(12) United States Patent
Haynes et al.

(10) Patent No.: US 8,282,557 B2
(45) Date of Patent: *Oct. 9, 2012

(54) DETERMINING RESPIRATORY OR CIRCULATORY HEALTH CONDITION IN ANIMALS FOR IMPROVED MANAGEMENT

(75) Inventors: John T. Haynes, Canyon, TX (US); William C. Pratt, Amarillo, TX (US)

(73) Assignee: MWI Veterinary Supply Co., Meridian, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/965,665

(22) Filed: Dec. 10, 2010

(65) Prior Publication Data

US 2011/0259283 A1 Oct. 27, 2011

Related U.S. Application Data

(63) Continuation of application No. 12/425,559, filed on Apr. 17, 2009, now Pat. No. 7,931,593, which is a continuation of application No. 11/292,412, filed on Nov. 30, 2005, now Pat. No. 7,670,292.

(60) Provisional application No. 60/631,646, filed on Nov. 30, 2004.

(51) Int. Cl.
*A61B 5/05* (2006.01)
*A61B 8/00* (2006.01)
*A01K 29/00* (2006.01)
*A01K 37/00* (2006.01)

(52) U.S. Cl. ........ 600/443; 600/427; 119/174; 119/712; 128/922

(58) Field of Classification Search .................. 600/437, 600/443, 410, 529; 119/51.01, 174, 712, 119/840; 128/922, 923

See application file for complete search history.

(56) References Cited

U.S. PATENT DOCUMENTS 2,786,449 A 3/1957 Dahlerup
2,891,722 A 6/1959 Nuttall et al.
(Continued)

FOREIGN PATENT DOCUMENTS

AU 2364297 A1 8/1997
(Continued)

OTHER PUBLICATIONS

"Answer to Request No. 20—List of Patents, Articles, and other prior art references," Fax Transmission from Mullin, Hoard & Brown to Klarquist Sparkman, 12 pp. (Dec. 2001).

(Continued)

*Primary Examiner* — Long V. Le
*Assistant Examiner* — Katherine Fernandez
(74) *Attorney, Agent, or Firm* — Klarquist Sparkman, LLP

(57) ABSTRACT

A method and system for managing at least one animal is disclosed. The method can include imaging, such as ultrasound imaging, a lung of a live animal, such as a ruminant or bovine. The imaging can be performed to determine a degree of respiratory damage from past respiratory illness. After imaging, information regarding respiratory damage can be used to select at least one aspect of the treatment, care or disposition of the animal. For example, the information can be used to select the amount or type of feed provided to the animal at a feedlot. The information also can be used to select how long the animal should be housed at the feedlot prior to slaughter. If an animal is diagnosed with a respiratory illness, information about its degree of respiratory damage from past respiratory illness also can be used to select the appropriate medical treatment or lack of treatment.

32 Claims, 81 Drawing Sheets

U.S. PATENT DOCUMENTS

| | | |
|---|---|---|
| 3,077,861 A | 2/1963 | Eide |
| 3,465,724 A | 9/1969 | Broadbent |
| 3,545,407 A | 12/1970 | Moore |
| 3,848,112 A | 11/1974 | Weichselbaum et al. |
| 3,929,277 A | 12/1975 | Byrne et al. |
| 4,049,950 A | 9/1977 | Byrne et al. |
| 4,129,096 A | 12/1978 | Nickel |
| 4,135,241 A | 1/1979 | Stanis et al. |
| 4,280,448 A | 7/1981 | Ostermann |
| 4,288,856 A | 9/1981 | Linseth |
| 4,336,589 A | 6/1982 | Smith et al. |
| 4,461,240 A | 7/1984 | Ostler |
| 4,461,241 A | 7/1984 | Ostler |
| 4,463,706 A | 8/1984 | Meister et al. |
| 4,512,096 A | 4/1985 | Heidecker |
| 4,517,923 A | 5/1985 | Palmer |
| 4,532,892 A | 8/1985 | Kuzara |
| 4,589,372 A | 5/1986 | Smith |
| 4,617,876 A | 10/1986 | Hayes |
| 4,687,107 A | 8/1987 | Brown et al. |
| 4,712,511 A | 12/1987 | Zamzow et al. |
| 4,733,971 A | 3/1988 | Pratt |
| 4,745,472 A | 5/1988 | Hayes |
| 4,767,212 A | 8/1988 | Kitahashi et al. |
| 4,785,817 A | 11/1988 | Stouffer |
| 4,786,925 A | 11/1988 | Landwehr |
| 4,815,042 A | 3/1989 | Pratt |
| 4,889,433 A | 12/1989 | Pratt |
| 4,910,024 A | 3/1990 | Pratt |
| 4,939,574 A | 7/1990 | Petersen et al. |
| 4,963,035 A | 10/1990 | McCarthy et al. |
| 5,008,821 A | 4/1991 | Pratt et al. |
| 5,028,918 A | 7/1991 | Giles et al. |
| 5,060,515 A | 10/1991 | Kanda et al. |
| 5,069,160 A | 12/1991 | Street et al. |
| 5,071,298 A | 12/1991 | Conzett |
| 5,140,942 A | 8/1992 | Flocchini |
| 5,140,988 A | 8/1992 | Stouffer et al. |
| 5,164,793 A | 11/1992 | Wolfersberger et al. |
| 5,184,733 A | 2/1993 | Arnarson et al. |
| 5,194,036 A | 3/1993 | Chevalier et al. |
| 5,218,344 A | 6/1993 | Ricketts |
| 5,219,224 A | 6/1993 | Pratt |
| 5,224,175 A | 6/1993 | Gouge et al. |
| 5,241,365 A | 8/1993 | Haagensen |
| 5,241,924 A | 9/1993 | Lundin et al. |
| 5,303,708 A | 4/1994 | Stouffer |
| 5,315,505 A | 5/1994 | Pratt et al. |
| 5,316,003 A | 5/1994 | Stouffer |
| 5,339,815 A | 8/1994 | Liu et al. |
| 5,340,211 A | 8/1994 | Pratt |
| 5,351,644 A | 10/1994 | Everett |
| 5,355,833 A | 10/1994 | Legrain |
| RE34,776 E | 11/1994 | Pratt |
| 5,369,032 A | 11/1994 | Pratt |
| 5,398,290 A | 3/1995 | Brethour |
| 5,401,501 A | 3/1995 | Pratt |
| 5,457,627 A | 10/1995 | Cureton et al. |
| 5,478,990 A | 12/1995 | Montanari et al. |
| 5,483,441 A | 1/1996 | Scofield |
| 5,487,603 A | 1/1996 | Hoff et al. |
| 5,525,967 A | 6/1996 | Azizi et al. |
| 5,552,772 A | 9/1996 | Janky et al. |
| 5,573,002 A | 11/1996 | Pratt |
| 5,579,719 A | 12/1996 | Hoff et al. |
| 5,596,945 A | 1/1997 | van der Lely |
| 5,617,864 A | 4/1997 | Stouffer et al. |
| 5,636,118 A | 6/1997 | Brewster et al. |
| 5,668,718 A | 9/1997 | Liu et al. |
| 5,673,647 A | 10/1997 | Pratt |
| 5,771,837 A | 6/1998 | van der Lely |
| 5,803,906 A | 9/1998 | Pratt et al. |
| 5,836,880 A | 11/1998 | Pratt |
| 5,853,244 A | 12/1998 | Hoff et al. |
| 5,867,820 A | 2/1999 | Cureton et al. |
| 5,873,323 A | 2/1999 | van den Berg et al. |
| 5,878,402 A | 3/1999 | Brester et al. |
| 5,944,598 A | 8/1999 | Tong et al. |
| 5,960,105 A | 9/1999 | Brethour |
| 6,000,361 A | 12/1999 | Pratt |
| 6,017,564 A | 1/2000 | Owens et al. |
| 6,032,084 A | 2/2000 | Anderson et al. |
| 6,058,379 A | 5/2000 | Odom et al. |
| 6,082,304 A | 7/2000 | Crain |
| 6,099,473 A | 8/2000 | Liu et al. |
| 6,131,744 A | 10/2000 | Pratt |
| 6,135,055 A | 10/2000 | Pratt |
| 6,200,210 B1 | 3/2001 | Pratt et al. |
| 6,211,789 B1 | 4/2001 | Oldham et al. |
| 6,216,053 B1 | 4/2001 | Cureton et al. |
| 6,231,435 B1 | 5/2001 | Pilger |
| 6,242,191 B1 | 6/2001 | Fluharty et al. |
| 6,318,289 B1 | 11/2001 | Pratt |
| 6,342,839 B1 | 1/2002 | Curkendall et al. |
| 6,427,627 B1 | 8/2002 | Huisma |
| 6,497,197 B1 | 12/2002 | Huisma |
| 6,516,270 B2 | 2/2003 | Pavlak et al. |
| 6,516,744 B1 | 2/2003 | Bjork et al. |
| 6,516,746 B2 | 2/2003 | Pratt |
| 6,547,726 B2 | 4/2003 | Pratt et al. |
| 6,554,188 B1 | 4/2003 | Johnson et al. |
| 6,579,236 B2 | 6/2003 | Pratt |
| 6,592,517 B2 | 7/2003 | Pratt et al. |
| 6,622,651 B1 | 9/2003 | Dessing |
| 6,664,897 B2 | 12/2003 | Pape et al. |
| 6,736,272 B2 | 5/2004 | Pratt |
| 6,745,126 B1 | 6/2004 | Pavlak et al. |
| 6,805,075 B2 | 10/2004 | Pratt |
| 6,837,189 B2 | 1/2005 | Schick |
| 6,889,197 B2 | 5/2005 | Lidow |
| 6,900,731 B2 | 5/2005 | Kreiner et al. |
| 6,901,369 B2 | 5/2005 | Cureton et al. |
| 6,974,373 B2 | 12/2005 | Kriesel |
| 7,129,423 B2 | 10/2006 | Baarsch et al. |
| 7,240,807 B2 | 7/2007 | Hoff et al. |
| 7,347,161 B2 | 3/2008 | Pratt |
| 7,464,666 B2 | 12/2008 | Pratt |
| 7,464,667 B2 | 12/2008 | Pratt |
| 7,603,284 B2 | 10/2009 | Stroman et al. |
| 7,607,405 B2 | 10/2009 | Pratt |
| 7,670,292 B2 | 3/2010 | Haynes et al. |
| 7,681,527 B2 | 3/2010 | Pratt |
| 7,714,729 B2 | 5/2010 | Pape et al. |
| 7,726,258 B2 | 6/2010 | Pratt |
| 7,748,345 B2 | 7/2010 | Pratt |
| 7,810,451 B2 | 10/2010 | Pratt |
| 7,827,015 B2 | 11/2010 | McGoogan et al. |
| 7,827,934 B2 | 11/2010 | Pratt |
| 7,836,849 B2 | 11/2010 | Pratt |
| 7,836,850 B2 | 11/2010 | Pratt |
| 7,870,840 B2 | 1/2011 | Valencia et al. |
| 7,904,284 B2 | 3/2011 | Engelke et al. |
| 7,931,593 B2 | 4/2011 | Haynes et al. |
| 2002/0065765 A1 | 5/2002 | Schuler et al. |
| 2002/0077718 A1 | 6/2002 | Harburda et al. |
| 2002/0103688 A1 | 8/2002 | Schneider |
| 2002/0158765 A1 | 10/2002 | Pape et al. |
| 2003/0062001 A1 | 4/2003 | Andersson |
| 2003/0083913 A1 | 5/2003 | Wolfe et al. |
| 2004/0023612 A1 | 2/2004 | Kriesel |
| 2004/0208343 A1 | 10/2004 | Golden et al. |
| 2005/0024988 A1 | 2/2005 | Hoff et al. |
| 2005/0049498 A1 | 3/2005 | Roche et al. |
| 2006/0054092 A1 | 3/2006 | Valencia et al. |
| 2006/0185605 A1 | 8/2006 | Renz et al. |
| 2006/0201432 A1 | 9/2006 | Pratt |
| 2006/0216332 A1 | 9/2006 | Freeman et al. |
| 2007/0145068 A1 | 6/2007 | Hoff et al. |
| 2007/0159918 A1 | 7/2007 | Hoff et al. |
| 2008/0059263 A1 | 3/2008 | Stroman et al. |
| 2008/0059264 A1 | 3/2008 | Stroman et al. |
| 2008/0059330 A1 | 3/2008 | Stroman et al. |
| 2008/0059534 A1 | 3/2008 | Stroman et al. |
| 2008/0065444 A1 | 3/2008 | Stroman et al. |
| 2008/0065473 A1 | 3/2008 | Stroman et al. |

| 2008/0077481 | A1 | 3/2008 | Stroman et al. |
| 2008/0097809 | A1 | 4/2008 | Stroman et al. |
| 2008/0190369 | A1 | 8/2008 | Pratt |

FOREIGN PATENT DOCUMENTS

| CA | 1295045 | | 1/1992 |
| CA | 2115999 | | 7/1999 |
| CA | 2181479 | | 11/1999 |
| CA | 2298074 | | 5/2000 |
| CA | 2111937 | | 6/2000 |
| CA | 2146308 | | 12/2006 |
| EP | 0945060 | A2 | 9/1999 |
| EP | 1 026 516 | | 10/2006 |
| GB | 2 303 211 | | 2/1997 |
| GB | 2 273 774 | | 4/1997 |
| GB | 2 304 191 | | 9/1999 |
| SU | 1704730 | | 1/1992 |
| WO | WO 00/62263 | | 10/2000 |

OTHER PUBLICATIONS

"Articles Received from Future Beef," pp. 1-5.
"Bovine Respiratory Disease," http://www.mycattle.com/health/updates/lesions.cfm, printed Sep. 14, 2004.
"Cattle Scanning Systems," Rapid City, South Dakota, 2 pp. (undated).
"Executive Summary National Beef Quality Audit," Published by the National Cattlemen's Association in Coordination with Colorado State University and Texas A&M University, 24 pp. (1992) (month not in issue, year sufficiently early—"the year of publication [without the month] will be accepted if the applicant points out in the information disclosure statement that the year of publication is sufficiently earlier than the effective U.S. filing date and any foreign priority date so that the particular month of publication is not in issue" MPEP 609).
"Introducing Sorting with the MSI Scanner," Stockmen's Livestock Exchange, Dickinson, North Dakota (Feb. 1995).
"Lung Lesions are Prevalent, Looks Can be Deceiving: Research Shows Costly Lung Lesions are Prevalent—Even in Treated Cattle," 3 pp. (date unknown).
"Oklahoma Researchers Look for Link Between Healthy Cattle and Eating Quality," American Society of Animal Science, American Dairy Science Association, News from the Midwest Sectional Meetings, Des Moines, Iowa, 2 pp. (Mar. 1998), http://www.asas.org/Midwestern/press/okmeat.html., printed Sep. 14, 2004.
"On the Humanside," *CALF News Cattle Feeder*, 1 p. (Aug. 1994).
"Scanner Cuts Feed Costs by 14%," CBW, 1 p. (Aug. 1993).
"The MSI Scanner," Primeline® Livestock Marketing advertisement, 2 pp. (Jan. 1994).
"The Shape of Things to Come," *Feed Lot*, 2 pp. (Apr./May/Jun. 1994).
"XIIIth World Congress on Diseases of Cattle," Durban Republic of South Africa, World Buiatrics Association, *Proceedings* vol. 1 (Sep. 1984).
Abdullah et al., "Relationships Between Objective and Subjective Measurements of Carcass Muscularity," *Proceedings of the New Zealand Society of Animal Production*, vol. 53, pp. 397-402 (1993) (month not in issue, year sufficiently early).
Abraham et al., "Factors Affecting Beef Carcass Cutability: An Evaluation of the USDA Yield Grades for Beef," *J. Animal Science*, 50(5):841-851 (1980) (month not in issue, year sufficiently early).
Allen et al., "Relationship of Physically Separable Muscle, Fat and Bone from the Left Side of Steer Carcasses to Yields of Retail Cuts, Fat Trim and Bone of the Right Side," pp. 311-315 (Circa more than one year prior to Oct. 31, 1994).
Article from *Feed Management*, vol. 36, No. 3, pp. 55-58 (Mar. 1985).
Aughtry, *SMS Feedlot Management System*, and attachments (54 pp.).
Baker, M., "Beef Cattle Comments," vol. 11, No. 6 (Jun. 2002), http://www.ansci.cornell.edu/beef/bcc0602.html., printed Sep. 14, 2004.
Barber et al., "Charolais and Angus Steers Slaughtered at Equal Percentages of Mature Cow Weight. I. Effects of Slaughter Weight and Diet Energy Density on Carcass Traits," pp. 218-230 (Circa more than one year prior to Oct. 31, 1994).
Beltran et al., "Growth Patterns of Two Lines of Angus Cattle Selected Using Predicted Growth Parameters," *J. Animal Science*, 70:734-741 (1992) (month not in issue, year sufficiently early).
Bishop et al., "Divergent Selection for Postweaning Feed Conversion in Angus Beef Cattle: I. Mean Comparisons," *J. Animal Science*, 69:4348-4359 (1991) (month not in issue, year sufficiently early).
Bond et al., "Effects of Feeding Level on Growth, Composition of Gain, Carcass Quality and Mature Body Size in Steers at Ages up to Six Years," *Growth*, pp. 388-403 (1982) (month not in issue, year sufficiently early).
Borland Software Co., "Delphi Case Study: Triple Point Technology, Inc.," (Jun. 6, 2001).
Brackebusch et al., "Relationship Between Longissimus Composition and the Composition of Other Major Muscles of the Beef Carcass," *J. Animal Science*, 69:631-640 (1991) (month not in issue, year sufficiently early).
Braun et al., "Ultrasonographic Findings in Cattle with Pleuropneumonia," *Veterinary Record*, 141:12-17 (Jul. 1997).
Braun et al., "Ultrasonography of the Lungs, Pleura, and Mediastinum in Healthy Cows," *Am J Vet Res*, 57(4):432-438 (Apr. 1996).
Braun, U., "Diagnostic Ultrasonography in Bovine Internal Diseases," $23^{rd}$ World Buiatrics Congress, Quebec, Canada, 5 pp. (Jul. 2004).
Brethour et al., "Quality Management in the Cattle Industry," Roundup 1992, *KAES Report of Progress No. 653*, Fort Hays Branch Experiment Station, Kansas State University, pp. 1-25 (Apr. 1992).
Brethour, "Estimating Marbling Score in Live Cattle from Ultrasound Images Using Pattern Recognition and Neural Network Procedures," Kansas State University, Fort Hays Branch Experiment Station, 8 pp. (incomplete) (Circa more than one year prior to Oct. 31, 1994).
Brethour, "Relationship of Ultrasound-Measured Backfat to Feedlot Performance of Beef Steers," Roundup 1991, *KAES Report of Progress No. 627*, Fort Hays Branch Experiment Station, Kansas State University, pp. 1-30 (Apr. 1991).
Brethour, "Technology to Implement Quality into Beef Production," *KAES Report of Progress No. 706*, Fort Hays Branch Experiment Station, Kansas State University, pp. 13-17 (Circa more than one year prior to Oct. 31, 1994).
Brethour, "The Repeatability and Accuracy of Ultrasound in Measuring Backfat of Cattle," *J. Animal Science*, vol. 70, pp. 1039-1044, 1992.
Brethour, "Using Ultrasound Technology to Increase Cattle Feeding Profits,"1989 Roundup, *KAES Report of Progress No. 570*, Fort Hays Branch Experiment Station, Kansas State University, pp. 5-12 (Apr. 1989).
Brown and Shrode, "Body Measurements of Beef Calves and Traits of Their Dams to Predict Calf Performance and Body Composition as Indicated by Fat Thickness and Condition Score," *J. Animal Science*, 33(1):7-12 (1971) (month not in issue, year sufficiently early).
Brown et al., "Evaluating Relationships Among Immature Measures of Size Shape and Performance of Beef Bulls, II. The Relationships Between Immature Measures of Size, Shape and Feedlot Traits in Young Beef Bulls," *J. Animal Science*, 36(6):1021-1031 (1973) (month not in issue, year sufficiently early).
Busch et al., "Body Measurements, Subjective Scores and Estimates of Certain Carcass Traits as Predictors of Edible Portion in Beef Cattle," South Dakota State University, Brookings, pp. 557-566 (Circa more than one year prior to Oct. 31, 1994).
Butcher and Webb, "Equipment for Farm Use in the National Cooperative Dairy Herd Improvement Program," National Cooperative Dairy Herd Improvement Program Handbook, 4 pp. (1985) (month not in issue, year sufficiently early).
Butts et al., "Relationships Among Definable Characteristics of Feeder Calves, Subsequent Performance and Carcass Traits. I. Objective Measurements," *J. Animal Science*, 51(6):1297-1305 (1980) (month not in issue, year sufficiently early).
Butts et al., "Relationships Among Definable Characteristics of Feeder Calves, Subsequent Performance and Carcass Traits II. Subjective Scores," *J. Animal Science*, 51(6):1306-1313 (1980) (month not in issue, year sufficiently early).

Caswell and Gagea, "Recognizing the Gross Lesions of Mycoplasma Bovis in Feedlot Beef Calves," Ontario Ministry of Agriculture, Food and Rural Affairs, 2 pp., http://www.gov.on.ca/OMAFRA/english/livestock/ceptor/2002/june02a6.htm., printed Aug. 21, 2005.

Clayton, "Prediction of Feedlot Performance and Carcass Characteristics Using Feeder Cattle Traits," Thesis, Colorado State University (1982) (month not in issue, year sufficiently early).

Coleman et al., "Body and Carcass Composition of Angus and Charolais Steers as Affected by Age and Nutrition," *J. Animal Science*, 71:86-95 (1993) (month not in issue, year sufficiently early).

Coleman Natural Products, Inc., "Coleman Natural Beef: Certified Organic by Coleman Natural Products, Inc.," (2000).

Corah et al., "Feeding Your Cows by Body Condition", November Kansas State University, Agricultural Experiment Station and Cooperative Extension Services (1991) (month not in issue, year sufficiently early).

Cornett, "Sorting by Computer Eye: System Measures Body so Arrivals can be Grouped to hit Carcass Specs." *Beef*, pp. 74, 76, 78 (Apr. 1994).

Cornett, S., "Fast Track Sorting," *Beef*, pp. 16-19 (Aug. 1994).

Crockett et al., "Preweaning, Feedlot and Carcass Characteristics of Calves Sired by Continental, Brahman and Brahman-Derivative Sires in Subtropical Florida," *J. Animal Science*, vol. 49, pp. 900-907, 1979.

Crouse et al., "Prediction of Feeder Calf Performance and Subsequent Carcass Characteristics," *J. Animal Science*, 38(2):256-263 (1974) (month not in issue, year sufficiently early).

Cundiff et al., "Breeding Cattle for Improved Product Consistency," Presented 1994 National Cattlemen's Convention and Trade Show, Reno, Nevada, pp. 1-28 (1994) (month not in issue).

CVP Brand Name—Nonproprietary Name Index, pp. N-1-N-28 (Circa more than one year prior to Oct. 31, 1994).

CVP Withdrawal Time Charts, pp. W-1-W-40, (Circa more than one year prior to Oct. 31, 1994).

Daley, "Prediction of Beef Carcass Composition Using Preslaughter Linear Measures," Thesis, Colorado State University (1981) (month not in issue, year sufficiently early).

Daley, "Relationship of Pre-weaning Measures and Performance Traits in Beef Cattle," Dissertation, Colorado State University (1984) (month not in issue, year sufficiently early).

Daniel et al., "Adding Value to Lamb by Evaluating and Reducing the Incidence of Lung Lesions," 3 pp. (date unknown).

Doye and Northcutt, "Integrated Resource Management (IRM) Tools: Standard Performance Analysis Cow-Calf Software," Oklahoma Cooperative Extension Service, Oklahoma State University, F-222, pp. 222.1-222.4 (May 1994).

eBay, Inc., "Internet Shopping Network and eBay partner to Expand Auction Capabilities," (Jan. 13, 1998).

Edwards et al., "Using Ultrasound, Linear Measurements and Live Fat Thickness Estimates to determine the Carcass Composition of Market Lambs," *J. Animal Science*, 67:3322-3330 (1989) (month not in issue, year sufficiently early).

Effertz, N., "Anxiously Awaiting Alliances," *Beef Today*, pp. 18-20 (Aug. 1994).

Epley et al., "Prediction of Weight and Percent of Retail Cuts of Beef Using Five Carcass Measurements," *J. Animal Science*, 30:872-879 (1970) (month not in issue, year sufficiently early).

Epperson, W., "A Pilot Study of the Impact of Metaphylactic Treatment at Processing on Lung Lesions at Slaughter," 4 pp., http://ars.sdstate.edu/beefext/BeefReports/2000/a_pilot_study_of_the_impact_of.htm, printed Aug. 21, 2005.

Examiner's First Report, dated Sep. 21, 2009, from the Australian Intellectual Property Office, for Australian Patent Application No. 2006206287, 2 pp.

Extended European search report, dated May 12, 2010, issued by the European Patent Office for EPC Patent Application No. 05852562.7, 6 pp.

Faulkner et al., "Prediction of Fat Cover and Carcass Composition from Live and Carcass Measurements," *J. Animal Science*, 68:604-610 (1990) (month not in issue, year sufficiently early).

Fee, R., "High-Tech, High-Spec Cattle Feeding," *Successful Farming*, 2 pp., (Jan. 1994).

Feuz et al., "Analysis of the Efficiency of Four Marketing Methods for Slaughter Cattle," *Agribusiness*, 9(5):453-463 (1993) (month not in issue, year sufficiently early).

Final Office Action, dated May 13, 2009, issued by the U.S. Patent and Trademark Office for U.S. Appl. No. 11/292,412, 20 pp.

Fox and Black, "A System for Predicting Body Composition and Performance of Growing Cattle," *J. Animal Science*, 58(3):725-739 (1984) (month not in issue, year sufficiently early).

Fox and Perry, "Predicting Individual Feed Requirement, Incremental Cost of Gain, and Carcass Composition in Live Cattle Varying in Body Size," 8 pp. (Circa more than one year prior to Oct. 31, 1994).

Fox et al., "A Manual for Using the Cornell Net Carbohydrate and Protein System for Evaluating Cattle Diets," Revised for CNCPS Release 2, pp. 1-43 (Aug. 1993).

Fox et al., "A Net Carbohydrate and Protein System for Evaluating Cattle Diets: III. Cattle Requirements and Diet Adequacy," *J. Animal Science*, 70:3578-3596 (1992) (month not in issue, year sufficiently early).

Fox et al., "Cornell Cattle Systems 5, Cattle Growth and Profit Prediction Model for All Classes of Growing Cattle, Users Guide," pp. 1-58 (Circa more than one year prior to Oct. 31, 1994).

Gardner et al., "Health of Finishing Steers: Effects on Performance, Carcass Traits and Meat Tenderness," *J. Animal Science*, 77:3168-3175 (1999), Abstract, http://www.asas.org/jas/abs/1999/dec3168.html., printed Sep. 14, 2004.

Gerke, J., "Consider Disposition in Genetic Selection," *Drovers Journal*, Section: Tools and Strategies, (Jun. 1, 2001).

Gibb, "Relationships Among Feeder Cattle Characteristics and Subsequent Production Traits," Thesis, Colorado State University, 214 pp. (1985) (month not in issue, year sufficiently early).

Gill and Lusby, "Limit Feeding Light-Weight Cattle High Nutrient Density Diets: Programmed Feeding for Calves (PROGFED2) (Revision 2)," *Oklahoma Cooperative Extension Service Current Report*, Oklahoma State University, CR-3025, pp. 3025.1-3025.8 (Jul. 1992).

Gill et al., "Spreadsheet Programs for Calculation of Complete Diets for Beef Cattle, Checking for Nutrient Balance and Estimating Gain (AUTONRCA & AUTONRCD)," *Oklahoma Cooperative Extension Service Current Report*, Oklahoma State University, CR-3027, pp. 3027.1-3027.4 (Apr. 1994).

Gjermundson, C., "Auction Scanners Classify Beef Shape, Size," *Electronic Efficiency*, 1 p. (date unknown).

Grafel, D., "Electronic Tracking Expands Role," *Drovers Journal*, p. 12 (Circa more than one year prior to Oct. 31, 1994).

Greathead et al., "The Relationship Between Ultrasonic Point Readings in Live Cattle and Carcass Fat Cover," *J. Agric. Sci.*, pp. 651-657 (1984) (month not in issue, yaer sufficiently early).

Gross, C., "Computer Judgements in the Feedlot," *Calf News*, pp. 6, 28, 29, (Aug. 1984).

Hakanson, W., "The Future is Now in the Health Care Industry," *Automatic I.D. News*, p. 49, (May 1987).

Halberg, N., "Indicators of resource use and environmental impact for use in a decision aid for Danish livestock farmers," *Agriculture, Ecosystems & Environment*, vol. 76, pp. 17-30 (1999).

Hankins and Berk, "Relationships Among Production and Grade Factors of Beef," Technical Bulletin No. 665, US Department of Agriculture, 19 pp. (Nov. 1938).

Hardin, B., "DECI (Decision Evaluator for the Cattle Industry): Information Age Tool for the Cattle Industry," *Agricultural Research*, (May 1998).

Harrison, V., "Optimizing Marketing Dates for Steers by Accounting for Individual Differences," *Agriculture Economic Report*, No. 372, U.S. Department of Agriculture, 31 pp. (Jun. 1977).

Hedrick, "Methods of Estimating Live Animal and Carcass Composition," *J. Animal Science*, Vo. 57, pp. 1316-1327, 1983.

Henderson, G., "Superior Genetics, Guaranteed Health," *Drovers Journal*, Section: Tools and Strategies, (Sep. 1, 2001).

Herring et al., "Evaluation of Machine, Technician, and Interpreter Effects on Ultrasonic Measures of Backfat and Longissimus Muscle Area in Beef Cattle," *J. Animal Science*, 72:2216-2226 (1994) (month not in issue).

Hicks et al., "Daily Dry Matter Intake by Feedlot Cattle: Influence of Breed and Gender," *J. Animal Science*, 68:245-253 (1990) (month not in issue, year sufficiently early).

Hicks et al., "Dry Matter Intake by Feedlot Beef Steers: Influence of Initial Weight, Time on Feed and Season of Year Received in Yard," *J. Animal Science*, 68:254-264 (1990) (month not in issue, year sufficiently early).

Hillman et al., "Report of the Committee on Livestock Identification," *United States Animal Health Association* (USAHA), 2004 Report, Oct. 26, 2004, (pp. 342-426), (Website: http://www.usaha.org/committees/reports/report-id-2004.pdf).

Hooda et al., "A review of water quality concerns in livestock farming areas," *The Science of the Total Environment*, vol. 250, pp. 143-167 (2000).

Houghton and Turlington, "Application of Ultrasound for Feeding and Finishing Animals: A Review," *J. Animal Science*, 70:930-941 (1992) (month not in issue, year sufficiently early).

Hyer et al., "The Relationship of Body Composition and Feed Intake of Beef Steers," *Animal Science Research Report*, Agriculture Experiment Station, Division of Agriculture, Oklahoma State University, pp. 96-100 (May 1986).

Ishmael, W., "Huntin' Daylight—Pre-Conditioned Pay-Back," Cattle Today Online, 4 pp., http://www.cattletoday.com/archive/2003/October/CT293.shtml., printed Aug. 21, 2005.

Jeffrey et al., "Weight-based Adjustment for Ultrasonically Derived Carcass Traits Amoung Performance Tested Angus Bulls," *Animal Science Research Report*, pp. 49-54, (1993) (month not in issue, year sufficiently early).

Kay, S., "New Scanner May Change Industry," *Cattle Buyer's Weekly*, 1 p. (circa Sep. 1993).

Kent et al., "Estimates of Beef Carcass Intermuscular Fat," *J. Animal Science*, 69:4836-4844 (1991) (month not in issue, year suffifciently early).

Koch et al., "Characterization of Biological Types of Cattle—Cycle II: III. Carcass Composition,Quality and Palatability," *J. Animal Science*, 49(2):448-460 (1979) (month not in issue, year sufficiently early).

Koch et al., "Characterization of Biological Types of Cattle. III. Carcass Composition, Quality and Palatability," *J. Animal Science*, 43(1):48-62 (1976) (month not in issue, year sufficiently early).

Koch, R., "Selection in Beef Cattle. III. Correlated Response of Carcass Traits to Selection for Weaning Weight, Yearling Weight and Muscling Score in Cattle," *J. Animal Science*, 47(1):142-150 (1978) (month not in issue, year sufficiently early).

Larson, B., "A New Look at Reducing Infectious Disease in Feedlot Cattle," 2005 Plains Nutrition Council Spring Conference, San Antonio, Texas, Publication No. AREC 05-20, Texas A&M University, pp. 9-18 (Apr. 2005).

Lee et al., "Effect of Cattle Type and Energy Intake on Carcass Traits and Adipose Tissue Cellularity," *J. Animal Science*, 57(3):621-627 (1983) (month not in issue, year sufficiently early).

Leu, B., "Cow Herd Improvement Program Services (CHIPS): 2001 Update," *Iowa State University Extension*, (2001).

Lusby and Gill, "Spreadsheet for Calculating Livestock Rations (RATIONII)," *OSU Extension Facts*, No. 3024, Oklahoma State University, pp. 3024.1-3024.2 (Jul. 1991).

Lusby and Gill, "Stocker Cattle Nutrition I—Basic Considerations for Rations and Supplements," *OSU Extension Facts*, No. 3012, Oklahoma State University, pp. 3012.1-3012.2 (Mar. 1982).

Lusby and Gill, "Stocker Cattle Nutrition II—Formulating Complete Rations," *OSU Extension Facts*, No. 3013, Oklahoma State University, pp. 3013.1-3013.4 (Mar. 1982).

Lusby and Gill, "Stocker Cattle Nutrition III: Formulating Supplements," *OSU Extension Facts*, No. 3014,Oklahoma State University, pp. 3014.1-3014.4 (Jul. 1982).

Maday, J., "Building a Value Chain," *Drovers Journal*, Section: Tools and Strategies, (Sep. 14, 2001).

Maday, J., "Cattle Sorting Enters a New Age," *DJ Feeder Management*, pp. 1, 4-5, 8 (Sep. 1994).

Maday, J., "Different Strokes," *Drovers Journal*, Section: Food Systems International, (Mar. 1, 2001).

McEllhiney, R., "Micro Systems: Revolutionizing Proportioning," *Feed Management*, 36(3):54-58 (Mar. 1985).

McPeake, C., "Hip Height and Frame Score Determination," *OSU Extension Facts*, F-3271, Oklahoma State University, pp. 3271.1-3271.2 (Circa more than one year prior to Oct. 31, 1994) (Circa more than one year prior to Oct. 31, 1994).

Midwest MicroSystems, LLC, "Cow Sense: Herd Management Software."

Miller et al., "Evaluation of Live and Carcass Techniques for Predicting Beef Carcass Composition," *Meat Science*, 23:111-129 (1988) (month not in issue, year sufficiently early).

Murray et al., "Effects of Three Different Growth Rates on Empty Body Weight, Carcass Weight and Dissected Carcass Composition of Cattle," *J. Agric Sci.*, 82:535-547 (1974) (month not in issue, year sufficiently early).

Nour and Thonney, "Technical Note: Chemical Composition of Angus and Holstein Carcasses Predicted from Rib Section Composition," *J. Animal Science*, 72:1239-1241 (1994) (month not in issue).

Office Action, dated Apr. 2, 2008, issued by the U.S. Patent and Trademark Office for U.S. Appl. No. 11/977,625, 10 pp.

Office Action, dated Jul. 1, 2008, issued by the U.S. Patent and Trademark Office for U.S. Appl. No. 11/977,511, 22 pp.

Office Action, dated Oct. 2, 2008, issued by the U.S. Patent and Trademark Office for U.S. Appl. No. 11/292,412, 20 pp.

Office Action for Canadian Patent Application No. 2,161,749, issued by the Canadian Intellectual Property Office, pp. 1-9, Oct. 23, 2008.

Office Action for Canadian Patent Application No. 2,493,331, issued by the Canadian Intellectual Property Office, pp. 1-5, Nov. 12, 2008.

Office Action, dated Dec. 10, 2009, issued by the U.S. Patent and Trademark Office for U.S. Appl. No. 12/251,927, 21 pp.

Office Action, dated Dec. 23, 2009, issued by the U.S. Patent and Trademark Office for U.S. Appl. No. 12/417,548, 23 pp.

Office Action, dated May 27, 2010, issued by the U.S. Patent and Trademark Office for U.S. Appl. No. 12/425,559, 29 pp.

Old and Garrett, "Effect of Energy Intake on Energetic Efficiency and Body Composition of Beef Steers Differing in Size at Maturity," *J. Animal Science*, 65:1371-1380 (1987) (month not in issue, year sufficiently early).

Olson, K., "Effect of Winter Environment (Range vs Drylot) on Replacement Heifer Development and Behavior," *KAES Report of Progress No. 597*, Fort Hays Branch Experiment Station, Kansas State University, pp. 1-33 (Apr. 1990).

Oltjen and Garrett, "Effects of Body Weight, Frame Size and Rate of Gain on the Composition of Gain of Beef Steers," *J. Animal Science*, 66:1732-1738 (1988) (month not in issue, year sufficiently early).

Oringderff, B., "A Little Black Box," pp. 39-44 (Circa more than one year prior to Oct. 31, 1994).

Owens et al., "Factors that Alter the Growth and Development of Ruminants," *J. Animal Science*, 71:3138-3150 (1993) (month not in issue, year sufficiently early).

Park et al., "Divergent Selection for Postweaning Feed Conversion in Angus Beef Cattle: III. Linear Body Measurements of Progeny," *J. Animal Science*, 71:334-340 (1993) (month not in issue, year sufficiently early).

Perkins et al., "Evaluation of Ultrasonic Estimates of Carcass Fat Thickness and Longissimus Muscle Area in Beef Cattle," *J. Animal Science*, 70:1002-1010 (1992) (month not in issue, year sufficiently early).

Phillips et al., "Effect of Pre- and Postweaning Management System on the Performance on Brahman Crossbred Feeder Calves," *J. Animal Science*, 69:3102-3111 (1991) (month not in issue, year sufficiently early).

Pratt, W., U.S. Appl. No. 10/903,963, Cattle Management Method and System (filed Jul. 30, 2004).

Prior et al., "Influence of Dietary Energy and Protein on Growth and Carcass Composition in Different Biological Types of Cattle," *J. Animal Science*, 45:132-146 (1977) (month not in issue, year sufficiently early).

Qualcomm, Inc., "Qualcomm Wireless Business Solutions," (2001).

Quansah et al., "Farmers' perceptions and management of soil organic matter—a case study from West Africa," *Nutrient Cycling in Agroecosystems*, vol. 61, pp. 205-213 (2001).

Sainz and Oltjen, "Improving Uniformity of Feeder Steers Using Ultrasound and Computer Modelling," *Proceedings, Western Section, American Society of Animal Science*, vol. 45, pp. 179-181 (1994) (month not in issue).
SCA Technologies, LLC, "Solutions: Case Histories: Saving Significant Costs by Restructuring McDonald's Various Meat Supply Chains," (2001).
Scofield and Boyd, "MSI Messenger," *Cattle Scanning Systems Newsletter*, vol. 1, No. 1, 2 pp., (Apr. 1994).
Shackelford et al., "Predicting Beef Carcass Cutability," *J. Animal Science*, 73:406-413 (1995).
Smith et al., "Traceback, Traceability and Source Verification in the U.S. Beef Industry," Presented at the XXI World Buiatrics Congress, (Dec. 5, 2000).
Smith, G.C., "Increasing Value in the Supply Chain," Presented at the 81st Annual Conference of the Canadian Meat Council in Vancouver, British Columbia, Canada (Feb. 9, 2001).
Smith, R., "Impact of Disease on Feedlot Performance: A Review," *J. Anim. Sci.*, 76:272-274 (1998).
Stough, J., "A National System," *Drovers Journal*, Section: Tools and Strategies, (Feb. 1, 2000).
Stough, J., "A New View of Your Herd," *Drovers Journal*, Section: Tools and Strategies, (Jan. 1, 2000).
Summers, L., "Bullish on Technology," *The Lane Report*, pp. 23-26 (Aug. 2001).
Swatland et al., "A Review of Probes and Robots: Implementing New Technologies in Meat Evaluation," *J. Animal Science*, 72:1475-1486 (1994) (month not in issue).
Tatum et al., "Carcass Characteristics, Time on Feed and Cooked Beef Palatability Attributes," *J. Animal Science*, 50(5):833-840 (1980) (month not in issue, year sufficiently early).
Tatum et al., "Evaluation of Ultrasound and Visual Appraisal for Estimation of Fat Thickness and Ribeye Area in Live Cattle," pp. 99-103 (Circa more than one year prior to Oct. 31, 1994).
Tatum et al., "Influence of Diet Growth Rate and Carcass Composition of Steers Differing in Frame Size and Muscle Thickness," *J. Animal Science*, 66:1942-1954 (1988) (month not in issue, year sufficiently early).
Tatum, J., "Effects of Management History, Breed-Type and Carcass Characteristics on Palatability Attributes of Beef," Dissertation, Texas A&M University (Aug. 1978).
Thomson, D., "Mortality in Feedyard Cattle," 2005 Plains Nutrition Council Spring Conference, San Antonio, Texas, Publication No. AREC 05-20, Texas A&M University, pp. 1-8 (Apr. 2005).
Thornton et al., "Feed Intake by Feedlot Beef Steers: Influence of Initial Weight and Time on Feed," *Animal Science Research Report*, Oklahoma Agricultural Experiment Station, pp. 320-331 (1985) (month not in issue, year sufficiently early).
Triple Point Technology, Inc., "Triple Point Technology Launches Next-Generation Commodity Trading System—Tempest XL," (Aug. 23, 2001).
U.S. Department of Agriculture and U.S. Environmental Protection Agency: Office of Wastewater Management, "Unified National Animal Feeding Operations (AFO) Strategy: Executive Summary," (Mar. 9, 1999).
U.S. Department of Agriculture, "Agricultural Marketing Service: Rule 7 CFR Part 205," (Dec. 21, 2000).
U.S. Department of Agriculture, "Institutional Meat Purchase Specifications: For Fresh Beef Products Series 100," (Jun. 1996).
U.S. Federal Trade Commission, "Internet Auctions: A Guide for Buyers and Sellers," (Sep. 2000).
Waldner et al., "Validation of Real-Time Ultrasound Technology for Predicting Fat Thicknesses, Longissimus Muscle Areas, and Composition of Brangus Bulls from 4 Months to 2 Years of Age," *J. Animal Science*, 70:3044-3054 (1992) (month not in issue, year sufficiently early).
Whittaker et al., "Principles of Ultrasound and Measurement of Intramuscular Fat," *J. Animal Science*, 70:942-952 (1992) (month not in issue, year sufficiently early).
Williams et al., "Comparison of Ultrasound Measurements for Predicting Retail Product and Trimmable Fat in Beef Carcasses," Abstracts from *J. Animal Science*, vol. 66, Supplement 1, abstract 213 (1988) (month not in issue, year sufficiently early).
Williams et al., "Simulated Influence of Postweaning Production System on Performance of Different Biological Types of Cattle. II. Carcass Composition, Retail Product, and Quality," Roman L. Hruska US Meat Animal Research Center, Clay Center, Nebraska, pp. 1-28 (Circa more than one year prior to Oct. 31, 1994).
Williams et al., "The Effects of Muscle Thickness and Time on Feed on Hot Fat Trim Yields, Carcass Characteristics and Boneless Subprimal Yields," *J. Animal Science*, 67:2669-2676 (1989) (month not in issue, year sufficiently early).
Zinn et al., "Feedlot and Carcass Grade Characteristics of Steers and Heifers as Influenced by Days on Feed," *J. Animal Science*, 31:302-306 (1970) (month not in issue, year sufficiently early).
Allen, "Tendon and Ligament Ultrasound in the Equine Athlete," Allen-Schneider Equine Hospital, paper, 7 pp., no date provided.
Badertscher, "Ultrasonographic Evaluation of the Urinary System and Prostate Gland in the Dog and Cat," Veterinary Imaging Professionals, 4 pp., no date provided.
Burns, "Veterinary Ultrasound Equipment and Scanning Techniques," Animal Ultrasound Seminar and Wet-Lab, 77 pp., Oct. 13-15, 1989.
Cole, "Intake Control Systems," USDA, Agricultural Research Service, pp. 156-161, no date provided.
Corometrics Medical Systems, Inc. "Aloka 500V" veterinary ultrasound system brochure, 2 pp., Dec. 1989.
Doornenbal et al., "Comparison of Methods Used for Carcass Evaluation in Swine," *Journal of Animal Science*, vol. 21, No. 3, 3 pp., Aug. 1962.
Feder, "Managing the Technological Frontiers," *New York Times*, 2 pp., Jan. 13, 1993.
Forrest et al., "A Review of Potential New Methods of On-Line Pork Carcass Evaluation," Measuring Effectiveness of Growth Modifiers on Carcass Value Symposium, ASAS 80th Ann. Mtg., 7 pp., Sep. 12, 1988.
Geers, "Electronic identification, monitoring and tracking of animals," CAB International, Abstract, 3 pp., 1997.
Gibb et al., "Bunk attendance of feedlot cattle monitored with radio frequency technology," *Canadian Journal of Animal Science*, vol. 78, Issue 4, pp. 707-710, Dec. 1998.
Gillis, "An Evaluation of Indices of Carcass Yield, Physical Composition and Chemical Composition in Swine; and Ultrasonic Measurement of the *Longissimus dorsi* area and Fat Thickness in Beef and Swine," excerpts from A Thesis Presented to the Faculty of the Graduate School of Cornell University, 6 pp., Jan. 1971.
Grant Award, U.S. Department of Agriculture, Sep. 23, 1992.
Gresham et al., "Commercial Adaptation of Ultrasonography to Predict Pork Carcass Composition from Live Animal and Carcass Measurements," *Journal of Animal Science*, vol. 70, 9 pp., 1992.
Growsafe.com web pages, Growsafe, 2 pp., Jan. 2001, retrieved from Archive.org Jan. 7, 2011.
Hamby et al., "Muscle Metabolism and Real-Time Ultrasound Measurement of Muscle and Subcutaneous Adipose Tissue Growth in Lambs Fed Diets Containing a Beta-Agonist," *Journal of Animal Science*, vol. 63, pp. 1410-1417, 1986.
Holloway, "Relationships of Empty-Body Composition and Fat Distribution to Live Animal and Carcass Measurements in *Bos Indicus-Bos Taurus* Crossbred Cows," *Journal of Animal Science*, vol. 68, 5 pp., 1990.
Landais et al., *Ultrasonic News* magazine, 26 pp., Winter 1960.
McAllister et al., "Electronic identification: Applications in beef production and research," *1999 annual meeting of the Canadian Society of Animal Science*, pp. 381-392, 1999.
Mutalib, "Studies on the Pathogenesis of Staphylococcal Osteomyelitis in Chickens. I. Effect of Stress on Experimentally Induced Osteomyelitis," *Avian Diseases*, vol. 27, No. 1, 16 pp., Jan.-Mar. 1983.
Perry et al., "The Use of Electronic Identification and Monitoring to Evaluate Feed Consumption, Weight Gain and Feed Efficiency of Feedlot Cattle," *San Joaquin Experimental Range Research Notes*, CATI Publication #970502, 3 pp., May 1997.
Powis, "Seeing 10,000 Things in Ultrasound," *Syllabus, 2nd Annual AIUM Animal Ultrasound Seminar & WET-LAB*, 84 pp., Sep. 28-30, 1990.

Schwartzkopf-Genswein, "Validation of a radio frequency identification system for monitoring feed patterns of feedlot cattle," *Livestock Production Science*, vol. 60, pp. 27-31, 1999.

Schwartzkopf-Genswein, "Feedbunk Detective," *Beef*, 3 pp., Oct. 1, 1998.

Simko et al., "Mild Exercise, Effect on Body Composition and Metabolism," *New York State Journal of Medicine*, vol. 74, No. 8, 5 pp., Aug. 1974.

Simm, "The Use of Ultrasound to Predict the Carcass Composition of Live Cattle—A Review," *Animal Breeding Abstracts*, vol. 51, No. 12, 23 pp., Dec. 1993.

Sowell et al., "Feeding and Watering Behavior of Healthy and Morbid Steers in a Commercial Feedlot," *Journal of Animal Science*, vol. 77, pp. 1105-1112, 1999.

Stouffer et al., "A Review of Ultrasonic Applications in Animal Science," *Journal of Clinical Ultrasound*, vol. 5, No. 2, 5 pp., Apr. 1977.

Stouffer et al., "Development and Application of Ultrasonic Methods for Measuring Fat Thickness and Rib-Eye Area in Cattle and Hogs," *Journal of Animal Science*, vol. 20, No. 4, 8 pp., Nov. 1961.

Stouffer et al., "Ultrasonics for Evaluation of Live Animal and Carcass Composition," *Proceedings of the Twelfth Research Conference Sponsored by the Research Advisory Council of the American Meat Institute Foundation at the University of Chicago*, 7 pp., 1960.

Stouffer et al., Ultrasound for Animal Evaluation, *New York's Food and Life Sciences*, vol. 10, No. 3, 2 pp., 1977.

Stouffer, "Application of Ultrasound in the Livestock and Meat Industry," paper, 6 pp., 1966.

Stouffer, "Carcass Evaluation and its Research Applications," *Proceedings of the 14$^{th}$ Recip. Meat Conf.*, 5 pp., 1961.

Stouffer, "Die Anwendung von Ultraschallmessungen in den USA," *Aus dem Institut für Tierzucht und Haustiergenetik der Universität Göttingen, Sonderdruck aus Züchtungskunde, Band 36, Heft 2*, Feb. 1964.

Stouffer, "Meat Evaluation in Live Animals," *Proceedings 1966, Frontiers in Food Research*, 7 pp., Apr. 12-13, 1966.

Stouffer, "Objective Technical Methods for Determining Carcass Value in Live Animals with Special Emphasis on Ultrasonics," *EAAP Symposium on Carcass Value, World Review of Animal Production*, 9 pp., 1966.

Stouffer, "Real Time Ultrasound Evaluation," Selecting Beef Cattle for Optimum Productivity, paper, 1 p, Jun. 19, 1988.

Stouffer, "Relationship of Ultrasonic Measurements and X-Rays to Body Composition," *Annals of the New York Academy of Sciences*, vol. 110, Park I, 8 pp., Sep. 26, 1963.

Stouffer, "Status of the Application of Ultrasonics in Meat Animal Evaluation," paper, 13 pp., 1959.

Stouffer, "Techniques for the Estimation of the Composition of Meat Animals," Techniques and Procedures in Animal Sciences, 13 pp., 1969.

Stouffer, The Ultrasonic Approach to Measuring Fat and Muscling in Live Beef Cattle, paper, 2 pp., no date provided.

Stouffer, "Ultrasonic Determination of Body Composition," Aerospace Medical Research Laboratory, 50 pp., Dec. 1968.

Stouffer, "Ultrasonic Research in Europe," paper, 2 pp., no date provided.

Stouffer, "Ultrasonics for Live Lamb and Carcass Evaluation," NC-111 Technical Committee for Increased Efficiency of Sheep Production, Sheep Industry Development Program, symposium proceedings, 5 pp., Jun. 15, 1988.

Stouffer, "Ultrasound for Disease Detection in Animals," FSIS-USDA Seminar brochure, 4 pp., Sep. 18, 1985.

Stouffer, "Using Ultrasound to Objectively Evaluate Composition and Quality of Livestock," *21$^{st}$ Century Concepts Important to Meat-Animal Evaluation*, 3 pp., Feb. 1991.

The CSB System: Grading Hog Carcasses: The CSB Ultra-Meater brochure, 2 pp., no date provided.

Wasserman et al., "Meat and Poultry Inspection, The Scientific Basis of the Nations's Program," Prepared by the Committee on the Scientific Basis of the Nation's Meat and Poultry Inspection Program, 11 pp., 1985.

Westervelt et al., "Estimating Fatness in Horses and Ponies," *Journal of Animal Science*, vol. 43, No. 4, 3 pp., 1976.

Wongkhalaung, "Pregnancy Detection and Changes During Gestation in Swine Determined with Ultrasound," excerpts from A Thesis Presented to the Faculty of the Graduate School of Cornell University, 2 pp., Jun. 1975.

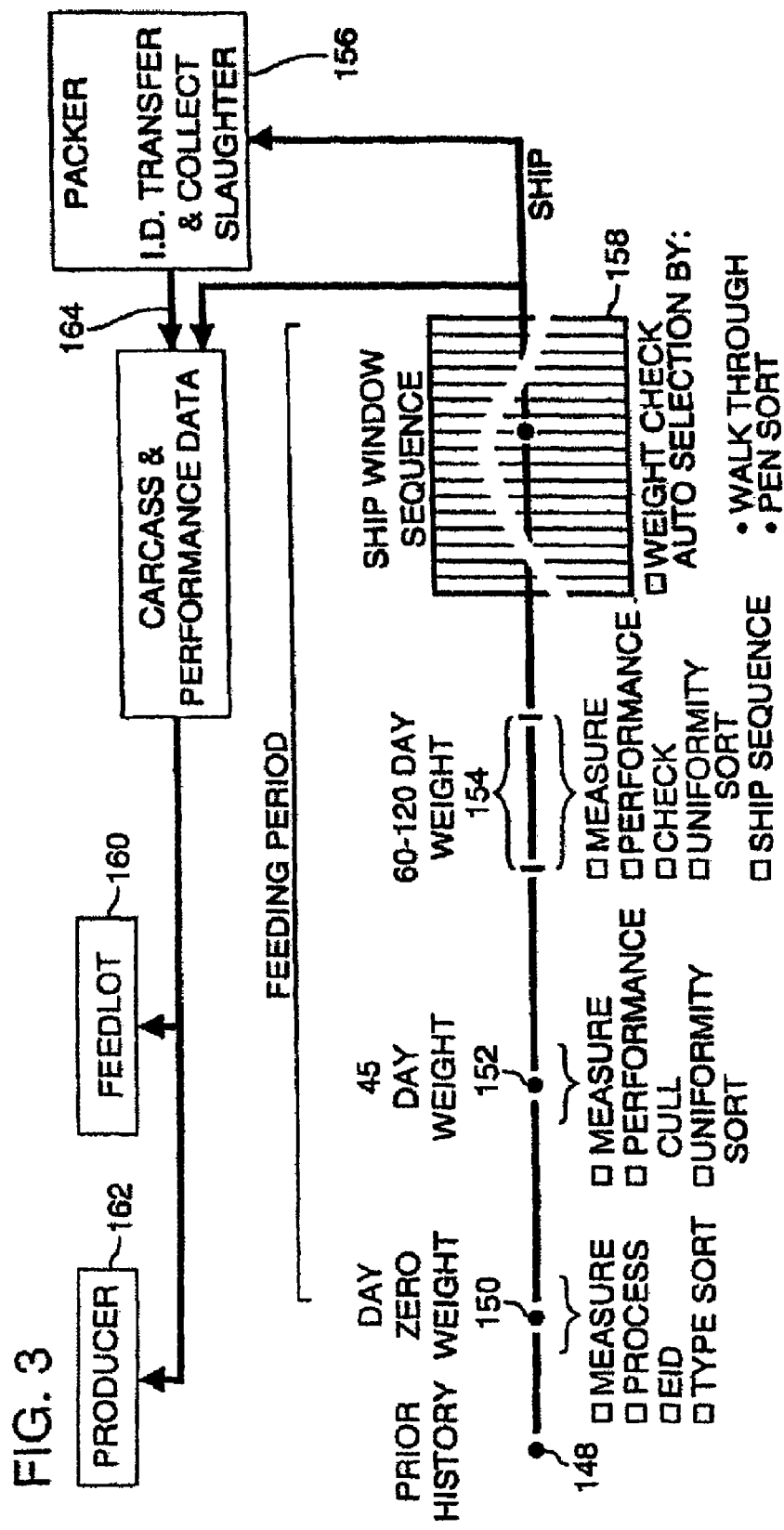

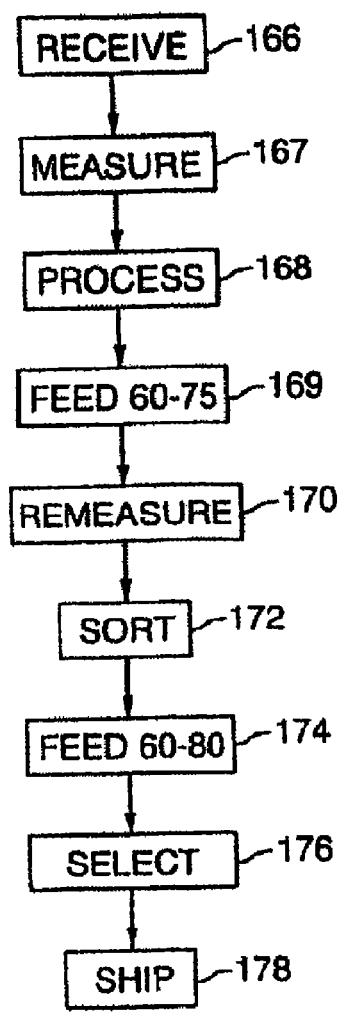
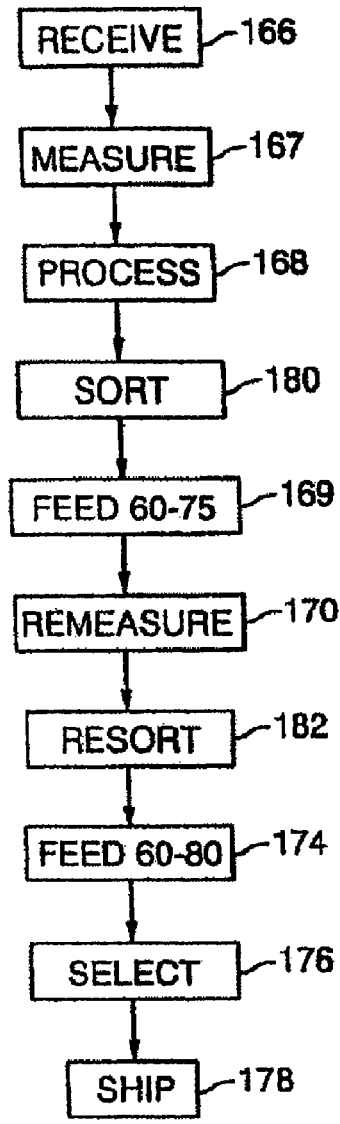
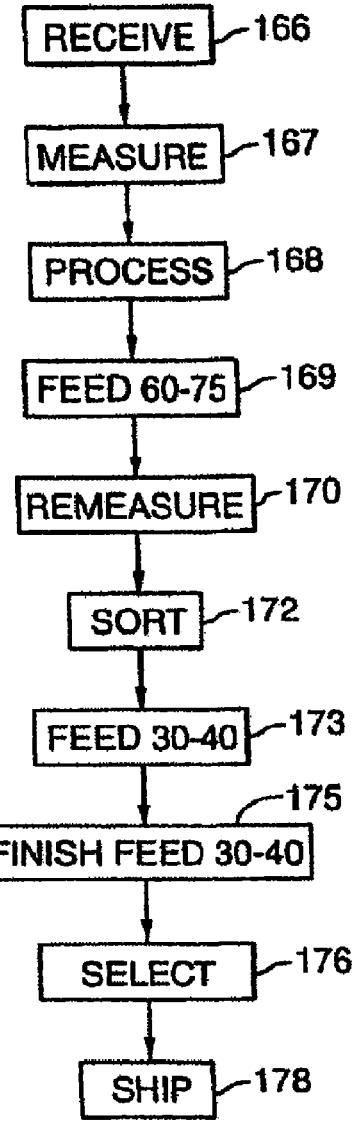

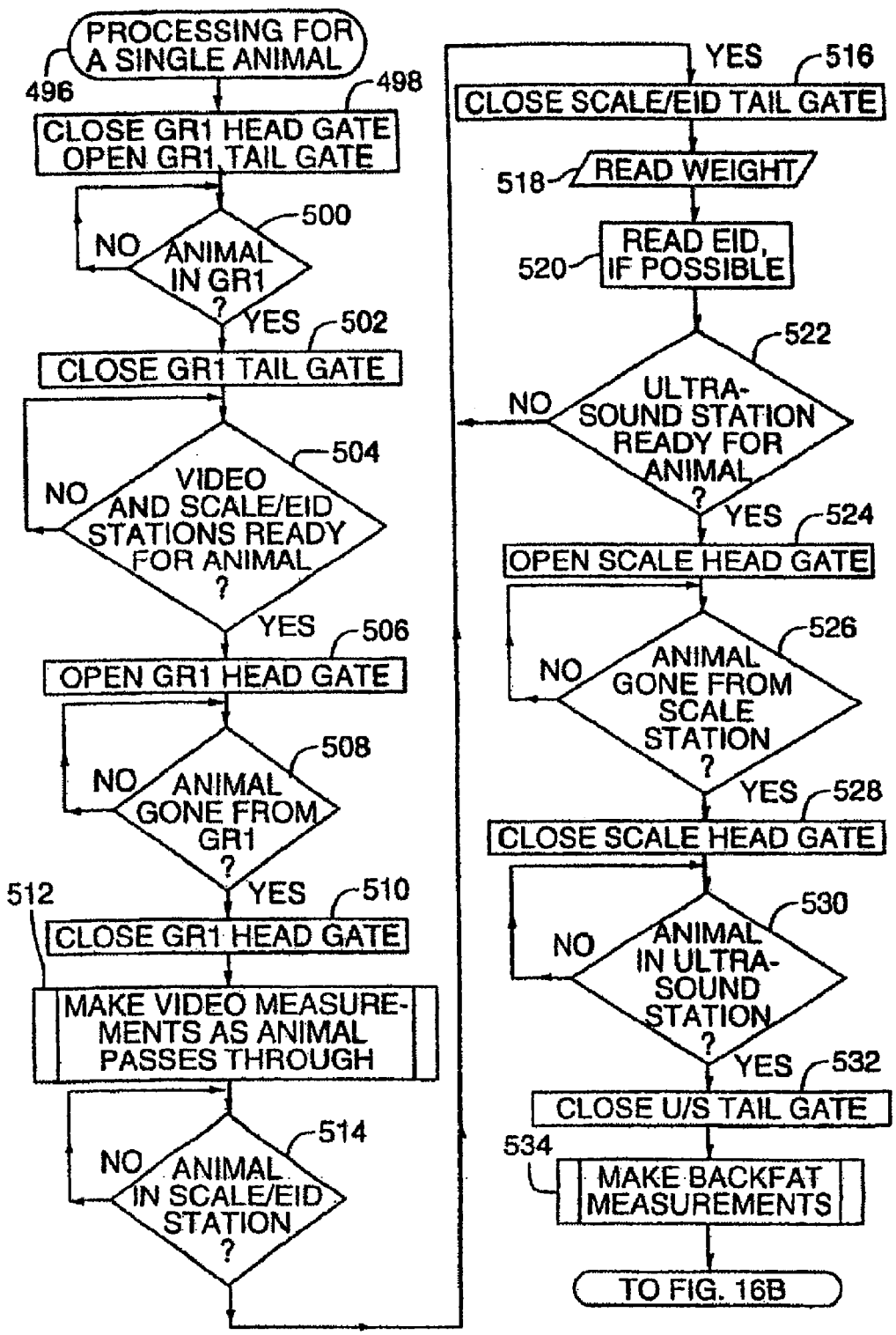

FIG. 14B
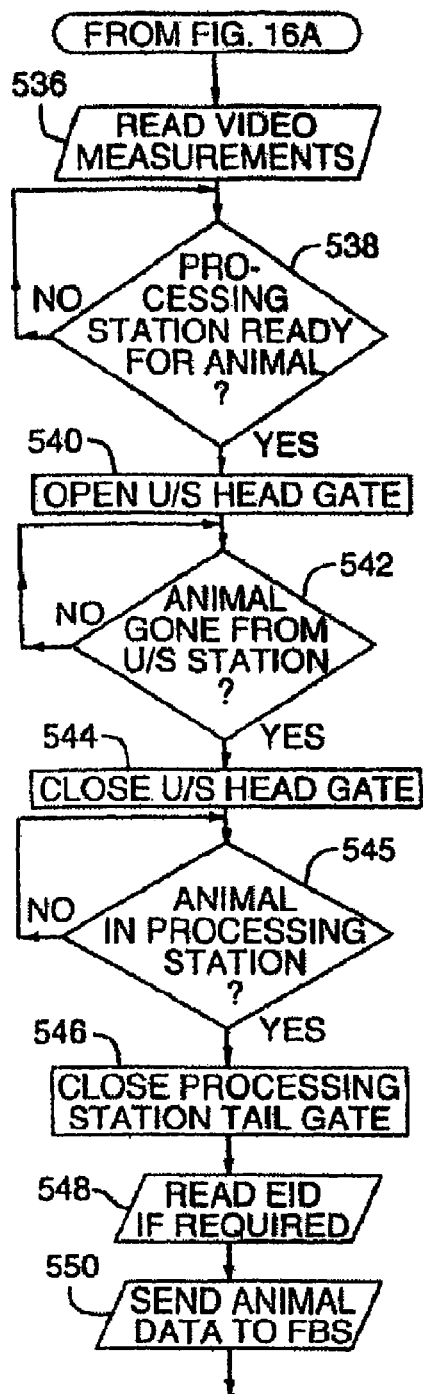
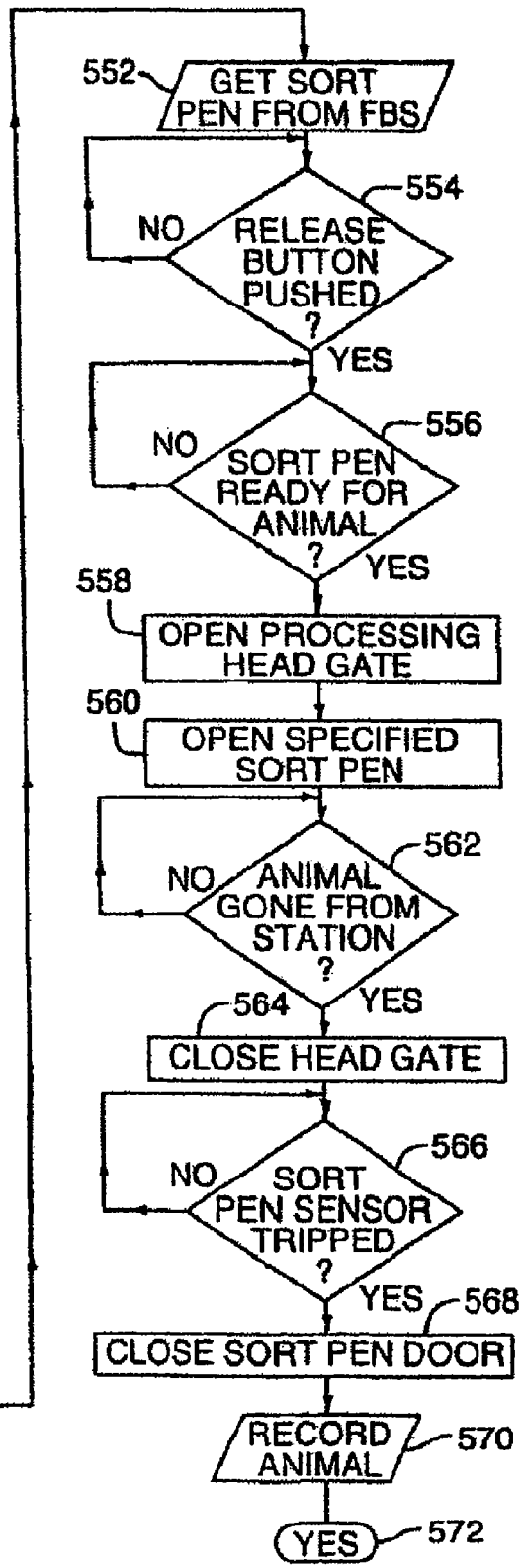

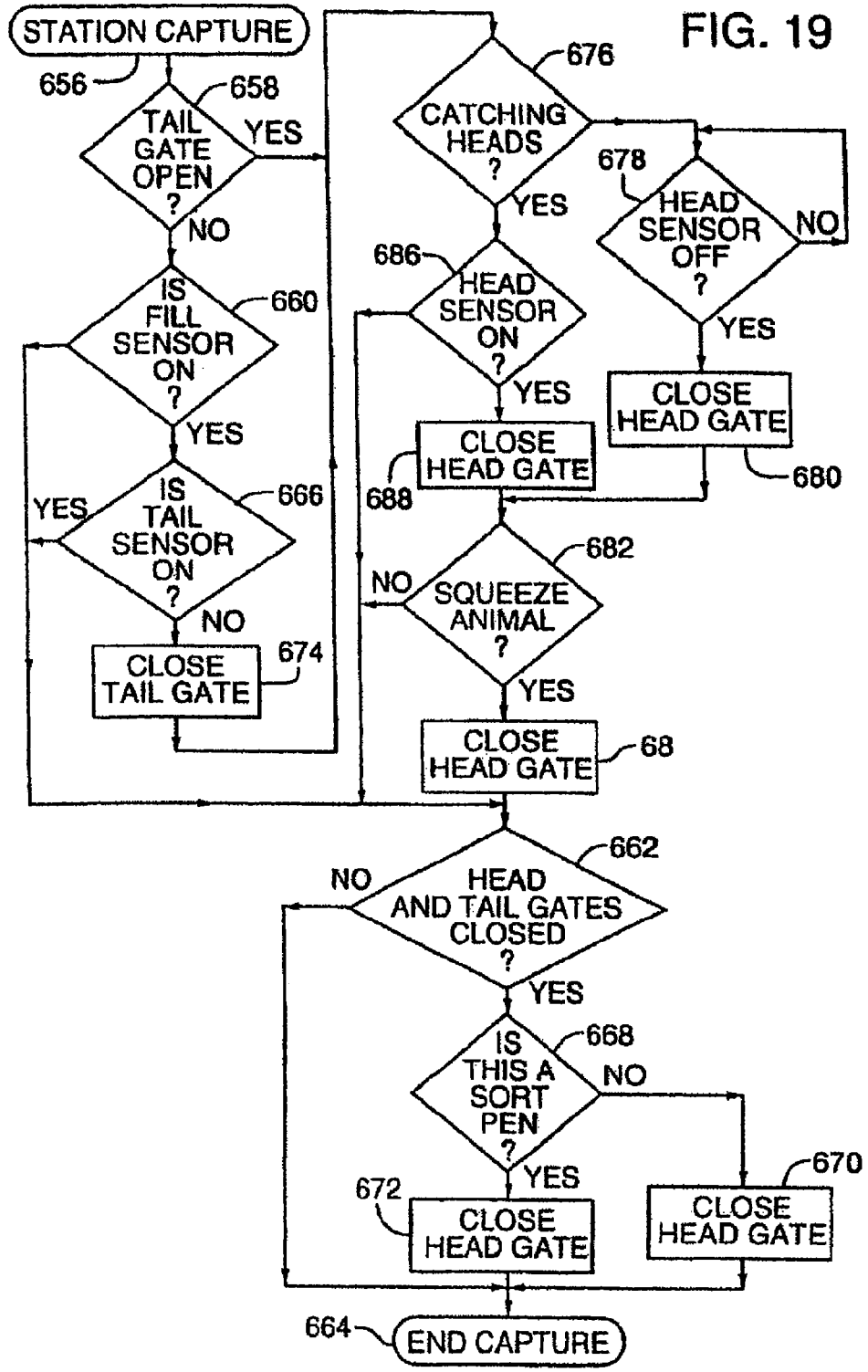

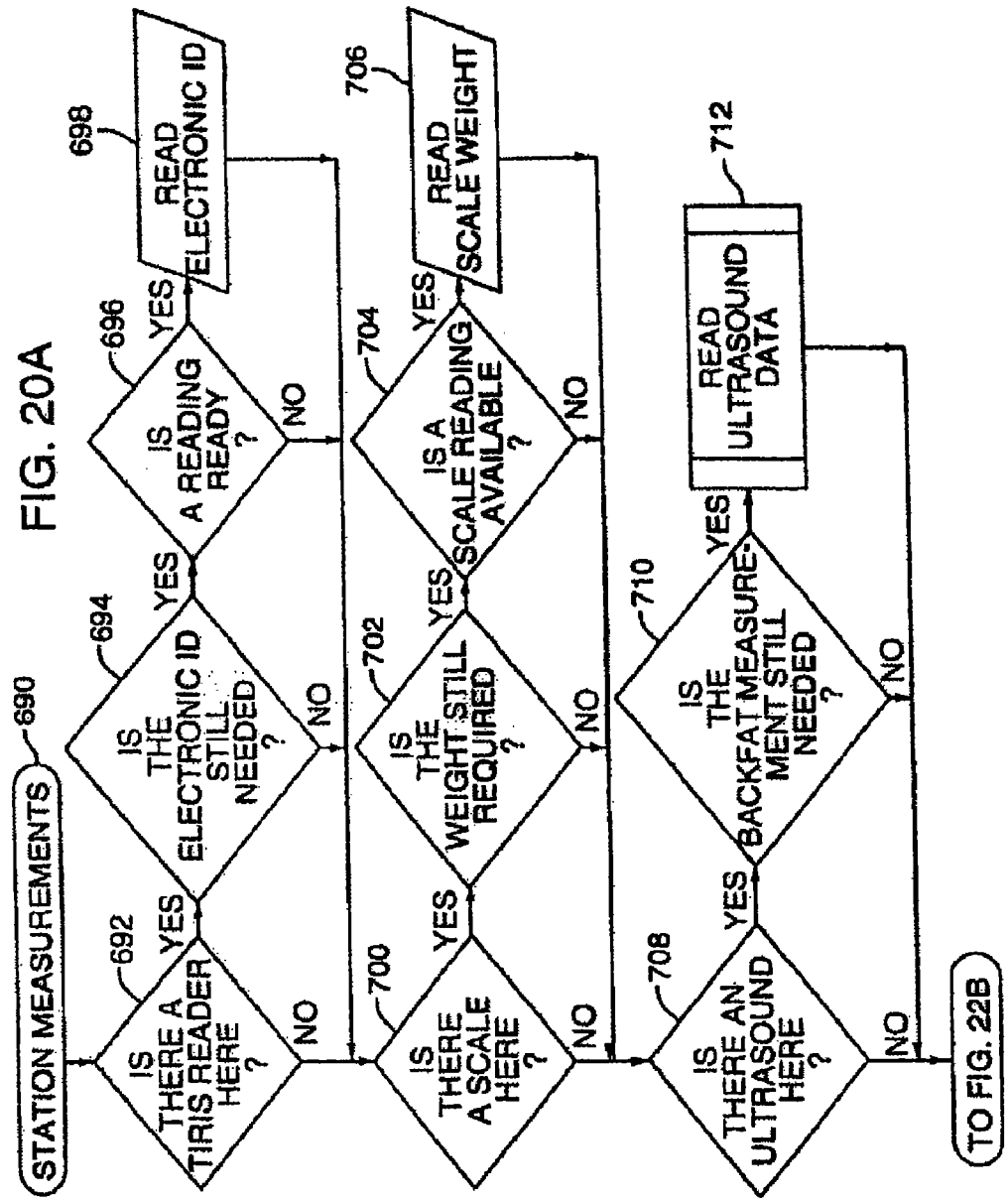

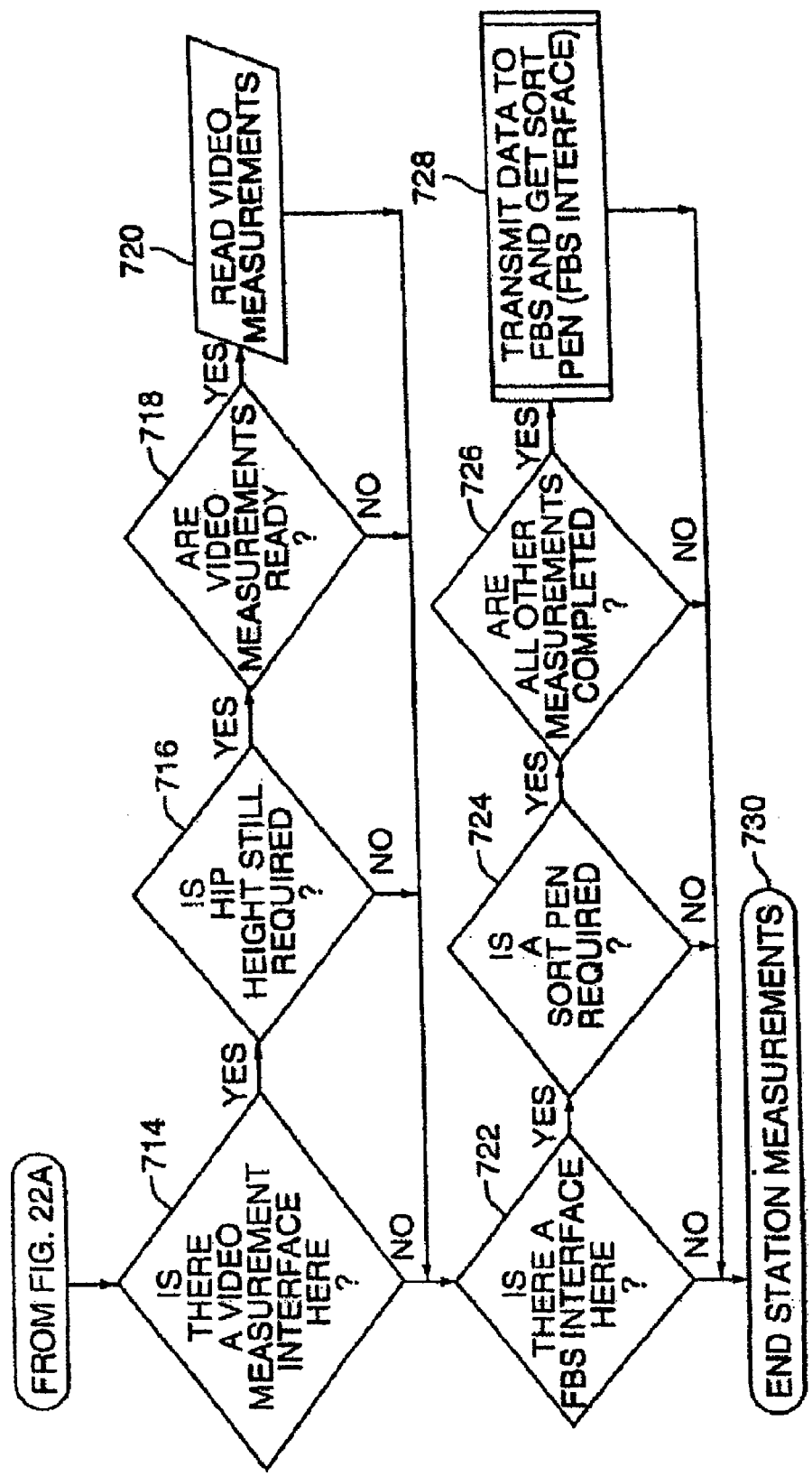

FIG. 28b

2) Calculate DMI ratios to be used from the remeasurement date to the next measurement to prorate feed to each lot/pen, by inputting Hip Height, Backfat, Current Weight and OFW. When a final weight is calculated for each animal (after slaughter), the Cornell Cattle Systems model will be used to determine DMI ratios for each animal to reapportion total feed fed per pen to calculate individual animal consumption in each lot/pen. Inputs are Initial Weight, Final Weight and Condition Score (based on actual Backfat)

Example Calculation:

| Animal # | Weight | Current Wt | Hip Height | Backfat | FS | CS | OFW |
|---|---|---|---|---|---|---|---|
| 85 | 829 | 1028 | 45.8 | 0.14 | 4.50 | 6 | 1136 |
| 10 | 867 | 1066 | 47.2 | 0.18 | 5.14 | 6 | 1183 |
| 68 | 738 | 937 | 43.3 | 0.2 | 3.45 | 6 | 1059 |
| 36 | 777 | 976 | 45.2 | 0.12 | 4.37 | 5 | 1127 |

| Animal # | CP¹ DMI | Ratio | CP Feed Fed | CP Prorated Feed | NP² DMI | Ratio | NP Feed Fed | NP Prorated Feed |
|---|---|---|---|---|---|---|---|---|
| 85 | 19.47 | 0.255646 | | 767 | 21.13 | 0.253206 | | 1519 |
| 10 | 20.13 | 0.264312 | | 793 | 21.81 | 0.261354 | | 1568 |
| 68 | 17.92 | 0.235294 | | 706 | 19.81 | 0.237388 | | 1424 |
| 36 | 18.64 | 0.244748 | | 734 | 20.7 | 0.248053 | | 1488 |
| Total | 76.16 | 1 | 3000 | 3000 | 83.45 | 1 | 6000 | 6000 |

| Animal # | HCW | Actual BF | Final Wt. | DMI Overall | Feed Fed | Prorated Feed | Feed/Gain |
|---|---|---|---|---|---|---|---|
| 85 | 716 | 0.25 | 1128 | 20.50 | | 2440 | 8.17 |
| 10 | 745 | 0.3 | 1163 | 21.26 | | 2531 | 8.54 |
| 68 | 667 | 0.35 | 1034 | 19.22 | | 2288 | 7.72 |
| 36 | 710 | 0.25 | 1118 | 20.16 | | 2400 | 7.03 |
| | | | | 81.14 | 9660 | 9660 | |

¹CP - Current Period (initial measurement to remeasurement)
²NP - Next Period - DMI ratios to be used for period from remeasurement to next measurement.

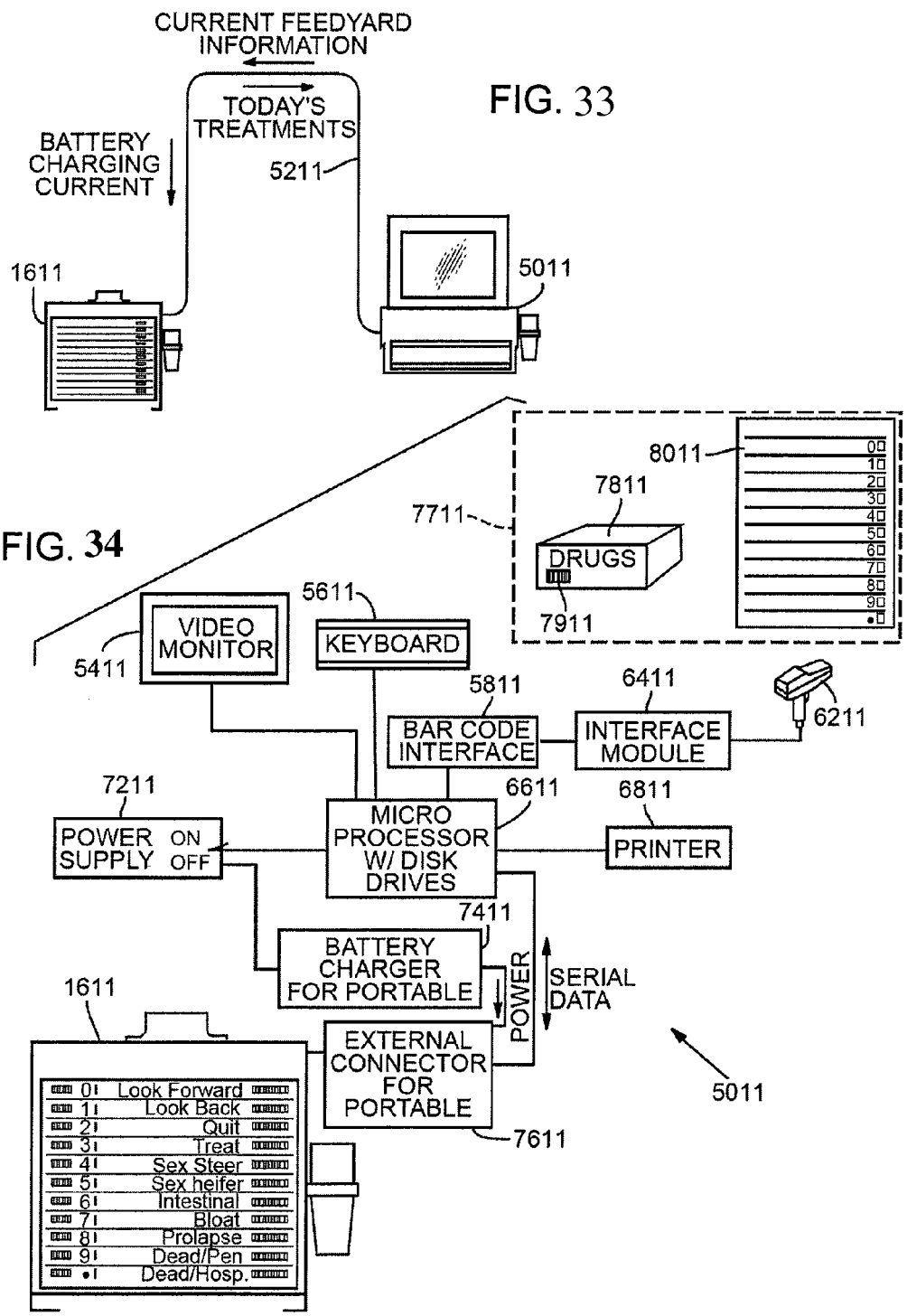

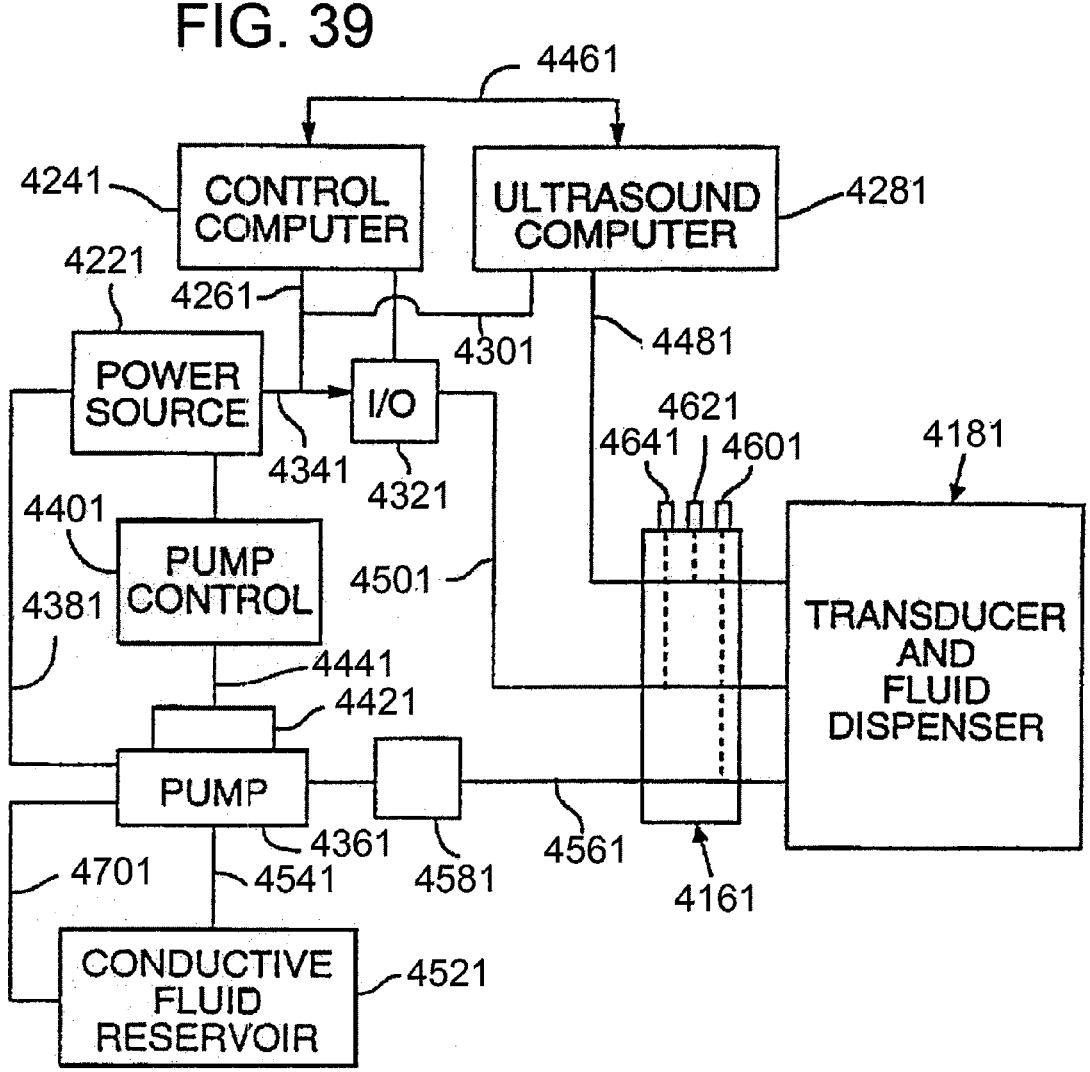

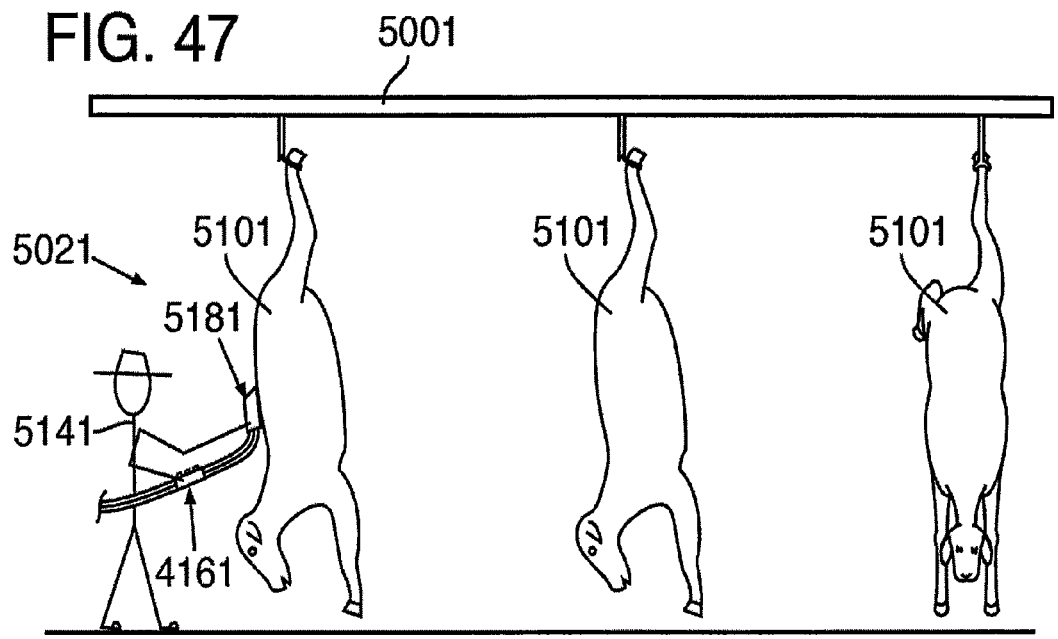
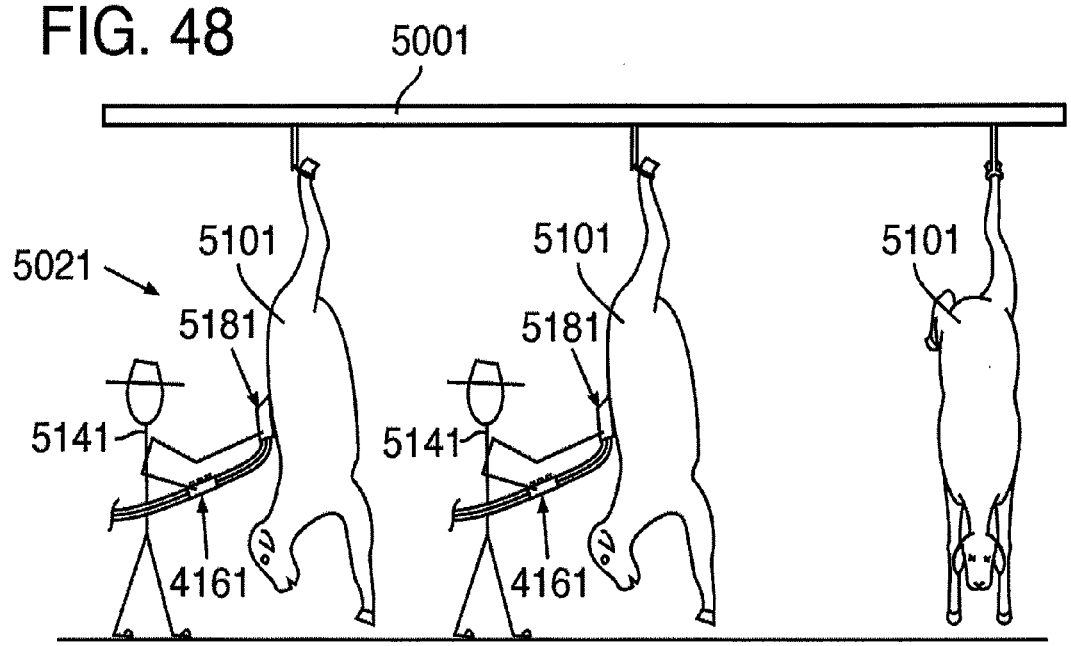

FIG. 55A

MOVE-OUT Confirmation Report*
BIE Documents Id    FC44AA8F09/0

Date of Event         08/05/09
Source Premise       S200971       Stocker S200971
Destination Premise  F201565       Feedlot F201565
Number of Animals   38 Confirmed – 0 Non Reconciled

| Identifier | Type | Species | Premise | Dates at Premise |
|---|---|---|---|---|
| 841903000065870 | UAIN | Bovine | Confirmed | 06/24/2005 – 04/28/2006 |
| 10920167 | DAINVI | | Confirmed | 04/29/2006 – 04/30/2006 |
| | | | Confirmed | 05/01/2006 – 08/05/2006 |
| | | | Confirmed | 08/06/2006 - |
| 841800000674852 | UAIN | Bovine | Confirmed | 06/24/2005 – 04/28/2006 |
| 841800000674852 | DAINRF | | Confirmed | 04/29/2006 – 04/30/2006 |
| 100920185 | DAINVI | | Confirmed | 05/01/2006 – 08/05/2006 |
| | | | Confirmed | 08/06/2006 - |
| 841800000674816 | UAIN | Bovine | Confirmed | 06/24/2005 – 04/28/2006 |
| 841800000674816 | DAINRF | | Confirmed | 04/29/2006 – 04/30/2006 |
| | | | Confirmed | 05/01/2006 – 08/05/2006 |
| | | | Confirmed | 08/06/2006 - |
| 841903000065824 | UAIN | Bovine | Confirmed | 06/24/2005 – 04/28/2006 |
| 100920110 | DAINVI | | Confirmed | 04/29/2006 – 04/30/2006 |
| | | | Confirmed | 05/01/2006 – 08/05/2006 |
| | | | Confirmed | 08/06/2006 - |
| 841903000065824 | UAIN | Bovine | Confirmed | 06/24/2005 – 04/28/2006 |
| 100920138 | DAINVI | | Confirmed | 04/29/2006 – 04/30/2006 |
| | | | Confirmed | 05/01/2006 – 08/05/2006 |
| | | | Confirmed | 08/06/2006 - |
| 8419000065804 | UAIN | Bovine | Confirmed | 06/24/2005 – 04/28/2006 |
| 100920086 | DAINVI | | Confirmed | 04/29/2006 – 04/30/2006 |
| | | | Confirmed | 05/01/2006 – 08/05/2006 |
| | | | Confirmed | 08/06/2006 - |
| 841800000674811 | UAIN | Bovine | Confirmed | 06/24/2005 – 04/28/2006 |
| 841800000674811 | DAINRF | | Confirmed | 04/29/2006 – 04/30/2006 |
| 100920144 | DAINVI | | Confirmed | 05/01/2006 – 08/05/2006 |
| | | | Confirmed | 08/06/2006 - |
| 841903000065916 | UAIN | Bovine | Confirmed | 06/24/2005 – 04/28/2006 |
| 841800000674885 | DAINRF | | Confirmed | 04/29/2006 – 04/30/2006 |
| 100920218 | DAINVI | | Confirmed | 05/01/2006 – 08/05/2006 |
| | | | Confirmed | 08/06/2006 - |
| 841904000033767 | UAIN | Bovine | Confirmed | 06//2005 – 04/28/2006 |
| 100904809 | DAINVI | | Confirmed | 04/29/2006 – 04/30/2006 |
| | | | Confirmed | 05/01/2006 – 08/05/2006 |
| | | | Confirmed | 08/06/2006 - |

*Confirmation means: 1) Premise ID valid. 2) UAIN's assigned valid. 3) Traceback is as reported MOVE-IN Confirmation Report*
BIE Document Id    FC15D07E7C/0

FIG. 55B

Date of Event       08/24/03
Source Premise      C200683        Cow/Calf C200683
Destination Premise A201547        Auction A201547
Number of Animals   0 Confirmed – 7 Non Reconciled

| Identifier | Type | Species | Premise | Dates at Premise |
|---|---|---|---|---|
| 841902000019074 | UAIN | Bovine | Confirmed | 12/19/2002 – |
| 100353460 | DAINVI | | Confirmed NON-RECONCILED | 08/24/2003 – 08/25/2003 |
| 841902000019097 | UAIN | Bovine | Confirmed | 12/19/2002 – |
| 100353485 | DAINVI | | Confirmed NON-RECONCILED | 08/24/2003 – 08/25/2003 |
| 841902000019081 | UAIN | Bovine | Confirmed | 12/19/2002 – |
| 100353468 | DAINRF | | Confirmed NON-RECONCILED | 08/24/2003 – 08/25/2003 |
| 841902000019070 | UAIN | Bovine | Confirmed | 12/19/2002 – |
| 100353456 | DAINVI | | Confirmed NON-RECONCILED | 08/24/2003 – 08/25/2003 |
| 841902000019098 | UAIN | Bovine | Confirmed | 12/19/2002 – |
| 841800000108153 | DAINRF | | Confirmed | 08/24/2003 – 08/25/2003 |
| 1003533486 | DAINVI | | NON-RECONCILED | |
| 841902000019055 | UAIN | Bovine | Confirmed | 12/19/2002 – |
| 100353440 | DAINVI | | Confirmed NON-RECONCILED | 08/24/2003 – 08/25/2003 |
| 841902000019065 | UAIN | Bovine | Confirmed | 12/19/2002 – |
| 100353451 | DAINVI | | Confirmed NON-RECONCILED | 08/24/2003 – 08/25/2003 |

*Confirmation means: 1) Premise ID valid. 2) UAIN's assigned valid. 3) Traceback is as reported TAG-APPLIED Confirmation Report*
BIE Document Id    FC5663F4A3/0

FIG. 55C

Date of Event        04/19/07
Source Premise       C200638      Cow/Calf C200638
Destination Premise  C200638      Cow/Calf C200638
Number of Animals    193 Confirmed – 0 Non Reconciled

| Identifier | Type | Species | Premise | Dates at Premise |
|---|---|---|---|---|
| 841800001073992 | UAIN | Bovine | Confirmed | 4/19/2007 - |
| 841800001073992 | DAINRF | | | |
| 101319325 | DAINVI | | | |
| 841901000153086 | UAIN | Bovine | Confirmed | 4/19/2007 - |
| 841800001073876 | DAINRF | | | |
| 101319209 | DAINVI | | | |
| 841901000153067 | UAIN | Bovine | Confirmed | 4/19/2007 - |
| 101319209 | DAINVI | | | |
| 841901000153042 | UAIN | Bovine | Confirmed | 4/19/2007 - |
| 101319155 | DAINVI | | | |
| 841901000153165 | UAIN | Bovine | Confirmed | 4/19/2007 - |
| 841800001073969 | DAINRF | | | |
| 841901000153135 | UAIN | Bovine | Confirmed | 4/19/2007 - |
| 841800001073931 | DAINRF | | | |
| 841901000153160 | UAIN | Bovine | Confirmed | 4/19/2007 - |
| 101319296 | DAINVI | | | |
| 841901000153050 | UAIN | Bovine | Confirmed | 4/19/2007 - |
| 841800001073833 | DAINRF | | | |
| 101319166 | DAINVI | | | |
| 841800001073922 | UAIN | Bovine | Confirmed | 4/19/2007 - |
| 841800001073922 | DAINRF | | | |
| 101319255 | DAINVI | | | |
| 841901000153079 | UAIN | Bovine | Confirmed | 4/19/2007 - |
| 841800001073868 | DAINRF | | | |
| 101319201 | DAINVI | | | |
| 841901000153080 | UAIN | Bovine | Confirmed | 4/19/2007 - |
| 841800001073869 | DAINRF | | | |
| 841901000153128 | UAIN | Bovine | Confirmed | 4/19/2007 - |
| 841800001073924 | DAINRF | | | |
| 101319257 | DAINVI | | | |
| 841901000153113 | UAIN | Bovine | Confirmed | 4/19/2007 - |
| 841800001073906 | DAINRF | | | |
| 101319241 | DAINVI | | | |

*Confirmation means: 1) Premise ID valid. 2) UAIN's assigned valid. 3) Traceback is as reported

FIG. 55D

SLAUGHTERED Confirmation Report*
BIE Document Id    FC55E30C08/0

Date of Event         04/03/07
Source Premise        P201668         Packer P201668
Destination Premise   P201668         Packer P201668
Number of Animals     18 Confirmed – 0 Non Reconciled

| Identifier | Type | Species | Premise | Dates at Premise |
|---|---|---|---|---|
| 841901000102410 | UAIN | Bovine | Confirmed | 12/28/2005 – 07/29/2006 |
| 841800000790399 | DAINRF | | Confirmed | 07/30/2006 – 07/31/2006 |
| 101035732 | DAINVI | | Confirmed | 08/01/2006 – 04/03/2007 |
| | | | Confirmed | 04/03/2007 – 04/03/2007 |
| 841901000102470 | UAIN | Bovine | Confirmed | 12/28/2005 – 07/29/2006 |
| 101035803 | DAINVI | | Confirmed | 07/30/2006 – 07/31/2006 |
| | | | Confirmed | 08/01/2006 – 04/03/2007 |
| | | | Confirmed | 04/03/2007 – 04/03/2007 |
| 841901000102468 | UAIN | Bovine | Confirmed | 12/28/2005 – 07/29/2006 |
| 101035800 | DAINVI | | Confirmed | 07/30/2006 – 07/31/2006 |
| | | | Confirmed | 08/01/2006 – 04/03/2007 |
| | | | Confirmed | 04/03/2007 – 04/03/2007 |
| 841901000102463 | UAIN | Bovine | Confirmed | 12/28/2005 – 07/29/2006 |
| 101035792 | DAINVI | | Confirmed | 07/30/2006 – 07/31/2006 |
| | | | Confirmed | 08/01/2006 – 04/03/2007 |
| | | | Confirmed | 04/03/2007 – 04/03/2007 |
| 841800000790430 | UAIN | Bovine | Confirmed | 12/28/2005 – 07/29/2006 |
| 841800000790430 | DAINRF | | Confirmed | 07/30/2006 – 07/31/2006 |
| 101035763 | DAINVI | | Confirmed | 08/01/2006 – 04/03/2007 |
| | | | Confirmed | 04/03/2007 – 04/03/2007 |
| 841901000102449 | UAIN | Bovine | Confirmed | 12/28/2005 – 07/29/2006 |
| 841800000790445 | DAINRF | | Confirmed | 07/30/2006 – 07/31/2006 |
| | | | Confirmed | 08/01/2006 – 04/03/2007 |
| | | | Confirmed | 04/03/2007 – 04/03/2007 |
| 841901000102461 | UAIN | Bovine | Confirmed | 12/28/2005 – 07/29/2006 |
| 841800000790457 | DAINRF | | Confirmed | 07/30/2006 – 07/31/2006 |
| 101035790 | DAINVI | | Confirmed | 08/01/2006 – 04/03/2007 |
| | | | Confirmed | 04/03/2007 – 04/03/2007 |
| 841800000790475 | UAIN | Bovine | Confirmed | 12/28/2005 – 07/29/2006 |
| 841800000790475 | DAINRF | | Confirmed | 07/30/2006 – 07/31/2006 |
| 101035808 | DAINVI | | Confirmed | 08/01/2006 – 04/03/2007 |
| | | | Confirmed | 04/03/2007 – 04/03/2007 |
| 841800000790423 | UAIN | Bovine | Confirmed | 12/28/2005 – 07/29/2006 |
| 841800000790423 | DAINRF | | Confirmed | 07/30/2006 – 07/31/2006 |
| | | | Confirmed | 08/01/2006 – 04/03/2007 |
| | | | Confirmed | 04/03/2007 – 04/03/2007 |

*Confirmation means: 1) Premise ID valid. 2) UAIN's assigned valid. 3) Traceback is as reported

Animal Tracking
Animal identifier - 123 456 789 012 345

| Date | Premise | |
|------|---------|---|
| 01-12-05 | AB12345 | Tag is allocated to premises |
| 03-15-05 | AB12345 | Sighting |
| 07-16-05 | GHI90JK | Movement in |
| 09-08-05 | GHI90JK | Sighting |
| 12-20-05 | GHI90JK | Movement out |
| 01-01-06 | T789UVW | Movement in |
| 12-25-09 | T789UVW | Slaughtered |

FIG. 58

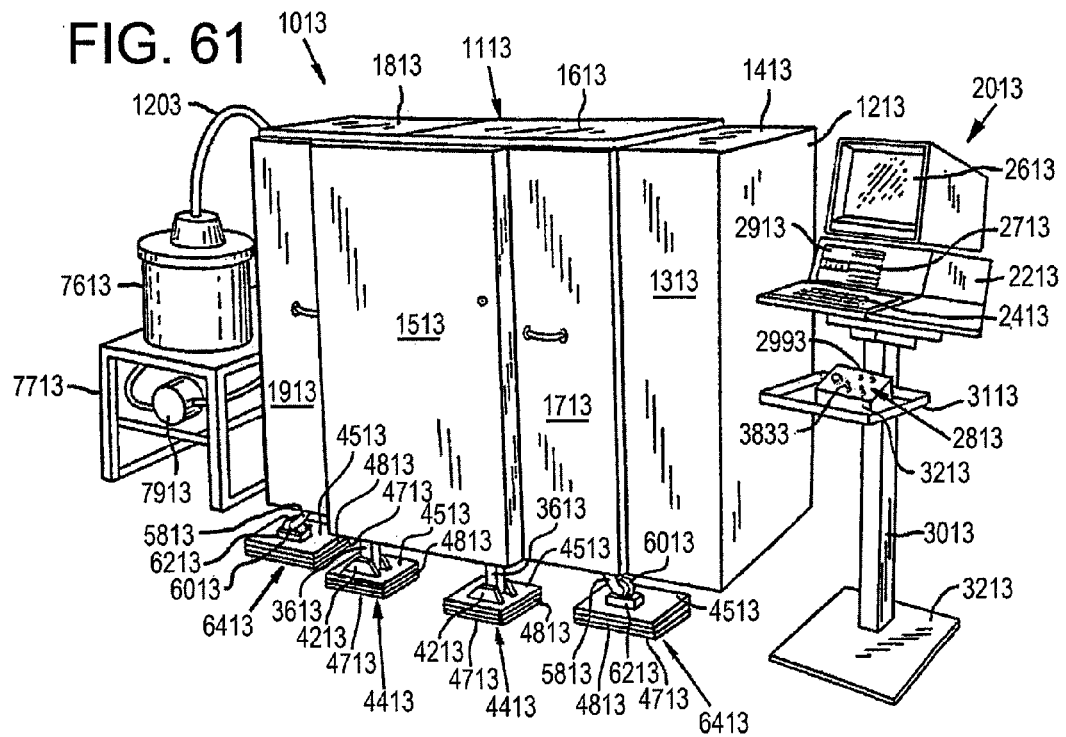
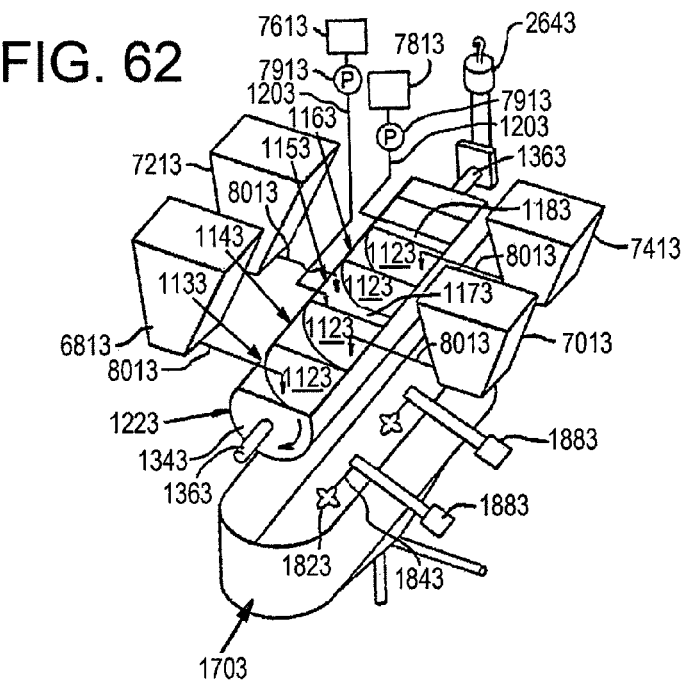

DETERMINING RESPIRATORY OR CIRCULATORY HEALTH CONDITION IN ANIMALS FOR IMPROVED MANAGEMENT

CROSS REFERENCE TO RELATED APPLICATIONS

This is a continuation of U.S. application Ser. No. 12/425,559, filed Apr. 17, 2009, now U.S. Pat. No. 7,931,593 which is a continuation of U.S. application Ser. No. 11/292,412, filed Nov. 30, 2005, now U.S. Pat. No. 7,670,292, which claims the benefit of the earlier filing date of U.S. Provisional Application No. 60/631,646, filed Nov. 30, 2004, all of which are incorporated herein by reference.

FIELD

This disclosure relates generally to the evaluation of internal tissue characteristics in animals, such as by imaging, and the management of animals based on the results of such evaluation.

BACKGROUND

Respiratory and circulatory diseases cause significant economic losses to the commercial meat industry. For example, bovine respiratory disease (BRD) has been estimated to account for 65% to 79% of the sickness and up to 72% of the deaths of feedlot cattle. BRD includes several more specific forms of respiratory diseases, including upper respiratory tract infections, diphtheria and pneumonia. Both viral and bacterial agents can cause BRD. These agents can be difficult or impossible to control. Cattle have natural defense systems for combating these agents, but these defense systems often are compromised by stress, such as stress associated with normal cattle management.

A significant percentage of livestock experience respiratory or circulatory disease at one or more times during their life. In most cases, the animals recover from the disease, but experience some degree of permanent internal damage. For example, studies on carcasses have shown that about one third to about one half of all cattle have lung lesions at slaughter that are the result of past respiratory disease.

To control respiratory diseases, such as BRD, many livestock managers actively diagnose and treat outbreaks. When detected, infected livestock typically are quarantined and treated with antibiotic and/or antiviral medications. These remedial efforts can be expensive and often fail to cure the disease. The success of treatment depends largely on the respiratory heath of the animal prior to onset of the disease. It has been shown, for example, that animals with significantly damaged respiratory systems from past respiratory disease are much less likely to respond well to treatment than animals with relatively undamaged respiratory systems.

In addition to affecting how animals respond to treatment, respiratory damage from past respiratory disease can adversely affect an animal's performance at the feedlot. For example, feedlot cattle with greater amounts of respiratory damage have been shown to gain less weight than feedlot cattle with lesser amounts of respiratory damage. In addition, the meat derived from cattle with greater amounts of respiratory damage often is of lower quality than the meat derived from cattle with lesser amounts of respiratory damage. Finally, the presence of respiratory damage from past respiratory disease may cause meat to fail to qualify as kosher, thereby decreasing its market value.

SUMMARY

Disclosed herein is a method for managing at least one animal based on its respiratory condition. The method can include imaging, such as ultrasound imaging, at least one lung of a live animal, such as a bovine animal or other ruminant animal. The imaging can be performed to determine a degree of respiratory damage in the animal, such as a degree of respiratory damage from past respiratory illness. In some embodiments, the animal has substantially no symptoms of active respiratory illness at the time of imaging. Determining the degree of respiratory damage can include evaluating scarring, fibrosis, necrosis or other lung lesions caused by the past respiratory illness.

After imaging, information regarding respiratory damage can be used to select at least one aspect of the treatment, care or disposition of the animal. For example, the respiratory damage information can be used to select the amount or type of feed provided to the animal. Respiratory damage information also can be used to select how long the animal should be housed at the feedlot prior to slaughter. If an animal is diagnosed with an active respiratory illness, information about its degree of respiratory damage from past respiratory illness also can be used to select the appropriate medical treatment or lack of treatment. This can include, for example, selecting whether or not to administer drugs to the animal.

Some disclosed embodiments include imaging at least one lung of each of a plurality of live animals so as to determine a degree of respiratory damage in each of the plurality of animals. Each animal then can be assigned a respiratory damage designation corresponding to the animal's degree of respiratory damage. These respiratory damage designations can be entered into an electronic database and associated with an identifier for each animal. This may allow a user to review the respiratory damage designation for each animal from a location remote from the animals. In some embodiments, the respiratory damage designation is referenced to inform a management decision involving one or more of the animals. For example, at least one aspect of the treatment, care or disposition of each of the plurality of animals can be selected based on each animal's respiratory damage designation. In some embodiments, a respiratory damage designation is provided to a buyer to aid the buyer in a decision regarding the purchase of an animal.

An animal management system also is disclosed. This system can include an identification device for distinguishing individual animals from other animals in a group of animals, a measuring station, and a computer for storing respiratory damage information for the animals and for matching each animal's identifier with the animal's respiratory damage. In some embodiments, the measuring station includes a data entry device for recording respiratory damage in the animals.

BRIEF DESCRIPTION OF DRAWINGS

FIG. 3 is a cattle processing timeline to exemplify a method of processing and managing cattle.

FIGS. 4A, 4B, and 4C are cattle processing diagrams illustrating three alternative methods of processing and managing cattle in a feedlot.

FIGS. 14A and 14B are a flow diagram of a computer program used to control the processing sequence for each animal proceeding through the various measuring and processing stations in the single-file chute of FIG. 5.

FIG. 19 is a flow diagram of a computer program used to ensure the capture of an animal within a measuring or processing station before measurements or processings are initiated at the station in the single-file chute shown in FIG. 5.

FIGS. 20A and 20B are a flow diagram of a computer program used for making measurements at the various measuring stations of the single-file chute, including weight, external dimension and internal measurements.

FIGS. 28a and 28b are a flow chart illustrating the process of determining feed proration to individual animals in a feedlot following a second and subsequent sets of animal measurements in the feedlot.

FIG. 33 is an illustration of the portable hospital unit in communication with a host computer.

FIG. 34 is a schematic diagram of the animal health computer of FIG. 33.

FIG. 39 is a schematic diagram showing a complete system of one embodiment of an ultrasound tissue imaging and analysis apparatus.

FIG. 47 is a schematic drawing illustrating an operator using an ultrasound tissue analyzer in a packing plant for analyzing backfat on a stunned ruminant conveyed to the operator after being stunned and bled.

FIG. 48 is a schematic drawing illustrating an alternative method for measuring internal tissue characteristics of a stunned ruminant using a first operator to apply a conductive liquid to a stunned ruminant conveyed to the first operator after being stunned and bled, and a second operator to take ultrasound measurements on the ruminant following the application of conductive liquid.

FIGS. 55A-D are sample lists illustrating the type of data sent in a traceback report.

FIG. 58 is a table illustrating a traceback report.

FIG. 61 is a perspective view showing the major components of a feed delivery apparatus.

FIG. 62 is a schematic perspective view illustrating the internal components of the main cabinet shown in FIG. 61.

DETAILED DESCRIPTION

Figure 1:
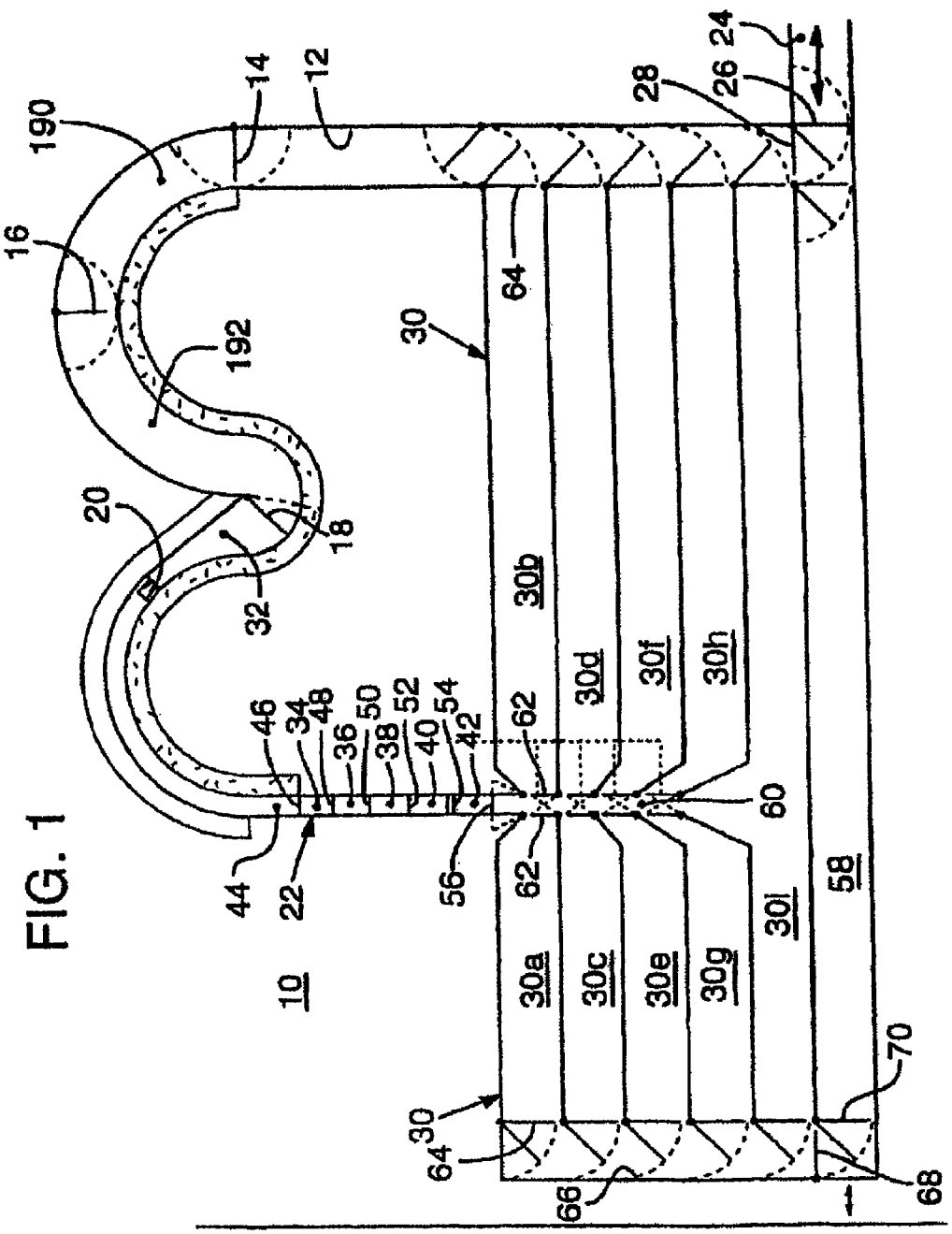
FIG. 1 is a schematic diagram of the layout of the single-file cattle processing chute and sorting pen portion of a feedlot.

Throughout this disclosure, the singular terms "a," "an," and "the" include plural referents unless the context clearly indicates otherwise. Similarly, the word "or" is intended to include "and" unless the context clearly indicates otherwise. The word "animal" is intended to include the broad genus of animals as well as the subgenera of ruminant animals, animals raised for food production, and cattle, unless the context clearly indicates otherwise. As used herein, the word "respiratory" is intended to refer to the entire respiratory system and immediately adjacent structures, including the lungs, pleura and mediastinum, unless the context clearly indicates otherwise. As used herein, the phrase "degree of respiratory damage" is intended to include the presence or absence of damage, as well as the extent of damage, unless the context clearly indicates otherwise.

Disclosed herein are a method and a system for evaluating respiratory or circulatory condition in animals and for managing the animals accordingly. Unlike external animal characteristics, the condition of an animal's respiratory and circulatory systems is not readily apparent from a superficial examination. Respiratory and circulatory condition, however, such as respiratory damage from past respiratory disease, is one of the most important aspects of an animal's health.

Although the majority of this disclosure is directed to the evaluation of respiratory condition, it should be apparent that similar techniques can be used for the evaluation of circulatory condition. For example, the ultrasonic and radiographic imaging techniques described below can be used to generate images of an animal's heart or lymph nodes in addition to its lungs. Information from these images then can be used to make management decisions regarding the animal.

Imaging

Some embodiments of the disclosed method include imaging at least one lung of a live animal. Several techniques can be used to image the lungs of live animals, such as ultrasonography, radiography (e.g., standard x-ray and computerized axial tomography) and magnetic resonance imaging. Of these techniques, ultrasonography is the least expensive and is particularly well suited to use on large animals raised for commercial food production.

Ultrasound imaging involves the direct introduction of high frequency sound waves from a transducer into the tissue to be evaluated. The echo resulting from these sound waves can be recorded as an image that provides valuable information about the internal characteristics of the tissue. The time delay between transmitting the sound waves and recording the echo can be used to indicate the depth of the tissue being imaged. The intensity of the echo can be used to distinguish between different types of tissue, because different materials have different levels of acoustical impedance. In this way, internal structures can be visualized, including overall organs and structures on or within organs, such as lesions.

Ultrasound imaging conventionally has been used in the obstetric care of livestock and to measure various livestock characteristics, such as back fat thickness and marbling. In very limited circumstances, ultrasound imaging also has been used to view the thoracic organs of live animals, including the lungs. There are two journal articles that describe ultrasound imaging of the lungs of cattle: U. Braun, et al., "Ultrasonographic Findings in Cattle with Pleuropneumonia," Vet. Rec. 141: 12-17 (1997) and U. Braun, et al., "Ultrasonography of the Lungs, Pleura, and Mediastinum in Healthy Cows," Am. J. Vet. Res. 57(4): 432-8 (1996). These articles are incorporated herein by reference. Both of these articles describe ultrasound imaging for the purpose of diagnosis of current disease rather than to evaluate damage from past disease.

Some embodiments of the disclosed method include imaging the lungs of live animals while the animals have substantially no symptoms of active respiratory illness. In these and other embodiments, imaging is not performed for the purpose of diagnosing current disease, but rather for the purpose of gathering information about respiratory condition that can be useful for future management decisions. Lung imaging can be conducted at various times during the lifecycle of an animal. At certain times, information about an animal's respiratory condition is more useful than at other times. In some disclosed embodiments, lung imaging is conducted shortly before a management decision, such as the sale of an animal or the slaughter of an animal. For example, lung imaging can be conducted at auction before an animal is sold, upon purchase of an animal for grazing or feeding or while the animal is undergoing finish feeding at a feedlot. Lung imaging also can be conducted at a time unrelated to the timing of a management decision. Information from such lung imaging can be recorded for later use. The process of recording and using information from lung imaging is described in greater detail below.

Most livestock require periodic maintenance. To improve efficiency, lung imaging can be conducted in conjunction with other maintenance. For example, lung imaging of cattle can be conducted while the cattle are receiving treatment in a chute or cattle working area. Some embodiments of the disclosed system include a measuring station. The imaging equipment can be stationary or mobile. Efficiency can be improved by successively imaging the lungs of two or more animals.

The procedure for imaging the lungs of animals can be derived from the imaging procedures used in other contexts. For example, ultrasound imaging procedures for imaging the lungs can be derived from obstetric ultrasound imaging procedures. For example, the lungs of cattle can be imaged with the same equipment used in back fat and marbling measurements. Suitable ultrasound devices include the Alkoa 500 with a 3.5 MHz transducer.

The transducer used in ultrasound imaging can be positioned externally or internally. If positioned externally, the skin on the thorax in the region of the lungs may be prepared prior to imaging. This preparation can include removing hair and applying a transmission gel or liquid. In cattle, the lungs generally can be observed in the area between the seventh intercostal space and the twelfth intercostal space. To produce images of the lungs, the transducer can be scanned along each intercostal space with its long axis parallel to the long axis of the ribs. The transducer can be positioned internally, for example, by sedating the animal and routing the transducer through the animal's esophagus. This technique is best for imaging the mediastinum rather than the outer portions of the lungs.

In some disclosed embodiments, ultrasound imaging is combined with an auditory evaluation of internal tissue characteristics. For example, a device can be used that includes both an ultrasound transducer and a stethoscope. Combining these instruments allows for the simultaneous visual and auditory evaluation of the internal tissue. The combined device can include, for example, a stethoscope mounted to an ultrasound transducer such that the diaphragm of the stethoscope is substantially coplanar with the portion of the transducer intended to contact the animal. The acoustical tubing leading to the diaphragm can be integrated with the wiring leading to the transducer. Sounds generated within the internal tissue also can be detected electronically. These sounds then can be reproduced in an earpiece or some other transmission device.

Evaluation of Images

A significant amount of information can be gathered from images of the lungs of live animals. For example, these images can provide information concerning both present and past respiratory disease. Present respiratory disease may be observed, for example, as an accumulation of fluid in the pleura. Damage from past respiratory disease may be observed, for example, as scarring, fibrosis, necrosis or other types of lung lesions. Some embodiments of the disclosed method are directed primarily to the evaluation of damage from past respiratory disease.

Evaluation of the images can be performed at the time of imaging or at a later time. In some disclosed embodiments, a technician images the lungs and records the images, which then can be evaluated by another technician or a veterinarian. Each animal can be assigned a respiratory damage designation corresponding to the animal's degree of respiratory damage. For example, the evaluator may assign a qualitative designation (e.g., good, average or poor) or a quantitative designation (e.g., the percentage of damage).

Lung lesions in animals are similar in appearance to lung lesions in humans. Thus, information regarding evaluating lung lesions in humans can be used as a guide in the evaluation of lung lesions in animals. Similarly, information regarding evaluating lung lesions in one type of animal can be used as a guide in the evaluation of lung lesions in another type of animal.

Both ultrasound and radiographic images typically are grayscale images. In such images, a healthy animal lung typically appears with a dark gray border and a lighter gray interior. Lung tissue affected by an active respiratory disease typically appears darker than healthy lung tissue. Lung tissue damaged by a past respiratory disease typically appears even darker than lung tissue affected by an active respiratory disease. In some cases, lung tissue damaged by a past respiratory disease is very dark gray or black. Thus, darkened portions of ultrasound and radiographic images of the lung are evidence of active or past respiratory disease. Additional information can be gathered from the locations of the darkened portions. Respiratory disease typically is most severe in the bottom portion of the lung. Therefore, ultrasound or radiographic images that show dark gray or black areas in this bottom portion are strong evidence of active or past respiratory disease. The exact grayscale intensity differences between healthy lung tissue, lung tissue affected by active respiratory disease and lung tissue damaged by past respiratory disease can be discerned by comparing images from several animals, including animals with each of these conditions.

Livestock Management

Information gathered from images of the lungs of live animals can be used to make management decisions regarding the animals. Such management decisions can include decisions regarding the treatment, care or disposition of the animals. Some examples of animal management decisions, as well as other relevant information, can be found in U.S. Provisional Patent Application No. 60/645,462 and U.S. Pat. Nos. 6,805,075, 6,736,272, 6,592,517, 6,579,236, 6,547,726, 6,516,746, 6,318,289, 6,200,210, 6,135,055, 6,131,744, 6,000,361, 5,836,880, 5,803,906, 5,673,647, 5,573,002, 5,401,501, 5,369,032, RE34,776, 5,340,211, 5,315,505, 5,219,224, 5,008,821, 4,910,024, 4,889,433, 4,815,042, 4,733,971, which are incorporated herein by reference.

After evaluating respiratory damage, such as from an ultrasound or radiographic image, the designation corresponding to the degree of respiratory damage can be recorded. To facilitate recordation of the respiratory damage designation, some embodiments of the disclosed system include a data entry device near the measurement station where the respiratory damage is imaged or evaluated. Each designation can be associated with a unique identifier for the animal being assessed. This facilitates later reference to the respiratory damage designation to inform future management decisions.

In some disclosed embodiments, the respiratory damage designation is entered and stored in an electronic database. In these and other embodiments, a user may be able to review the respiratory damage designation for each of a plurality of animals from a location remote from the animals.

As discussed above, livestock with significant amounts of respiratory damage from past respiratory disease typically do not perform as well as other livestock at the feedlot, do not respond as well as other livestock to treatment for active respiratory disease and produce lower quality meat than other livestock. According to some embodiments of the disclosed method, livestock managers can use the knowledge that certain animals will or will not have these undesirable characteristics to make better management decisions.

One management decision that can be informed by knowledge of respiratory damage is the purchase of an animal. Some disclosed embodiments include providing a respiratory damage designation to a buyer to aid the buyer in a decision regarding the purchase of an animal. Naturally, animals with a greater degree of respiratory damage may be purchased for a lower price than animals with a lesser degree of respiratory damage. In some cases, a lower purchase price may offset the additional risks associated with investing in an animal with significant respiratory damage.

Aside from purchase of an animal, respiratory damage information also may be useful for determining whether to treat an animal for a respiratory illness diagnosed after the respiratory damage information is gathered. As discussed above, treatment can include the administration of drugs, which can be expensive. A decision may be made, for example, not to incur the expense associated with treatment of animals with significant respiratory damage from past respiratory disease because these animals are less likely to recover than other animals. Alternatively, a decision may be made to treat animals with significant respiratory damage from past respiratory disease more aggressively than other animals if such treatment may prevent the otherwise likely death of such animals.

Other management decisions that may be affected by an animal's respiratory condition include how the animal should be fed and housed prior to slaughter. Typically, livestock are fed at a feedlot for several months prior to slaughter. Animals with significant respiratory damage gain less weight per day at a feedlot than other animals. Thus, a decision can be made to lessen or avoid the expense associated with the animal's stay at a feedlot. For example, animals with significant respiratory damage can be housed at a feedlot for shorter amounts of time than other animals or sent directly to slaughter without spending any time at a feedlot. The rates of respiratory disease increase dramatically while an animal is housed at a feedlot and animals with significant respiratory damage are less likely to recover from respiratory disease than other animals. Thus, bypassing the feedlot stage or shortening the amount of time an animal is housed at a feedlot also may help prevent the premature death of animals with significant respiratory damage. If an animal is sent to a feedlot, the animal's respiratory condition may affect management decisions regarding how the animal should be fed. Animals with significant respiratory damage, for example, may require less feed than other animals.

Electronic Cattle Management

This subsection describes various process steps and system components for electronic animal management. These process steps and system components can be used in conjunction with evaluation of an animal's respiratory or circulatory condition, as discussed above. For example, information gather by imaging and evaluating an animal's respiratory or circulatory system, such as respiratory damage designations, can be entered into the described electronic system components and processed alone or with other animal characteristics as described below.

FIG. 1 illustrates a feedlot 10 which would typically include a series of feed pens (not shown) where cattle would be fed selected feed rations and watered during their stay in the feedlot. For example, four feed pens A, B, C and D are illustrated schematically in FIG. 7. In addition to feed pens, a feedlot incorporating the cattle management system and method includes an alley 12 leading through a series of manually or power-operated gates 14, 16, 18 and a one-way gate 20 to a chute 22.

The alley 12 leads from an alley 24, which communicates with both feed pens and receiving and holding pens, where cattle are received and held for a short period upon their delivery to the feedlot from a producer. The intersection of alley 24 and the alley 12 leading to the chute 22 is gated as indicated at 26 and 28 to control the admission of cattle into alley 12 leading to the chute and to control the exit of cattle from sorting pens indicated at 30.

Gates 14, 16 and 18 subdivide the upper curved portion of the alley 12 into cattle holding sections 190, 192 of about 40 head apiece so as to control the delivery of cattle into a crowding section 32 through a crowd gate 18. The crowding section 32 narrows from its entrance to the one-way gate 20 so that cattle are forced single file through the gate 20 and into the chute area 22 which is a single-file chute.

Chute section 22 is subdivided into a series of longitudinally arranged stations 34, 36, 38, 40 and 42. These five stations are separated from one another and from the entrance 44 to the chute by entrance and exit gates 46, 48, 50, 52, 54, 56. The stations defined by these gates are only large enough to receive one animal at a time. The opening and closing of these gates are controlled by position sensors such as photoelectric cells under computer control to control the one at a time movement of animals through the chute. A larger scale depiction of the chute will be seen in FIG. 5.

Just downstream of the single-file chute are a series of the previously mentioned sorting pens 30, there being nine such pens illustrated in FIG. 1, including pens 30A, 30B, 30C, 30D, 30E, 30F, 30G, 30H and 30I. Below these pens in FIG. 1 is an alley 58 leading from the left-hand pen exits to the alleys 12 and 24. In addition, there is a single-file narrow alley 60 between the left-hand series of sorting pens 30A, 30C, 30D, 30E, 30G and the right-hand series of sorting pens 30B, 30D, 30F and 30H. From the layout of FIG. 1 it will be apparent that any animal proceeding through the chute and not sorted into one of the sorting gates 30A-30H will automatically end up in sorting pen 30I.

Alley 60 is normally isolated from the entrances to each of the eight sorting pens 30A-30H by a computer-operated entrance gate 62 at the entrance to each sorting pen. It will be noted that there is no entrance gate to the final sorting pen 30I. Each sorting pen also has an exit gate 64 at its opposite end opening into an alley used to direct the cattle from the sorting pens to another destination to be described in greater detail below. The exit gates 64 on pens 30A, 30C, 30E and 30G on the left-hand side of the alley 60 in FIG. 1 open into an alley 66 leading through control gates 68, 70 back to alley 58 where cattle can be directed either back through alley 12 or into alley 24 leading to the feed pens.

Each station of the single file chute 22 is set up either to prepare each animal for measurement or processing, or to actually measure or process the animal. For example, in FIG. 1, station 34 is termed the "get ready" station where one animal is admitted from the chute entrance area 44. Once the animal enters the "get ready" station 34, gate 46 closes and gate 48 remains closed so the animal remains isolated at that station. Then gate 48 is opened so that the animal enters the next station 36. Station 36 is where certain external dimensions of each animal are measured. This is preferably done through a video-imaging device or scanner suitable for this purpose such as one known commercially as an MSI Scanner available from Cattle Scanning Systems (C.S.S.) of Rapid City, S. Dak. Another video-imaging measurement system for cattle is disclosed in Hayes, U.S. Pat. No. 4,745,472.

After the animal's external dimensions are measured, gate 50 is opened and the animal proceeds into the third station 38 in the chute, which contains a scale on which the animal is weighed. The scale used can be any of a number of commercially available scales but should be capable of generating an electronic signal for recording the weight at a remote location. Also at the scale station or at another desired station, an electronic identification (EID) tag is attached to the animal's ear. This EID tag remains attached to the animal throughout its residence in the feedlot and its shipment to the packing plant where it is removed upon slaughter. Through this EID tag, the animal can not only be identified but its location can be tracked and its measurement and performance data correlated to the animal throughout the duration of its feedlot stay, through its shipment to the packing plant, and until slaughter. One suitable EID tag for this purpose is manufactured by Allflex International and is described in greater detail in U.S. Pat. No. 5,315,505. The disclosure of U.S. Pat. No. 5,315,505 is incorporated herein by reference. The Allflex EID tag is a transponder which operates through a nearby antenna and an integrator reader also available from Allflex International. Each EID tag emits a signal unique to the animal to which it is attached, which is electronically "read" by the antenna and communicated to a host computer via a computer interface unit.

After an animal's weight is recorded and its EID tag attached, it moves through gate 52 to the next measuring station 40 where its internal backfat content is measured using an ultrasound measuring means and technique. For this purpose, the animal must be held fairly still, station 40 is a "squeeze chute," well known in the feedlot industry. The squeeze chute has a rear gate that pushes against the rear of an animal while its head is stabilized in a "head catcher." The ultrasound measuring system used at station 40 is similar to the experimental system used by Professor John Brethour at Kansas State University's Fort Hays Experiment Station, described in the September, 1994 issue of D J Feeder Management magazine. While the animal is within measuring station 40, circulatory or respiratory system imaging also can be performed, as discussed above.

After backfat measurement, the gate 54 is opened and the animal proceeds to station 42 for processing. Station 42 is also a squeeze chute. Typically, processing at station 42 will include individual drug administration, growth hormone implantation, castration and dehorning. After processing, the chute gate 56 is opened and the animal is sorted into one of the sorting pens in a manner to be described hereinafter.

Figure 5:
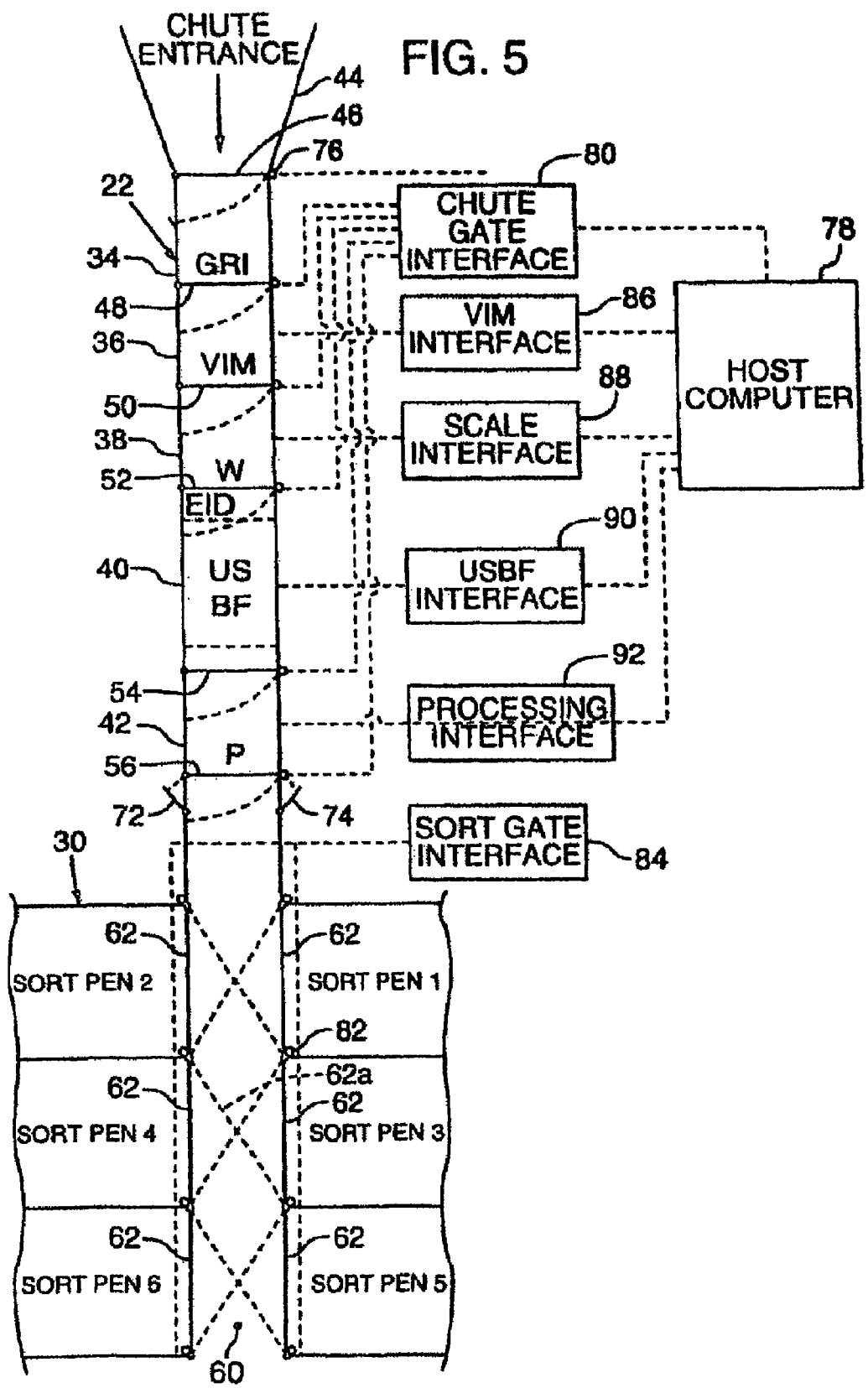
FIG. 5 is an enlarged schematic diagram of the single-file measuring chute and adjacent sorting pens similar to those shown in FIG. 1, but on an enlarged scale and showing schematically a control means for controlling the operation thereof.

The enlarged schematic version of the single-file chute 22 shown in FIG. 5 is sufficiently similar to the chute 22 shown schematically in FIG. 1 that the same reference numerals will be used in describing both chutes. With reference to FIG. 5, it includes the same five processing and measuring stations 34, 36, 38, 40 and 42 as in FIG. 1. However, at the downstream end of the chute 22 of FIG. 5 there are only seven sorting pens 30 shown and designated sort pens 1-7, rather than nine such pens as shown in FIG. 1.

As shown most clearly in FIG. 5, the single-file chute includes at its downstream end just downstream of chute exit gate 56 from the processing station 42 a pair of access gates 72, 74 for the admission of feedlot personnel into the chute when necessary. These gates may be manually operated.

From FIG. 5 it will also be apparent that sorting into one of the several sorting pens is accomplished after each animal proceeds through all five stations of the chute by opening an entrance gate to one of the sorting pens while the others remain closed. Thus, for example, if an animal is to be sorted into sorting pen 3 in FIG. 5 its entrance gate 62 would open to the position 62a shown while the entrance gate 62 to all other sorting pens remain closed, thereby directing the animal into sorting pen 3.

As previously mentioned, each sorting pen entrance gate 62 and each of the chute gates 46, 48, 50, 52, 54 and 56 is operated via position sensors indicated schematically at 76 in FIG. 5 in conjunction with a host computer 78 through chute gate interfaces indicated schematically at 80. Similarly, sort pen entrance gates 62 are operated by the position sensors 82 controlled by the host computer 78 through the sort gate interfaces 84.

The measurement taken at each of the measuring stations 36, 38 and 40 of the chute, for each animal passing through the chute, transmits a signal indicative of the measurement for that animal through an appropriate interface to the host computer 78, where the measurement data is entered and stored for use in calculating various performance characteristics of the animal.

Each measurement is correlated with a specific animal through the animal's EID tag as it passes from station to station through the chute. More specifically, the video imaging measurement (VIM) data is transmitted through a VIM interface 86 to the host computer 78. Weight data for the same animal is transmitted from the scale at station 38 through a scale interface 88 to the host computer 78. Then the ultrasound data for the same animal is transmitted through the USBF interface 90 to the host computer 78. The ultrasound data can include, for example, backfat data and respiratory condition data. Finally, any drugs administered to the animal or other procedures performed on the animal at the processing station 42 are transmitted through the processing interface 92 to the host computer where such data is correlated with the animal processed.

Reference is made to the aforementioned U.S. Pat. No. 5,315,505 for a detailed description of how animal health data and drug administration data would be entered into the host computer from a processing station for a given animal.

Figure 2:
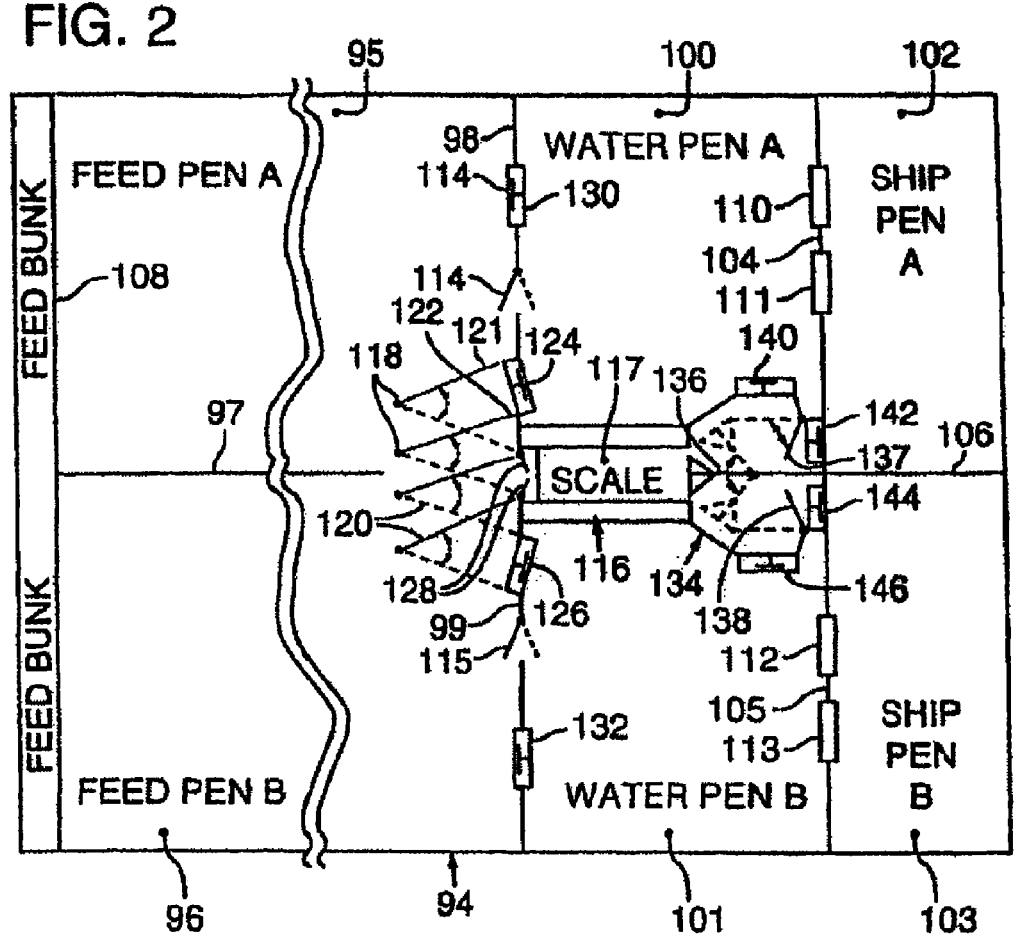
FIG. 2 is a schematic diagram of the layout of a pen sorter including feed pens, water pens and shipping pens for a feedlot.

With reference to FIG. 2, a pen sorter 94 is disclosed. There could be one or several pen sorters 94 in a feedlot. Also, it is possible that the sorting portion of the pen sorter 94, which portion is to be described presently, could be designed as a portable unit that would be transported to a particular feed pen within the feedlot for use there within the 30 days or so prior to scheduled shipment of the group of animals within the feed pen so that the shipment date for each animal in the pen could be optimized for maximum feed efficiency and value.

In any case, the pen sorter is designed to enable weighing of individual animals on a frequent basis, such as daily or even more frequently, without removing the animals from their feed pens and without the need to send them back through the single-file chute described with respect to FIGS. 1 and 5.

The illustrated pen sorter 94 is subdivided into two feed pens 95, 96 designated feed pen A and feed pen B, separated by a partition or fence 97. Each feed pen in turn is also separated by partitions 98, 99 from adjacent water pens 100, 101, designated water pen A and water pen B. Water pens A and B are, in turn, separated from adjacent shipping pens 102, 103 by partitions 104, 105, the shipping pens being designated ship pen A and ship pen B. The ship pens in turn are separated from one another by another fence or partitions 106. Each feed pen includes a feed bunk 108 into which the daily feed ration of the animals in those pens is deposited and to which the animals in the feed pen have ready access. The water pens and ship pens are provided with respective watering troughs 110, 111, 112 and 113 so that the animals within those pens can access drinking water as desired.

The heart of the pen sorter 94 is its array of gates for directing animals in the feed pens A and B to desired locations within the larger confines of the pen sorter 94, on an individual animal basis, based on measured performance characteristics of each animal, other data such as market conditions, and a desired shipping date.

First it should be noted that animals within feed pen A are free to pass between such pen and its adjacent water pen A through a two-way gate 114 to access feed and water as desired. The same is true with respect to animals within feed pen B through a two-way gate 115 between feed pen B and water pen B. However, unless desired by feedlot personnel or dictated by the management system, cattle cannot pass from one feed pen to another or from one water pen to another and cannot pass from either water pen into either shipping pen.

A single scale stall 116 is positioned between water pen A and water pen B and is sized to accept one animal at a time. The scale stall is equipped with one scale at 117, which can be of a type similar to that used in the scale station of the single-file chute as previously described. The scale is set up to transmit automatically the weight reading of an animal through a suitable interface to the host computer. To identify the animal being weighed, the stall is also equipped with an EID tag identification means as previously described for receiving and transmitting the identification of an animal being weighed to the host computer.

Access to the scale stall is either from feed pen A or feed pen B, as desired, through one of two shuttle gates 118, 120. Both shuttle gates 118 and 120 comprise a pair of parallel gate arms 121, 122 which move in unison from a scale entrance position, as shown with respect to shuttle gate 120, to a scale blocking position, as shown with respect to shuttle gate 118 in FIG. 2. When in its scale blocking position, each shuttle gate has its arms 121, 122 directed toward a one-way gate leading into the adjacent water pen. For example, feed pen A shows shuttle gate 118 with its shuttle arms in a position for directing animals through the one-way gate 124 into water pen A. When shuttle gate 120 is in a comparable position, its arms would direct cattle through a one-way gate 126 into water pen B. Thus, depending on the position of shuttle gate 118, animals from feed pen A can be directed either through one-way gate 124 into water pen A or into the scale stall 117. A one-way gate 128 at the entrance to the scale stall prevents an animal that has entered the scale stall from backing out. Similarly, an animal within feed pen B can be directed by shuttle gate 120 either into the scale stall 117 to be weighed or through the one-way gate 126 into water pen B.

Of course, it will apparent that an animal in feed pen A or in feed pen B can at any time pass through the two-way gates 114 and 115 between those pens and their respective water pens A and B, and back again to their respective feed pens. It will also be apparent that any animal within water pen A can also pass through a one-way gate 130 back to feed pen A.

However, unless other control gates are operated, an animal in water pen A cannot pass to either shipping pen A or shipping pen B or into feed pen B. Similarly, any animal in water pen B can pass through either the two-way gate 115 or a one-way gate 132 back to feed pen B but cannot pass into shipping pen B, feed pen A or water pen A without operation of appropriate control gates.

Once an animal is within the scale stall 116, it must pass forwardly out of the stall through a complex array of sorting gates indicated generally at 134 into one of four pens, either water pen A, shipping pen A, water pen B, or shipping pen B. The operation of the sorting gate array 134 is under computer control. The scale stall 116 is provided with an EID tag antenna to identify the animal within the scale stall to the computer system, which then determines which pen the animal is to proceed to from the scale stall, after which the computer operates the sorting gate array 134 in a manner to direct the animal to the appropriate pen.

Sorting gate array 134 includes three controllable shuttle gates 136, 137 and 138. In addition, it includes a one-way gate 140 leading from the sorting area just downstream from the scale stall into water pen A, a one-way gate 142 leading from the same sorting area into shipping pen A, a third one-way gate 144 leading from the sorting area into shipping pen B and a fourth one-way gate 146 leading from the sorting area into water pen B.

The following will illustrate that an animal in, for example, feed pen A can be directed through the scale stall 116 and then either back to feed pen A, to feed pen B, to shipping pen A or to shipping pen B. The same is true with respect to an animal in feed pen B. Thus, pen sorter 94 is capable of effecting a four-way sort.

To illustrate, an animal in feed pen A with the shuttle gate 118 in the position shown, can pass freely between feed pen A and water pen A and back to feed pen A. However, with the shuttle gate 118 shifted to its position shown in dashed lines in FIG. 2, an animal in feed pen A will be directed through the one-way gate 128 into the scale stall 116 where it will be weighed and identified to the computer through its EID tag. The computer will then determine to which pen it should be sorted from the scale stall and actuate the appropriate gates to accomplish the desired sort. For example, if it is desired to return the animal to feed pen A, sorting gate 136 is shifted downward to its dashed line position shown thereby allowing the animal to move through the sorting area and through the one-way gate 140 back to water pen A where it can move freely back to feed pen A, either through the two-way gate 114 or the one-way gate 130.

If it is desired that the animal be sorted from feed pen A to feed pen B, sort gate 136 is shifted upward to its dashed line position shown, allowing the animal to travel from the scale stall freely through the sorting area and one-way gate 146 to water pen B, from which the animal can move freely through either two-way gate 115 or one-way gate 132 to feed pen B.

If it is desired that the animal move from the scale stall 116 to shipping pen A, sort gate 136 is moved to its downward position in FIG. 2 and control gate 137 is moved to its upward position shown in dashed lines in FIG. 2, enabling the animal to travel through the sorting area and through one-way gate 142 into shipping pen A.

If it is desired that the animal move from the scale stall to shipping pen B, sorting gate 136 is moved upward, control gate 138 is moved downward to its dashed line position, and the animal can thus move freely through the sorting area and one-way gate 144 into shipping pen B.

From the foregoing it will be understood that animals within feed pens A and B can be weighed as frequently as desired and sorted four ways without moving the animals any appreciable distance. Thus the pen sorter 94 provides an ideal finishing pen for use in determining the exact day within a shipping window of several days when an animal should be shipped to the packing plant for slaughter to realize the maximum return on the investment in such animal, considering animal performance, market conditions and feed efficiency.

FIG. 3 illustrates a hypothetical timeline in the management of cattle. Upon arrival of a lot of cattle in the feedlot, or before, the prior history of the lot would be entered in the host computer 78, as indicated at 148. Such prior history data is illustrated, for example, in the cattle received report by "load" shown in Table 3A. The report indicates such things as the date the load was received, the load number, the number of head in the load, the sex of the cattle in the load and the average weight of the animals in the load. It also indicates cost information. It also gives information such as the age of the cattle, the breed, the type of pasture the load has been on and health, nutrition, stress and weather conditions applicable to the load. It also indicates the number of days the load has been feeding on pasture. Some or all of this data may be used in later calculations by the computer to determine the optimum end date (OED) or days to finish (DTF), of the group or individual animals in the group. This date is also sometimes referred to as the optimum marketing or shipping date.

On the day of their arrival, indicated on the timeline at 150, each animal in the load is measured, processed and electronically identified with an EID tag in the one-way single-file chute 22 previously described. Then, if desired, the measured and processed animals may be sorted into the sorting pens 30 in a rough sort by type (breed), weight, age, or a first estimated OED or DTF, although such a first "rough" first sort is optional.

From the sorting pens, the animals are moved to feed pens, either by sort or on an ad hoc basis, where they are fed for a period of time, such as 45 days as shown in FIG. 3, although possibly substantially longer than that.

If a 45 day weight or measurement is desired for the animals, they would be moved from their feed pens on the 45th day as indicated at 152 back through the single-file chute, where they would be remeasured. From the initial measurement and remeasurement data, the performance of each animal would be calculated by the computer, and its performance assessed. The animals would then be sorted into the sorting pens 30 according to their performance characteristics. Poorly performing animals would be culled from the group and removed from the feedlot operation as "salvage." The remaining resorted animals would be returned to the feed pens according to their sorts. Animals with respiratory or circulatory damage indicated by imaging also can be moved to the salvage group.

Then 60-120 days into the feeding period, indicated by the range 154 in FIG. 3, the animals from at least two feed pens at once would be moved from their pens back through the single-file chute for remeasuring once again on an individual basis. The data from these measurements together with prior data for each animal would be used by the computer to calculate a new OED or DTF for each animal and other performance criteria, such as average daily gain (ADG) and feed proration for each animal. From the single-file chute the animals would be resorted once again according to predetermined criteria such as DTF or OED. A projected shipping sequence for each animal could also be calculated at this time. Then the animals would be returned to the feed pens according to the newly determined sorts. The animals then could be removed from their pens for shipment according to their calculated shipping sequence. Whenever an animal is moved in the feedlot, its identification and data, via computer, moves with it. Its location at any time can be determined remotely by computer, and its performance data assessed.

Alternatively, a portable pen sorter of the type shown in FIG. 2 could be installed in the feed pen. Each animal would be carefully monitored and weighed, perhaps on a daily basis, until it reached its optimum shipping weight or value, at which time it would be shipped to the packer, indicated at 156.

Alternatively, animals within the feed pens could be sent to a finishing pen such as the pen sorter 94 shown on FIG. 2 where it would be confined, monitored and weighed frequently within a shipping window such as a 30 day shipping window. Within that shipping window indicated at 158, each animal as determined by frequent weight checks and market conditions, would be directed from its feed pen, such as feed pen A or feed pen B in FIG. 2, to appropriate shipping pen A or B when it is ready for shipment.

Alternatively, during an animal's shipping window, the animal could be weight checked simply by sending it back through the single-file chute periodically until it reaches its ideal shipping weight, at which time it would be shipped to the packer 156.

Alternatively, a specific shipping date for a given animal could be determined by issued inspection while the animals are within their 30-day shipping window.

When the animal leaves the feedlot, its EID tag travels with it. Its historical and performance data records would be maintained by the feedlot, indicated at 160, and also transmitted to the producer, indicated at 162. At the same time, the packer would record the carcass data for each slaughtered animal, identified by its EID tag, and transmit the carcass data, as indicated at 164, to the feedlot and producer for correlation with the animal's live performance data from the feedlot.

The correlation can be useful to the feedlot in projecting optimum end dates (OED), initial feed proration and production costs for future animals of a given type and similar history. This data can also be useful to cattle producers in determining which breeds and individual breeding animals are most desirable from the standpoint of market value and producing the best quality of beef. The important thing to note is that the performance of each animal is tracked on an individual basis from the time it arrives in the feedlot until the time it is shipped and slaughtered, when its carcass data is collected and correlated with its performance data for use by the feedlot and producer in managing future beef production.

Another important feature of the system is its ability to update an individual animal's performance projections on a daily basis. For example, the DTF for an animal will be current for the day the projection is assessed. The same is true for other projections such as projected weight, etc.

Although FIG. 3 illustrates one possible processing sequence of cattle including measuring and remeasuring steps and sorting and resorting steps for optimum feed efficiency and return, many other sequences are possible as illustrated in FIGS. 4A, 4B and 4C. For example in the sequences of FIGS. 4A, 4B and 4C the 45 day remeasurement is eliminated and instead a single 60-75 day remeasurement and uniformity sort are performed.

Referring to FIG. 4A, a load of cattle is received in the feedlot at 166 and within a few hours, measured at 167 and processed at 168 in the single-file chute. From the chute they are directed into the feed pens at 169 without an initial sort. They are fed in the feed pens for 60-75 days, and then returned to the single-file chute for remeasuring at 170 and possibly reimplantation of a growth hormone, if necessary. After remeasuring, the animals undergo a uniformity sort as determined by the computer, and directed into the appropriate sorting pens 172. Upon completion of the sorting operation, they are returned to the feeding pens 174 according to their sort groups and there fed for a period of 60 to 80 days. As the cattle within the feed pens approach their individual optimum end dates they would be selected for shipment either visually, by remeasurement at the single-file chute, or by frequent reweighing in a portable pen sorter of the type shown in FIG. 2. Following selection at step 176 the animal would be shipped as at 178 to the packer.

The processing sequence of FIG. 4B for an individual animal is the same down through the initial receiving, measuring and processing steps. However after measuring and processing, according to FIG. 4B there is an initial sort step 180 that can be a rough type sort as in FIG. 3 or can be based on a first rough estimated optimum end date for each individual animal. Following the first sort 180, the animals are directed by sort group into feed pens at 169 for a feeding period of 60-75 days. At the end of the 60-75 day period the animals are removed from their pens, either individually or in groups, and returned to the single-file chute for remeasuring at 170.

After remeasuring in the single-file chute, each animal is resorted at 182 by the computer, which opens the appropriate sorting gates of the sorting pens 30. From the sorting pens, the animals are redirected back to the feed pens at 174 and placed into the pens according to their sorting groups. They remain in the feed pens for a period of 60-80 days, after which they are individually, or by group, selected for shipment, according to their last calculated OED. As previously indicated, this selection for shipment can be fine-tuned through the use of either a portable pen sorter or the pen sorter 94 of FIG. 2. After selection, the selected animals are shipped at step 178 to the packing plant for slaughter, where the carcass data and EID tag are collected.

The optional cattle processing procedure of FIG. 4C is the same as the procedure outlined in FIG. 4A down through the initial sorting step 172. However, thereafter the animals, according to the procedure in FIG. 4c, are directed back to the feed pens according to sorting group at step 173 for a feeding period of only 30-40 days. Thereafter, the animals, or at least selected animals, from the feed pens are removed to finish feed pens, such as pen sorters 94 in FIG. 2, for a finish feeding step 175 for an additional 30-40 days, which represents the shipping window 158 indicated in FIG. 3. Within the finish feeding pens, the animals can be sorted, resorted, weighed, reweighed and selected on an individual animal basis for sorting to one of the two shipping pens A and B for shipment to the packer at step 178.

Figure 7:
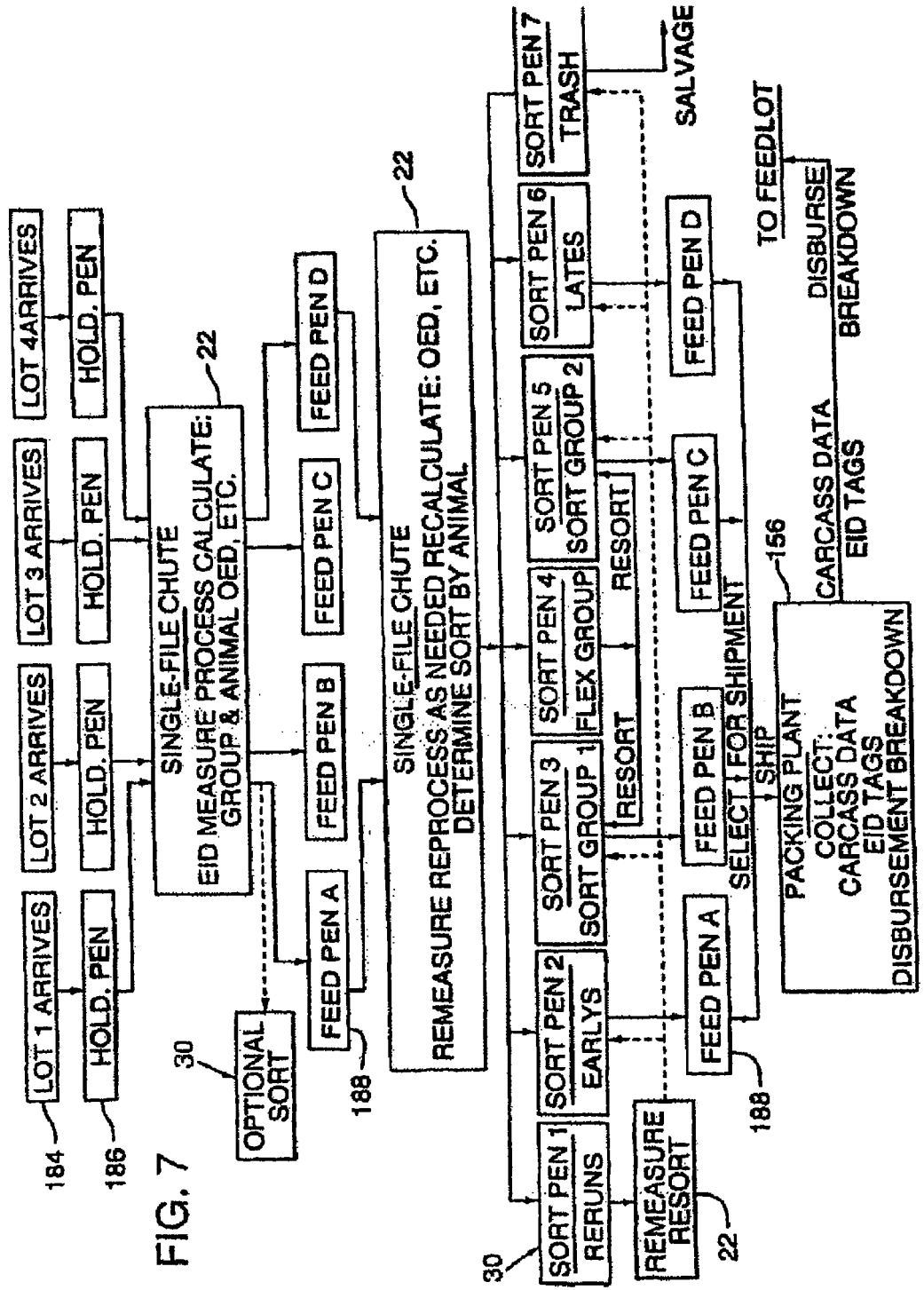
FIG. 7 is a cattle processing diagram but in considerably greater detail than those of FIGS. 4A, 4B and 4C.

FIG. 7 illustrates, in greater detail, a representative cattle processing sequence in a feedlot. Steps in the processing sequence are numbered 1-9 along the left-hand side of FIG. 7.

In step 1, as indicated at 184, several lots of cattle arrive at the feedlot at about the same time, indicated as lots 1-4. When they arrive, the previous history data of the lots and individual animals in the lots is entered into the host computer by data entry means (not shown) such as a computer keyboard. The previous history, as already mentioned, may include information such as shown in Table 3A.

According to step 2, after the cattle arrive they are directed into receiving or holding pens 186, typically by lot, where they are held just prior to initial processing. The time spent in the holding pens 186 will depend on when the lots arrived in the feedlot. For example, when they arrive in the middle of a night, they would be retained in the holding pens until feedlot personnel arrive early the next morning to process them. When ready for processing, the cattle from the holding pens 186 are directed through the appropriate alleys to the one-way single-file chute 22 where they are one-by-one led through the various chute stations, sequentially, including the get ready station 34, the video image measuring station 36, the weighing station 38 and the ultrasound measuring station 40. During this process the EID and visual ear tags are applied as well, and the measurement data from each of these stations is transmitted through the appropriate interfaces to the host computer 78 for recording, collection and storage. At the processing station 42 each animal is implanted with a growth hormone, given medication as needed, and dehorned and castrated as needed.

Using available information and data on the group being processed and the individual animals in the group, an initial optimum end date (OED) is determined, either through calculation by the computer or by the operator. A marketing target grade for each animal and for the group (an average) is also assigned, either by the operator from a list of data or through calculation by the computer, depending on the capability of the computer program used. In addition, at this point a projected feed intake for each animal is calculated and assigned and used in prorating the total feed ration used by a group of animals within a single feed pen, so that a fairly accurate cost of feed per animal can be calculated and assessed to the owner.

Figure 25:
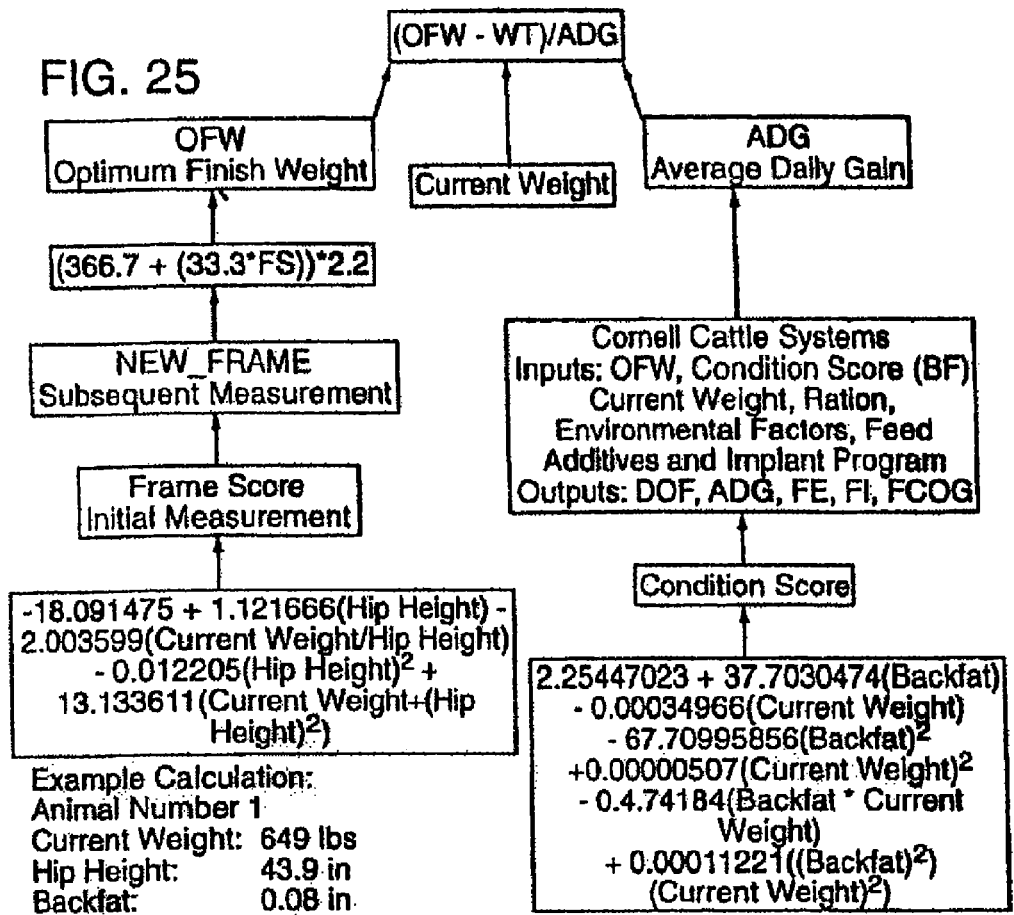
FIG. 25 is a flow diagram illustrating the process and formulas for calculating "Days to Finish," followed by an example calculation based on hypothetical animal measurements.

Referring to FIG. 25, the process and formulas for calculating "days to finish" (DTF) is illustrated, followed by an example calculation based on hypothetical measurements of an animal passing through the single-file chute.

Figure 26:
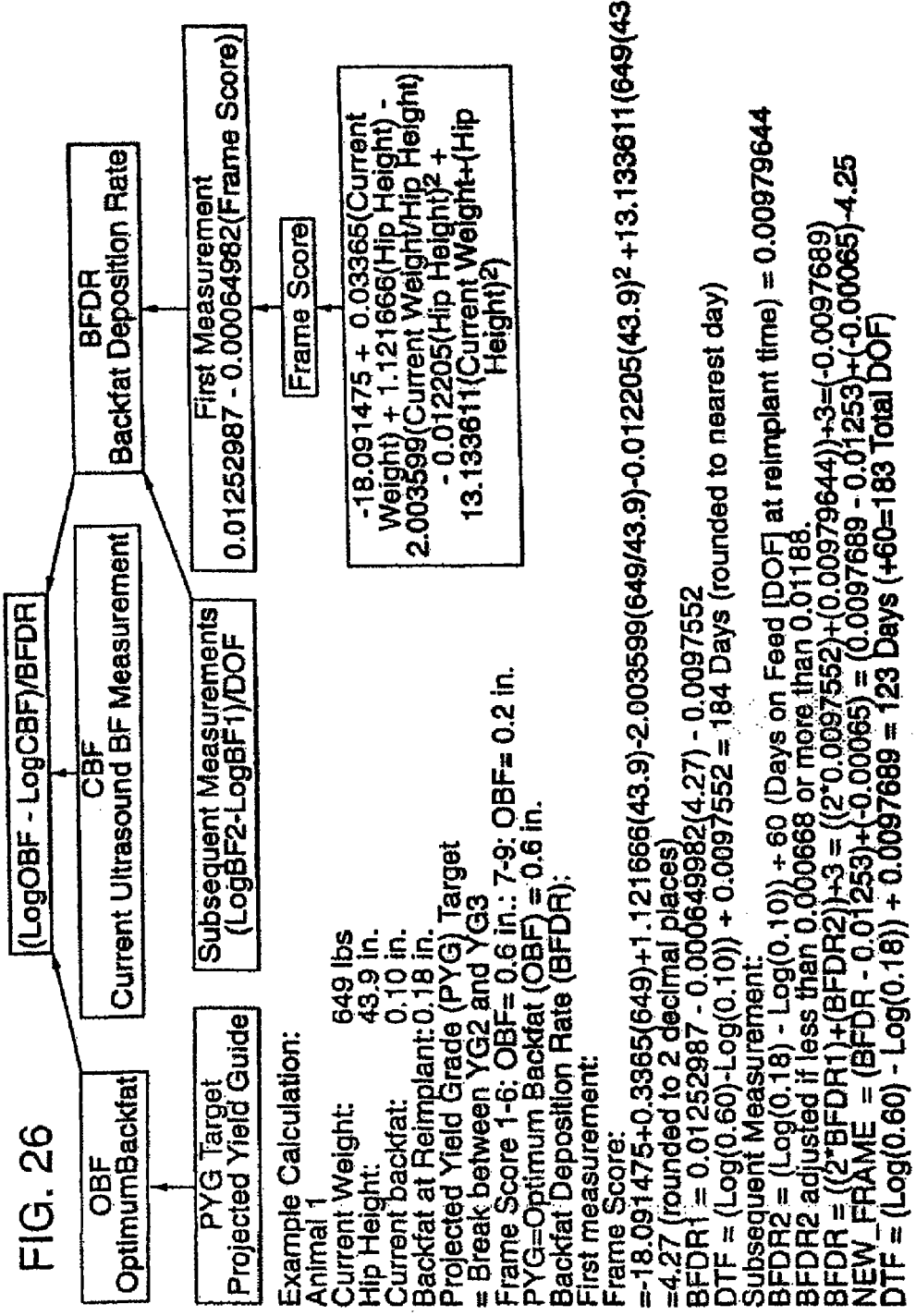
FIG. 26 is a flow diagram illustrating an alternative method to that of FIG. 25 for calculating "Days to Finish" for an individual animal, followed by an example calculation based on hypothetical measurements of the animal.

Referring to FIG. 26, an alternative method of calculating DTF for an individual animal is disclosed. Following the figure is an example calculation based on hypothetical measurements taken at two different measuring dates during an animal's feeding period at the feedlot.

Using the method of FIG. 25, an animal arriving at the feedlot, after being measured in the single-file chute, is calculated to have a projected DTF of 141 days. This represents the total number of days the animal is projected to be at the feedlot before it is ready for shipment to the packing plant. However, according to FIG. 26, the same animal using the different method of FIG. 26 is calculated to have a DTF of 165 days, based on its initial measurements upon arrival at the feedlot.

In Table 1 there are set forth limiting factors to DTF projections based on maximum and minimum live weight for the animal. An example calculation follows. According to the calculation, if a maximum hot carcass weight of 800 pounds and a minimum hot carcass weight of 500 pounds is desired in the end product, the maximum live weight of the animal should be 1230 pounds and the minimum live weight of the animal should be limited to 768 pounds. Thus, if the OFW (optimum finish weight) as used in the example calculation following FIG. 25 results in a maximum live weight that exceeds 1230 pounds or a minimum live weight of less than 768 pounds, the maximum or minimum live weights from the example calculation of Table 1 should be used in the FIG. 25 calculation rather than the optimum finish weight (OFW) originally used.

It will be noted that the formula and calculation of FIG. 25 includes a "Cornell Cattle Systems" formulation. This is a well-known formula in the cattle industry which includes inputs of OFW, condition score (backfat measurement), current weight, ration, environmental factors, feed additives and input program used.

Figure 27:
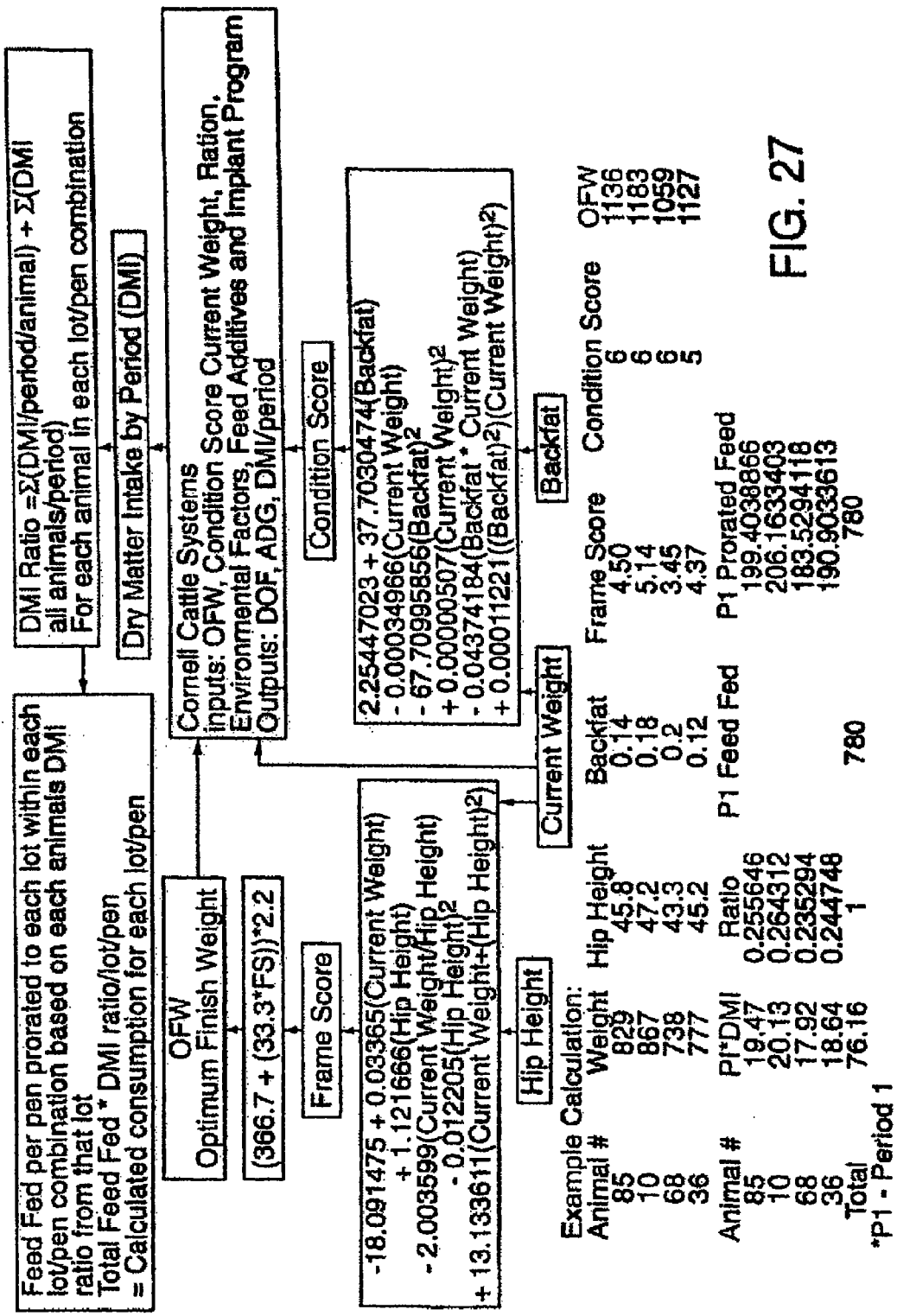
FIG. 27 is a flow diagram illustrating the process of determining feed proration to individual animals following a first set of animal measurements in the feedlot.
Figure 28A:
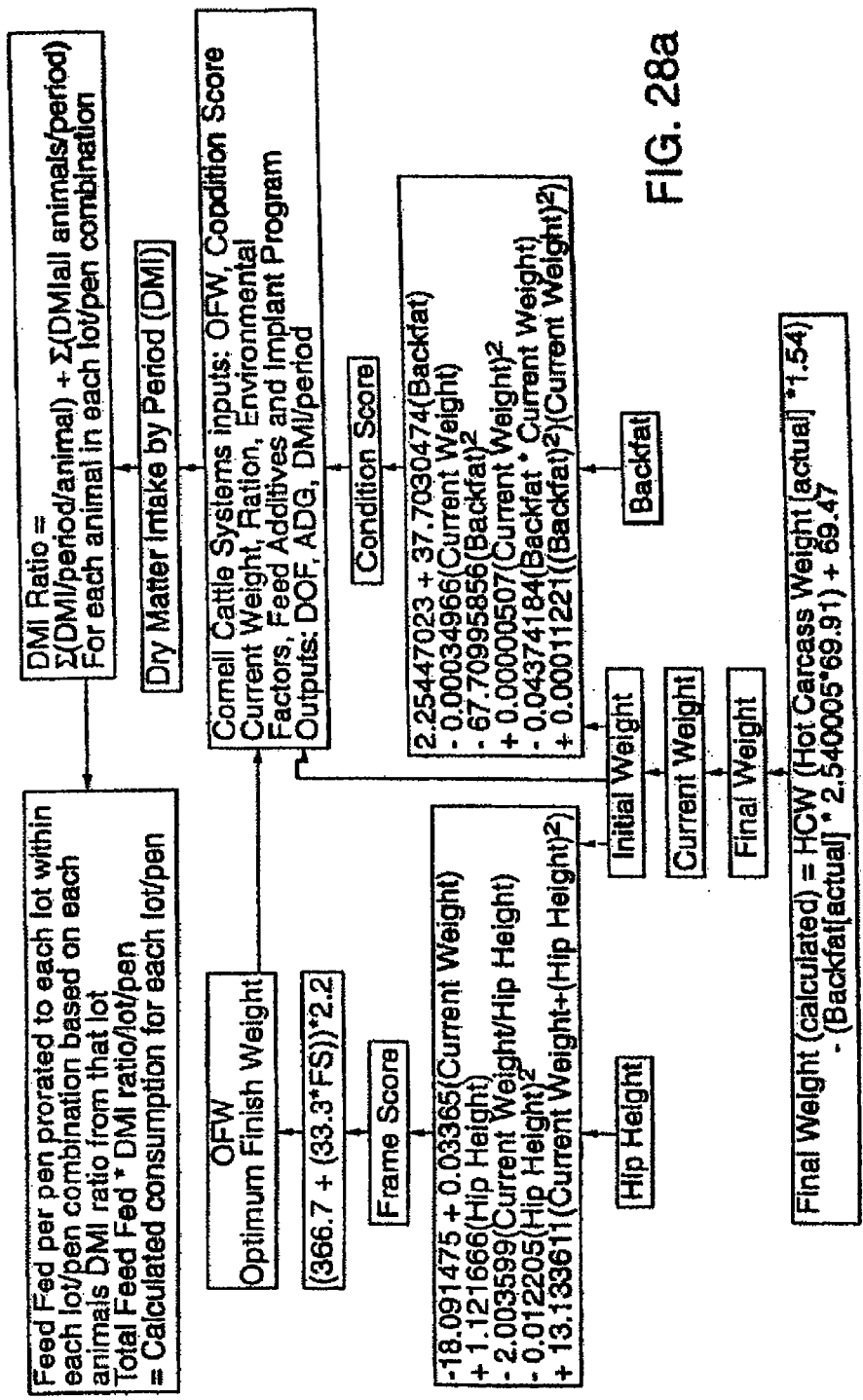

FIG. 27 shows the calculation and the process of calculating feed proration to each animal as determined following the first set of measurements at the single-file chute. FIG. 27 is followed by an example calculation using the formula and method indicated in the figure. In the figure DMI indicates dry matter intake for a given feed period and is indicated hereinafter as (DMI). In the same method of calculation the ADG indicates the average daily gain for a given animal. All other measurements used in the formula will be self-explanatory. As indicated in the formula, the frame score is determined by a formula using both hip height and current weight. The condition score for an animal is determined using both the backfat measurement and current weight. In the example, the proration of feed fed in a given period (P1) is calculated for each animal. From the calculation a proration ratio is indicated and applied to the 780 total pounds of feed fed to a pen of four animals during the P1 feed period, resulting in a feed period total proration of feed among the four animals as indicated in the last column of the calculation. It will be noted that of the four animals, the proration ranges from a low of 190.9 pounds to a high of 206.2 pounds. This feed proration formula and calculation is used only for the first feed period following the first measurement of the animals. Following the second and subsequent measurements, a different feed proration formula and calculation is used as indicated in FIGS. 28a and 28b.

Figure 29:
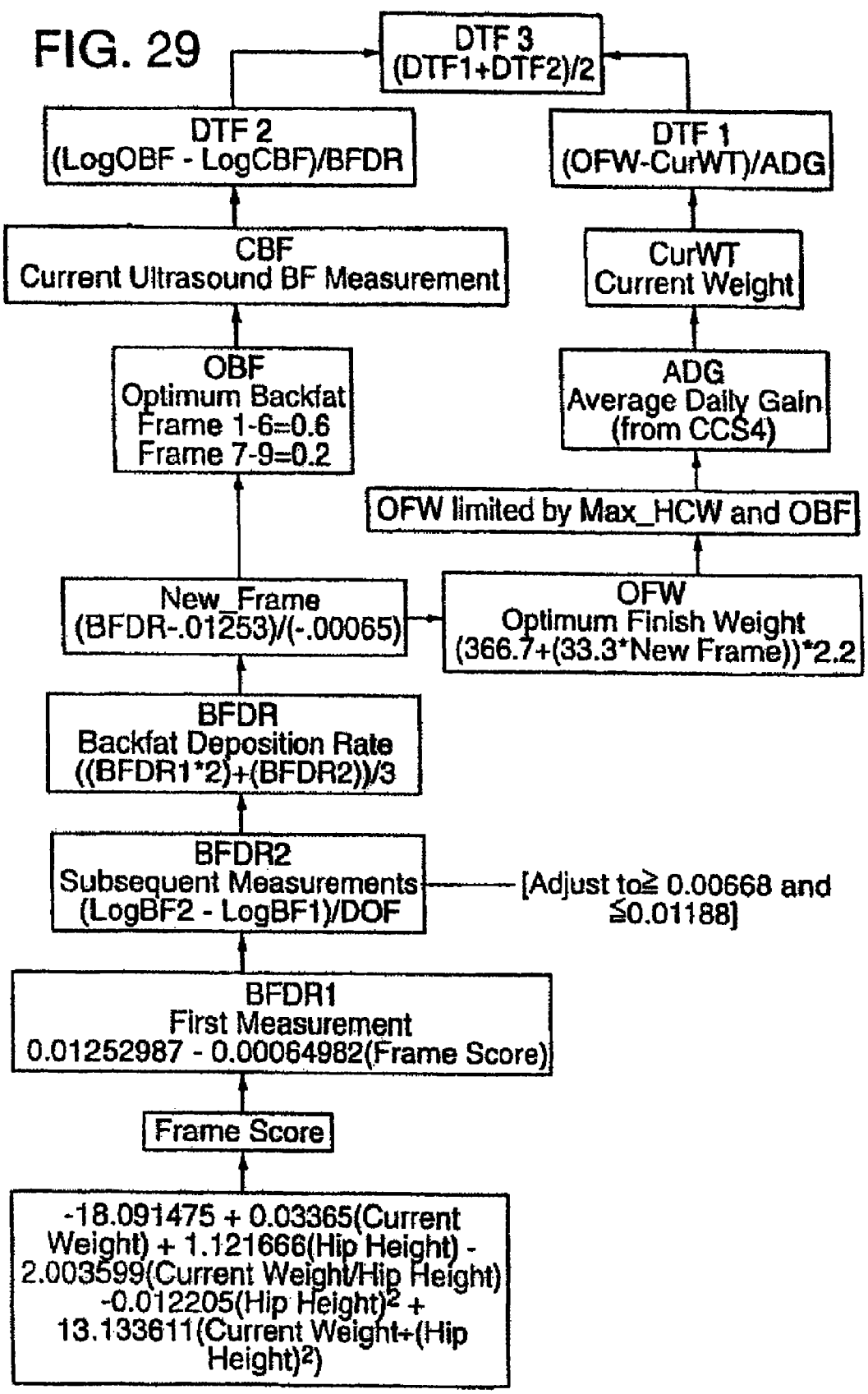
FIG. 29 is a flow diagram showing how calculations of "Days to Finish" from FIGS. 25 and 26 can be used to create an average "Days to Finish" for projecting when an individual animal will be ready to ship from a feedlot.

FIG. 29 illustrates how the calculations of DTF from 2 FIGS. 25 and 26 (DTF1 and DTF2) can be used to create an average DTF (DTF3) for use in projecting when an individual animal will be ready to be shipped from the feedlot. The numbers used in 6 FIGS. 25, 26 and FIG. 29 are coefficients that are obtained empirically from experience feeding cattle at a prototype feedlot. The coefficients are defined and correlated with the coefficient numbers used, in Table 2.

TABLE 1

Limiting factors to DTF Projections
Maximum Live Weight (Max_LW)
Minimum Live Weight (Min_LW)

| | |
|---|---|
| Max_LW = (Max_HCW*1.54) − (OBF*2.540005*69.91) + 69.47 | |
| Min_LW = (MinHCW*1.54) − (OBF*2.540005*69.91) + 69.47 | |
| Maximum Hot Carcass Weight (Max_HCW): | User Input |
| Minimum Hot Carcass Weight (Min_HCW): | User Input |
| Optimum Backfat (OBF): | User Input |
| Example Calculations | |
| User Inputs: | |
| Max_HCW: | 800 lbs |
| Min_HCW: | 500 lbs |
| OBF: | 0.40 in. for frame score 4 |
| Max_LW = (800*1.54) − (0.40*2.540005*69.91) + 69.47 = 1230 lbs | |
| Min_LW = (500*1.54) − (0/40 *2.540005*69.91) + 69.47 = 768 lbs | |

TABLE 2

DTF Calculation Coefficients

Frame-Linear Regression Equation

C-1  Intercept for Regression Equation (=18.091475)
C-2  Estimate for Weight parameter (0.03365)
C-3  Estimate for Hip Weight parameter (1.121666)
C-4  Estimate for the parameter of Current Weight divided by Hip Height (2.003599)
C-5  Estimate for the parameter of Hip Height Squared (−0.012205)
C-6  Estimate for the parameter of Current Weight divided by Hip Height Squared (13.133611)

BFDR-1 Linear Regression Equation

TABLE 2-continued

DTF Calculation Coefficients

| | |
|---|---|
| C-7 | Intercept (0.01252987) |
| C-8 | Estimate for Frame Score Parameter (−0.00064982) |
| | BFDR-2 Logarithmic Regression Equation |
| C-9 | Lower limit fat Deposition Rate (0.00668) |
| C-10 | Upper limit Fat Deposition Rate (0.01188) |
| | New Frame |
| C-11 | Upper Deposition Rate (−0.01253) |
| C-12 | Lower Deposition Rate (−0.00065) |
| | OBF-Conversion Tables for Frame to Back Fat |
| | DTF1-Logarithmic Regression Equation |
| | OFW-Regression Equation |
| | OFW-Regression Equation |
| C-13 | Intercept (366.7) |
| C-14 | Estimate for OFW (33.3) |
| C-15 | Pounds to Kilogram Conversion Factor (2.2) |
| | ADG-Cornell Model Output of ADG |

Figure 30:
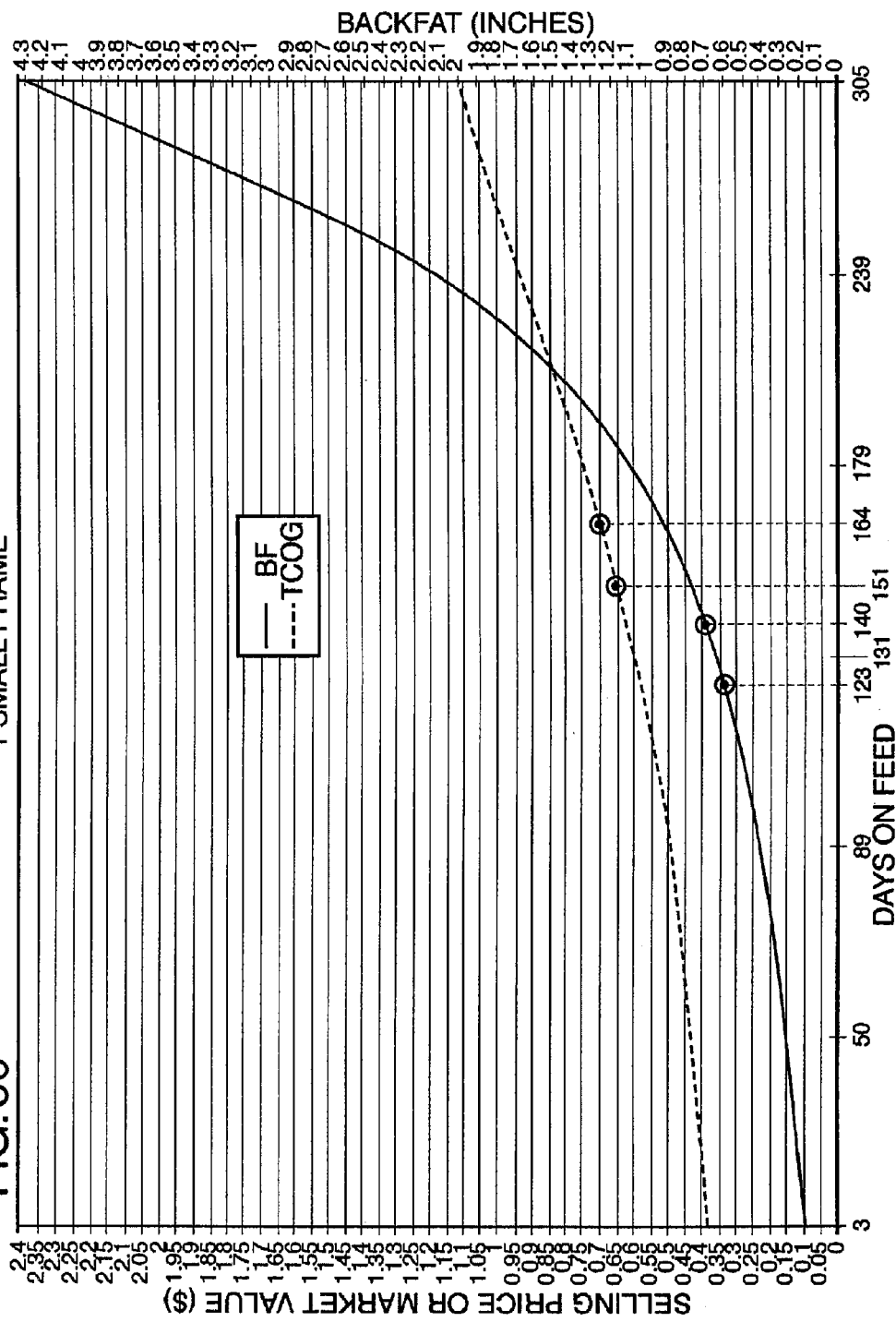
FIG. 30 is a graph plotting selling price against animal backfat along two different curves during the time that an animal is on feed in a feedlot.

The following example illustrates how a final DTF calculation can be made for determining exactly when an animal should be shipped to slaughter, based on economics (value) and the prior DTF1 and DTF2 calculations of FIGS. 25 and 26. FIG. 30 is a graph that plots selling price (left-hand vertical line) and backfat on the animal (right-hand vertical line) along two different curves, in terms of the number of days the animal is on feed (DOF). From the calculations and plotting it is determined, in the example, that the point P4 on the backfat curve should be selected for shipment of the animal. This is at 140 days into the feeding period, the most economical point for shipping. Beyond that point, the animal's backfat will exceed 0.7 inches, resulting in the animal's carcass being degraded and thus becoming less valuable. The P1 and P2 end points would result in a carcass with too much backfat. The P3 endpoint would be below the backfat limit, so the animal can be fed beyond this point to increase its value.

Example

Individual Animal Final DTF Calculation
1) Input: Sex, Beginning Weight, OFW, Mature Weight, Breed, Hide, Age, Number of Head, Purchase Date, Hip Height, Calculated Frame Score, Initial Back Fat, Flesh Condition Code, Ration Composition/Energy, Environmental Factors.
2) Run Cornell Calculation Method One.fwdarw.Outputs for 6 periods on feed.
Average Weight for Period.
Dry Matter Intake for Period.
ADG for Period
DOF for Period
3) Calculation Gain for Period=ADG. DOF Period.
4) Period Feed Cost of Gain=DMI.times.DOF Period.times.Cost Per Pound+(Yardage cost per day.times.DOF Period.div.Gain for Period)
5) Feed Interest Cost of Gain=Calculated for all except period one
6) Cattle Interest Cost of Gain for Period I=Daily interest rate.times.number of days in period=$.div.the gain (calculated by average weight for period less initial weight)
7) Total nos. 4)+5)+6)=Total incremental Cost of Gain
8) Calculate and project for all 6 periods and plot projection graph
9) Plot OFW (Mature Weight) on TCOG line at P-1 at 151 DOF to reach 1006 pounds (28% Body Fat Target).
10) Plot the location where total incremental COG=Selling Price ($0.70/lb) on TCOG line at P-2 at 164 DOF to reach 1041 pounds.
11) Plot Back Fat Deposition Rate-use Initial Back Fat in the DTF2 Method Two calculation to determine the rate. The rate is used to compound the initial back fat measurement daily for the entire period and is plotted on the graph as BF.
12) Plot the 0.6 BF Target on the Fat deposition rate line at P-3 for 0.6 at 123 DOF to reach 920 pounds.
13) Final DTF Number in this case is P-4, which is the predetermined maximum Back Fat limit which is selected by the computer program. This is calculated to be 140 DOF at 975 pounds. The final DTF number cannot be P-1, P-2 or P-3 because:
a) P-1 exceeds Maximum BF to incur a dollar discount.
b) P-2 exceeds Maximum BF to incur a dollar discount as well as causing incremental cost of gain to exceed selling price resulting in decreased profit.
c) P-3 is the original BF target but, since the animal is still making profit, it should be fed longer.

As soon as the animal exits the processing station 42 to enter the sorting pen area, the computer 78 has calculated the indicated characteristics of the animal, such as projected OFW, projected ADG, projected DTF and a projected feed proration ratio according to the formula and process outlined in FIG. 27. At this point a sort may or may not be done as indicated at step 3A of the management process. If a sort is to be done, it would likely be a rough sort by animal type, weight, or OED. At this point it would usually be too early to cull animals from the feedlot because there is no performance data yet accumulated on any animal.

In the illustration of FIG. 7 the measured and processed animals would go directly to step 4 of the process, which is directly to one of four feed pens 188, feed pen A, feed pen B, feed pen C or feed pen D. There they would be provided a selected feed ration and water for a selected period that may range from 45-75 days but more typically in the 60-75 day range. During this first feeding period each animal's records are maintained and the cost of the feed ration delivered to each pen would be prorated among the individual animals for assessment to their respective owners.

At the end of the first feeding period, two or more of the feed pen cattle groups in the feed pens A-D are selected for remeasurement at the same time. This selection may be based on one or more of several factors such as the similarity of their group average OED or DTF, breed type, marketing target yields or other factors. Each animal in the selected groups is directed back through, for example, the alley 24 from its feed pen through the gates 26, 28 and back through the alley 12 leading to the single-file chute. Once within the alley 12, the animals are led into two different holding sections of the alley as defined by the manually operated alley gates 14, 16, 18 defining holding sections 190, 192. Each of the holding sections 190, 192 is capable of holding approximately 40 head of cattle. From the holding section 192 the cattle are led through a hydraulically operated crowd gate 18 into the crowding section 32 where cattle are directed one-at-a-time through a hydraulically powered one-way gate 20 leading to a single-file entrance section 44 into the one-way chute 22.

Then the animals are admitted one at a time and single file into the chute 22 where they are measured externally and internally, and weighed once again. In the processing section 42 the animals may also be reimplanted with a growth hormone as needed. The measurement data for each animal is automatically entered into the computer 78 via data entry means coupled to the measuring apparatus and there correlated with the EID of the animal.

With the historical data, original measurement data and the remeasurement data for each animal, that animal's performance through the first feeding period can be accurately calculated and gauged, much more so than with the projected performance data from the original measurements alone. Thus, upon remeasurement, each animal's ADG, OFW and DTF (or OED) is recalculated and used as the basis for a prediction of future performance and a shipping date or at least shipping window, using the methods previously outlined with respect to FIGS. 25 and 26, and Table 1. In addition, each animal's feed proration is recalculated using the method and formula outlined in FIGS. 28a and 28b. This gives a much more accurate feed proration for each animal than the initial proration determined according to FIG. 27. This new feed proration will be used to calculate each animal's feed intake for the next feeding period. Of course, for the indicated calculations, both the rate of weight gain (ADG) and the total amount of change (gain) and the fat (fat deposition rate) and external dimensions (frame, muscular growth) are used in calculating the new projected DTF and OEW for each animal.

At the same time, each animal's DTF as calculated is checked against any drug withdrawal and safe-to-ship information available from the health history of the animal, also stored in the computer system according to the system described in the aforementioned U.S. Pat. No. 5,315,505. Any OED or DTF calculated by the computer or otherwise would be adjusted as dictated by the drug withdrawal and safe-to-ship information from the animal health system and prior to any assignment of the animal to any particular sort group. This drug withdrawal and safe-to-ship check might be done either by computer or manually by the operator. Also before any growth promotant drug or implant is administered to the animal in the processing station, a decision would be made on whether to administer at all based on the calculated DTF or OED, drug cost, and efficacy. In short, no growth promotant drug need be given if the animal is predicted to remain in the feedlot for only a short time following a remeasurement.

As each animal leaves the single-file chute, the computer has determined its sort group and allocated a particular sort pen in which to direct it from the chute. Steps 6 and 7 of the diagram of FIG. 7 represent a sorting procedure that may be used following a remeasurement. Essentially, each animal is directed to one of the seven sort pens of FIG. 5 temporarily. Each of the seven sort pens indicated in step 6 will receive animals selected according to seven different sort groups. The sort group to which a particular animal is assigned may be based on any one or more of several parameters but most likely will be based on their OED or DTF, their visual scores, their weights, their physical condition, or a combination thereof.

In the illustration of FIG. 7 there are seven sort groups. These are designated, "sort group 1," "sort group 2," "flex group," "earlies," "lates," "reruns," and "trash." Before the sorting procedure is over in step 6, these seven sort groups will be reduced to four, consisting of "sort group 1," "sort group 2," "earlies," and "lates." Each of those four groups will then be directed, in turn, according to step 8, into one of the four feed pens A, B, C or D according to their sort groups. Feed pens A-D in all likelihood will be the same feed pens as used in step 4.

To explain the sort groups further, "reruns" are cattle for which one or more measurements are missing or a process was omitted after a first pass through the single-file chute. As a result, cattle sorted into sort pen 1 as reruns will be run again through the single-file chute and there sorted into one of the other six groups, as indicated in step 7.

The "earlies" group consists of cattle that are predicted to have earlier OED's or DTF's than the rest of the cattle being sorted. In other words, they are predicted to have shipping dates to the packing plant considerably earlier than the cattle in the other groups. As indicated, cattle in the earlies group will be directed from sort pen 2 in step 6 to feed pen A in step 8. It should be noted that some of the reruns from sort pen 1, after being rerun, may end up in the earlies group of sort pen 2 and be eventually directed into feed pen A.

Sort pen 6, consisting of the "lates" group, include cattle that are predicted to have late shipping dates (DTF's or OED's), as compared to the other groups. As indicated in the diagram of FIG. 7, the lates group will be directed from sort pen 6 to feed pen D. The lates group may eventually include some of the reruns of sort pen 1 after the reruns are passed again through the single-file chute.

The "trash" group is composed of non-performing or poorly performing cattle and are sorted into sort pen 7. These are cattle that have poor ADG's or other physical problems, such as circulatory or respiratory damage, that render them unsuitable for beef production or that are unprofitable to keep in the feedlot. Cattle in the trash group are culled from the rest of the animals, removed from the feedlot and sold as salvage.

The three remaining groups are sort group 1, sort group 2 and the flex group. Whatever the parameters being used to sort, the flex group consists of animals that are close to the dividing line between sort group 1 and sort group 2. For example if sorting is by weight and sort group 1 consists of a range of lighter weight animals and sort group 2 a range of heavier weight animals, the flex group consists of animals that are somewhere in a weight range between the two principal sort groups.

For example, after a first pass through the single-file chute, sort group 1 might include 20 animals and sort group 2 might include 17 animals. The purpose of the flex group is to even out the number of animals in each of sort groups 1 and 2. In the given example, if there are 10 animals in the flex group, they would be resorted by sending them through the single-file chute again and redistributing them into either sort group 1 or sort group 2 according to weight. As a result of this resorting process with respect to the flex group, eventually there are no remaining animals in the flex group, as they have all been redistributed to either sort group 1 or sort group 2. In the given example, where sort group I originally includes 20 animals, sort group 2 17 animals and the flex group 10 animals, eventually sort group 1 may end up with 24 animals, sort group 2 with 23 animals and the flex group with none. When the flex group has been redistributed, the animals in sort groups 1 and 2 are directed respectively to feed pens B and C.

Flex sorting is a method of sorting a group of random animals into sort groups of predetermined size and quantity. The particular measurement that is used for ordering is of minor importance to the flex sorting method, but some examples are current weight, finish date, and finish weight. To achieve this sort, an ordered list of animals is maintained as the data is collected, and a sort group is assigned based on the position within the ordered list. As the sorting starts, insufficient data will exist to make reasonable sort decisions, so animals are placed in a flex group until enough data has been collected to be representative of the whole population. This sample size is expressed as a percent of the total population, and is configurable. Other animals that will also be placed in the flex group are ones that are too close to the split between sort groups to be certain to which group they belong. This area of uncertainty is defined by flex percent value, it is also configurable and is expressed as a percent of the data range (i.e. maximum value-minimum value). At the completion of sorting, the animals in the flex group are processed again, this time since all information is known about the population the correct sort decision can be made.

Example

| Setup parameters: | |
|---|---|
| Total Population | 5 head |
| Sort Distribution | 2 groups |
| First Group | 2 head (40% of total) |
| Second Group | 3 head (60% of total) |
| Sample Size | 30% |
| Flex Percent | 10% |

Sample weight data 625, 600, 675, 610, 640

1. First weight is 625, add to ordered list, compute new median, and the area of uncertainty.
Results

| Ordered List | Median Loc | Median Wt | Uncertainty |
|---|---|---|---|
| 625 | 1$^{st}$ element | 625 | N/A |

Since the number of weights (1) is less than sample size (1.5=*0.3) put this weight in flex group.
Results

| Sort Group 1 | Sort Group 2 | Flex Group |
|---|---|---|
| | | 625 |

2. Next weight is 600, add this weight to the ordered list, compute new median, and the area of uncertainty.
Results

| Ordered List | Median Loc | Median Wt | Uncertainty |
|---|---|---|---|
| 600 | ((2 − 1)*0.4) + 1 | AVG. (1 & 2) | (625 − 600)*0.1 |
| 625 | or between 1 & 2 | or 612.5 | + or −2.5 |

Since the number of weights (2) is greater than the sample size (1.5), check to see if new weight is in the area of uncertainty. The area of uncertainty is 610 to 615, the new weight is not in this area and is less than the median, so it belongs in sort group one.
Results

| Sort Group 1 | Sort Group 2 | Flex Group |
|---|---|---|
| 600 | | 625 |

3. Next weight is 675, add this weight to the ordered list, compute new median, and the area of uncertainty.
Results

| Ordered List | Median Loc | Median Wt | Uncertainty |
|---|---|---|---|
| 600 | ((3 − 1)*0.4) + 1 | AVG. (1 & 2) | (675 − 600)*0.1 |
| 625 | or between 1 & 2 | or 612.5 | + or −7.5 |

Since the number of weights (3) is greater than the sample size (1.5), check to see if new weight is in the area of uncertainty. The area of uncertainty is 605 to 620, the new weight is not in this area and is greater than the median, so it belongs in sort group two.
Results

| Sort Group 1 | Sort Group 2 | Flex Group |
|---|---|---|
| 600 | 675 | 625 |

4. Next weight is 610, add this weight to the ordered list, compute list, compute new median, and the area of uncertainty.
Results

| Ordered List | Median Loc | Median Wt | Uncertainty |
|---|---|---|---|
| 600 | ((4 − 1) * 0.4) + 1 | AVG. (2 & 3) | (675 − 600) * |
| 610 | or between 2 & 3 | or 617.5 | 0.1 + or − 7.5 |
| 625 | | | |
| 675 | | | |

Since the number of weights (4) is greater than the sample size (1.5), check to see if new weight is in the area of uncertainty. The area of uncertainty is 610 to 625, the new weight is in this area and must be placed in the flex group.
Results

| Sort Group 1 | Sort Group 2 | Flex Group |
|---|---|---|
| 600 | 675 | 625 |
| | | 610 |

5. The last weight is 640, add this weight to the ordered list, compute new median, and the area of uncertainty.
Results

| Ordered List | Median Loc | Median Wt | Uncertainty |
|---|---|---|---|
| 600 | ((5 − 1) * 0.4) + 1 | AVG. (2 & 3) | (675 − 600) * |
| 610 | or between 2 & 3 | or 617.5 | 0.1 + or − 7.5 |
| 625 | | | |
| 640 | | | |
| 675 | | | |

Since the number of weights (5) is greater than the sample size (1.5), check to see if new weight is in the area of uncertainty. This area of uncertainty is 610 to 625, the new weight is not in this area and is greater than the median, so it belongs in sort group two.

Results

| Sort Group 1 | Sort Group 2 | Flex Group |
|---|---|---|
| 600 | 675 | 625 |
|  | 640 | 610 |

6. Now it is time to do the flex pen, the first weight of 625 is already in the ordered list so we only need to determine which group it belongs in.
Results

| Ordered List | Median Loc | Median Wt | Uncertainty |
|---|---|---|---|
| 600 | ((5 − 1) * 0.4) + 1 | AVG. (2 & 3) | None |
| 610 | or between 2 & 3 | or 617.5 |  |
| 625 |  |  |  |
| 640 |  |  |  |
| 675 |  |  |  |

Since there is no area of uncertainty and the current weight is greater than the median, it belongs in group two.
Results

| Sort Group 1 | Sort Group 2 | Flex Group |
|---|---|---|
| 600 | 675 | 610 |
|  | 640 |  |
|  | 625 |  |

7. Now the last flex weight of 610 is already in the ordered list so we only need to determine which group it belongs to.
Results

| Ordered List | Median Loc | Median Wt | Uncertainty |
|---|---|---|---|
| 600 | ((5 − 1) * 0.4) + 1 | AVG. (2 & 3) | None |
| 610 | or between 2 & 3 | or 617.5 |  |
| 625 |  |  |  |
| 640 |  |  |  |
| 675 |  |  |  |

Since there is no area of uncertainty and the current weight is less than the median, it belongs in group one.
Results

| Sort Group 1 | Sort Group 2 | Flex Group |
|---|---|---|
| 600 | 675 |  |
| 610 | 640 |  |
|  | 625 |  |

The above example demonstrates a two-way sort, but it can sort any number of ways. For an n-way sort there are (n−1) median locations within the ordered list to keep track of, but only one flex pen is needed to hold the animals that we are uncertain about. Also, in the example given, the sort was done without any errors or animals in the wrong pen. It is possible for the sort to end up with a different head count in the sort group than expected, or for some head to be in the wrong pen based on their sorting measurement. These mistakes occur mostly at the splits between two sort groups, and involve animals with very close measurements. One thing that should be pointed out is that this sorting method, like a lot of other sorting methods, performs better if the data is random. The worst possible scenario is for the data to already be sorted either ascending or descending.

One additional feature of this sorting method is the ability to have a human make subjective sort decisions, such as color, before running through the flex sort, in effect having two flex sort sessions running concurrently.

With the animals in feed pens A, B, C and D for the second portion of the feeding period as indicated in step 8, they may remain in their respective pens until they are ready for shipment. During this second feeding period of typically 60-80 days, selected animals or selected groups of animals may again be remeasured and resorted through the single-file chute and sorting pens if desired or economically feasible. For example the timeline of FIG. 3 indicates two remeasurements and resorts during the feeding period. However FIG. 7 illustrates a single remeasuring and single uniformity sort more like the procedure outlined in FIG. 4A. All of the animals in feed pens A, D have new and more accurate pro rata feed intake ratios assigned to them using the method outlined in FIG. 28a and FIG. 28b, including data such as ADG, gain, external and internal measurements and other factors. Individual animal records are maintained for each animal during its remaining period of time in the feedlot. Additional weight checks or other measurements may be used to monitor actual performance during this second portion of the feeding period to confirm or modify the OED or DTF of each animal.

Also, as indicated in FIG. 4C, after a certain period within feed pens A-D, one or more of the groups may be sent to pen sorters such as pen sorter 94 in FIG. 2 for finish feeding for the time that these groups will be within their marketing window. This approach allows for "fine-tuning" of the optimum date of shipment for each individual animal based on market conditions and the individual animal's performance in its final days at the feedlot. This selection process, whether accomplished visually, by weight checks or by final feeding in a pen sorter, involves the selection process as indicated in step 8A for shipment of the animal to the packing plant. In the case of a pen sorter, this would involve sorting the animal selected for shipment from the feeding pen portion of the sorter to the shipping pen portion, as previously described.

Animals may be selected for shipment based on a selected marketing group of animals having the same average OED's or DTF's or on an individual animal basis, depending on how finely tuned the selection process desired. The selection process may be performed visually, by computer or by repeated weight checks as previously described.

Step 9 of the management system involves shipping the selected animals to the packing plant 156. At the packing plant, the animals are slaughtered for production of beef products for consumption. At the packing plant, the EID tag on each live animal is read and transferred by computer to match the identification on the resulting carcass so that the carcass data can be matched to the live animal performance and history data.

At the packing plant, the EID tags are removed from the animals and shipped in a container to a reconditioning operation where they are cleaned, tested and sorted for delivery back to the proper feedlot. The carcass data and the disbursements of funds breakdown for the original owners of the animals in a marketing group are transmitted to the appropriate feedlot. This data may also be transmitted to the original cattle producers for use in improving the genetics of the animals for future beef production.

The feed proration flow charts of FIGS. 27, 28a and 28b have been discussed. Following each table is an example calculation using the formulas and flow diagrams set forth in the figures. These examples set forth the data output from the computer when provided with software for carrying out the calculations set forth in FIGS. 27, 28a and 28b. The examples are for four animals identified as animals nos. 85, 10, 68 and 36. From the examples it will be seen that animal No. 85 had a starting weight of 829 pounds and a calculated optimum finish weight of 1136 pounds. During the initial feeding period P1 the ratio of feed allocated to it was 0.255646, so that out of a total of 780 pounds of feed fed during the first feeding period, 199.4038866 pounds of feed was prorated to it for allocating feed charges. During the next current period CP, the same ratio was used to prorate a total of 3,000 pounds of feed among the four animals, with 767 pounds being allocated to animal No. 85. However from the subsequent calculation, the DMI ratio for animal 85, based on remeasurements and original measurements, changed to 0.253206. As a result, animal 85 in the next feeding period ended up with 1,519 pounds of feed prorated to it out of a total of 6,000 pounds. It will also be noted from the calculations and data output from the computer that animal No. 85, when remeasured, had a weight of 1,028 pounds, up from an 829 pound initial weight. It also ended up with an actual weight of 1,128 pounds at final measurement compared to an original calculated optimum finish weight of 1,136 pounds.

When the four animals finally left the feedlot, their DMI numbers overall were recalculated to adjust their overall DMI ratios, resulting in a reallocation of the total feed fed to each animal. Animal No. 85 had 2,440 pounds of feed allocated to it out of a total of 9,660 pounds, based on its recalculated overall feed ratio of 0.25262. The final data output from the feed proration calculations is a ratio of feed to weight gain for each animal. Animal No. 85 ended up with a feed to weight gain ratio of 8.17, second highest in the group of four animals considered.

Figure 8:
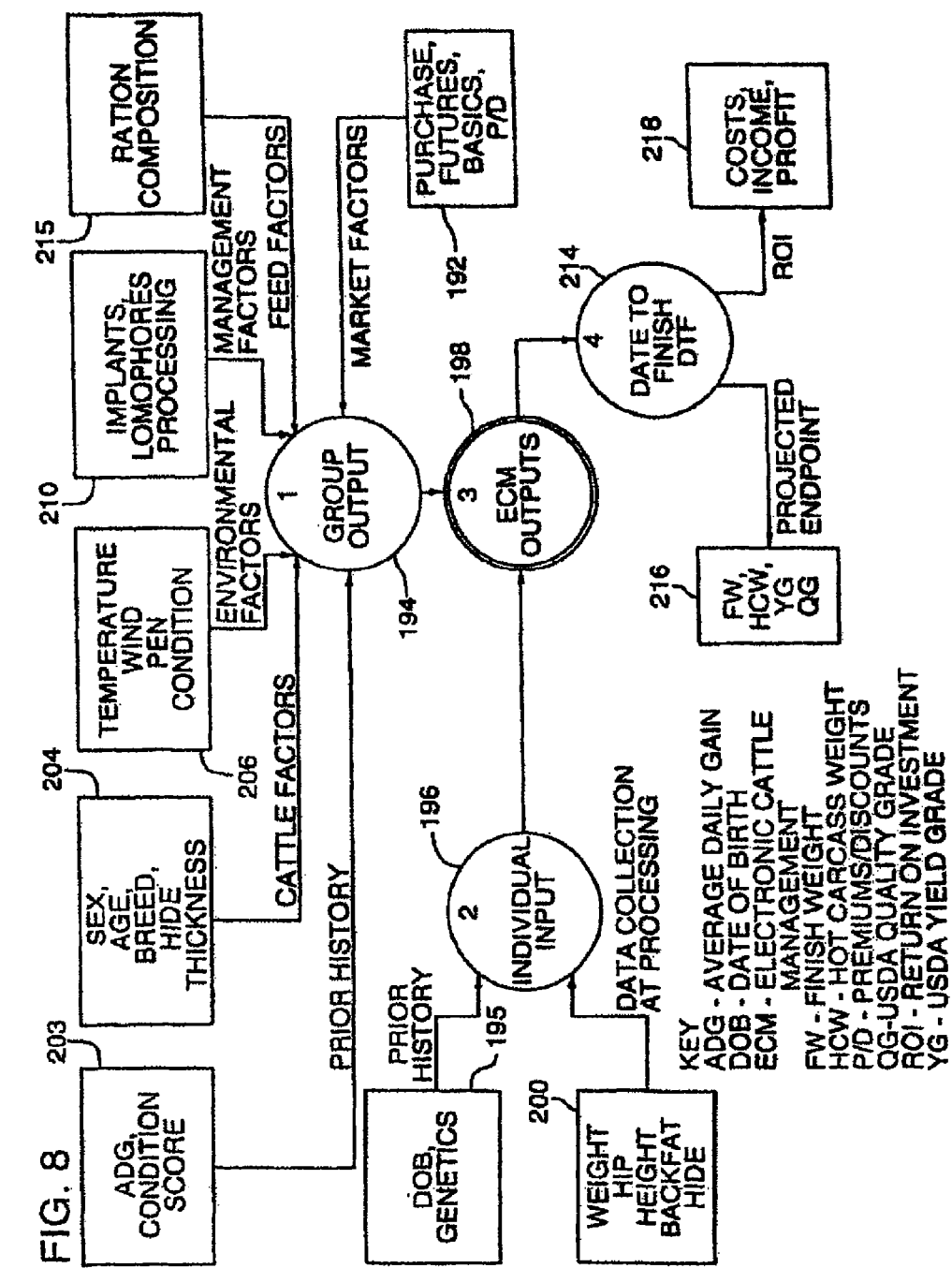
FIG. 8 is a data flow block diagram illustrating the data flow in a computerized control system.

FIG. 8 is a general block diagram of the data inputs and data outputs to the host computer system 78. There are two categories of inputs, including the group input category 194 and the individual animal input represented by interface 196. The individual prior history of each animal is entered upon each animal's arrival at the feedlot, as indicated by the prior history input 198. Such prior history would include each animal's date of birth and its genetic background. Also entered at initial processing and on subsequent remeasurements would be each animal's weight, hip height, backfat and hide condition as indicated at input 200. These measurements are obtained at the single-file chute in the manner previously described. These individual inputs in turn are transmitted by cable or radio frequency means to the host computer 78 for storage and use in calculating the previously discussed formulas. Group information when transmitted to the computer would include prior history data such as average daily gain while in the pasture and the group condition score, visually estimated at the time of arrival at the feedlot. Other information would include the sex, age, breed and hide thickness breakdown for the animals in the group. These "cattle factors" are also input into the computer through data entry means indicated at 204 and the group input interfaces 194.

Environmental factors such as air temperature, wind, and pen conditions where the animals came from are also collected and entered through data entry means 206 into the group input interface 194.

Management factors for each group including implants, ionophores and processing information, are collected and input through data entry means 208 into the computer through the group input interfaces 194. Finally, feed factors, such as ration composition, are input through data entry means 210 and the group input interfaces 194 into the host computer 78.

Market factors are also part of the data used to calculate the desired computer outputs, such factors including purchase price, cattle futures, basis and premium/discounts for the animals in the group. These market factors are entered through data entry means 12 and the group input interface 194 into the host computer 78.

With the data collected as described, and the appropriate software, the computer system is able to calculate, using formulas such as the ones disclosed in FIGS. 25, 26, 27, 28a, 28b, and Table 1, such outputs as a projected date to finish (DTF), optimum end weight (OEW), and projected end points such as finish weight, hot carcass weight, yield grade, and USDA quality grade. The computer system also calculates a return on investment including cost, incomes and profit as indicated at 218.

Examples of the type of data collected, calculated, stored and available in reports generated by the computer system are shown in Tables 3A. 3G.

Table 3A, the cattle received report by load, has already been discussed. It discloses the information available from the producer and entered into the computer through appropriate data entry means upon the arrival of a load of cattle at the feedlot. This is a "group" report and is the sort of information entered into the computer as indicated at data entry means 202, 204 and 206 of FIG. 8.

Table 3B is a pen assignment summary report, which is another group type report and gives the sorting pen assignments 1-7 for lot No. 495 of cattle that is to be fed in pens 59, 57 and 58. The number of head of cattle in each pen 10, 11 and 11 for sorting pens 1, 2 and 4 and feed pens 59, 57 and 58 is given. This information is available from the computer after at least one measurement and sort of a lot of animals.

Still referring to Table 3B, the remaining data in the pen assignment summary report should be self-explanatory, giving information concerning the projected finish weight, the current weight, the frame size and current backfat measurements, on average, for the animals in feed pens 59, 57 and 58. In addition to the averages for each of the indicated measurements, the pen assignment summary report also gives maximum and minimum ranges for the animals in each sort group.

Table 3C is a sample of a pen assignment detail report generated by the computer system. This report indicates the lot number, the feed pen number, the sort pen number, and the EID tag number of each of the 11 animals in feed pen 57. The report also indicates that the animals in this feed pen have a shipping window ranging from May 14, 1994 to Sep. 28, 1994, indicating that the animals in this group are expected to reach their optimum condition, such as optimum finish weight, sometime within this window. The pen assignment detail report also gives individual animal measurements and calculations including video image dimensions (VID), and projected days to finish (DTF) which is the number of days the animal is projected to require to reach its optimum finish weight. Also indicated is the projected optimum finish weight (OFW), the animal's current weight (CWT), and each animal's average daily gain (ADG). Finally, the pen assignment detail report gives each animal's frame measurement score (FM) and backfat measurement (BF).

Because of the amount of information available for each animal in each feed pen in the feedlot, and at any time during the animal's stay in the feedlot, it will be readily appreciated how animals can be selected, on an individual basis if desired, for shipment to the packing plant when each animal is in optimum condition for shipment. Simply by taking repeated measurements of each animal as it nears its projected shipping date or optimum finish weight, animals can be selected for shipment and slaughter based on their individual performances and market factors rather than the performances of any particular group, if desired.

Table 3D and Table 3E are marketing yard sheets that the computer system can generate for each animal in the feedlot. The marketing yard sheet of Table 3D is for the same group of animals as the marketing yard sheet of Table 3E. However the yard sheet of Table 3D gives individual animal data for lot No. 495 of animals on the measurement date of Mar. 30, 1994, while Table 3E gives the data for the same animals in lot No. 495 approximately three weeks later, on Apr. 22, 1994.

As will be seen by the columns in the marketing yard sheets, each animal is identified by tag number, pen number and lot number. Additional data available in the other columns of both marketing yard sheets include various projections that have been calculated for each animal, a comparison of purchase weight and current weight for each animal, days on feed (DOF) information for each animal, the ration information that applies to each animal, average daily gain (ADG) information for each animal and feed intake information for each animal. Finally, the projected and actual cost information based on various treatments, processing and other factors for each animal is listed.

Table 3F is a sample of a pen closeout report generated by the computer system as a result of the various inputs, including measurement inputs for each animal and each group of animals. This gives the income and expense information for a pen of animals, broken down to an average cost per head, including feed charges, cattle insurance, yardage fees and processing fees. Other pen information included in the pen closeout report includes such information as total pounds gained by all animals in the pen, broken down to an average gain per head. Also included are average daily gain for each animal, daily feed costs per head, daily total costs per head, total pounds of feed fed for the pen and total pounds per head. Also included is average daily consumption data. Other information includes the cost of the feed fed.

In the summary at the bottom of the pen closeout report, the profit or loss from the pen is given. In the sample, there was no profit for the indicated pen, which included 10 heifers. Based on the summary, the 10 heifers in the pen had an average incoming weight of 678 pounds and an average outgoing weight of 787 pounds. Each gained an average of 3.21 pounds per day for a total of 34 days on feed. The cost of the gain was $56.21.

The final sample report is shown in Table 3G which is a Closeout Summary By Lot report. In this case the lot number is 42894, which was included in pen 553, containing a total of 27 head. The total profit for the lot was $4,957.98. Each animal in the report is identified by its visual identification tag number (VID) and the profit from each animal is calculated. In addition, each animal's performance during its stay in the feedlot is calculated. Each animal is listed under its sire and dam. This sort of information is valuable to the cattle producer in determining which sires and dams produce the most profitable offspring. This information is then used in making future breeding decisions.

Figure 6:
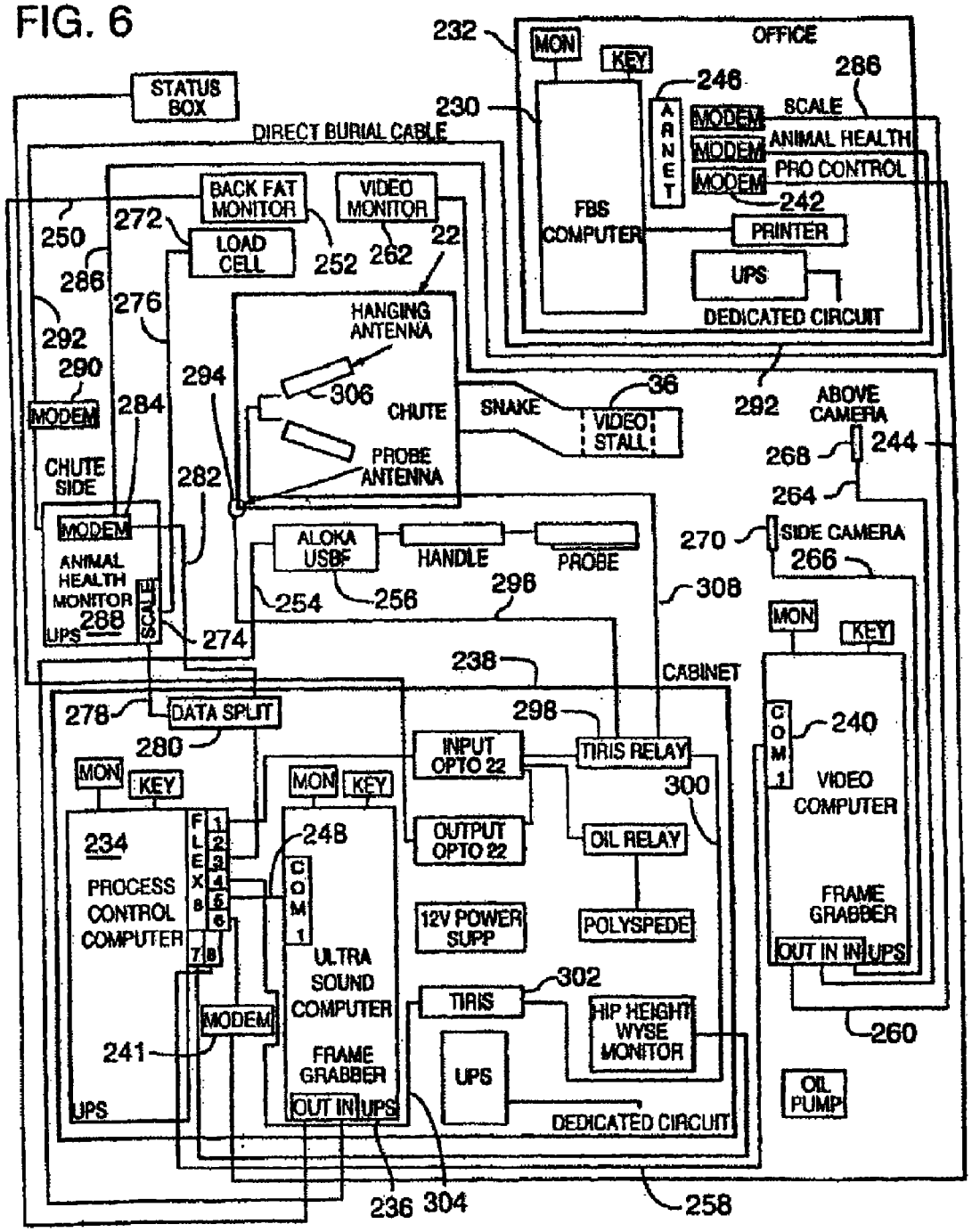
FIG. 6 is a block diagram of the computerized control system.

A layout of the computer system is shown in FIG. 6. Several different computers are used in the system. First there is a feedlot business systems (FBS) computer 230 located at the feedlot office 232. This computer stores the databases used in the system and performs most of the calculations needed in operating the system.

Remote from the FBS computer and closer to the chute area 22 are a separate process control computer 234 and an ultrasound computer 236 within a common control cabinet 238. Separate from the control cabinet and the other computers is a video computer 240.

Basically, the process control computer 234 controls the operation of all subsystems including the stall and sorting gates, weigh scale, ultrasound computer and the video computer. The process control computer communicates with the FBS computer through the modems 241, 242, line 244 and FBS interface 246. The ultrasound computer 236 communicates with the process control computer 234 through a line 248. The ultrasound computer 240 also has an output line 250 to a backfat monitor 252 and an input line 254 from the ultrasound scanner 256 at the single-file chute stall 40.

The video computer 240 communicates with the process control computer 234 through a commline 258. It also has an output line 260 to a video monitor 262, and input lines 264, 266 to video cameras, including an overhead camera 268 and a side-view camera 270.

Each animal is weighed by a scale loadcell 272 at the weigh stall 38. The loadcell communicates with the scale 274 through a line 276. The scale in turn communicates with the process control computer through a line 278 and data split 280. Data from the data split also can be communicated via line 282 and a modem 284 and line 286 directly to the FBS computer 230 through the FBS interface 246.

Data concerning drugs, other animal health treatments and other information about an individual animal at the processing station or stall 42 can be entered into an animal health computer or monitor 288 at the processing station and from there communicated directly through the modem 290 and line 292 and interface 246 to the FBS computer.

As previously noted, each animal has an EID tag applied to it in the single-file chute to give each animal a unique electronic identification. This identification is transmitted from the EID tag by a probe antenna 294 at the EID/USBF stall 40 through a line 296 from the chute to a tiris relay 298 and from the relay through a line 300 to a tins EID reader 302. The tiris reader 302 transmits the animal's EID identification through a line 304 to the process control computer 234. Alternatively, each animal's EID tag signal can be received by a hanging antenna 306 at the single-file chute and transmitted via line 308 to the tiris relay 298 and thence through line 300 to the tiris reader 302 and through the line 304 to the process control computer 234.

The FBS computer not only collects data and uses it to calculate projections, costs and other information used in the management method and system, it also collects data from other sources not shown. For example, the FBS computer performs the regular feedlot accounting functions and generates financial reports. It may also receive and store data from a computerized animal drug inventory control and animal health history and drug treatment system as disclosed in the previously mentioned U.S. Pat. No. 5,315,505. The FBS computer may also collect and store data from a computerized feed additive delivery system such as disclosed in U.S. Pat. No. 4,733,971 and the related patents previously mentioned. The FBS computer may also receive and store data concerning the amount of feed ration delivered to each of the feed pens in a feedlot, including such data collected from a computerized bunk reader system such as disclosed in U.S. Pat. No. 5,008,821. All such information, including the drug usage information, feed ration usage information, and feed additive usage information can be used together with the data concerning each animal collected from the system and other data that may be collected and stored in the FBS computer database to prorate feed ration and feed additive costs to individual animals and thereby calculate the cost of production value and other pertinent information about each animal in the feedlot according to various formulas, a few of which are disclosed as examples and discussed.

Tables 4A, 4E are sample pages of prompts that are generated by the computer programs that are used in the computer system 78 that operates the described system. The described management system is known as the electronic cattle management system (ECM) which is the computer symbol used to initiate the program. The ECM program includes four session types, one of which is entered to begin the system's operation. In Table 4B it will be seen that certain animal measurements can be keyed in, automatically entered or not recorded.

Item 7 in Table 4B gives the prompts for entering the type of sorting that is desired such as, for example, a flex sort as previously described.

At the top of Table 4C, the prompts for entering the number of animals to be sorted into the various sort pens are indicated.

Table 4D lists the various prompts for processing each animal at the single-file chute. By entering the proper prompt, the computer can be instructed to process the identified animal in a particular way such as by weight, by reading its EID, by ultrasound measurement and/or by taking external video measurements.

Additional prompts for setting the parameters for measuring and sorting are given in Table 4E and 4F.

The electronic cattle management system can use a number of different computer programs to run the system as described, the operation and sequencing of which are all controlled by the previously described process control computer 234 shown in FIG. 6. These programs will now be described with reference to their respective flow charts.

Figure 9A:
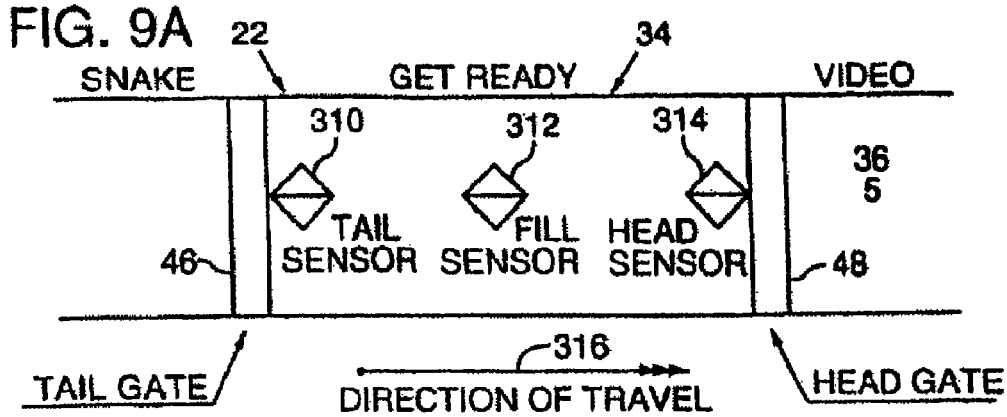
FIG. 9A is an enlarged schematic diagram of the get ready stall of the single-file chute shown in FIGS. 1 and 5, including the locations of sensors used in such stall.

First, control of the operation of the entrance and exit gates at the various stalls or stations in the single file chute will be described. First with reference to FIG. 9A, the get-ready station 34 in the single-file chute includes the entrance or tail gate 46 and the exit or head gate 48 defining the stall. Within the stall are three sensors including a tail sensor 342, a fill sensor 344 and a head sensor 346. These sensors, which may be photoelectric sensors or some other automatic sensors, detect the presence of an animal within the stall space, and when all three sensors detect the presence of an animal, the animal will be contained within the space, whereupon the tail gate 46 can be closed after being opened initially to allow entrance of the animal into the stall space. FIG. 9A also indicates the direction of travel of the animal through the single-file chute and the stall space as indicated by the arrow 316.

Figure 9B:
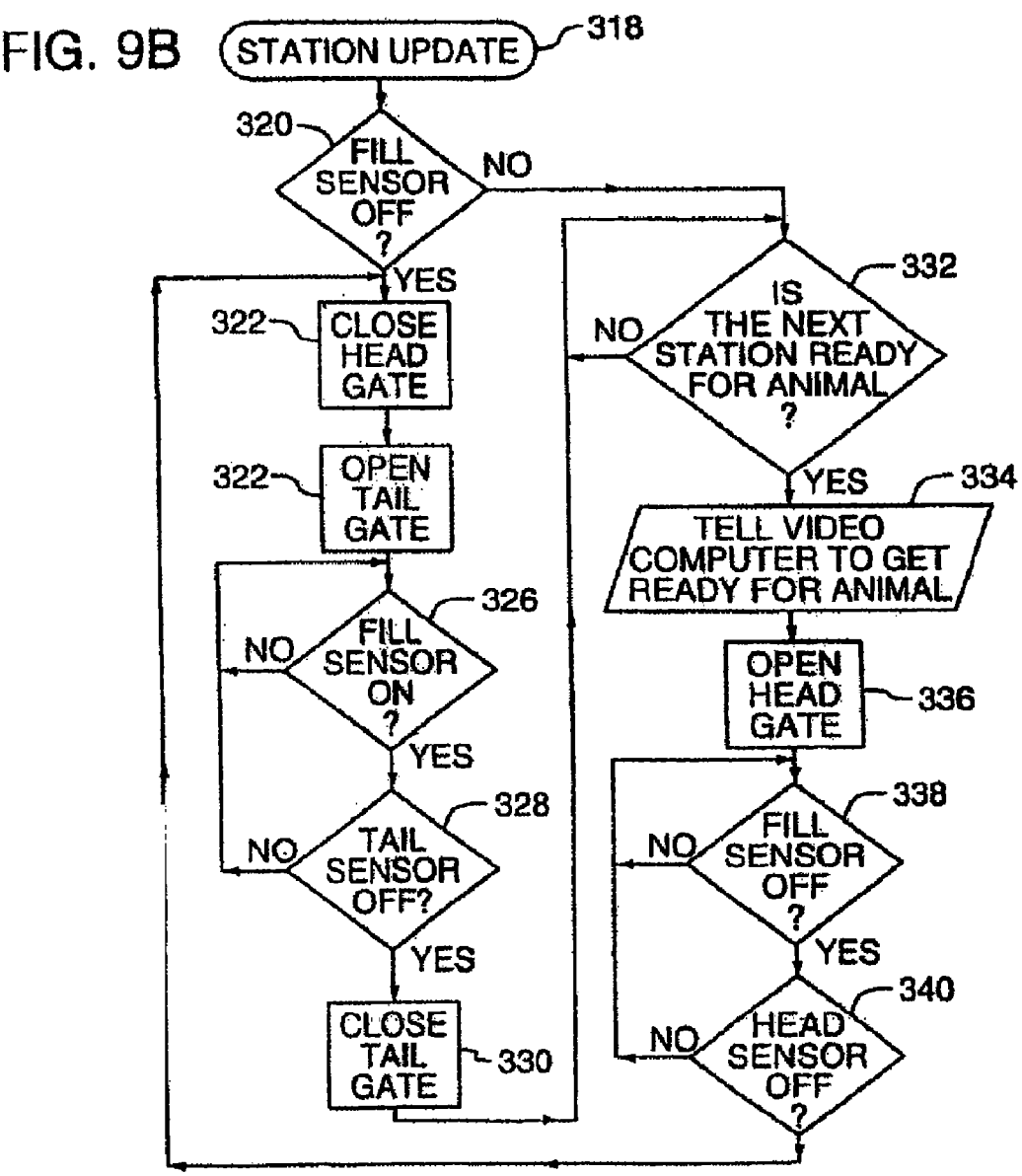
FIG. 9B is a flow diagram of the computer program used to operate the entrance (tail) gate and exit (head) gate in conjunction with the sensors of FIG. 11A for the get ready station.

Referring now to FIG. 9B, the computer program for controlling the operation of the tail and head gates 46, 48 is disclosed. This computer program resides in the process control computer 234 of FIG. 6. Although not shown, obviously the sensors associated with the get ready stall and all other stations in the single-file chute and the sort pens, to be described, are in communication with the process control computer.

First the program is conditioned by another program to be described to get ready to receive the next animal that will proceed through the single file chute, as indicated at step 318. At this point, if the fill sensor is off as indicated at 320, the program assumes that the get ready stall is empty and so commands that the head gate be closed as indicated at step 322. Then the program commands opening of the tail gate 324 to allow the next animal to enter the get ready stall. After the tail gate opens, the program waits until the fill sensor at 326 detects the presence of an animal in the stall. The program then proceeds to the next step to detect when the tail sensor is turned off, at step 328. When this occurs, the program commands closing of the tail gate at step 330. If at step 326 the fill sensor does not detect the presence of an animal, the tail gate will not close. Also, as indicated at 328, if the tail sensor remains on, the tail gate will not close. Only when the fill sensor is on and the tail sensor is off can the tail gate close.

After the tail gate closes, the program inquires at step 322 whether the next station, namely the video station 86, is ready for the next animal. At this point nothing happens until the processing computer receives an indication that the video station is ready for the next animal. When this occurs, the program, as step 334, signals the video computer 240 to get ready for the next animal. At this point the head gate 48 is opened as indicated at 336. The program then inquires at step 338 as to whether the fill sensor 312 in the get ready stall is off and at step 340 whether the head sensor is off. When both the fill sensor 312 and the head sensor 314 are off, indicating that an animal has left the get ready stall and entered the video stall, the program commands the head gate 48 to reclose as indicated at step 322, and then commands the tail gate at step 324 to reopen to ready the stall for the next animal.

Figure 10A:
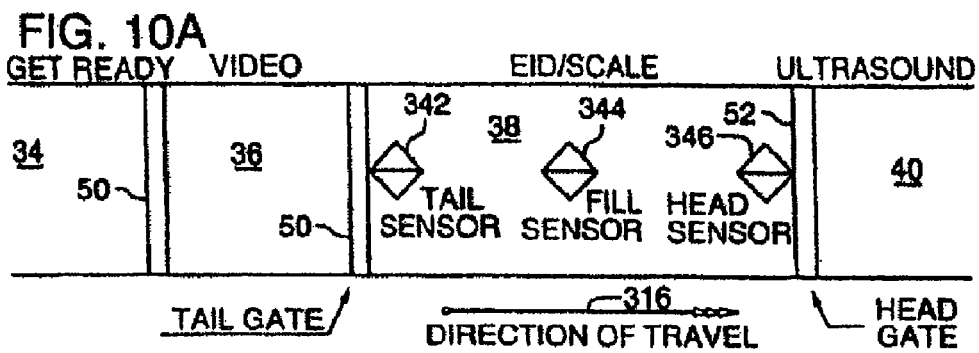
FIG. 10A is an enlarged schematic diagram of the video and EID/scale stations of the single-file chute shown in FIGS. 1 and 5, showing the locations of sensors used in operating the tail and head gates for the EID/scale station.

Referring to FIG. 10A, after the animal leaves the get ready stall 34 it walks through the video stall 36 where it is scanned for external dimensions, and proceeds, without stopping, through the open tail gate 50 directly into the EID/scale stall 38 where the animal is weighed and an EID tag is applied to the animal if necessary and read to identify it. Because of the continuous movement of the animal through the video stall, there are no tail, fill or head sensors in that stall. However the subsequent EID/scale stall requires the animal to stop while it is weighed. Thus, both the tail gate 50 and the head gate 52 must be closed while the animal is contained within the EID/scale stall, identified and weighed. Thus such stall includes a tail sensor 342, a fill sensor 344 and a head sensor 346, all of which communicate with the process control computer. Again, the direction of travel of the animal is indicated by the arrow 316.

Figure 10B:
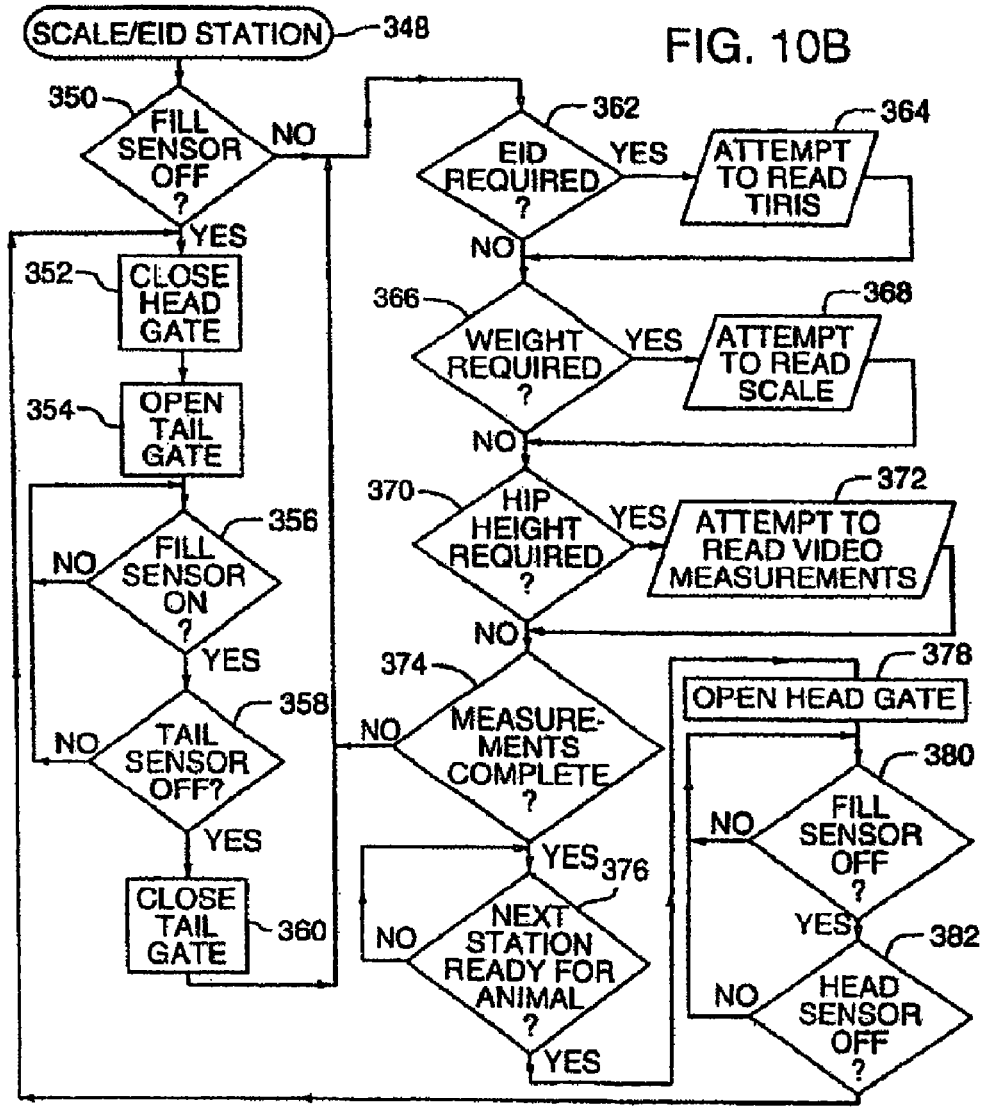
FIG. 10B is a flow diagram of the computer program used to control the operations of the tail and head gates for the EID/scale station of FIG. 10A in conjunction with the sensors of such station.
Figure 11A:
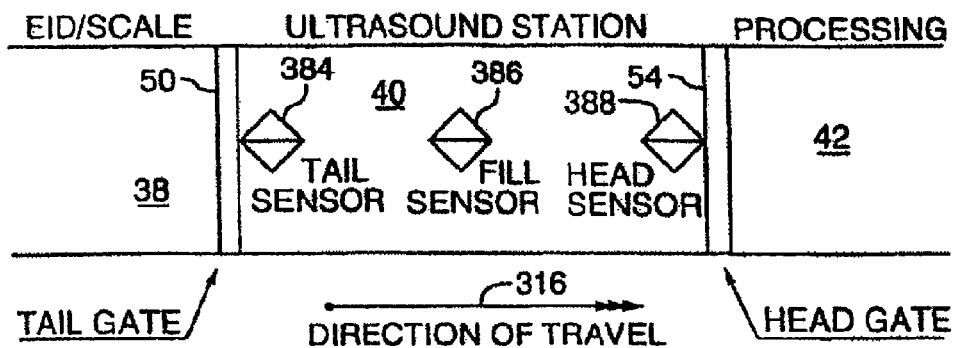
FIG. 11A is an enlarged schematic diagram of the ultrasound station portion of the single-file chute shown in FIGS. 1 and 5 showing the locations of sensors used in operating the control gates for such station.

Referring to FIG. 10B, the computer program for operating the tail gate 50 and head gate 52 at the EID/scale station is disclosed. As an animal proceeds through the video stall 36, tail gate 50 will be open if the EID/scale station is ready for the next animal, which will be determined by whether or not the head gate of such station is closed and its fill sensor and head sensors 344, 346 are off. At this point, the EID/scale station computer program 348 is initialized and ready to start its sequence of operation. First, at step 350, the program inquires whether the fill sensor 344 is off. If so, it commands the head gate 52 to close at step 352. Thereafter, at step 354 the tail gate 50 is commanded to open, allowing the next animal to enter the EID/scale stall. Next the program, at step 356, inquires whether the fill sensor is on. If so, it inquires at step 358 whether the tail sensor is off. If so, at step 360, the program commands the tail gate 50 to reclose, whereupon the animal is ready to be weighed and have its EID tag attached if necessary, and read.

With the animal in the EID/scale stall, the program inquires at step 362 whether an EID identification of the animal is required. If so, the process control computer 234 is commanded to attempt to read the tiris EID reader 302 at step 364. If no EID is required, the program next inquires whether a weight is required at step 366. If so, the process control computer at step 368 is commanded to read the animal's weight from the scale 274. After this, or if no weight is required, the program will inquire at step 370 whether a hip-height measurement of the animal is required. If so, the process control computer is commanded at step 372 to read and record the video measurements communicated from the video computer 240. After the measurements are recorded, if required, the program inquires at step 374 whether measurements are complete. If not, the program will return to step 362 and again proceed through the program to attempt to read the video measurements. Once the measurements have been recorded, the program proceeds at step 376 to inquire whether the next station, namely the ultrasound station 40, is ready for the next animal. Unless the next station is ready for the animal, the head gate 52 will not open. When the next station signals that it is ready, through the process control computer, the head gate 52 is commanded to open at step 378. Next, the program inquires whether the fill sensor 344 is off, at step 380. If not, the program will not proceed to the next step and reclose the head gate. When the fill sensor is off, the program inquires whether the head sensor is off. If the head sensor is off, indicating that the animal has left the EID/scale stall, the program commands the process control computer to reclose the head gate 52. At this point the weighed and identified animal will have entered the ultrasound stall 40, and the program returns to step 352 to command reclosing the head gate in preparation for the next animal.

Referring to FIG. 9A, the ultrasound station 40 is disclosed as having a tail sensor 384, a fill sensor 386 and a head sensor 388. It also includes the tail gate 52, which is the same gate 52 that serves as the head gate for the preceding EID/scale stall 38. It also includes the head gate 54 which serves as the tail gate for the next processing stall 42. Again, the direction of travel of the animal through the ultrasound station and through the single-file chute is indicated by the arrow 316.

Figure 11B:
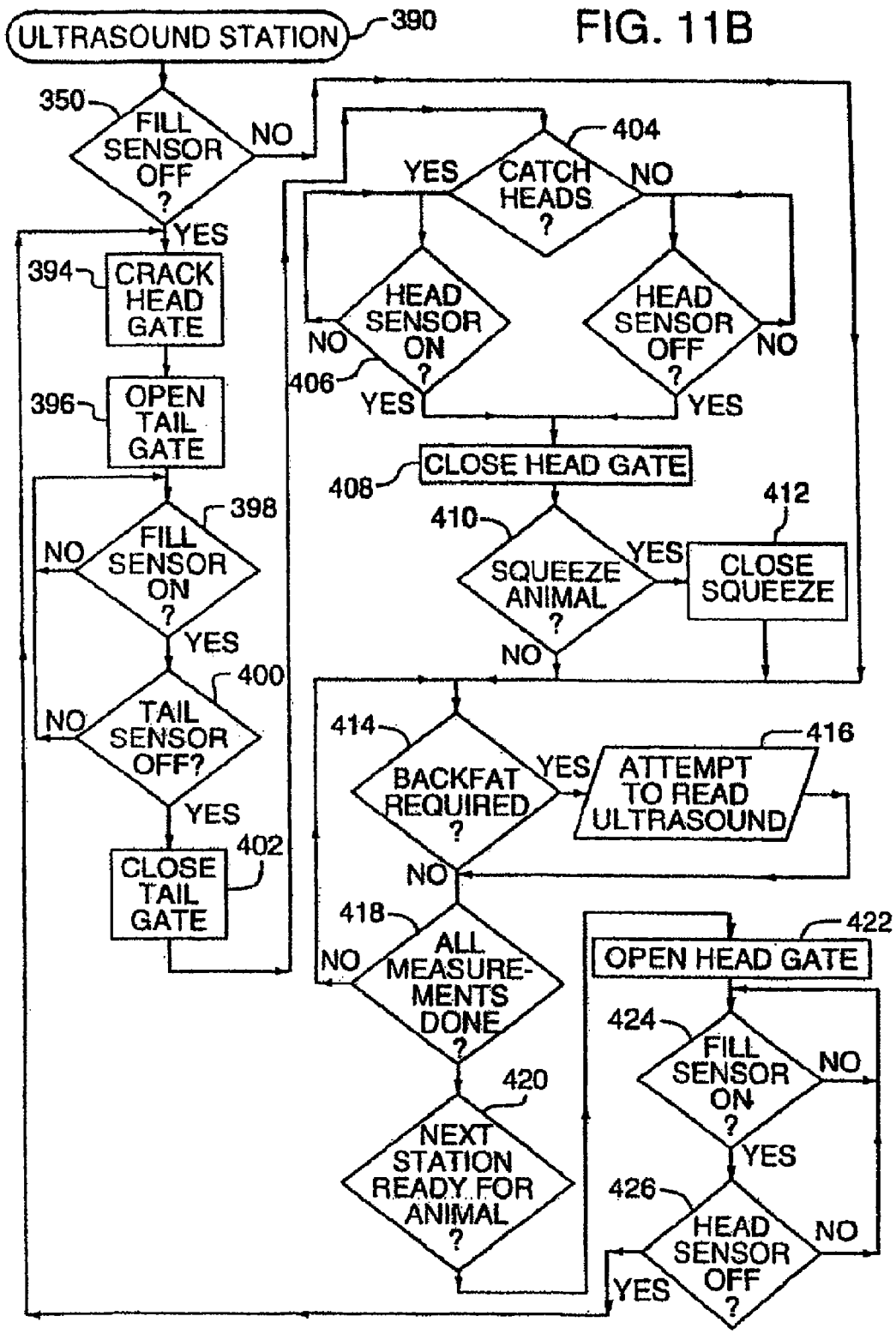
FIG. 11B is a flow diagram of a computer program used to control the operation of the tail gate and head gate of the ultrasound station of FIG. 11A in conjunction with the sensors for such station.

Referring now to FIG. 11B, the computer program for controlling the operation of the gates and thus the animal within the ultrasound station is indicated at 390. Once initiated, it first inquires at step 392 whether the fill sensor 386 is off. If not, because the preceding animal has not yet left the station, the program will return to determine whether the animal has not yet completed its ultrasound scan. However, assuming that the preceding animal has left the ultrasound station and the head gate 54 is closed, the program commands at step 394 that the head gate be cracked open. Then at step 396 the program commands the processing computer to open the tail gate. When the tail gate is opened, the program inquires whether the fill sensor is on, at step 398. If so, indicating that the next animal has entered the ultrasound station, the program inquires whether the tail sensor is off, at step 400. When the tail sensor goes off, the computer program instructs the computer to close the tail gate, at step 402, whereupon the next animal is fully within the ultrasound station and ready to be prepared for measurement. Once the tail gate is closed, the program inquires at step 404 whether the head catcher is to be employed to stabilize the animal in the station. If it is, the program inquires whether the head sensor is on at step 406. If it is, the program, at step 408, commands closing of the head gate.

Once the head gate is closed, the program at step 410 inquires whether the animal is to be "squeezed" within the station. This has reference to the device at the station commonly referred to as a "squeeze gate," which in effect squeezes the animal from behind into tight confinement within the stall so that it cannot move to any appreciable extent. If the answer is yes, the squeeze gate at 412 is commanded to close at step 412. If the answer is no, the squeeze gate is not actuated. In either case, the next programming sequence is an inquiry as to whether the animal's backfat is to be measured, at step 414. If the answer is yes, the program will attempt to take a reading from the ultrasound computer at step 416 to record the backfat measurement. If the answer is no, the program inquires whether all measurements are completed at step 418. This is also the next step after a backfat ultrasound reading is attempted at step 416. If the answer is no, the program will again attempt to take a backfat measurement. If the answer is yes, the program inquires whether the next station in the chute is ready for the animal, at step 420. If not, nothing further happens until the next station is ready for the animal. When that occurs, the head gate 54 is commanded to open at step 422. When the head gate is open, the program inquires at step 426 whether the fill sensor is off. If not, nothing further happens until the fill sensor is off. When that occurs, the program inquires at step 426 whether the head sensor is off. If not, nothing further happens until the head sensor is off. When that occurs, the program returns to step 394 to cause the head gate to crack, ready for the next animal.

Figure 12A:
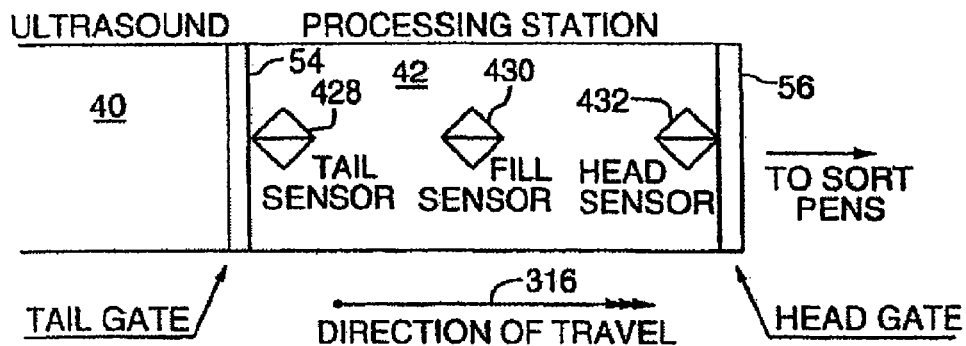
FIG. 12A is an enlarged schematic diagram of the processing station of the single-file chute of FIGS. 1 and 5 showing the location of sensors for operating the control gates of such station.

Referring to FIG. 12A, the animal proceeds from the ultrasound station 40 into the processing station 42 through the head gate 54 of the ultrasound station, which becomes the tail gate 54 of the processing station. Within the processing station are three sensors, a tail sensor 428, a fill sensor 430 and a head sensor 432.

Figure 12B:
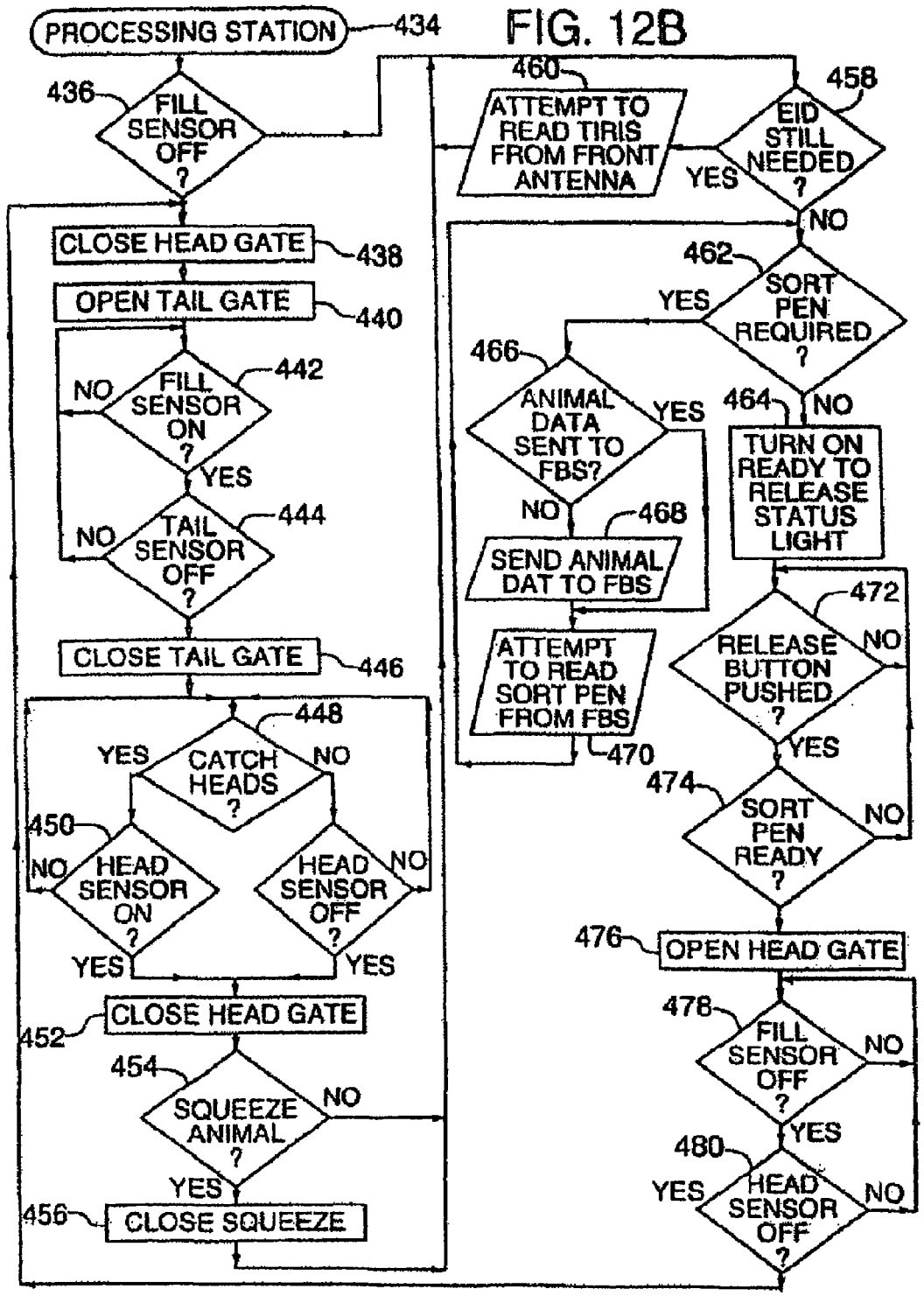
FIG. 12B is a flow diagram of a computer program used to control the operation of the tail gate and head gate for the processing station of FIG. 12A in conjunction with the sensors at such station.

Referring to FIG. 12B, the computer program for the processing station, indicated at 434, first inquires whether the fill sensor 430 is off, at step 436. If not, the head gate 56 will not close until the fill sensor does indicate that the preceding animal has left the processing station. When the fill sensor is off, head gate 56 is commanded to close at step 438 and the tail gate 54 is commanded to open at step 440 to admit the next animal into the processing station.

Next, the program inquires whether the fill sensor is on at step 442. If not, nothing further happens until the fill sensor is on. When that occurs, the program inquires whether the tail sensor 428 is off, at step 444. If the tail sensor is not off, the tail gate 54 will not close. When the tail sensor is off, indicating that the animal is completely within the processing station, the tail gate 54 is commanded to close at step 446. When the tail gate is closed the program, at step 448, inquires whether there is to be a head catch. If the answer is yes, the program inquires at step 450 whether the head sensor 432 is on. If not, nothing further happens until the head sensor is on. If the answer is yes, the head gate 56 is closed at 452 to catch the animal's head.

Next, the program inquires whether the animal is to be squeezed by the squeeze gate within the processing station, at step 454. If not, the program proceeds to the next processing sequence. If the answer is yes, the squeeze gate at the processing station is commanded to close at step 456 to confine the animal within the station. After the squeeze gate is closed, the program proceeds to the next processing sequence.

The next inquiry, at step 458, is whether the animal needs to be identified by its EID. If the answer is yes, the program instructs the process control computer at step 460 to attempt to read an identification from the tiris. Nothing further happens until the animal is identified. When the animal has been identified or if no identification is needed, the program inquires whether a sort pen for the animal is required, at step 462. If not, a status light on a control panel (not shown) at the processing station is commanded to indicate, at step 464, that the animal is ready to be released from the single-file chute.

If a sort pen is required, the program at step 466 inquires whether the animal data has been sent to the FBS computer. If the answer is no, the data is sent to the FBS computer, at step 468. If the animal data has already been sent to the FBS computer, the program bypasses step 468 and attempts to read the correct sort pen for the animal as determined by the FBS computer at step 470. The program then returns to the sort pen required inquiry step 462. If a sort pen is still required then the just described steps are repeated. If a sort pen identity is not required, then the program proceeds on through the sequence and the ready to release status light is illuminated on the aforementioned control panel.

Thereafter, an operator must manually press a release button to release an animal from the single-file chute into the alley between the sort pens. At this point the computer inquires whether the release button has been pushed, at step 472. If the answer is no, nothing further happens until the release button is pushed. When the release button has been pushed, the program inquires whether the sort pen is ready, at step 474. If not, nothing further happens until either the release button is pushed or the sort pen is ready. When the sort pen is ready, head gate 56 is commanded to open, at step 476. When the head gate is open, the program inquires whether the fill sensor is off, at step 478. If not, nothing further happens until the fill sensor is off. When it is off, the program next inquires whether the head sensor is off, at step 480. If not, nothing further happens until the head sensor is off. When it is off, the program returns to step 438 to close the head gate and prepare the stall for the next animal.

Figure 13A:
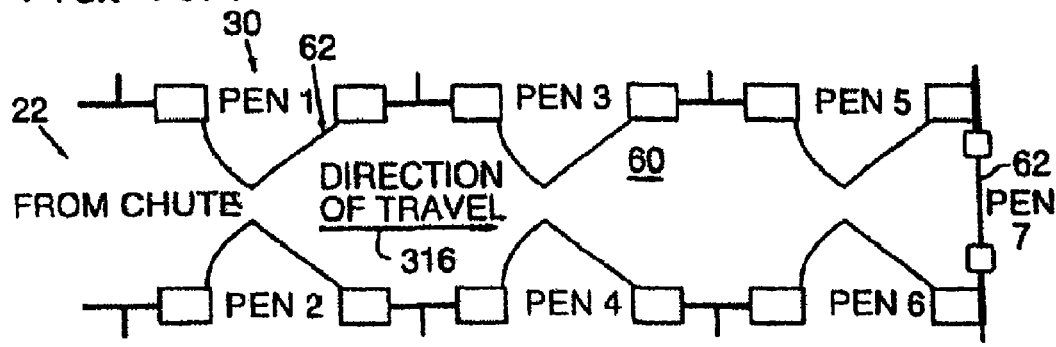
FIG. 13A is an enlarged schematic diagram of the sort pen entrance gates for the sort pens shown in FIG. 5.

Referring now to FIG. 13A, the seven sort pens 62 and their respective sorting pen entrance gates 62 are illustrated schematically. The direction of travel of the animals through the alley 60 between the two rows of sorting pens is indicated by the arrow 316 as they leave the single-file chute indicated generally at 22.

Figure 13B:
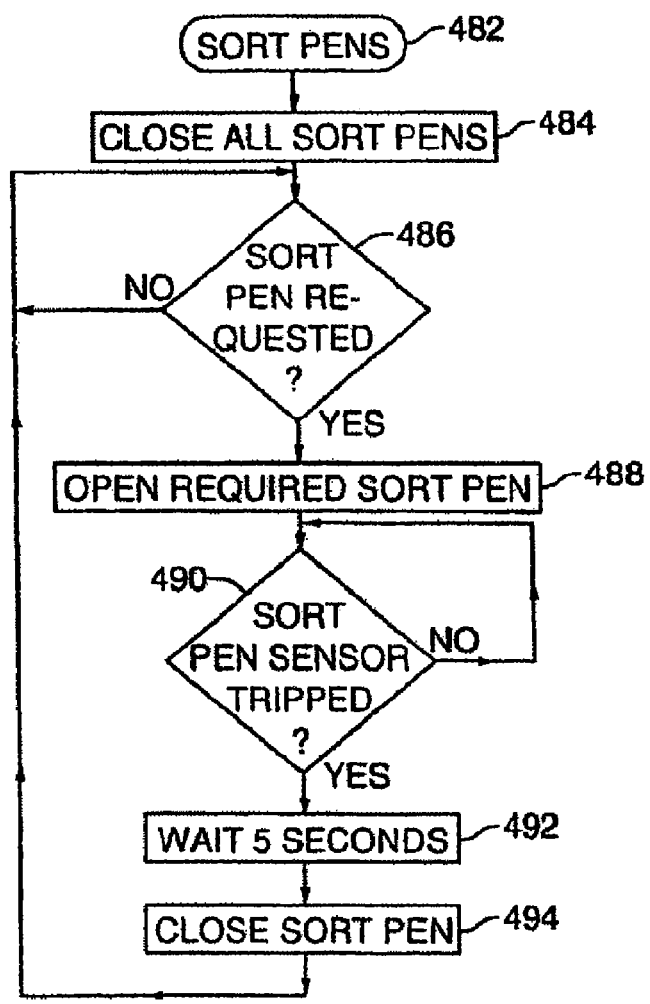
FIG. 13B is a flow diagram of a computer program used to control the operation of the entrance gates to the sort pens of FIG. 13A.

FIG. 13B is a flow diagram of the computer program 482 for operating the sort pen entrance gates 62. The first step in the programming sequence is to make sure all sort pen gates are closed at step 484. Next, the program at step 486 inquires of the process control computer whether a sort pen is requested. If not, nothing further happens and the sort pen gates remain closed, and each animal would travel through the alley 60 to an appropriate feed pen through the open gate 62 of feed pen 7 as indicated in FIG. 13A.

If a sort pen is requested, the designated sort pen is commanded to open at 488. When the sort pen gate is open the program inquires whether the sort pen gate sensor (not shown) has been tripped, at step 490. When the sort pen gate sensor is tripped, it would indicate that an animal has entered the sort pen through the open gate. The sort pen sensor, such as a photocell, would be located at the gate entrance so that its beam would be interrupted when an animal passes through the entrance into the pen with the gate open. After the sort pen sensor has been tripped, there is a five second delay, indicated at step 492, to give the animal time to pass through the open gate into the designated pen. Thereafter, the entrance gate is commanded to close again, as indicated at step 494. When the designated sort pen gate is closed, the program returns to step 486 to inquire if a sort pen is requested for the next animal. Nothing further happens until a sort pen is again requested.

FIG. 14 is a flow diagram for the computer program in the process control computer that operates in conjunction with the measuring and processing station and sort pen operating programs to control the sequence of operation of the various station head and tail gates and sort pen entrance gates. The FIG. 14 program, indicated generally at 496, is for controlling the movement of a single animal through the single-file chute and its measuring and processing stations and into one of the selected sort pens. The processing sequence program 496 starts at step 498 by closing the GR1 stall head gate and opening the GR1 stall tail gate. Then at step 500 it asks whether there is an animal in the GR1 stall. If not, nothing further happens until an animal enters the GR1 stall.

When there is an animal in the stall as indicated by the fill and tail sensors in the stall, the GR1 tail gate is closed at step 502. Then the program asks if the video and scale/EID stations are ready for an animal, at step 504. If not, nothing further happens until those stalls are empty and ready for the next animal. When they are, the GR1 head gate opens at 506. Then, at step 508, when the sensors in the GR1 stall indicate that the stall is empty, the GR1 head gate closes at step 510. As the animal passes from the GR1 stall through the video stall the video measurements are made under control of the video computer, as indicated at step 512.

The animal passes from the video stall into the scale/EID station or stall as indicated at step 514. When the sensors in the scale/EID station indicate that an animal is in the station, the scale/EID tail gate is closed at step 516. Thereafter, the animal is weighed in the scale/EID station as indicated at 518. Next, there is an attempt to read the animal's EID identification at step 520. Thereafter, the program inquires whether the ultrasound station is ready for the animal at step 522. If not, nothing further happens until the ultrasound station is ready. When ready, the head gate of the scale/EID station is opened at step 524 so the animal can pass into the ultrasound station. Next, the program asks at step 526 whether the animal is gone from the scale/EID station. If not, nothing further happens until the program is told that the animal has left the station. When the animal is gone from the scale/EID station the scale/EID head gate is closed at step 528.

Next, the program asks at step 530 whether there is an animal in the ultrasound station. If not, nothing further happens until an animal is detected in the ultrasound station. Then the ultrasound tail gate is closed at step 532. Thereafter, the ultrasound computer operates the ultrasound machine to make the backfat measurements at step 534, and the process control computer is commanded to read the video measurements at step 536 by the processing station program.

Next, the processing station program asks whether the processing station is ready for the animal, at step 538. If not, nothing further happens until the processing station has cleared the previous animal and is ready for the next animal. Then, the ultrasound head gate is opened at step 540, allowing the animal to proceed into the processing station. Thereafter, the program asks whether the animal is gone from the ultrasound station, as indicated at step 542. If not, nothing further happens until the animal has cleared the ultrasound station. Thereafter, the ultrasound station head gate is closed at step 544.

Next, the program asks whether the animal has entered the processing station at step 544. If not, nothing further happens until the animal is fully within the processing station, after which the processing station tail gate is closed at step 546. After the animal is within the processing station, its EID identification is read at step 548, its measurement data from the previous measuring stations is transmitted to the FBS computer at step 550, and the FBS computer transmits to the process control computer the assigned sort pen for the animal at step 552.

At this point, within the processing station, the animal may be implanted with growth promotants or undergo additional treatment that may be indicated. When this processing is completed, a button is manually pushed by an operator to indicate that the animal is ready to leave the processing station. The computer program then asks whether the release button has been pushed at step 554 and if not, nothing further happens and the animal cannot leave the processing station. When the release button has been pushed, the program inquires whether the assigned sort pen is ready for the animal, at step 556. Until the designated sort pen is ready, nothing further happens and the animal remains in the processing station. When the sort pen is ready, the processing station head gate is opened at step 558 and the specified sort pen gate is also opened at step 560, so the animal can leave the processing station and proceed into the sort gate alley and into the open sort pen.

Next, the computer program asks whether the animal has left the processing station at step 562. If so, the head gate of the processing station is closed at step 564. Next, the program asks whether the sort pen sensor has been tripped by the animal entering through the sort pen gate, at step 566. If so, the designated sort pen gate is closed at step 568. Finally, the identification of the animal entering the sort pen is recorded at step 570 and the processing sequence program ends for that particular animal at step 572.

Figure 15:
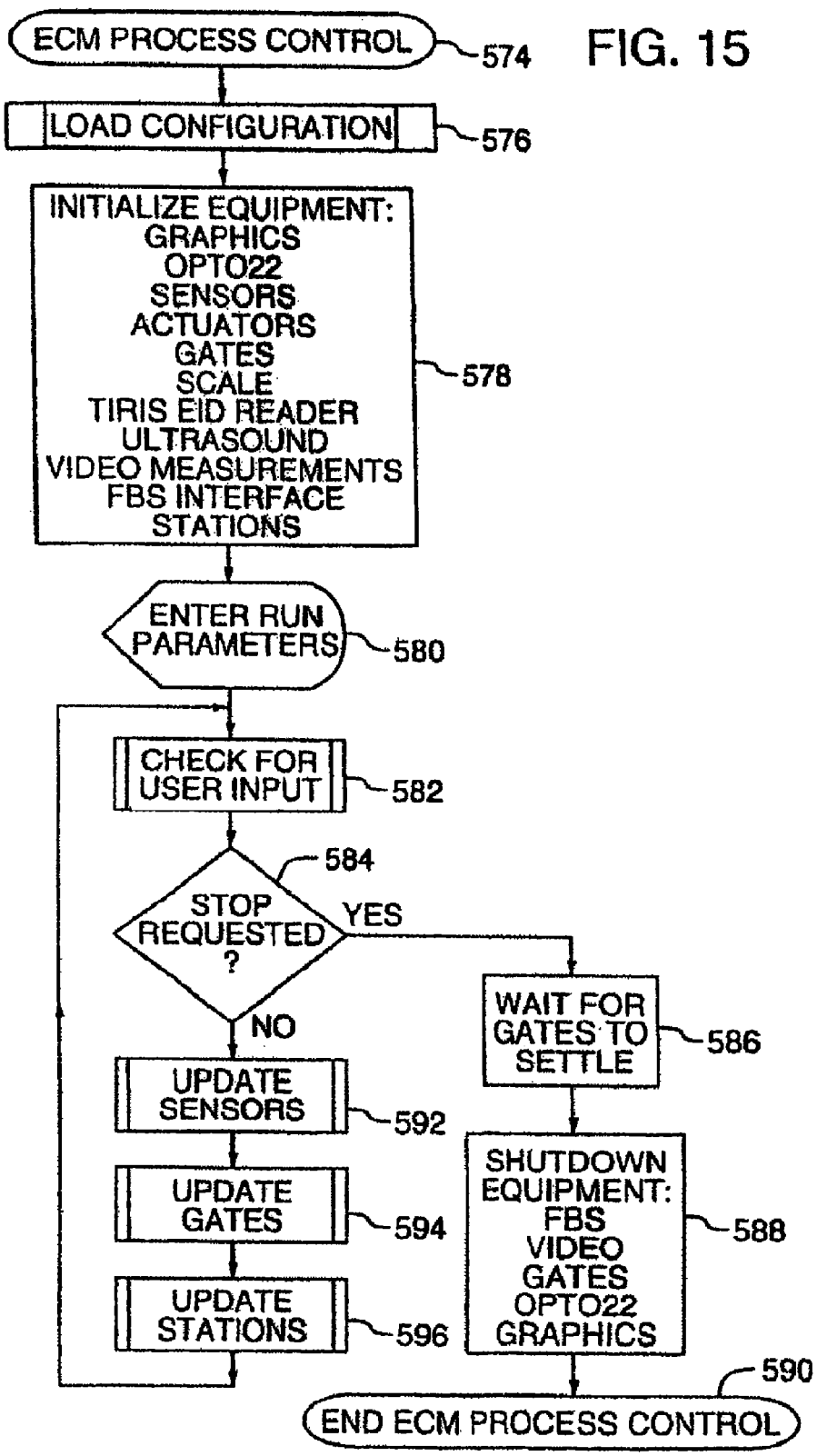
FIG. 15, is a flow diagram of the overall process control computer program for controlling the operation of the various computer-operated devices and equipment of a cattle management system.

FIG. 15 is the overall ECM process control program in the process control computer that controls identification and shutdown of the various equipment used in the system including the sort pen gate sensors, the measuring and processing station sensors, the station gate actuators, the tiris EID reader, the ultrasound computer, the video measurement computer, the FBS computer interface and the like. The program is indicated generally at 574.

First, the particular configuration of the feedlot management system being used is loaded into the computer at step 576, and thereafter the various computers, interfaces, actuators, sensors, sort pen gates, and the like are initialized at step 578. Next, the various parameters to be used in the system are entered at step 580 through a data entry means. Next, the program checks for user inputs at step 582, and inquires whether any stopping of the operation of the system has been requested at step 584. If a stop has been requested, the system waits for the gates to settle at step 586 and then shuts down the equipment under its control at step 588 to end the ECM process control program at step 590.

If no stop of the system has been requested, then the program updates the sensors at step 592, updates the gates at 594 and updates the measurement and processing stations at step 596. Thereafter, the program returns to the portion of the program at step 582 that checks for user inputs and the program then continues to operate for the next animal proceeding through the system.

Figure 16:
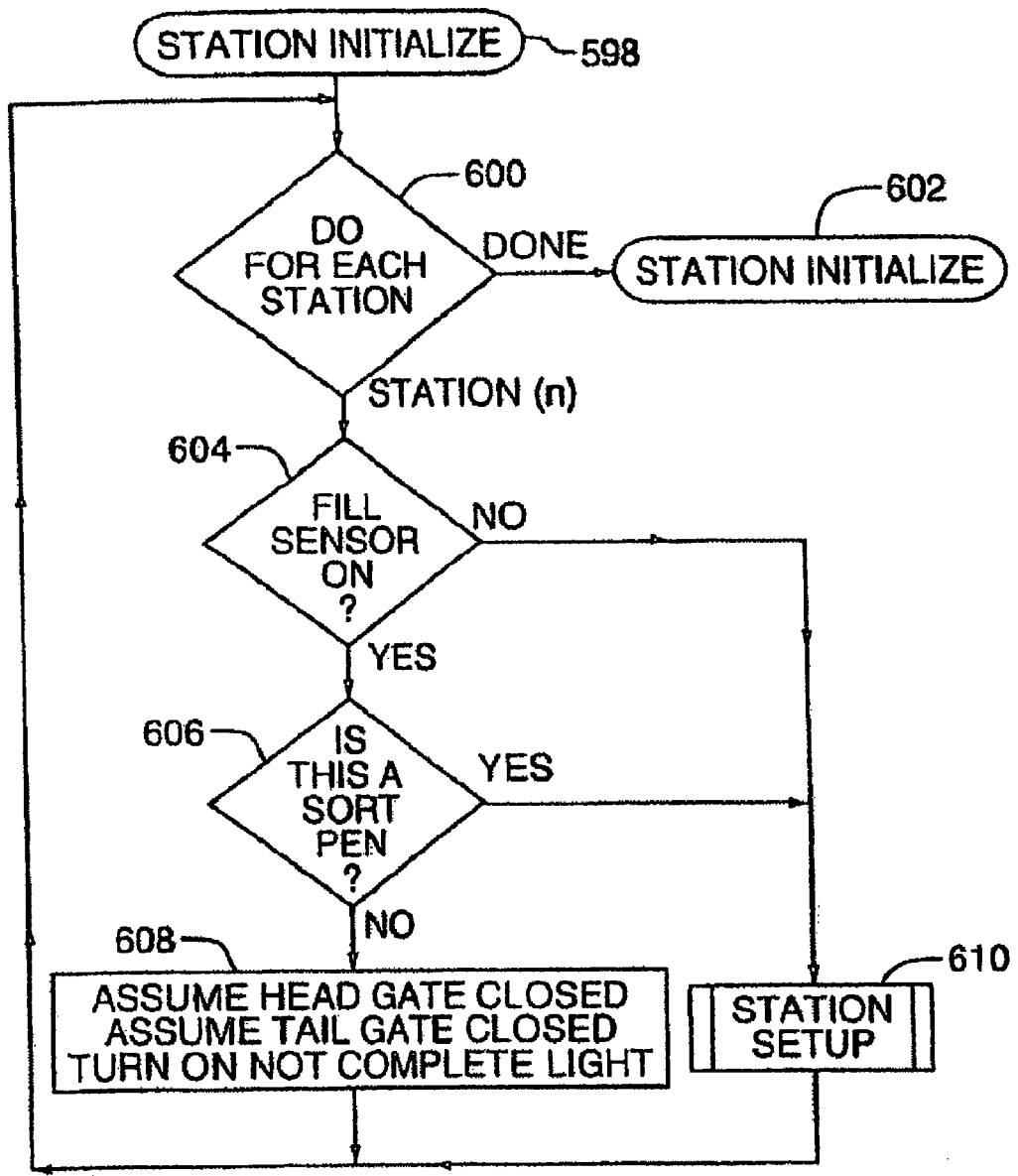
FIG. 16 is a flow diagram of a station initialization computer program for the various measuring and processing stations of the single-file chute shown in FIG. 5.

FIG. 16 is the station initialization program 598 that conditions each measuring and processing station for the receipt of the next animal. Each station is initialized at step 600, and when completed for all stations, the station initialization program ends at step 602. To initialize each station or pen, the program inquires whether the fill sensor in that station is on, at step 604. If the fill sensor is on, the program inquires whether this is a sort pen at step 606. If not, the program then assumes that the head gate is closed and that the tail gate is closed for that particular station at step 608, and then the program returns to its start at step 600 and repeats the sequence for each of (n) stations or pens. If at any station the program detects that a fill sensor is not on, at step 604 the program proceeds to a station setup step 610 and then back to the start of the programming sequence at step 600. If at step 606 of the programming sequence the program detects that this is a sort pen being initialized, then the program proceeds to the station setup step 610 before proceeding back to the start of the programming sequence at step 600.

Figure 17:
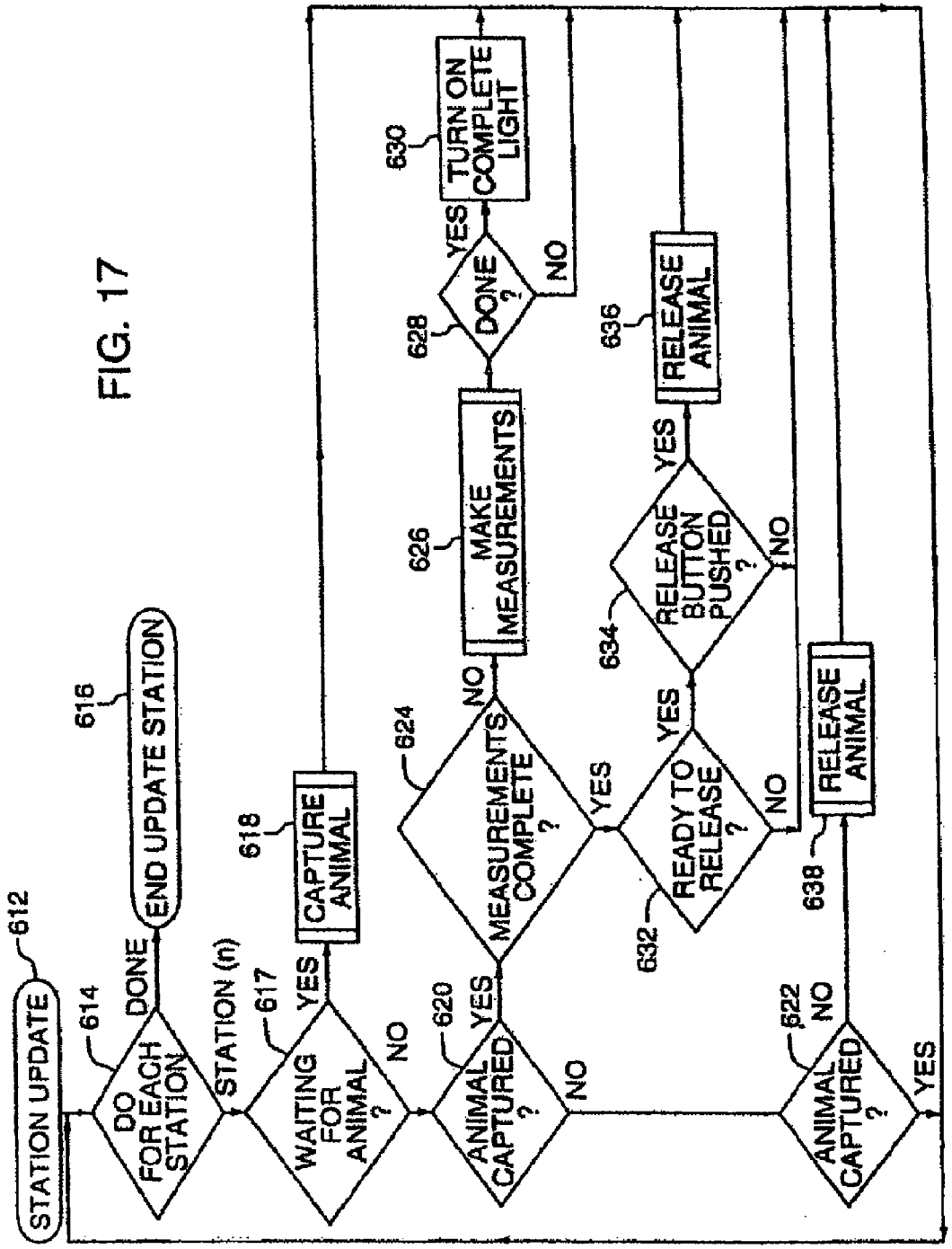
FIG. 17 is a flow diagram of a computer program used to update the data for each computer-operated measuring apparatus at each measuring and processing station.

FIG. 17 is the flow chart for the "update stations" program 612. The first step in the program sequence is to update each station for the next animal as indicated at step 614. When each station of the total number of stations (n) has been updated, the update program for that station ends at step 616. The program resequences until all stations have been updated.

To update a station, the next step 616 of the program asks a station whether it is waiting for an animal. If it is, then it initiates the capture animal program at step 618, which will be described subsequently. After the capture animal program for a particular station has been run, the program sequences back to its start at step 614 and then proceeds to update the next station. If a particular station at sequencing step 616 of the program is not waiting for an animal, the program then asks whether an animal has been captured at step 620. If an animal has not been captured, it then asks at step 622 whether an animal has been released from the station. If an animal has been released, the program resequences to the beginning at step 614 to rerun the program for the next station. If for a particular station an animal is captured when the inquiry is made at step 620, the program next asks at step 624 whether the measurements are complete at that station. If the measurements are not complete, the program waits until the measurements are made at step 626.

Next, the program asks if the measurements have been completed at step 628 and if the answer is yes a light on the control panel is turned on at step 630 to indicate that the measurements are complete, and the program sequences back to the beginning at step 614. If the measurements are not complete, the program sequences back to the beginning and reruns until the measurements are complete and the "complete light" can be turned on.

If, at step 624 when the program inquires whether the measurements are complete and the answer is yes, the program then asks at step 632 whether the animal is ready for release. If the answer is no, the program sequences to the beginning and reruns through the sequences until the animal is ready for release. When the animal is ready for release at step 632 of the program, it then asks at step 634 whether the release button has been pushed. If it has, then the animal is released at step 636. If it has not, then the program sequences back to the beginning to rerun until the animal is released. If at step 622 of the program an animal has not been released, then the program commands that the animal be released at step 638 after which the program sequences back to the beginning to update the station for the next animal.

Figure 18:
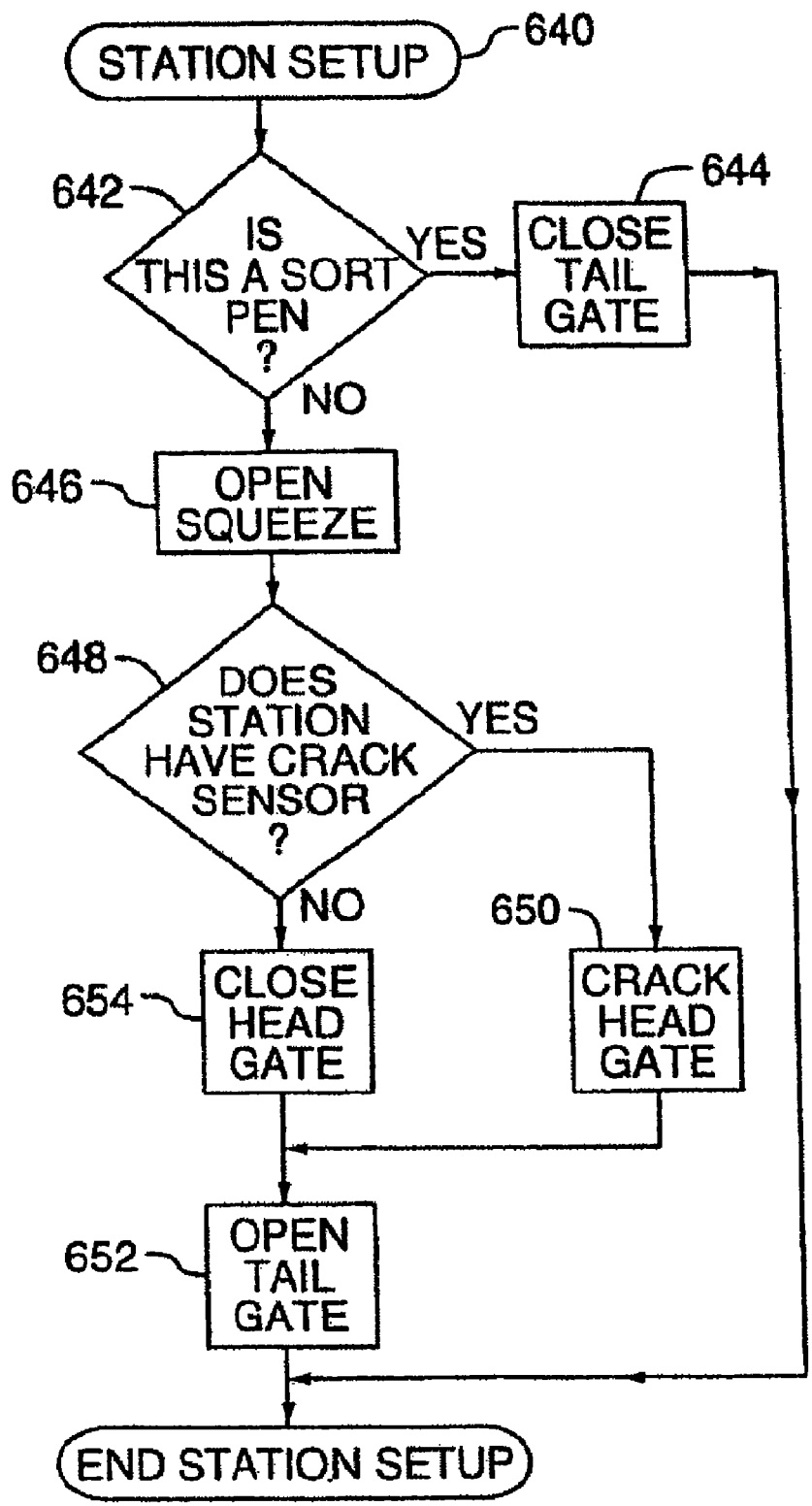
FIG. 18 is a flow diagram of a station setup computer program used to prepare each station for the receipt of an animal for measuring and processing.

FIG. 18 shows the flow chart for the "station setup" computer program 640. In the first step of the programming sequence the program asks whether this is a sort pen. If it is a sort pen, the sort pen entrance gate (indicated in the flow chart as the "tail gate" at step 644 is closed to end the station setup program for the sort pen.

If the station setup program is not being run for a sort pen, then the program commands that the squeeze gate, if any, be opened at 646. Next, the program inquires at step 648 whether the station has a crack sensor. If it does, then the program commands that the head gate be cracked at step 650. Then the program commands that the tail gate be opened at step 652 to end the setup program for that particular station.

If at the sequencing step 648 the station does not have a crack sensor, then the program commands that the station head gate be closed at step 654 and then that the tail gate be opened at step 652 to end the station setup program, at which point the station is ready to receive the next animal.

FIG. 19 is the flow chart for the "capture animal" program for each station, which, like the preceding programs, is run by the process control computer. The program, indicated at 656, first inquires whether the tail gate for a station is open at step 658. If the tail gate is not open, it inquires whether the fill sensor at the station is on at step 660. If the fill sensor is not on the program sequences to a point where it asks whether the head and tail gates are closed at step 662. If the head and tail gates are not closed, the program sequences to its end at step 664 because there is no animal present to be captured.

Returning to step 660 of the programming sequence, if the fill sensor is on, the program then inquires whether the tail sensor is on at step 666. If the tail sensor is on the program then sequences to step 662 to inquire whether the head and tail gates are closed. If the head and tail gates are closed, the programs inquires whether this is a sort pen at step 668. If it is not a sort pen, the program commands that the status light on the control panel be turned on to indicate that the measuring or processing at the station is not complete, at step 670. If at step 668 it is a sort pen, then the program commands that the animal's identity be recorded at step 672.

Returning to step 666, if the tail sensor is not on but the fill sensor is on, then the program commands that the tail gate be closed at step 674. Once the tail gate is closed, the program at step 676 inquires whether there is a head catcher at the station and if so whether the head is to be caught by it.

If the station has no head catcher, then the program at step 678 inquires whether the head sensor is off. If it is not off, nothing further happens until it does go off. Then the program commands the head gate to close at step 680. When the head gate closes the program inquires whether the station has a squeeze gate and if so whether the animal is to be squeezed, at step 682. If the animal is to be squeezed, the squeeze gate is commanded to close at step 684. After the squeeze gate is closed, the program sequences through the steps previously described at 662, 668, and 672 to the end of the capture program at 664.

If at step 676 there is an indication that there is a head catcher to be operated, the program inquires at step 686 whether the head sensor is on. If it is on then the head gate is commanded to close at step 688, and the program sequences through steps 682, 684, 662, 668 and 672 as previously described.

If at step 686, the head sensor is not on, then the program sequences to step 662 to inquire whether the head and tail gates are closed.

The next program to be described is the "make measurements program, the flow diagram for which is shown in FIG. 20 and indicated generally at 690. This is the program of the process control computer that controls the operation of the computers that control the equipment for making the three basic measurements, namely a weight measurement, an external measurement via the video scanner, and an ultrasound measurement for backfat via the ultrasound machine. The program also controls the reading of the measurement data and its transmission to the FBS computer.

The first step 692 in the program is to inquire whether an animal needs to be identified through its EID tag, by asking whether there is a tiris reader. If there is a tiris reader the program inquires whether an electronic ID of the animal is still needed at step 694. If an electronic identification is needed, the program inquires whether an identity reading is ready at step 696. If the reading is ready, the program instructs the computer to read the animal's electronic identification at step 698. If at any step in the foregoing sequence, it is indicated that no electronic ID is needed or that the reading is not ready, the program proceeds to the next sequence of steps.

The sequence involves weighing, and the first step in the sequence is to inquire whether there is a scale at the station. If there is a scale at the station, the program inquires at step 708 whether a weight is required. If a weight is required the program asks if the scale reading is available at step 710. If the scale reading is available, the program instructs the computer to read the scale weight at step 712. If at any point in the foregoing weigh sequence it is indicated that a weight is not required or a weight reading is not available, the program sequences to the next series of steps for backfat measurement. The backfat steps start with an inquiry at step 708 whether there is an ultrasound machine at the station. If there is, the program inquires whether a backfat measurement is required at step 710. If a backfat measurement is required, the program commands the appropriate computer to read the ultrasound data at step 712. If a backfat measurement is not available or needed, or once the ultrasound data has been read, the program sequences to the next series of steps relating to video measurements.

The first inquiry at the next sequence of steps as indicated at step 714 is whether there is a video measurement interface at the particular station. If there is, the program inquires whether a hip-height measurement is still required at step 716. If it is, the program inquires whether the video measurements are ready to be read at step 718. If they are, a reading of the video measurements of the animal is made at step 720, and the program sequences to the next series of steps beginning at step 722. If at any point in the video measurement sequence of steps it is indicated that a measurement is not required or that the video measurements are not available to be read, the program sequences to the next series of steps.

At step 722 the program inquires whether there is an FBS computer interface at the station. If there is, the program inquires whether a sort pen is required at step 724. If one is required, the program inquires whether all measurements are completed at step 726. If all measurements are completed, then the program transmits the recorded measurement data to the FBS computer. It also requests the FBS computer to assign a sort pen to the animal at step 728. If at any point in the foregoing sequence of steps, beginning at step 722, there is no sort pen required or all measurements are not complete, the program proceeds to the end at step 730.

From the foregoing description of the "make measurements" program it will be apparent that this program can be used to control the appropriate computer and equipment at each measurement station to make the appropriate measurements, then record them and transmit the measurement data to the FBS computer, and in turn receive a sort pen assignment from the FBS computer based on such measurement data.

Figure 21:
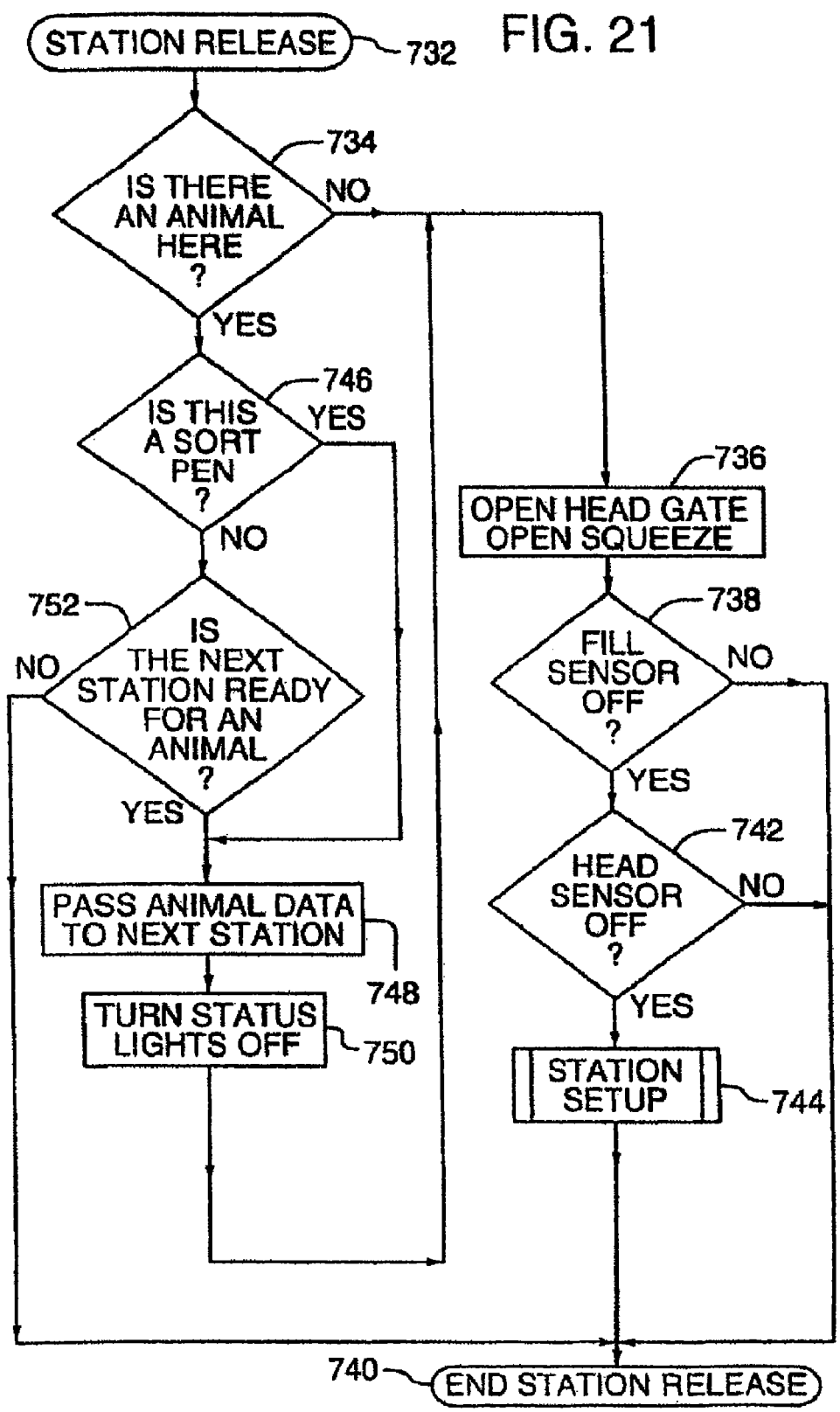
FIG. 21 is a flow diagram of a computer program used for preparing a station or a sort pen for releasing an animal from the station or sort pen to another destination.

The next program to be described is the "release animal" program, the flow diagram of which is shown in FIG. 21 and indicated generally at 732.

The first step in the release animal programming sequence, at step 734, is to inquire whether there is an animal at the particular station. If there is no animal, the program sequences to command the head gate to open and the squeeze gate to open at step 736. Then the program sequences to inquire whether the fill sensor is off at step 738. If the fill sensor is not off, the program sequences to the end of the station release program at step 740 and the animal is not released.

If the fill sensor is off at step 738 then the program inquires whether the head sensor is off at step 742. If the head sensor is off, then the program commands the station setup program to start at step 744 and completes its sequencing at step 740. If the head sensor is not off at step 742, the program sequences to the end of the program and the animal is not released.

If at step 734 of the program sequence there is an animal in the station, the next inquiry is whether this is a sort pen, at step 736. If it is a sort pen, then the program sequences to pass the animal data to the next station at step 748 and then to turn the status lights off on the control panel at step 750. Thereafter, the program sequences to step 736 to open the squeeze and head gates to release the animal.

If at step 746 in the sequence the indication is that the station is not a sort pen then the program sequences to the next step 752 to inquire whether the next station is ready for an animal. If the answer is no, the program sequences to the end at step 740 and the animal is not released. If the answer is yes at step 752, then the animal data is passed to the next station at step 748, the status lights are turned off at step 750 and the program sequences to step 736 to release the animal.

Figure 22:
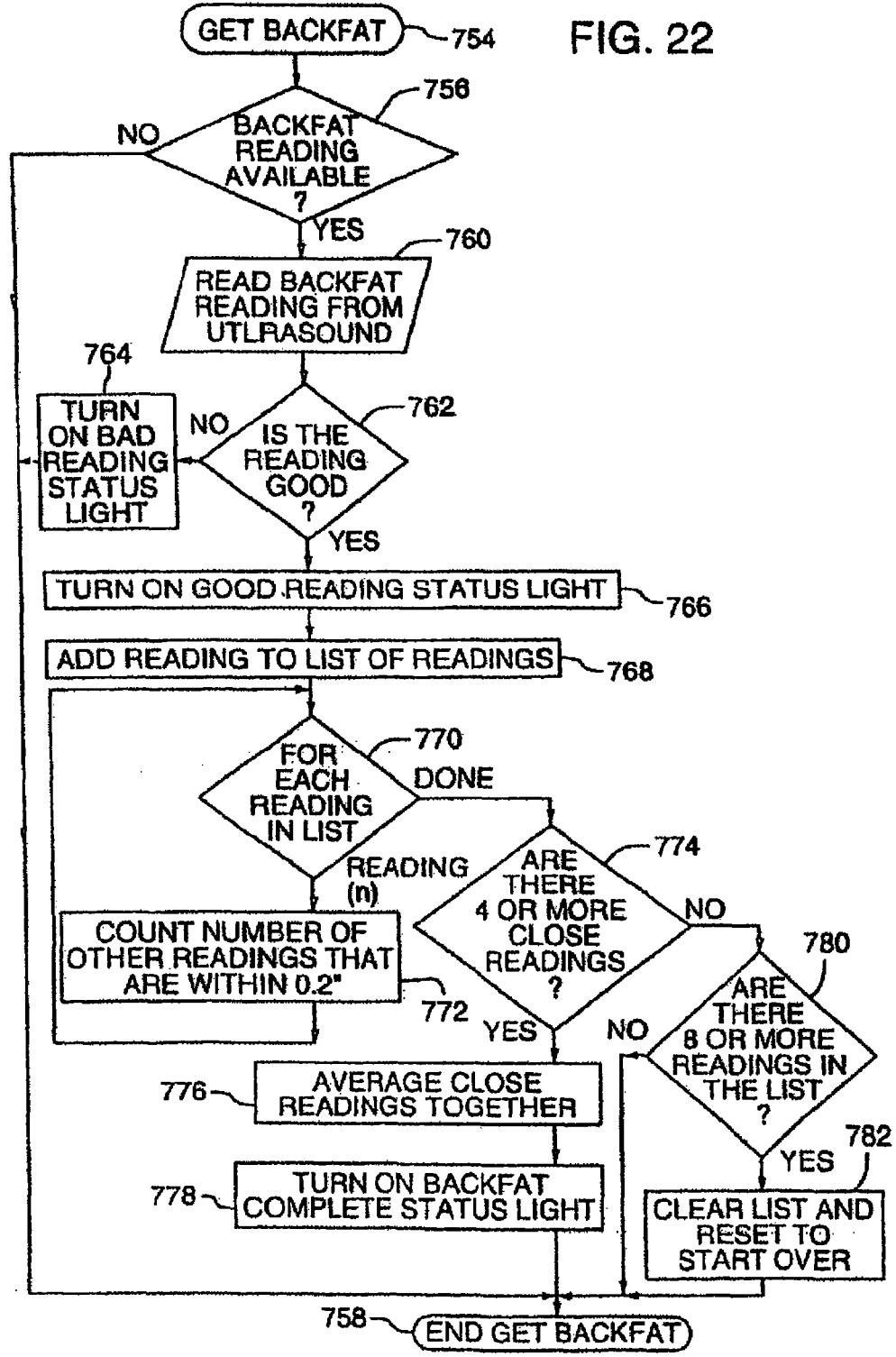
FIG. 22 is a flow chart of a computer program used for reading the ultrasound backfat data of an animal at the ultrasound measuring station of the single-file chute shown in FIG. 5.

The next program to be described, with reference to the flow diagram of FIG. 22, is the "read ultrasound data" program 754. The first step in the program sequence is to inquire whether a backfat reading is available from the ultrasound computer at step 756. If one is not available, the program sequences to the end at step 758. If a reading is available, the computer is instructed to read the backfat reading from the ultrasound at step 760. Next, the program inquires whether the backfat reading is good at step 762. If it is not, then the program commands the computer to turn on the bad reading status light on the control panel at 764 and the program sequences to the end. If the reading is good then the "good reading" status light is turned on at the control panel at step 766. Then the good reading is added to the list of backfat readings for that animal at step 768.

After the reading, the program commands the computer at step 770 to count the number of other readings that are within 0.2 inches, as indicated at step 772. When that has been done, the program sequences back to step 770 until all such readings in the list have been counted as indicated. When that is done, the program sequences to step 774 and inquires whether there are four or more close readings. If there are four or more close readings, the next step 776 is to average the close readings. Then the computer turns on the "backfat complete" status light on the control panel at step 778 and the program ends.

If at step 774 there are not four or more close readings, then the program sequences to step 780 and asks if there are eight or more readings in the list. If there are not, the program sequences to the end at step 758. If there are, the program instructs the computer to clear the list and reset to start over at step 782 and then sequences to the end of the program at step 758.

Figure 23:
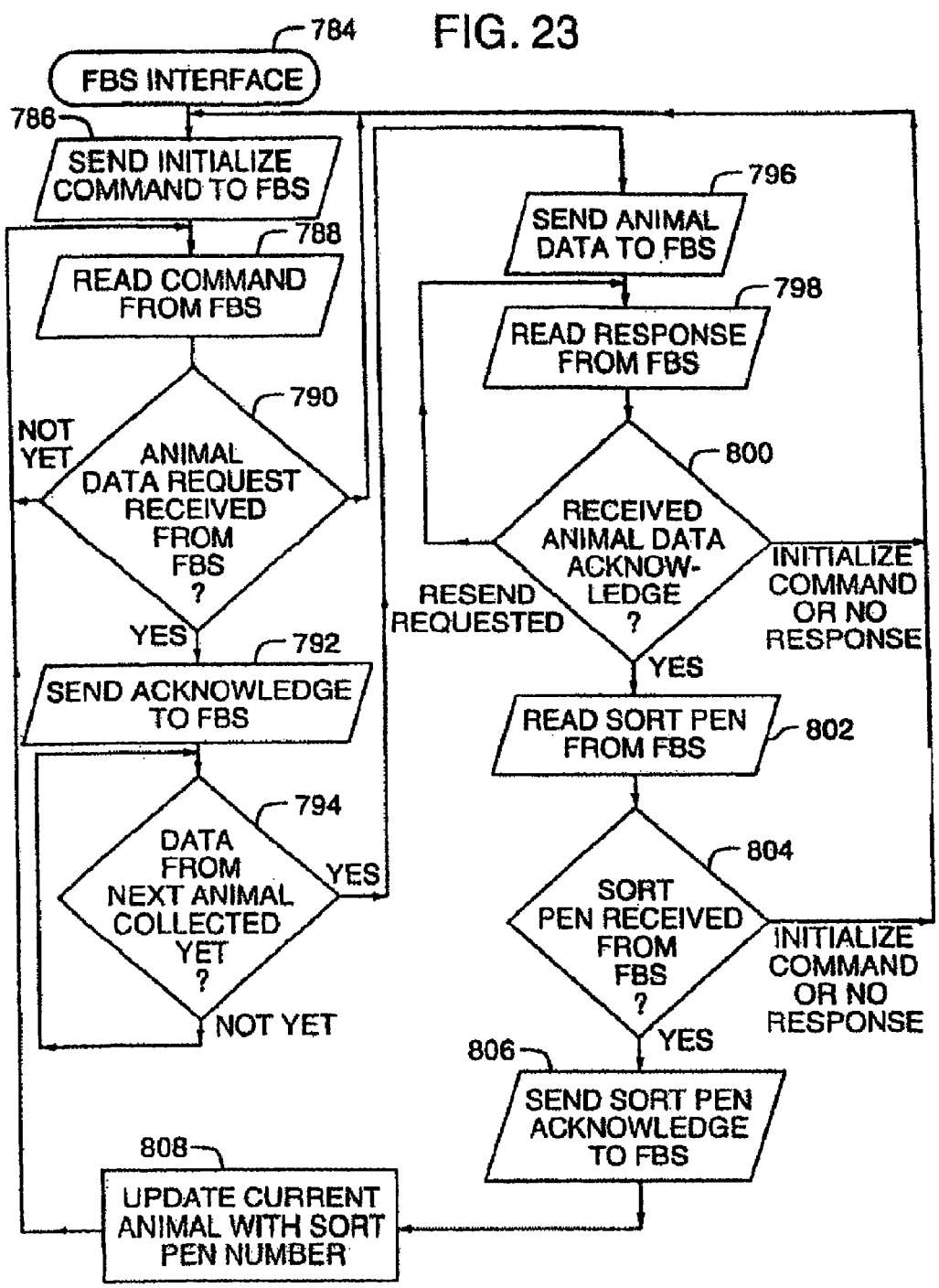
FIG. 23 is a flow chart of a computer program used to interface the process control and other computers used for collecting data at the various feedlot measuring, processing and sorting stations or pens with the main feedlot business system (FBS) computer so that data can be passed back and forth between the FBS computer and the various processing computers used in the overall computer control system.

The next program to be described is the FBS computer interface program 784 described with reference to the flow diagram of FIG. 23. This program operates the FBS interface indicated at 246 in FIG. 6. The first step 786 in the program is to send an initialize command to the FBS computer. The next step 788 in the program is to read a command from the FBS computer. The next 790 step in the program is to inquire whether an animal data request has been received from the FBS computer. If not, the program sequences back to step 788 to await a command from the FBS computer. If there is no command from the FBS computer or no response, the program sequences back to the beginning to send an initialize command to the FBS computer.

If at step 790 an animal data request is received from the FBS computer, an acknowledgement is sent to the FBS computer at step 792. Next, the program inquires whether data from the next animal is collected yet, at step 794. If the data has not yet been collected, the program returns to step 794 to await the collection of data. When data for the next animal has been collected, the program sequences to step 796 and sends the animal data to the FBS computer. Next, at step 798 the program waits to read a response from the FBS computer. Then, the program awaits receipt of an animal data acknowledgement from the FBS computer at step 800. If not received, the program requests the FBS computer to resend an acknowledgement. Upon an initialize command or no response from the FBS computer, the program sequences back to the initial step 786.

If the program receives an acknowledgement from the FBS computer that the animal data was received, the program next reads the sort pen assignment received from the FBS computer at step 802. Next, at step 804, the program inquires whether the sort pen assignment was received from the FBS computer. At this point if there is an initialize command from the FBS computer or no sort pen assignment from the FBS computer, the program sequences back to the initial step 786.

If there is a sort pen assignment received from the FBS computer, the program sends a sort pen acknowledgement to the FBS computer at step 806. Then, at step 808 the program commands the computer to update the current animal with its assigned sort pen number, in other words, to correlate the new sort pen assignment with the identified animal. The program then returns to step 788, awaiting a command from the FBS computer.

Figure 24:
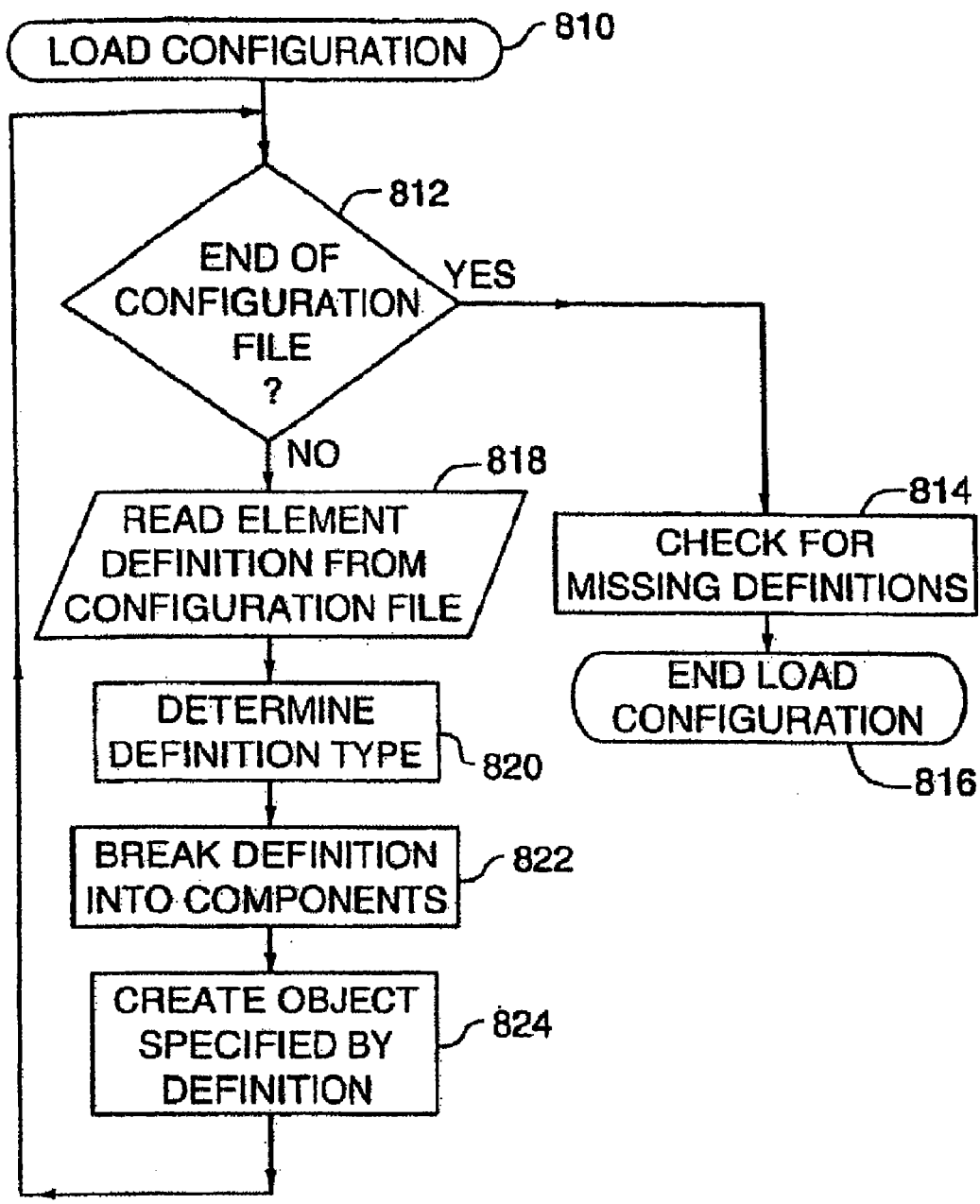
FIG. 24 is a flow diagram of a computer program used for loading station configuration information into the computer system for a particular feedlot cattle management system.

Finally, there is a program for loading the ECM (cattle management system) station configuration information into the process control computer. This program is diagrammed in FIG. 24 and indicated generally at 810. In the first step of its sequence the program inquires whether this is the end of the configuration file, at step 812. If the answer is yes, then the program sequences to step 814 to check for any missing definitions. Then the load configuration program ends at step 816. If the configuration file is not fully loaded, then from step 812 the program sequences to read the element definition from the configuration file at step 818. Then the program determines the definition type at step 820 and breaks the definition into its components at step 822 and creates the object specified by the definition at step 824 before sequencing back to the beginning of the load configuration program.

From the foregoing it will be appreciated that the disclosed computerized cattle management system and method provides a highly flexible system and method for measuring, sorting and processing animals, either on a group basis or an individual basis or in a combination of group and individual basis. It furthermore proves a means and method for projecting, on an individual animal basis, when that animal will be ready to be shipped from the feedlot to the packing plant for slaughter and what that animal's optimum finish weight will be. The system also provides a means and method whereby the costs of maintaining animals in the feedlot can be determined on an individual animal basis so that such costs, on an individual animal basis, can be assessed to the animal's owners, thereby providing a highly efficient cost management tool.

With the management system, no longer is it necessary to treat a group of animals received in a feedlot as a group throughout its period of stay in the feedlot. Instead, different groups of animals as received in a feedlot can be mixed with other groups regardless of ownership, based on management criteria such as animal type, DTF, OEW or other factors. Since each animal can be identified electronically at any time and at any place during its stay in the feedlot, with its ownership easily determined, it can be grouped with other animals with similar physical characteristics or OED's rather than being kept in a common ownership group while in the feedlot. Similarly, when animals are ready for slaughter, they can be sent to the packing plant without regard to ownership because their EID tags will identify them at packing plant as to ownership and thus costs and proceeds can be properly assessed and credited without regard to group.

From the foregoing, it should be apparent that a particular animal may be in one group or lot when it arrives in a feedlot, may be moved to a different group within a feed pen during the feeding period, and may be sorted into a marketing group different than its pen feeding group when it is finally ready for shipment to the packing plant. All of this is made possible by the ability to electronically identify each animal by ownership and physical characteristics and costs at any time, irrespective of the group it happens to be in at any given time.

TABLE 3A

Cattle Received Report by Load

Period: Mar. 18, 1994 to Mar. 20, 1994  
Research Division  
Agri-Research  
Feeders  
Lot: 495

CIR117  
Seq 13  
Page

| Pen No. | Date Rcvd. | Load No. | Head | Sex | Weight Average Pay | Rec | Shrink | Totals Pay | Rec | Purchase Cost Total | S/CWT |
|---|---|---|---|---|---|---|---|---|---|---|---|
| L4 | Mar. 19, 1994 | 1 | 32 | HF | 678 | 678 | 0.00% | 21,680 | 21,680 | 16,476.80 | 76.00 |
| | AGE | | | | YEARLING | | | 160.00 | | | |
| | BACKGROUND | | | | WHEAT PASTURE | | | 100.00 | | | |
| | BREED OF FEEDER | | | | ANGUS CROSS | | | 25.00 | | | |
| | | | | | CHAROLAIS | | | 6.25 | | | |
| | | | | | HEREFORD | | | 28.00 | | | |
| | | | | | HOLSTEIN CROSS | | | 18.75 | | | |
| | | | | | SHORTHORN X | | | 22.00 | | | |
| | DAYS IN PASTURE | | | | 154-161 | | | 100.00 | | | |
| | DISPOSITION | | | | DOCILE | | | 95.00 | | | |
| | HEALTH SCORE | | | | EXCELLENT | | | 100.00 | | | |
| | MARKET TYPE | | | | DIRECT | | | 100.00 | | | |
| | NUTRITION | | | | WHEAT PASTURE | | | 100.00 | | | |
| | STRESS SCORE | | | | EXCELLENT | | | 100.00 | | | |
| | WEATHER/ARRIVAL | | | | SUNNY & MILD | | | 100.00 | | | |
| Number of Loads: | | 1 | 32 | | 678 | 678 | 0.00% | 21,680 | 21,680 | 16,476.80 | 76.00 |
| HF-HEIFERS | | 1 | 32 | | 678 | 678 | 0.00% | 21,680 | 21,680 | 16,476.80 | 76.00 |
| | AGE | | | | YEARLING | | | 100.00% | | | |
| | BREED OF FEEDER | | | | ANGUS CROSS | | | 25.00% | | | |
| | | | | | CHAROLAIS | | | 6.25% | | | |
| | | | | | HEREFORD | | | 28.00% | | | |
| | | | | | HOLSTEIN CROSS | | | 18.75% | | | |
| | | | | | SHORTHORN X | | | 22.00% | | | |
| | BACKGROUND | | | | WHEAT PASTURE | | | 100.00% | | | |
| | DISPOSITION | | | | DOCILE | | | 95.00% | | | |
| | HEALTH SCORE | | | | EXCELLENT | | | 100.00% | | | |
| | MARKET TYPE | | | | DIRECT | | | 100.00% | | | |
| | NUTRITION | | | | WHEAT PASTURE | | | 100.00% | | | |
| | DAYS ON PASTURE | | | | 154-161 | | | 100.00% | | | |
| | STRESS SCORE | | | | EXCELLENT | | | 100.00% | | | |
| | WEATHER/ARRIVAL | | | | SUNNY & MILD | | | 100.00% | | | |

TABLE 3B

Pen Assignment Summary
Source Lot: 495  
Source Pen: 59  
Sort Type: DAYS TO FINISH

| Pen | 1 | 2 | 3 | 4 | 5 | 6 | 7 |
|---|---|---|---|---|---|---|---|
| Lot | 495 | 495 | | 495 | | | |
| Feed Pen | 59 | 57 | | 58 | | | |
| Head | 10 | 11 | | 11 | | | |
| Average | 98 | 79 | | 83 | | | |
| STD | 38 | 41 | | 56 | | | |
| Max | 154 | 154 | | 164 | | | |
| Min | 36 | 17 | | 9 | | | |
| Range | 118 | 137 | | 155 | | | |

Projected Finish Weight

| | 1 | 2 | 3 | 4 | 5 | 6 | 7 |
|---|---|---|---|---|---|---|---|
| Average | 1066 | 1093 | | 997 | | | |
| STD | 158 | 137 | | 126 | | | |
| Max | 1260 | 1260 | | 1177 | | | |
| Min | 830 | 876 | | 815 | | | |
| Range | 430 | 384 | | 362 | | | |

Current Weight

| | 1 | 2 | 3 | 4 | 5 | 6 | 7 |
|---|---|---|---|---|---|---|---|
| Average | 787 | 875 | | 766 | | | |
| STD | 120 | 66 | | 66 | | | |
| Max | 1035 | 965 | | 843 | | | |
| Min | 627 | 766 | | 648 | | | |
| Range | 408 | 199 | | 195 | | | |

Frame

| | 1 | 2 | 3 | 4 | 5 | 6 | 7 |
|---|---|---|---|---|---|---|---|
| Average | 5 | 6 | | 4 | | | |
| STD | 1 | 1 | | 1 | | | |
| Max | 7 | 7 | | 7 | | | |
| Min | 3 | 3 | | 3 | | | |
| Range | 4 | 4 | | 4 | | | |

Current Back Fat

| | 1 | 2 | 3 | 4 | 5 | 6 | 7 |
|---|---|---|---|---|---|---|---|
| Average | .22 | .30 | | .33 | | | |
| STD | .12 | .11 | | .19 | | | |
| Max | .42 | .53 | | .75 | | | |
| Min | .09 | .17 | | .12 | | | |
| Range | .33 | .36 | | .63 | | | |

TABLE 3C

PEN ASSIGNMENT DETAIL

LOT: 495  
PEN: 57  
Sort Pen: 2  
Run Seq: 206  
Thu Apr. 28, 1994  
07:35:12  
Page 1

Ship Window: May 14, 1994 TO Sep. 28, 1994

| EID | VID | DTF | OFW | CWT | ADG | FM | BF |
|---|---|---|---|---|---|---|---|
| 16817175 | 11 | 16 | 876 | 826 | 3.13 | 3 | 0.53 |
| 16817094 | 4 | 32 | 1004 | 905 | 3.09 | 5 | 0.41 |
| 16817763 | 22 | 45 | 1034 | 942 | 2.04 | 5 | 0.25 |
| 16816164 | 9 | 59 | 1089 | 929 | 2.71 | 7 | 0.22 |
| 16814011 | 5 | 60 | 912 | 766 | 2.43 | 3 | 0.41 |
| 16816227 | 24 | 75 | 1024 | 798 | 3.01 | 5 | 0.36 |
| 16816430 | 16 | 83 | 1132 | 897 | 2.83 | 7 | 0.25 |
| 16815742 | 28 | 98 | 1260 | 965 | 3.01 | 7 | 0.17 |
| 16816005 | 34 | 115 | 1260 | 931 | 2.86 | 7 | 0.31 |
| 16814141 | 19 | 122 | 1175 | 843 | 2.72 | 7 | 0.17 |
| 16813043 | 32 | 153 | 1260 | 824 | 2.85 | 5 | 0.24 |

TABLE 3D

MARKETING YARD SHEET  
INDIVIDUAL ANIMAL LEVEL

Mar. 30, 1994  
17:55-:03  
Measurement Date: Mar. 30, 1994  
DIV: AGR  
SEX: HF  
Owner: Agri Research  
Origin: Little  
Type: Crossbred Heifers C1###  
page

| | | | | Projected | | | | Weights | | DOF | | | Ration | |
|---|---|---|---|---|---|---|---|---|---|---|---|---|---|---|
| TAG | PEN | HGp | LOT | DTF | Date | OFW | YG | BE | CURR | PUR | CPD | LPD | ID | No. | Days |
| 25 | 59 | | 495 | 38 | 0506 | 815 | 3.0 | 117.25 | 711 | 678 | 10 | | 10 | 8 | 10 |
| 11 | 59 | | 495 | 46 | 0514 | 876 | 3.0 | 117.25 | 757 | 678 | 10 | | 10 | 8 | 10 |
| 15 | 59 | | 495 | 53 | 0522 | 896 | 3.0 | 117.25 | 757 | 678 | 10 | | | 8 | 10 |
| 18 | 59 | | 495 | 59 | 0527 | 821 | 3.0 | 117.25 | 668 | 678 | 10 | | 10 | 8 | 10 |
| 4 | 59 | | 495 | 62 | 0530 | 1004 | 3.0 | 117.25 | 843 | 678 | 10 | | 10 | 8 | 10 |
| 3 | 59 | | 495 | 65 | 0602 | 848 | 3.0 | 117.25 | 679 | 678 | 10 | | 10 | 8 | 10 |
| 14 | 59 | | 495 | 68 | 0606 | 904 | 3.0 | 117.25 | 727 | 678 | 10 | | 10 | 8 | 10 |
| 22 | 59 | | 495 | 75 | 0612 | 1034 | 2.0 | 117.25 | 817 | 678 | 10 | | 10 | 8 | 10 |
| 9 | 59 | | 495 | 89 | 0626 | 1089 | 2.0 | 117.25 | 832 | 678 | 10 | | 10 | 8 | 10 |
| 5 | 59 | | 495 | 90 | 0627 | 912 | 3.0 | 117.25 | 679 | 678 | 10 | | 10 | 8 | 10 |
| 17 | 59 | | 495 | 92 | 0630 | 830 | 3.0 | 117.25 | 576 | 678 | 10 | | 10 | 3 | 10 |
| 20 | 58 | | 495 | 97 | 0705 | 972 | 3.0 | 117.25 | 704 | 678 | 10 | | 10 | 8 | 10 |
| 2 | 58 | | 495 | 98 | 0706 | 965 | 3.0 | 117.25 | 710 | 678 | 10 | | 10 | 8 | 10 |
| 24 | 58 | | 495 | 104 | 0712 | 1024 | 2.0 | 117.25 | 722 | 678 | 10 | | 10 | 8 | 10 |
| 26 | 53 | | 495 | 104 | 0712 | 1044 | 2.0 | 117.25 | 742 | 678 | 10 | | 10 | 8 | 10 |
| 30 | 58 | | 495 | 107 | 0715 | 1034 | 3.0 | 117.25 | 755 | 678 | 10 | | 10 | 8 | 10 |
| 13 | 58 | | 495 | 107 | 0715 | 1012 | 3.0 | 117.25 | 733 | 678 | 10 | | 10 | 8 | 10 |
| 16 | 58 | | 495 | 113 | 0720 | 1132 | 2.0 | 117.25 | 805 | 678 | 10 | | 10 | 8 | 10 |
| 21 | 58 | | 495 | 113 | 0720 | 990 | 3.0 | 117.25 | 697 | 678 | 10 | | 10 | 8 | 10 |
| 23 | 58 | | 495 | 119 | 0726 | 1260 | 2.0 | 117.25 | 915 | 673 | 10 | | 10 | 8 | 10 |
| 28 | 58 | | 495 | 128 | 0804 | 1260 | 2.0 | 117.25 | 890 | 678 | 10 | | 10 | 8 | 10 |
| 29 | 58 | | 495 | 128 | 0508 | 1090 | 3.0 | 117.25 | 738 | 678 | 10 | | 10 | 8 | 10 |
| 34 | 57 | | 495 | 144 | 0821 | 1260 | 2.0 | 117.25 | 841 | 678 | 10 | | 10 | 8 | 10 |
| 19 | 57 | | 495 | 152 | 0828 | 1175 | 3.0 | 117.25 | 757 | 678 | 10 | | 10 | 8 | 10 |

| | | | | ADG | | | Feed Intake | | | | Treats/HD | | PROCS/Hd | | TOTALS/Hd | |
|---|---|---|---|---|---|---|---|---|---|---|---|---|---|---|---|---|
| TAG | PEN | HGp | LOT | CPD | LPD | ID | PCP | ACP | L7D | ID | Proj | Act | Proj | Act | Proj | TD |
| 25 | 59 | | 495 | 5.4 | .0 | 5.4 | 18 | 22 | 23 | 22 | 1 | .00 | 5 | 4.75 | 6 | 4.75 |
| 11 | 59 | | 495 | 5.8 | .0 | 5.8 | 18 | 24 | 25 | 24 | 1 | .00 | 5 | 4.75 | 6 | 4.75 |
| 15 | 59 | | 495 | 5.8 | .0 | 5.8 | 18 | 24 | 25 | 24 | 1 | .00 | 5 | 4.75 | 6 | 4.75 |
| 18 | 59 | | 495 | 5.1 | .0 | 5.1 | 18 | 21 | 22 | 2 | 1 | .00 | 5 | 4.75 | 6 | 4.75 |
| 4 | 59 | | 495 | 6.4 | .0 | 6.4 | 18 | 27 | 28 | 27 | 1 | .00 | 5 | 4.75 | 6 | 4.75 |
| 3 | 59 | | 495 | 5.2 | .0 | 5.2 | 18 | 21 | 22 | 21 | 1 | .00 | 5 | 4.75 | 6 | 4.75 |
| 14 | 59 | | 495 | .6 | .0 | .6 | 18 | 23 | 24 | 23 | 1 | .00 | 5 | 4.75 | 6 | 4.75 |
| 22 | 59 | | 495 | 6.2 | .0 | 6.2 | 18 | 26 | 27 | 26 | 1 | .00 | 5 | 4.75 | 6 | 4.75 |
| 9 | 59 | | 495 | 2.4 | .0 | 2.4 | 18 | 26 | 27 | 26 | 1 | .00 | 5 | 4.75 | 6 | 4.75 |
| 5 | 59 | | 495 | 2.0 | .0 | 2.0 | 18 | 21 | 22 | 21 | 1 | .00 | 5 | 4.75 | 6 | 4.75 |
| 17 | 59 | | 495 | 4.4 | .0 | 4.4 | 18 | 18 | 19 | 18 | 1 | .00 | 5 | 4.75 | 6 | 4.75 |
| 20 | 58 | | 495 | 5.4 | .0 | 5.4 | 18 | 22 | 23 | 22 | 1 | .00 | 5 | 4.75 | 6 | 4.75 |
| 2 | 58 | | 495 | 5.4 | .0 | 5.4 | 18 | 22 | 23 | 22 | 1 | .00 | 5 | 4.75 | 6 | 4.75 |
| 24 | 58 | | 495 | 5.5 | .0 | 5.5 | 18 | 23 | 24 | 23 | 1 | .00 | 5 | 4.75 | 6 | 4.75 |
| 26 | 58 | | 495 | 5.7 | .0 | 5.7 | 18 | 23 | 24 | 23 | 1 | .00 | 5 | 4.75 | 6 | 4.75 |
| 30 | 58 | | 495 | 2.4 | .0 | 2.4 | 18 | 24 | 25 | 24 | 1 | .00 | 5 | 4.75 | 6 | 4.75 |
| 13 | 58 | | 495 | 5.6 | .0 | 5.6 | 18 | 23 | 24 | 23 | 1 | .00 | 5 | 4.75 | 6 | 4.75 |
| 16 | 58 | | 495 | 6.1 | .0 | 6.1 | 18 | 25 | 26 | 25 | 1 | .00 | 5 | 4.75 | 6 | 4.75 |

TABLE 3D-continued

MARKETING YARD SHEET
INDIVIDUAL ANIMAL LEVEL

| 21 | 58 | 495 | 5.3 | .0 | 5.3 | 18 | 22 | 23 | 22 | 1 | .00 | 5 | 4.75 | 6 | 4.75 |
| 23 | 58 | 495 | 7.0 | .0 | 7.0 | 18 | 29 | 30 | 29 | 1 | .00 | 5 | 4.75 | 6 | 4.75 |
| 28 | 58 | 495 | 6.8 | .0 | 6.8 | 18 | 28 | 29 | 28 | 1 | .00 | 5 | 4.75 | 6 | 4.75 |
| 29 | 58 | 495 | 5.6 | .0 | 5.6 | 18 | 23 | 24 | 23 | 1 | .00 | 5 | 4.75 | 6 | 4.75 |
| 34 | 57 | 495 | 6.4 | .0 | 6.4 | 18 | 27 | 28 | 27 | 1 | .00 | 5 | 4.75 | 6 | 4.75 |
| 19 | 57 | 495 | 5.8 | .0 | 5.8 | 18 | 24 | 25 | 24 | 1 | .00 | 5 | 4.75 | 6 | 4.75 |

TABLE 3E

MARKETING YARD SHEET
INDIVIDUAL ANIMAL LEVEL

Apr. 22, 1994     C1####  
17:55:11     Page 1  
Measurement Date: Apr. 22, 1994  
DIV: AGR  
SEX: HF  
Owner: Agri Research  
Origin: Little  
Tpe: Crossbred Heifers

| | | | | Projected | | | | | Weights | | DOF | | | Rution | |
|---|---|---|---|---|---|---|---|---|---|---|---|---|---|---|---|
| TAG | PEN | HGp | LOT | DTF | Date | OFW | YG | BE | CURR | PUR | CPD | LPD | ID | No. | Days |
| 25 | 59 | A | 495 | 21 | 0513 | 869 | 3.0 | 118.39 | 811 | 678 | 24 | 10 | 34 | 6 | 12 |
| 11 | 59 | A | 495 | 24 | 0156 | 888 | 3.0 | 118.04 | 826 | 678 | 24 | 10 | 34 | 6 | 12 |
| 15 | 59 | A | 495 | 32 | 0524 | 896 | 3.0 | 117.07 | 813 | 678 | 24 | 10 | 34 | 6 | 12 |
| 4 | 59 | A | 495 | 34 | 0526 | 993 | 3.0 | 117.82 | 905 | 678 | 24 | 10 | 34 | 6 | 12 |
| 3 | 59 | A | 495 | 36 | 0528 | 863 | 3.0 | 116.01 | 769 | 678 | 24 | 10 | 34 | 6 | 12 |
| 18 | 59 | A | 495 | 43 | 0604 | 856 | 3.0 | 114.76 | 744 | 678 | 24 | 10 | 34 | 6 | 12 |
| 14 | 59 | B | 495 | 43 | 0604 | 905 | 3.0 | 115.60 | 793 | 678 | 24 | 10 | 34 | 6 | 12 |
| 22 | 59 | B | 495 | 51 | 0612 | 1089 | 2.0 | 115.92 | 942 | 678 | 24 | 10 | 34 | 6 | 12 |
| 5 | 59 | B | 495 | 56 | 0617 | 912 | 3.0 | 113.99 | 766 | 678 | 24 | 10 | 34 | 6 | 12 |
| 17 | 59 | B | 495 | 58 | 0619 | 787 | 3.0 | 109.23 | 628 | 678 | 24 | 10 | 34 | 6 | 12 |
| 9 | 59 | B | 495 | 68 | 0629 | 1127 | 2.0 | 114.30 | 929 | 678 | 24 | 10 | 34 | 6 | 12 |
| 2 | 58 | A | 495 | 68 | 0629 | 970 | 3.0 | 113.64 | 793 | 678 | 24 | 10 | 34 | 6 | 12 |
| 16 | 58 | A | 495 | 68 | 0629 | 1095 | 2.0 | 113.62 | 897 | 678 | 24 | 10 | 34 | 6 | 12 |
| 20 | 58 | A | 495 | 74 | 0705 | 988 | 3.0 | 112.04 | 785 | 678 | 24 | 10 | 34 | 6 | 12 |
| 23 | 58 | A | 495 | 78 | 0709 | 1260 | 2.0 | 116.07 | 1035 | 678 | 24 | 10 | 34 | 6 | 12 |
| 24 | 58 | A | 495 | 82 | 0713 | 1035 | 2.0 | 110.62 | 798 | 678 | 24 | 10 | 34 | 6 | 12 |
| 26 | 58 | A | 495 | 82 | 0713 | 1038 | 2.0 | 110.69 | 801 | 678 | 24 | 10 | 34 | 6 | 12 |
| 21 | 58 | A | 495 | 82 | 0713 | 962 | 3.0 | 111.62 | 749 | 678 | 24 | 10 | 34 | 6 | 12 |
| 30 | 58 | A | 495 | 90 | 0721 | 1031 | 3.0 | 112.60 | 798 | 678 | 24 | 10 | 34 | 6 | 12 |
| 29 | 58 | A | 495 | 92 | 0723 | 1097 | 3.0 | 112.39 | 843 | 678 | 24 | 10 | 34 | 6 | 12 |
| 13 | 58 | A | 495 | 94 | 0725 | 1055 | 3.0 | 112.77 | 811 | 678 | 24 | 10 | 34 | 6 | 12 |
| 28 | 58 | A | 495 | 102 | 0802 | 1055 | 2.0 | 113.93 | 965 | 678 | 24 | 10 | 34 | 6 | 12 |
| 34 | 57 | A | 495 | 113 | 0813 | 1260 | 2.0 | 112.65 | 931 | 678 | 24 | 10 | 34 | 6 | 12 |
| 19 | 57 | A | 495 | 115 | 0815 | 1159 | 3.0 | 111.58 | 843 | 678 | 24 | 10 | 34 | 6 | 12 |

| | | | | ADG | | | Feed Intake | | | | Treats/HD | | PROCS/Hd | | TOTALS/Hd | |
|---|---|---|---|---|---|---|---|---|---|---|---|---|---|---|---|---|
| TAG | PEN | HGp | LOT | CPD | LPD | ID | PCP | ACP | L7D | ID | Proj | Act | Proj | Act | Proj | TD |
| 25 | 59 | A | 495 | 4.2 | 5.4 | 4.6 | 22 | 26 | 25 | 25 | 1 | .00 | 5 | 4.75 | 6 | 4.75 |
| 11 | 59 | A | 495 | 2.9 | 5.8 | 3.7 | 21 | 27 | 25 | 26 | 1 | .00 | 5 | 4.75 | 6 | 4.75 |
| 15 | 59 | A | 495 | 2.3 | 5.8 | 3.3 | 21 | 26 | 25 | 26 | 1 | .00 | 5 | 4.75 | 6 | 4.75 |
| 4 | 59 | A | 495 | 2.6 | 6.4 | 3.7 | 21 | 29 | 28 | 29 | 1 | .00 | 5 | 4.75 | 6 | 4.75 |
| 3 | 59 | A | 495 | 3.8 | 5.2 | 4.2 | 21 | 25 | 23 | 24 | 1 | .00 | 5 | 4.75 | 6 | 4.75 |
| 18 | 59 | A | 495 | 3.2 | 5.1 | 3.7 | 21 | 24 | 23 | 23 | 1 | .00 | 5 | 4.75 | 6 | 4.75 |
| 14 | 59 | B | 495 | 2.8 | 5.5 | 3.6 | 21 | 26 | 24 | 25 | 1 | .00 | 5 | 4.75 | 6 | 4.75 |
| 22 | 59 | B | 495 | 5.2 | 6.2 | 5.5 | 21 | 31 | 29 | 29 | 1 | .00 | 5 | 4.75 | 6 | 4.75 |
| 5 | 59 | B | 495 | 3.6 | 5.2 | 4.1 | 21 | 25 | 23 | 24 | 1 | .00 | 5 | 4.75 | 6 | 4.75 |
| 17 | 59 | B | 495 | 2.2 | 4.4 | 2.8 | 21 | 20 | 19 | 20 | 1 | .00 | 5 | 4.75 | 6 | 4.75 |
| 9 | 59 | B | 495 | 4.0 | 6.3 | 4.7 | 21 | 30 | 28 | 29 | 1 | .00 | 5 | 4.75 | 6 | 4.75 |
| 2 | 58 | A | 495 | 3.5 | 5.4 | 4.0 | 21 | 26 | 24 | 25 | 1 | .00 | 5 | 4.75 | 6 | 4.75 |
| 16 | 58 | A | 495 | 3.8 | 6.1 | 4.5 | 21 | 29 | 27 | 28 | 1 | .00 | 5 | 4.75 | 6 | 4.75 |
| 20 | 58 | A | 495 | 3.4 | 5.4 | 4.0 | 21 | 26 | 24 | 25 | 1 | .00 | 5 | 4.75 | 6 | 4.75 |
| 23 | 58 | A | 495 | 5.0 | 7.0 | 5.6 | 21 | 34 | 32 | 32 | 1 | .00 | 5 | 4.75 | 6 | 4.75 |
| 24 | 58 | A | 495 | 3.2 | 5.5 | 3.9 | 21 | 26 | 24 | 25 | 1 | .00 | 5 | 4.75 | 6 | 4.75 |
| 26 | 58 | A | 495 | 2.5 | 5.7 | 3.4 | 21 | 26 | 24 | 25 | 1 | .00 | 5 | 4.75 | 6 | 4.75 |
| 21 | 58 | A | 495 | 2.2 | 5.3 | 3.1 | 21 | 24 | 23 | 24 | 1 | .00 | 5 | 4.75 | 6 | 4.75 |
| 30 | 58 | A | 495 | 1.8 | 5.8 | 3.0 | 21 | 26 | 24 | 25 | 1 | .00 | 5 | 4.75 | 6 | 4.75 |
| 29 | 58 | A | 495 | 4.4 | 5.6 | 4.7 | 21 | 27 | 26 | 26 | 1 | .00 | 5 | 4.75 | 6 | 4.75 |

TABLE 3E-continued

MARKETING YARD SHEET
INDIVIDUAL ANIMAL LEVEL

| 13 | 58 | A | 495 | 3.3 | 5.6 | 3.9 | 21 | 26 | 25 | 25 | 1 | .00 | 5 | 4.75 | 6 | 4.75 |
| 28 | 58 | A | 495 | 3.1 | 6.8 | 4.2 | 21 | 31 | 29 | 30 | 1 | .00 | 5 | 4.75 | 6 | 4.75 |
| 34 | 57 | A | 495 | 3.8 | 6.4 | 4.5 | 21 | 30 | 28 | 29 | 1 | .00 | 5 | 4.75 | 6 | 4.75 |
| 19 | 57 | A | 495 | 3.6 | 5.8 | 4.2 | 21 | 27 | 26 | 26 | 1 | .00 | 5 | 4.75 | 6 | 4.75 |

TABLE 3F

Pen Closeout Report
Research-Division
As of Apr. 22, 1994
Lot 495 Pen 59 Owner AGRI Agri Research Center, Inc. 100.00

| | | Pounds | | Dollars | |
|---|---|---|---|---|---|
| Item | Head | Total | Avg | /CWT | /Head | Total |

INCOME

| Inventory | 10 | 7,867 | 787 | 73.25 | 576.28 | 5,762.80 |

EXPENSES

| Cattle: | 10 | 6,775 | 678 | 76.00 | 514.90 | 5,149.00 |

HEIFERS

| Feed and Other: | | | COG | /Head | Total |
|---|---|---|---|---|---|
| FEED CHARGES | | | 50.15 | 54.77 | 547.60 |
| CATTLE | | | 0.16 | 0.17 | 1.70 |

TABLE 3F-continued

Pen Closeout Report
Research-Division
As of Apr. 22, 1994
Lot 495 Pen 59 Owner AGRI Agri Research Center, Inc. 100.00

| INSURANCE YARDAGE | 1.56 | 1.70 | 17.00 |
| PROCESSING | 4.35 | 4.75 | 47.40 |
| Sub Total Feed and Other | 56.21 | 61.38 | 613.80 |
| Total | | 576.28 | 5,762.80 |
| Profit/Loss | | 0.00 | 0.00 |

Performance Data

| Total Pounds Gained | 1,092.00 | Total Proc & Med | 47.45 |
| /Head | 109.20 | /Head | 4.75 |
| Average Daily Gain | 3.21 | Total Deads | 0.00 |
| Daily Feed Cost/Head | 1.61 | % Death Loss | 0.00% |
| Daily Total Cost/Head | 1.81 | % Shrink into Yard | 0.00% |
| Total Pounds Fed | 8,040.86 | Total Feed Cost | 547.69 |
| Total Pounds Fed/Head | 804.09 | Avg Ration Cost/Ton | XXXXX |
| Avg Daily Consumption | 23.65 | Cost of Gain | 56.21 |
| Wet Conversion | 7.36 | (Deads in) | |
| Dry Conversion | 6.02 | Cost of Gain | 56.21 |
| In Mar. 19, 1994 Out: | | (Deads out) | |
| | | Total Head Days | 340.00 |
| | | Average Days on Feed | 34.00 |

SUMMARY
10 HEIFERS
In Wt 678 Out Wt 787
Gained 3.21 for 34 DOF
Cost of Gain: 56.21
Profit 0.00 (Before Interest)

TABLE 3G

Close-Out Summary
BY LOT

LOT: 42894
PENS: 553　　　　　　　　　　HEAD 27　　　　　　SEX S　　　　　　DATE Apr. 28, 1993
OTAL PFT: $4,957.98

| VID | PFT | TCOG | ADG | PE | QG | YG | HCW | DP % | LW | PWT | DOF | FCOG | PROC | TREAT | TCOG |
|---|---|---|---|---|---|---|---|---|---|---|---|---|---|---|---|
| SIRE: ANGUS DAM: BRAFORD |||||||||||||||| 
| 567 | 329.96 | 45.00 | 3.37 | 6.31 | CH− | 4.0 | 875 | 66.5 | 1315 | 634 | 202 | 43.00 | 11.36 | 0.00 | 45.00 |
| 563 | 64.18 | 45.00 | 3.64 | 6.25 | SE+ | 5.0 | 777 | 62.8 | 1238 | 648 | 162 | 42.00 | 11.36 | 0.00 | 45.00 |
| 564 | 76.03 | 57.00 | 2.97 | 7.16 | SE+ | 4.2 | 736 | 61.8 | 1190 | 590 | 202 | 48.00 | 11.36 | 33.25 | 57.00 |
| 565 | 233.46 | 42.00 | 3.93 | 5.79 | SE− | 5.0 | 915 | 66.6 | 1373 | 736 | 162 | 39.00 | 11.36 | 0.00 | 42.00 |
| 566 | 122.80 | 66.00 | 2.47 | 9.20 | SE− | 3.3 | 699 | 65.3 | 1070 | 620 | 182 | 62.00 | 11.36 | 0.00 | 56.00 |
| AVG | 165.29 | 51.00 | 3.28 | 6.94 | | 4.30 | 800 | 65 | 1237 | 646 | 182 | 46.80 | 11.36 | 6.65 | 51.00 |
| SIRE: ANGUS DAM: BRANGUS ||||||||||||||||
| 423 | 151.91 | 39.00 | 3.57 | 5.98 | SE− | 2.9 | 731 | 61.9 | 1181 | 460 | 202 | 36.00 | 11.36 | 0.00 | 39.00 |
| 421 | 296.59 | 40.00 | 3.87 | 5.69 | SE− | 3.9 | 811 | 62.6 | 1296 | 592 | 182 | 38.00 | 11.36 | 0.00 | 40.00 |
| 425 | 74.46 | 63.00 | 2.23 | 9.17 | CH | 3.2 | 661 | 64.7 | 1022 | 508 | 231 | 60.00 | 11.36 | 0.00 | 63.00 |
| 420 | 113.36 | 43.00 | 3.23 | 6.61 | SE+ | 2.7 | 693 | 62.2 | 1114 | 462 | 202 | 40.00 | 11.36 | 0.00 | 43.00 |
| 427 | 282.11 | 45.00 | 3.45 | 6.38 | SE+ | 3.5 | 775 | 64.1 | 1210 | 582 | 182 | 43.00 | 11.36 | 0.00 | 45.00 |
| 422 | 198.62 | 45.00 | 3.06 | 6.97 | CH− | 3.0 | 734 | 64.5 | 1138 | 480 | 215 | 42.00 | 11.36 | 0.00 | 45.00 |
| AVG | 186.18 | 45.83 | 3.24 | 6.80 | 0.00 | 3.20 | 734 | 63 | 1160 | 514 | 202 | 43.17 | 11.36 | 0.00 | 45.83 |

TABLE 3G-continued

Close-Out Summary
BY LOT

SIRE: ANGUS DAM: ANGUS

| | | | | | | | | | | | | | | |
|---|---|---|---|---|---|---|---|---|---|---|---|---|---|---|
| 619 | 254.93 | 42.75 | 3.25 | 7.60 | CH | 2.3 | 742 | 66.6 | 1114 | 574 | 166 | 38.73 | 10.04 | 0.00 | 42.75 |
| 616 | −129.50 | 58.02 | 2.59 | 9.50 | SE | 3.0 | 701 | 62.9 | 1114 | 558 | 215 | 50.27 | 10.04 | 19.50 | 58.02 |
| 633 | 231.38 | 46.77 | 3.17 | 8.50 | CH | 2.8 | 762 | 63.2 | 1205 | 562 | 203 | 43.17 | 10.04 | 0.00 | 46.77 |
| 628 | 222.01 | 53.51 | 3.08 | 8.60 | CH | 2.7 | 813 | 65.7 | 1238 | 612 | 203 | 45.61 | 10.04 | 25.58 | 53.51 |
| 661 | 255.60 | 43.86 | 3.15 | 7.90 | CH | 3.7 | 822 | 65.3 | 1258 | 660 | 190 | 40.12 | 10.04 | 0.00 | 43.86 |
| 929 | 154.05 | 52.96 | 2.58 | 9.70 | CH | 4.1 | 708 | 63.8 | 1109 | 554 | 215 | 48.81 | 10.04 | 0.00 | 52.96 |
| AVG | 164.75 | 49.65 | 2.97 | 8.63 | 0.00 | 3.10 | 758 | 65 | 1173 | 587 | 199 | 44.45 | 10.04 | 7.51 | 49.65 |

SIRE: ANGUS DAM: HERF

| | | | | | | | | | | | | | | |
|---|---|---|---|---|---|---|---|---|---|---|---|---|---|---|
| 907 | 178.77 | 45.63 | 3.05 | 8.20 | CH | 2.1 | 741 | 64.3 | 1152 | 646 | 166 | 41.34 | 10.04 | 0.00 | 45.63 |
| 908 | 257.39 | 42.53 | 3.60 | 6.80 | CH | 2.4 | 906 | 63.1 | 1435 | 652 | 215 | 36.16 | 10.04 | 25.58 | 42.53 |
| 902 | 266.58 | 42.83 | 3.25 | 7.70 | CH | 2.9 | 811 | 63.7 | 1181 | 642 | 166 | 38.81 | 10.04 | 0.00 | 42.83 |
| 903 | 181.05 | 44.14 | 3.15 | 7.90 | SE | 2.6 | 788 | 64.6 | 1219 | 696 | 166 | 39.99 | 10.04 | 0.00 | 44.14 |
| 906 | 203.41 | 50.74 | 2.74 | 9.00 | CH | 3.1 | 748 | 69.6 | 1075 | 620 | 166 | 45.97 | 10.04 | 0.00 | 50.74 |
| 905 | 183.21 | 42.67 | 3.26 | 7.60 | SE | 2.3 | 768 | 63.7 | 1205 | 664 | 166 | 38.66 | 10.04 | 0.00 | 42.67 |
| 904 | 216.42 | 44.13 | 3.10 | 8.10 | CH | 2.5 | 809 | 63.6 | 1272 | 606 | 215 | 40.68 | 10.04 | 0.00 | 44.13 |
| 910 | 171.61 | 49.23 | 2.75 | 9.00 | CH | 3.0 | 792 | 64.4 | 1229 | 632 | 215 | 45.38 | 10.04 | 0.00 | 49.23 |
| 911 | 172.01 | 50.52 | 2.75 | 9.10 | CH | 1.2 | 686 | 63.2 | 1035 | 628 | 166 | 45.77 | 10.04 | 0.00 | 50.52 |
| 909 | 245.58 | 43.41 | 3.15 | 7.90 | CH | 3.8 | 893 | 65.0 | 1373 | 696 | 215 | 40.01 | 10.04 | 0.00 | 43.41 |
| AVG | 202.6 | 45.583 | 3.083 | 8.13 | 0 | 2.6 | 794 | 65 | 1223 | 649 | 186 | 41.277 | 10.04 | 2.558 | 45.583 |

LOT AVERAGE

| | | | | | | | | | | | | | | |
|---|---|---|---|---|---|---|---|---|---|---|---|---|---|---|
| AVG | 183.63 | 43.34 | 2.61 | 6.42 | | 2.91 | 703 | 59 | 1090 | 548 | 174 | 39.60 | 9.65 | 3.58 | 43.34 |
| STD | | 15.02 | 1.22 | 3.06 | | 1.21 | 230 | 19 | 356 | 185 | 59 | 13.72 | 3.11 | 8.66 | 15.02 |
| MAX | 329.96 | 66.00 | 3.93 | 9.70 | | 5.00 | 915 | 70 | 1435 | 736 | 231 | 62.00 | 11.36 | 33.25 | 66.00 |
| MIN | −129.50 | 39.00 | 2.23 | 5.69 | | 1.20 | 661 | 62 | 1022 | 460 | 162 | 36.00 | 10.04 | 0.00 | 39.00 |
| RANG | 469.46 | 27.00 | 1.70 | 4.01 | | 3.80 | 254 | 8 | 413 | 276 | 69 | 26.00 | 1.32 | 33.25 | 27.00 |

TABLE 4A

Feedlot Business System

Type in three letters ahs to start the Animal Health Program
1. Type FMS
2. TERM = (ANSI) typeway150
   Feedlot Business System
   Agri Research Database
   ver. 4.1
   Mar. 03, 1994
   Enter user ID____
   Access Micro-System
3. Push the DEL key on the keyboard
4. S Type ECM
   ELECTRONIC CATTLE MANAGEMENT PROGRAM
   0 - Exit
   1 - Perform an ECM Session
   2 - Modify ECM Session Configuration
   3 - Print the Results of an ECM Session
5. Type 1 then press the Enter key
   ELECTRONIC CATTLE MANAGEMENT PROGRAM
   Currently defined Session Types:
       1   2   3   4
   Choose Session Type from above list
6. Type 2 then press the Enter key

TABLE 4B

| | |
|---|---|
| 1 - Session Types: 2 | |
| 2 - Description: Demo | |
| 3 - Process control computer present? | [yes] |
| 4 - Unused | [no] |
| 5 - Type of Sorting ? | [AR] |
| 6 - Read Electronic Ear Tags? | [yes] |
| 7 - Insert New Visual Ear Tags ? | [no] |
| 8 - Cattle Type? | [not Recorded] |
| 9 - Frame Type? | [not Recorded] |
| 10 - Flesh Type? | [not Recorded] |
| 11 - AGE? | [not Recorded] |
| 12 - Weight ? | [Automatically] |
| 13 - Back Fat ? | [Automatically] |

TABLE 4B-continued

| | |
|---|---|
| 14 - Loin Depth ? | [not Recorded] |
| 15 - Rump Height? | [Keyed In] |
| 16 - Rump Width ? | [not Recorded] |
| 17 - Shoulder Height ? | [not Recorded] |
| 18 - Shoulder Width? | [not Recorded] |
| 19 - Top Length ? | [not Recorded] |
| 20 - Body Length ? | [not Recorded] |
| 21 - Girth ? | [not Recorded] |
| Enter row = to change, 0 to finish | |
| or 99 to delete session | |
| 7. Type 0 then push the Enter key | |
| 1 - Sort Name: AR | |
| 2 - Description: | |
| 3 - Sorting Criteria? | [Optimum END date] |
| 4 - FLEX Sort? | [yes] |
| 5 - FLEX pen Number? | [3] |
| 6 - Sort Pen Count? | [3] |
| Number to change -or- 0 when finished | |
| 8. Type 0 then push the Enter key | |
| Number of head to be sorted in the Session | |

TABLE 4C

How many Animals should be sorted into each group

| | |
|---|---|
| 1 - Sort Pen | 1 final count____? |
| 2 - Sort Pen | 2 final count____? |
| 3 - Flex Pen | 3 final count____? |
| 4 - Sort Pen | 4 final count____? |

Number to Change -or- 0 when finished
9. Type 0 then press Enter key
ELECTRONIC CATTLE MANAGEMENT PROGRAM Animal ?? of ??

| Lot | Pen | Sort Pen | Head Count |
|---|---|---|---|
| EID | | | |
| Tag 0 | | 1 | 0 |
| Frame 0 | | 2 | 0 |
| Weight 0 | | FLEX | 0 |

TABLE 4C-continued

| | | |
|---|---|---|
| Rump Ht. | 4 | 0 |
| Back fat | 5 | 0 |
| OED Dec. 31, 1999 | 6 | 0 |

10. Are these cattle all from the same lot?
11. . . . And what is this lot?
12. Are these cattle all from the same pen?
13. . . . And what is this pen?
14. Enter the Date that sorting occurred (usually today's date)?
    Trying to establish communication with Process Control Computer

TABLE 4D

Process Control Setup

1. Power on computer
    C:ECM>
2. Type ECM
    *ENTER RUN PARAMETERS*
    LOG FILE NAME_____
3. Enter today's date 040194
    Sort Types:
    0 - No Sort
    1 - FBS Sort
    2 - Weight
    3 - Days of Feed Sort
    4 - Manual Sort
    Enter Sort Type ==
4. If you Enter 0 go to #9
5. If you Enter 1 go to #16
6. If you Enter 2 go to #17
7. If you Enter 3 go to #37
8. If you Enter 4 go to #60
    Sort Type 0
9. Catch Heads (Y N) ==
10. Squeeze Animals (Y N) ==
11. Weigh Animals (Y N) ==
12. Read Electronic ID (Y N) ==
13. Do Animals already have EID Tags (Y N) ==
14. Read Back Fat (Y N) ==
15. Take Video Measurements (Y N) ==
    ECM Computer is Ready to go

TABLE 4E

Sort Type 1

16. Is this a Flex Grop Sort (Y N) ==
    If Y the program will Start
    If N go to step #9
    Sort Type 2

17. Minimum Weght for Pen 1 ==
18. Maximum Weight for Pen 1 ==
19. Minimum Weight for Pen 2 ==
20. Maximum Weight for Pen 2 ==
21. Minimum Weight for Pen 3 ==
22. Maximum Weight for Pen 3 ==
23. Minimum Weight for Pen 4 ==
24. Maximum Weight for Pen 4 ==
25. Minimum Weight for Pen 5 ==
26. Maximum Weight for Pen 5 ==
27. Minimum Weight for Pen 6 ==
28. Maximum Weight for Pen 6 ==
29. Minimum Weight for Pen 7 ==
30. Maximum Weight for Pen 7 ==
31. Lot Number ==
32. Source Pen Number ==
33. Head Count ==
34. Breed Frame type ==
35. Average Weight ==
36. Go To #9

TABLE 4F

37. Sort Type 3
38. Minimum Weight for Pen 1 ===
39. Maximum Weight for Pen 1 ===
40. Minimum Weight for Pen 2 ===
41. Maximum Weight for Pen 2 ===
42. Minimum Weight for Pen 3 ===
43. Maximum Weight for Pen 3 ===
44. Minimum Weight for Pen 4 ===
45. Maximum Weight for Pen 4 ===
46. Minimum Weight for Pen 5 ===
47. Maximum Weight for Pen 5 ===
48. Minimum Weight for Pen 6 ===
49. Maximum Weight for Pen 6 ===
50. Minimum Weight for Pen 7 ===
51. Maximum Weight for Pen 7 ===
52. Lot Number ===
53. Source Number ===
54. Head Count ===
55. Breed, Frame Type ===
56. Average Weight ===
57. Out Weight ===
58. Average Daily Gain ===
    Days on Feed??? (calculated by computer)
59. Go To #9
60. Sort Type 4
61. Go To #9

Animal Health History

This subsection describes various process steps and system components for providing up-to-date health histories of animals. These process steps and system components can be used in conjunction with evaluation of an animal's respiratory or circulatory condition, as discussed above. For example, information gather by imaging and evaluating an animal's respiratory or circulatory system, such as respiratory damage designations, can be entered into the described electronic system components and processed alone or with other animal characteristics as described below.

Figure 31:
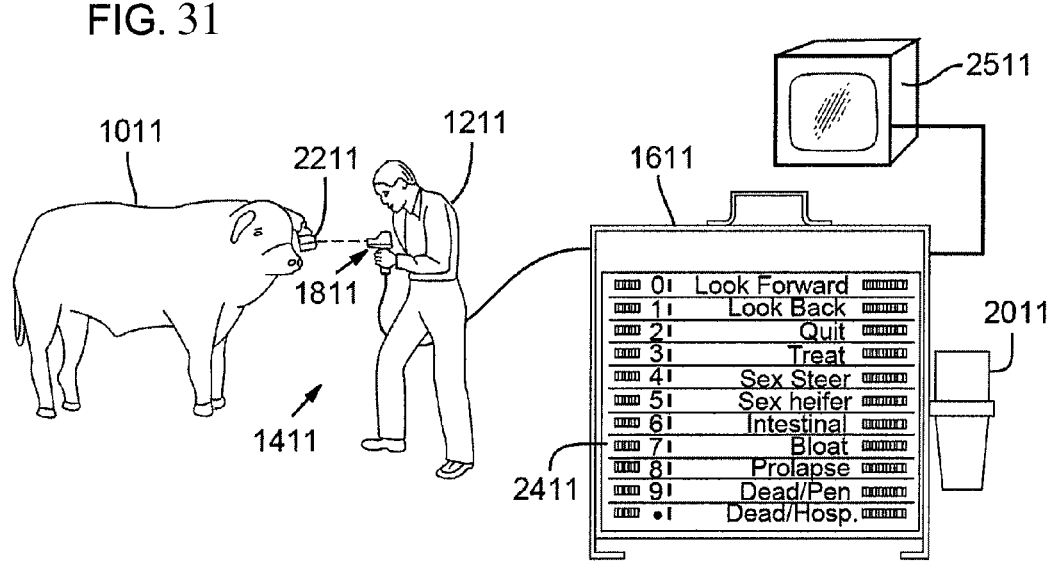
FIG. 31 is an illustration of a portable hospital unit.

Referring now to FIG. 31, there is shown an animal 1011 and an operator 1211 in an area of a cattle feedlot referred to as an animal hospital 1411. An animal 1011 may be brought to the hospital 1411 for a check on its physical condition, for treatments that are administered to all animals in a particular lot, and if an animal is to be individually treated for sickness. Typically, the animal hospital 1411 includes a cattle chute and a head gate (not shown) for holding the animal stationary while its weight and temperature are checked and any drugs are administered.

As indicated in FIG. 31, the system in this embodiment includes a portable hospital unit 1611 that can be transported to the hospital 1411 for use by the operator 1211. This portability enables the operator to care for cattle with a single unit at several hospitals located around the feedlot rather than at a single hospital to which all cattle must be directed. Coupled to the portable unit 1611 is a means for entering data into the unit such as an optical character reader, which in this first embodiment comprises a portable bar code scanner 1811 available from a number of sources including the MSI Data Corporation under the name SYMBOLTEC LS8100. The scanner 1811, which is stored in a holster 2011 mounted to a side of the unit 1611, is adapted to read indicia means such as an ear tag 2211 bearing optical characters such as a bar code for uniquely identifying each animal. Rather than having to write down the animal's identifying number on a sheet, therefore, the operator 1211 need only scan the ear tag 2211 and the identifying number is electronically read and accurately recorded within the unit 1611. The portable unit also includes a character menu sheet 2411 that bears optical characters such as bar codes corresponding to treatment data comprising the observed physical condition of the animal as well as drug treatments that may be administered. The sheet 2411 is mounted behind a clear plastic door of the unit 1611 and includes bar codes on the sheet's left and right margins. The bar codes on the left margin are for entering identification numbers of drugs, numerical quantities, and menu selection steps during program execution. The bar codes on the right margin are for entering sickness codes, sex of the animal, and commands for scrolling through the prior health history, for entering data and for quitting after observation or treatment is concluded. The operator can thus enter the identity of the animal and treatment data by simply scanning the menu sheet 2411 with the scanner 1811. The treatment data is recorded along with the animal's identifying number within the unit 1611. Visual feedback to the operator 1211 of the prior health history and the data just entered is provided by a display device such as video monitor 2511. The monitor 2511 also displays the program prompts provided to the operator 1211 by the unit 1611 for entering the data, as will be described in detail hereafter.

Figure 32:
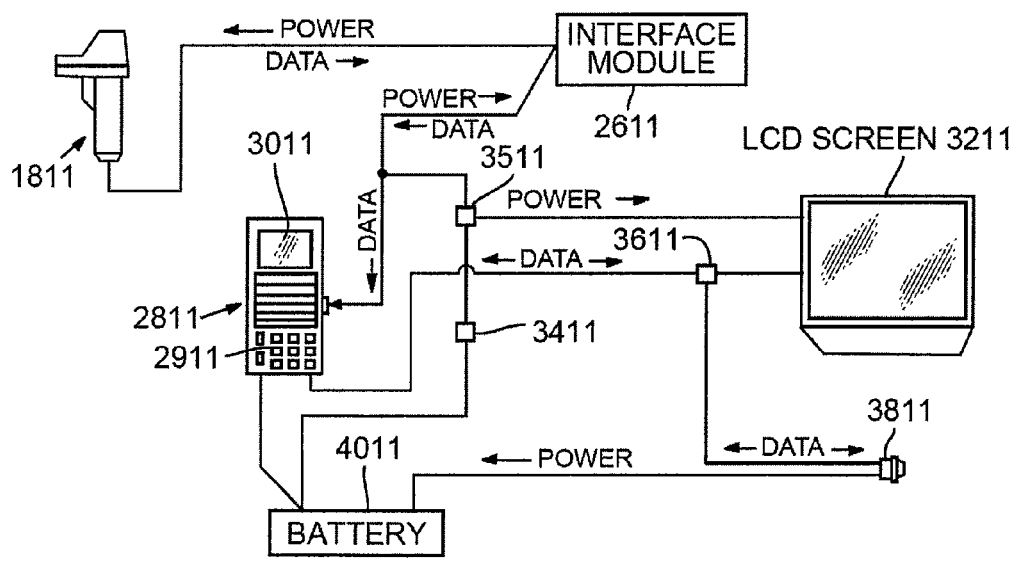
FIG. 32 is a schematic diagram of the portable hospital unit shown in FIG. 31.

FIG. 32 is a schematic diagram showing the elements within the chassis of the unit 1611. The scanner 1811 is connected via a spring cord to a conventional laser interface module 2611 such as MSI Data Corporation Model 1365 for communicating data represented by optical characters to a portable terminal 2811. The data terminal 2811 is of conventional design such as a PDTIII available from the MSI Data Corporation and includes a microprocessor, associated memory for storing an instruction program and for recording data, a keyboard 2911 for data entry, and a display 30 for displaying executing programs and recorded data. The keyboard 2911 is reached through the door opening of the unit 1611 and is an alternative to the scanner 1811 for entering data that is not bar coded, such as the time and date of treatment and the lot number of the animal, or if the scanner malfunctions. Also shown in the schematic is an optional liquid crystal display (LCD) screen 3211 connected to the terminal 28 through a reset switch 3411, a power switch 3511, and a selector switch 3611. The reset switch 3411 reinitializes the module 2611. The switch 3511 controls power to the scanner 1811 and LCD screen 3211 to electrically disconnect them when not required by the operator. The selector switch 3611 directs the data that is entered via the scanner 1811 into the terminal 2811 to either the LCD screen 3211 (visible through the transparent door of unit 1611 above the menu sheet 2411) or to the video monitor 2511 via a serial data connector 3811 such as an RS232 port. These additional display devices are optionally available because of the difficulty in reading the display 3011 from a distance. The LCD screen 3211 is normally selected by a single operator while the monitor 2511 is usually employed when a crew is working in the hospital 1411 and a number of the members must view the display simultaneously. The power source for the unit 1611 is a battery 4011 which is charged through a power supply line via the connector 3811.

Referring to FIG. 33, the data treatment recorded by the unit 1611 is periodically transferred to a host computer 5011 remote from the animal hospital 1411 to update the health histories of observed and treated animals. The host computer 5011 is intended for collecting data on feedlot operations in general and maintains the cumulative health history of each animal in the feedlot. The portable unit 1611 when transferring the data is coupled to the host computer 5011 via a conducting cable 5211. The computer 5011 in turn is adapted to collect the treatment data recorded within the portable unit 1611 and produce an accumulation of such data associated with each animal. This accumulation of data comprises the animal's health history. After the current data is transferred, the computer 5011 is programmed to transfer to unit 1611 in return the up-to-date health history of each animal as well as current feedlot information, such as newly established lot numbers. The cable 5211 also includes the power supply line for charging the battery 4011 within the unit 1611.

FIG. 34 is a schematic diagram showing the elements comprising the computer 5011. The computer itself is of conventional design and includes a video monitor 5411 for displaying data and a keyboard 5611 for data entry. The computer 5011 includes an interface board 5811 for receiving data entered via a second bar code scanner 6211 and a second laser interface module 6411. The interface board 5811 transfers the data to and from a central microprocessor 6611 equipped with internal memory and disk drives. Data and instruction programs stored in memory and on disk can be viewed on monitor 5411. The computer 5011 is also connected to a printer 6811 for printing the health histories and other related documents. Power is supplied to the computer through a conventional power supply 7211. The power supply 7211 is also coupled to a battery charger 7411 which supplies power for the unit 1611. The up-to-date animal health histories, programming, and other feedlot information are transmitted as serial data from the computer 5011 along with power to the unit 1611 via a connector 7611 coupled to the cable 5211.

The host computer 5011 serves a number of functions in addition to collecting treatment data to produce health histories for each animal treated. One related function is tracking inventory of drugs for treatment of the animals. Referring again to FIG. 34, computer 5011 is located adjacent to a drug room 7711 which stores drug inventory. Each drug container 7811 is labeled with a bar code 7911 for identifying the drugs therein and a menu sheet 8011 is present for entering the amount of drugs within each container when removed for drug treatment and the amount remaining in each container when returned for restocking or when additional amounts are added to inventory. The computer 5011 is programmed to compare the net amount of drugs taken from the inventory as communicated by the scanner 6211 against the amount of drugs used in treatment in the animal hospital 1411 as communicated by the scanner 1811. The difference between the two amounts over a predetermined time can thereby be determined for monitoring loss due to breakage, theft, etc. This difference, as well as the comparable amounts, are printed at request as a drug usage report as will be described.

Figure 35:
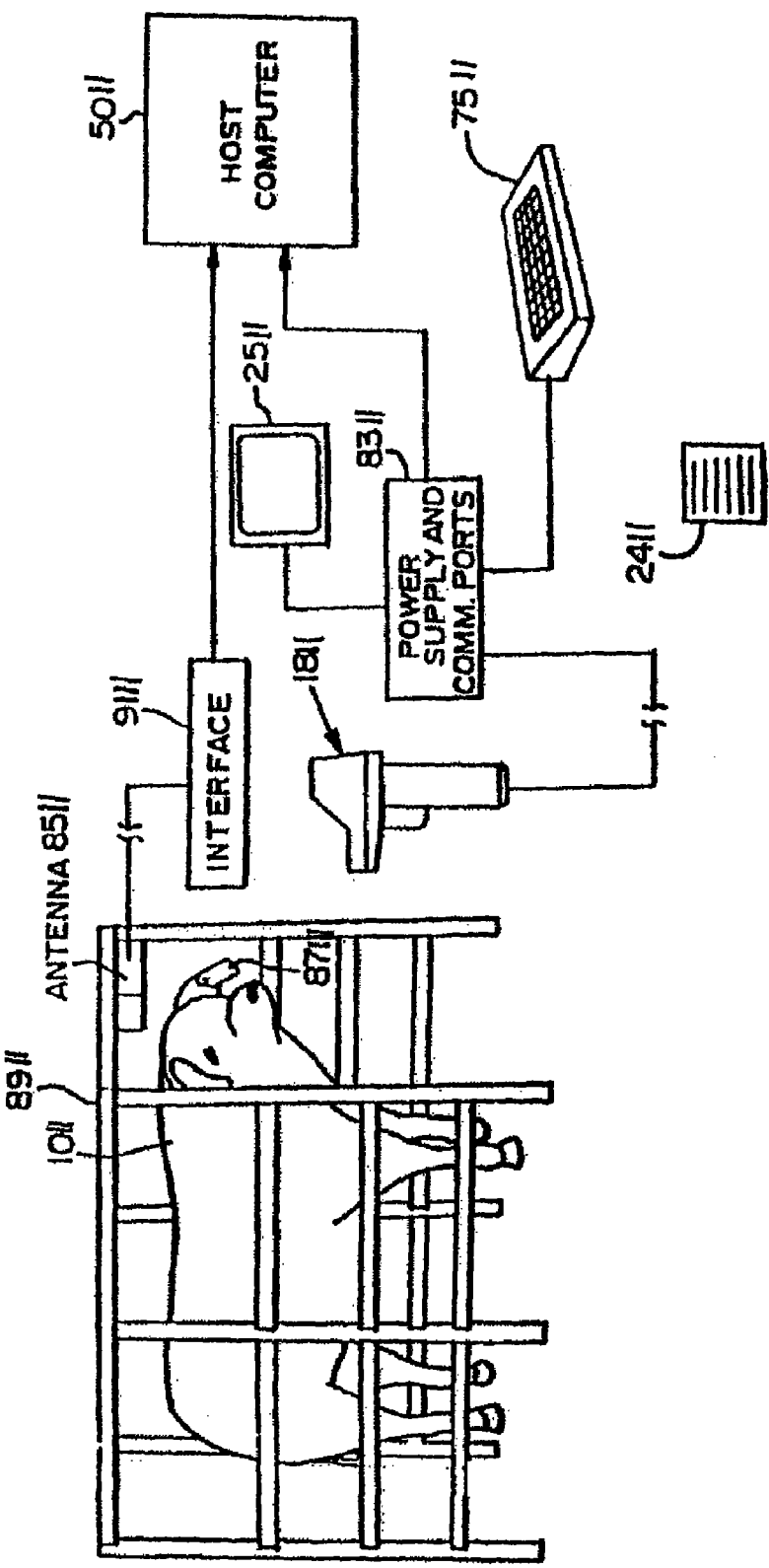
FIG. 35 is a schematic diagram of an animal health system.

FIG. 35 shows a second embodiment of the system for possible use where a continuous source of power such as AC power is available in the hospital 1411. The system includes a remote "dumb" terminal comprising the scanner 1811, the video display 2511, and a keyboard 7511, all in communication with the host computer 5011 through a node 8311 that includes communication ports and a power supply. The terminal acts an extension of host computer 5011, relaying treatment data to the computer in real time and displaying the up-to-date health histories transferred to the display from the host computer. This real time communication, when possible, avoids the need for physically moving the portable unit to the host computer and the delay in updating the prior health histories of the animals.

FIG. 35 also shows data entry means such as a transmitter-receiver antenna 8511 and indicia means such as transponder 8711 attached to an ear for identifying the animal 1011. The antenna is preferably of a type similar to an RDREO1, integrater reader available from Allflex International and the tag is preferably a transponder of the type similar to an EID ear tag also available from Allflex International. The antenna is mounted along side the cattle chute 8911 and emits a signal that reaches the transponder 8711 when animal 1011 passes by the antenna 8511. The tag 8711 in response emits a unique signal identifying the animal, which is electronically "read" by the antenna 8711 and communicated to the host computer 5011 via a computer interface unit 9111 such as a CIUMO1 from Allflex International. Alternatively, the transponder 8711 may be an active transmitter that continuously emits a radio signal for reception by a passive antenna 8511. This means for automatically identifying the animal avoids the delay associated with the operator having to move to each animal for identifying it by scanning the ear tag. The entry of treatment data, however, is handled in the same manner as in the first embodiment, with the scanner 1811 utilized to scan bar codes on menu sheet 2411 corresponding to physical conditions and any drug treatment administered to the animal. The keyboard 7511, however, is available if data cannot be entered via the antenna 8511 or scanner 1811.

Figure 36A:
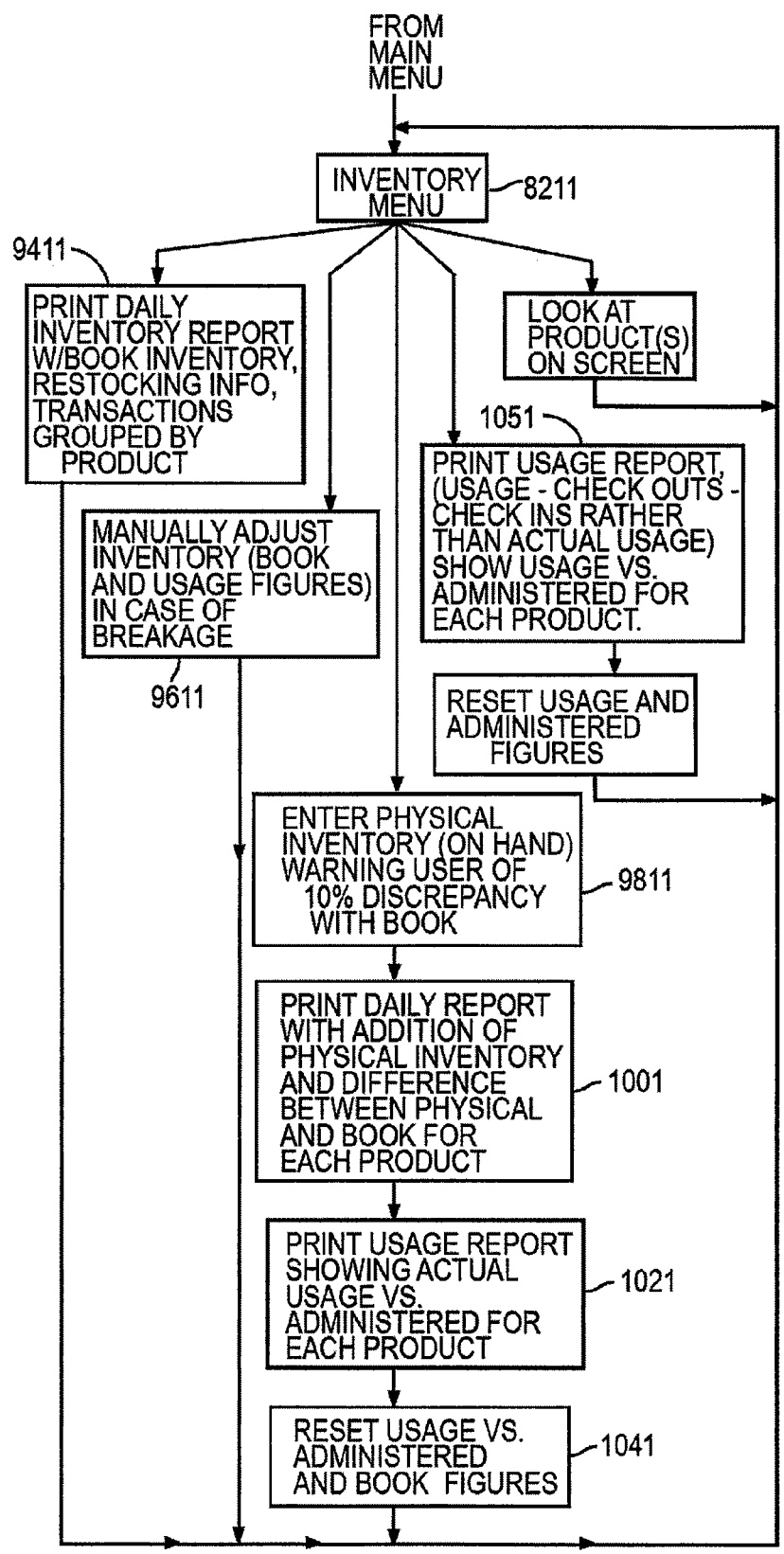
FIGS. 36A-B are flowcharts illustrating programming of the host computer.
Figure 36B:
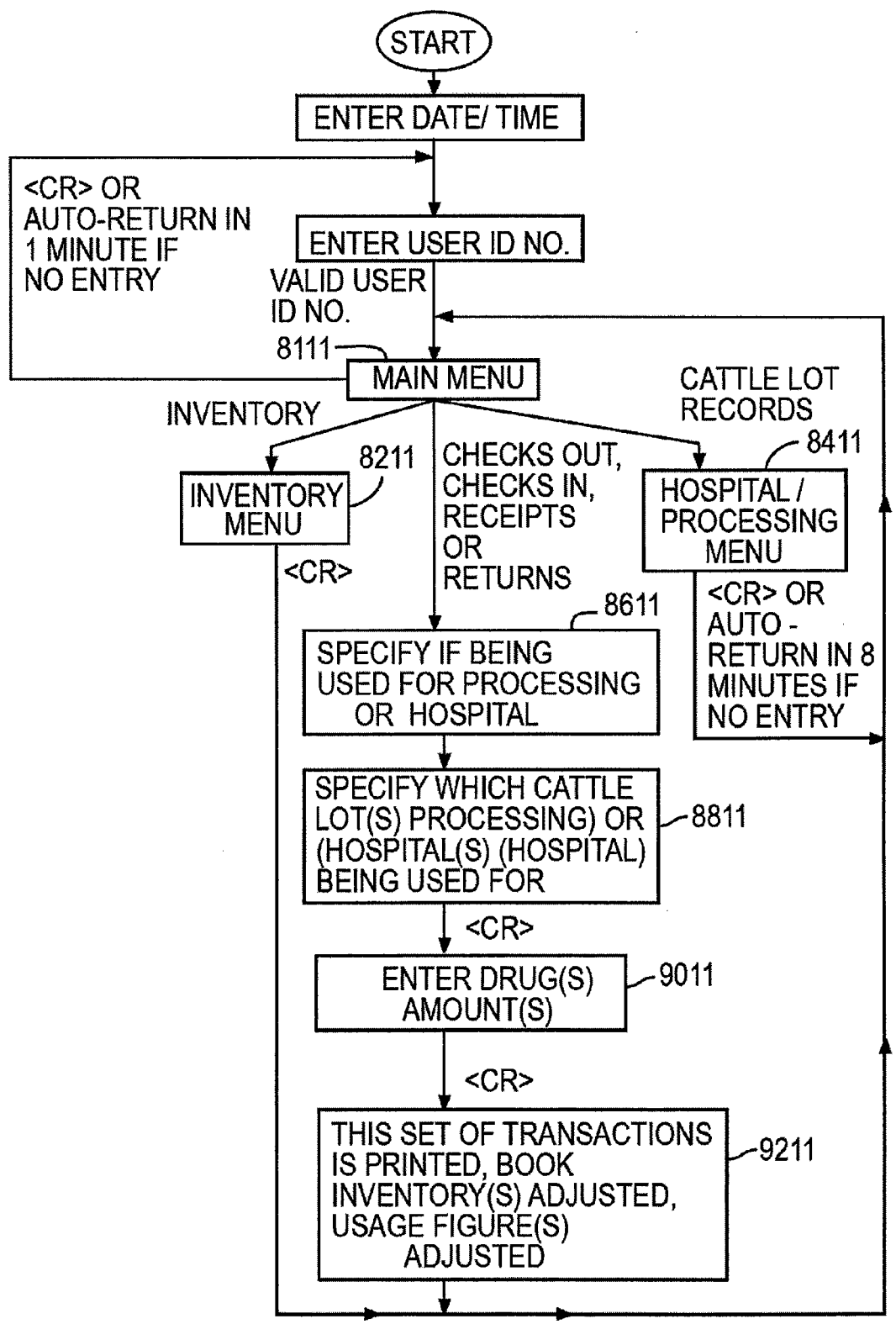

The computer 5011 and data terminal 2811 within unit 1611 are programmed in BASIC, according to the method illustrated in the flowcharts of FIGS. 36 through 38. FIGS. 36A and B show the options available to the operator upon logging onto the computer 5011. A main menu (8111) appears with three options. An inventory menu (8211) is selected for working with the drug inventory; a hospital/processing menu (8411) is selected for working with the cattle feedlot records; or the procedure for monitoring the removal and restocking of drugs is selected as drugs are to be used, such as in the animal hospital 1411. With this third option, the operator scans the bar code 7911 of the containers 7811 that contain drugs required for treatment. He is then prompted to specify the purpose of the drug (8611), specify the cattle lots the drug is being used for (8811), and to enter the drug amounts removed and restocked (9011). This data is used to adjust the book inventory stored within the computer's memory (9211). The entry of data is indicated by "carriage returns" (CR).

The inventory menu option (8211) is selected for monitoring the inventory. For example, one choice thereunder is to print the daily inventory report, with the book inventory, restocking information, and transactions grouped by product (9411). Another option is to manually adjust the inventory in case of a breakage of drugs within the inventory (9611). Other options include monitoring the difference between physical inventory as determined by a count and book inventory as determined by the checking in and checking out of drugs previously described. From the inventory menu (8211), the operator can also enter the physical inventory for comparison against the book inventory (9811). The difference between physical inventory and book inventory of each product (1001) can then be presented. The actual physical usage as determined by a physical inventory of the drugs can be compared with the amount administered (1021). The totals can then be adjusted as appropriate (1041). The operator can additionally print the net amount taken from inventory for drug treatment against the amount recorded from the portable unit 16 (1051) as administered.

The third option of the main menu (8111), the hospital/processing menu (8411), enables the operator to set up new lots for cattle brought into the feedlot and to prepare group drug treatments known as processing orders and hospital treatments which are administered to the animals. Referring now to FIG. 37B, a first option is a lot number menu (1061) appearing at the right of the figure and is selected whenever a new cattle lot is to be set up (1081). This menu allows the operator to add header information to the lot (110), change the header information (1121), or review the lots presently within the feedlot operation (1141). The lot menu (1061) also includes an option for deleting a cattle lot (1161) after the cattle within the lot have been shipped from the feedlot.

A second option under the hospital processing menu is a processing order menu (1181). Within this menu is a command for adding a processing order (1201). First, a number is assigned to a unique combination of drugs to be administered as the processing order or treatment (1221). The drugs desired are then selected (1241), and the dosages per head or per 100 pounds are entered (1261). The selection of drugs and dosages are then repeated until the processing order is complete (1271). The menu (1181) also permits the operator to print a list of current processing orders (1281) or delete an existing processing order (1301). An operator can also view a present processing order (1321) and change it if desired (1341) by changing the drugs or their amounts (1361).

Figure 37A:
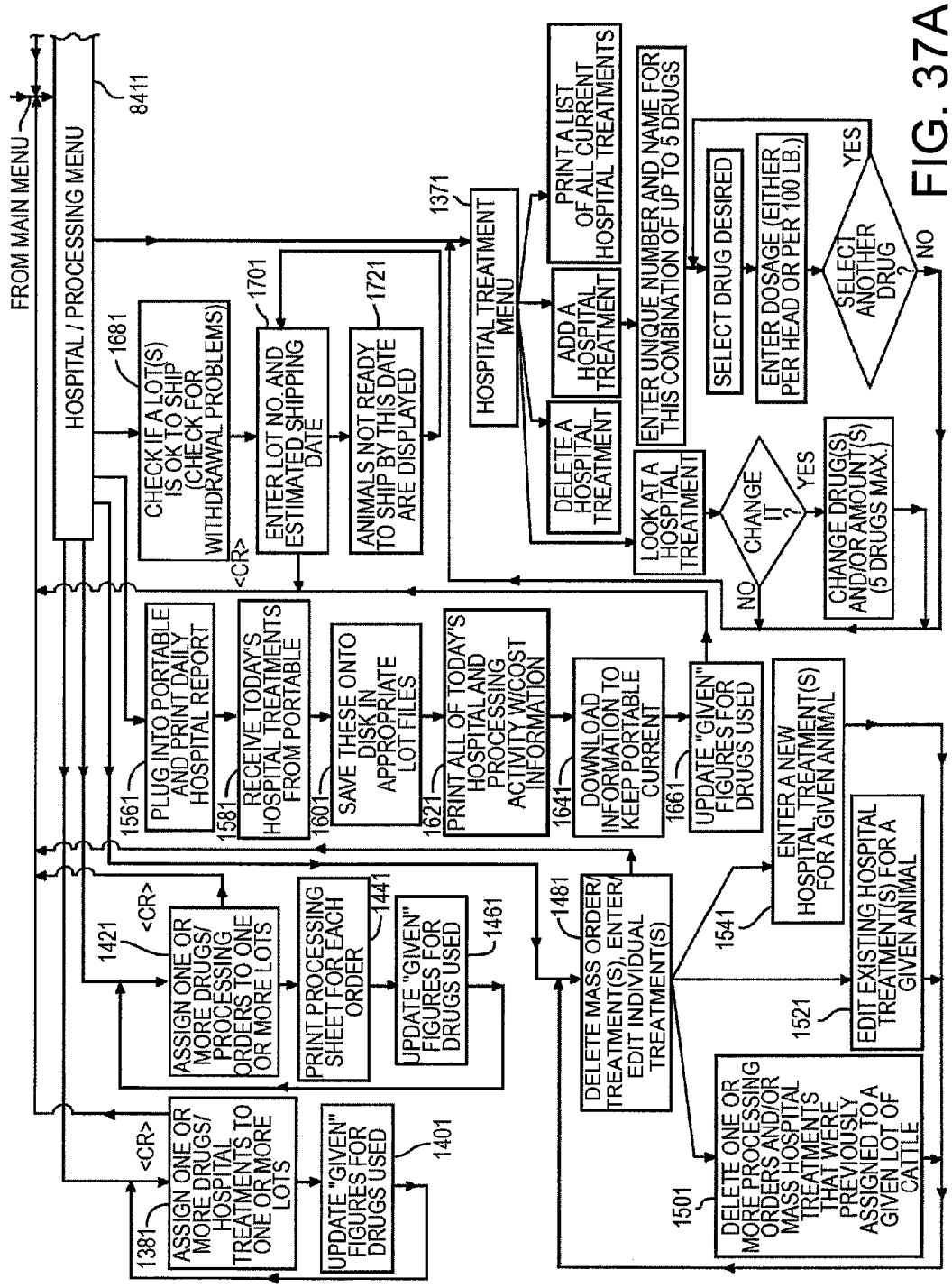
FIG. 37A is a flowchart illustrating in more detail a portion of the hospital/processing menu within the programming of the host computer.
Figure 37B:
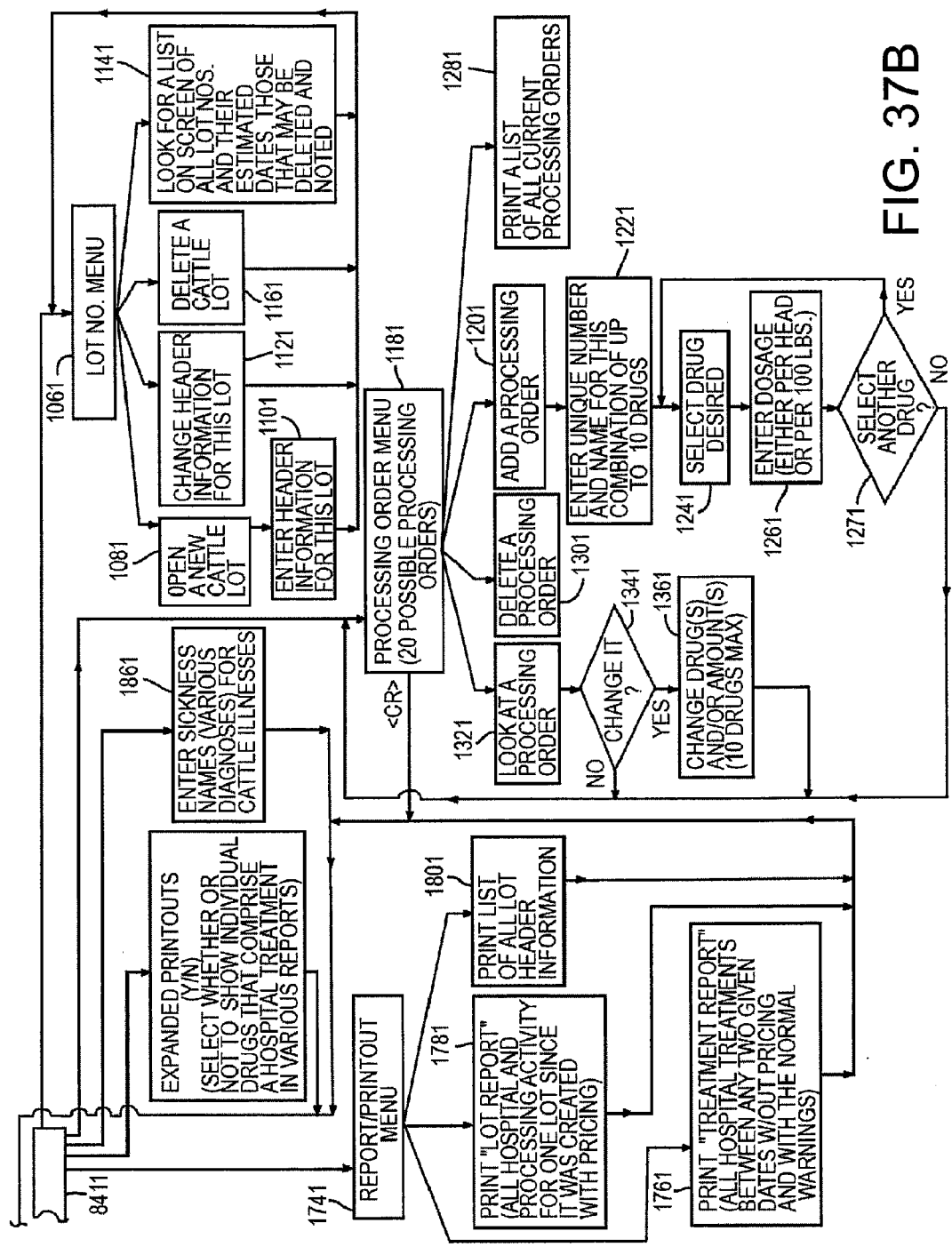
FIG. 37B is a flowchart illustrating in more detail a second portion of the hospital/processing menu within the programming of the host computer.

Referring now to FIG. 37A, a third option under the hospital/processing menu (8411) is a hospital treatment menu (1371). Hospital treatments differ from processing orders in that hospital treatments are normally intended for specific sicknesses and include a combination of drugs for treating that sickness. Processing orders, on the other hand, are not directed to specific sicknesses and are typically administered to all cattle in a lot, outside the animal hospital 1411. The hospital treatment menu (1371) includes basically the same selections as in the processing order menu (1181) and for brevity descriptions of the selections therein are not repeated here.

The other options under the hospital/processing menu (8411) include an option (1381) at the left of FIG. 37A enabling the operator to assign and record treatments for the animals without entering the data through the portable unit 16. This option minimizes data entry where it is known that all cattle in a given lot will receive a specified treatment. The option (1381) includes a command for updating the figures for drugs used in each hospital treatment (1401). A similar option (1421) allows the operator to assign one or more drugs or processing orders to one or more lots. The operator can print the processing sheet for each order (1441) and also has the ability to update figures in the orders for the drugs used (1461).

Just as he can assign drugs and treatments to lots, the operator has the option of deleting and editing treatments (1481). These options include deleting previously assigned treatments (1501), editing existing treatments for a given animal (1521), and entering new hospital treatments for a given animal (1541).

Communication via cable 5211 with the portable unit 1611 is also handled through the hospital/processing menu (8411). The menu (8411) allows the operator to print the daily hospital report (1561) of the animals treated as well as receive the day's hospital treatment from the portable (1581). The daily treatments are stored on disk in appropriate lot files (1601). The operator can also print the day's hospital and processing activity with cost information (1621). The updated health history and new lot numbers are then be downloaded into the portable unit 16 to keep it current (1641). The program also updates in memory the amount of drugs used in treating each animal (1661).

One concern of feedlots is the shipping of cattle not yet suitable for consumption. A further option under the menu (8411) allows the operator to check when a lot may be shipped (1681) by entering the lot number and estimated shipping date (1701). Animals that are not ready for shipping within the lot are then displayed by number (1721).

Referring again to FIG. 37B, an operator selects the report/printout menu option (1741) whenever a report on treatments administered for each lot is required. Under menu (1741), an operator can print a treatment report which indicates all hospital treatments between any two given dates (1761). The operator may also print the lot reports which indicate all treatment with drug cost, both processing and hospital, administered to a specified lot since a lot was created (1781). A third selection is for summarizing information on each lot by simply printing the header (1801).

One other option shown allows the operator under menu (8411) to enter the sickness names such as bloat, prolapse, etc., that will be recognized by the portable unit 1611 and will appear on menu sheet 2411 (1861). If the sickness codes are changed at the hospital/processing menu, the menu sheet 2411 is also updated.

Figure 38A:
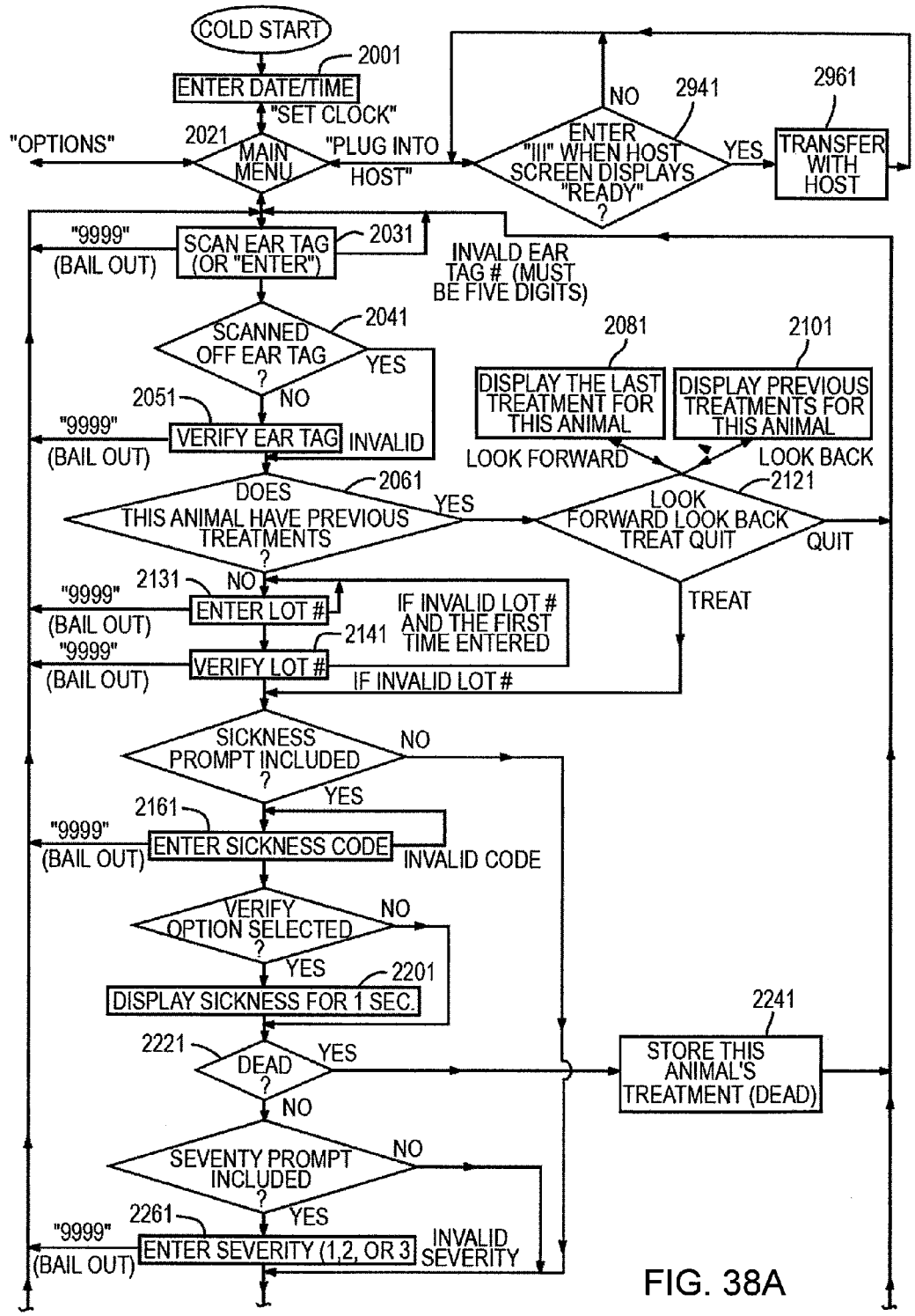
FIG. 38A is a flowchart illustrating a portion of the programming of the portable unit.
Figure 38B:
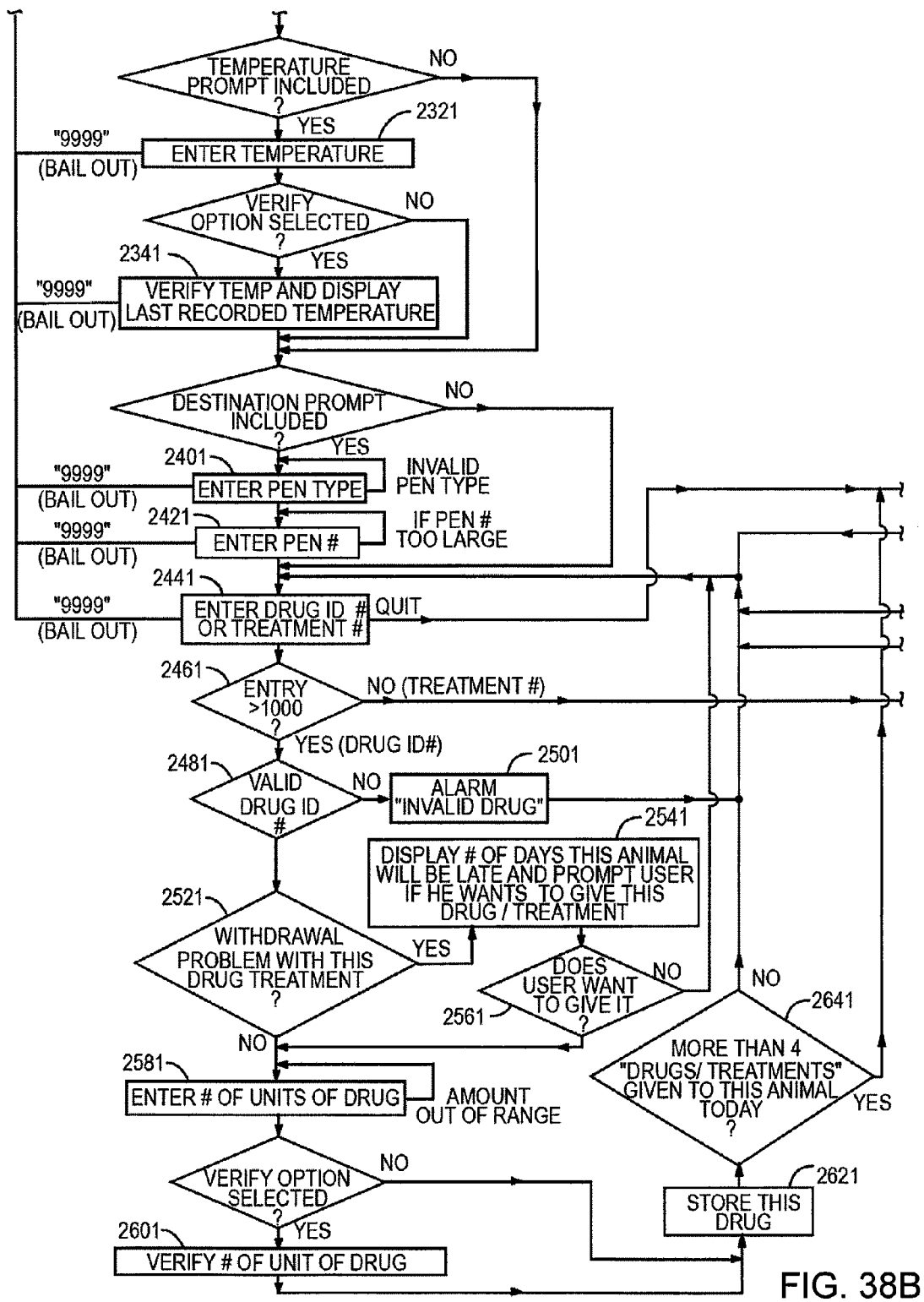
FIG. 38B is a flowchart illustrating a second portion of the programming of the portable unit.
Figure 38C:
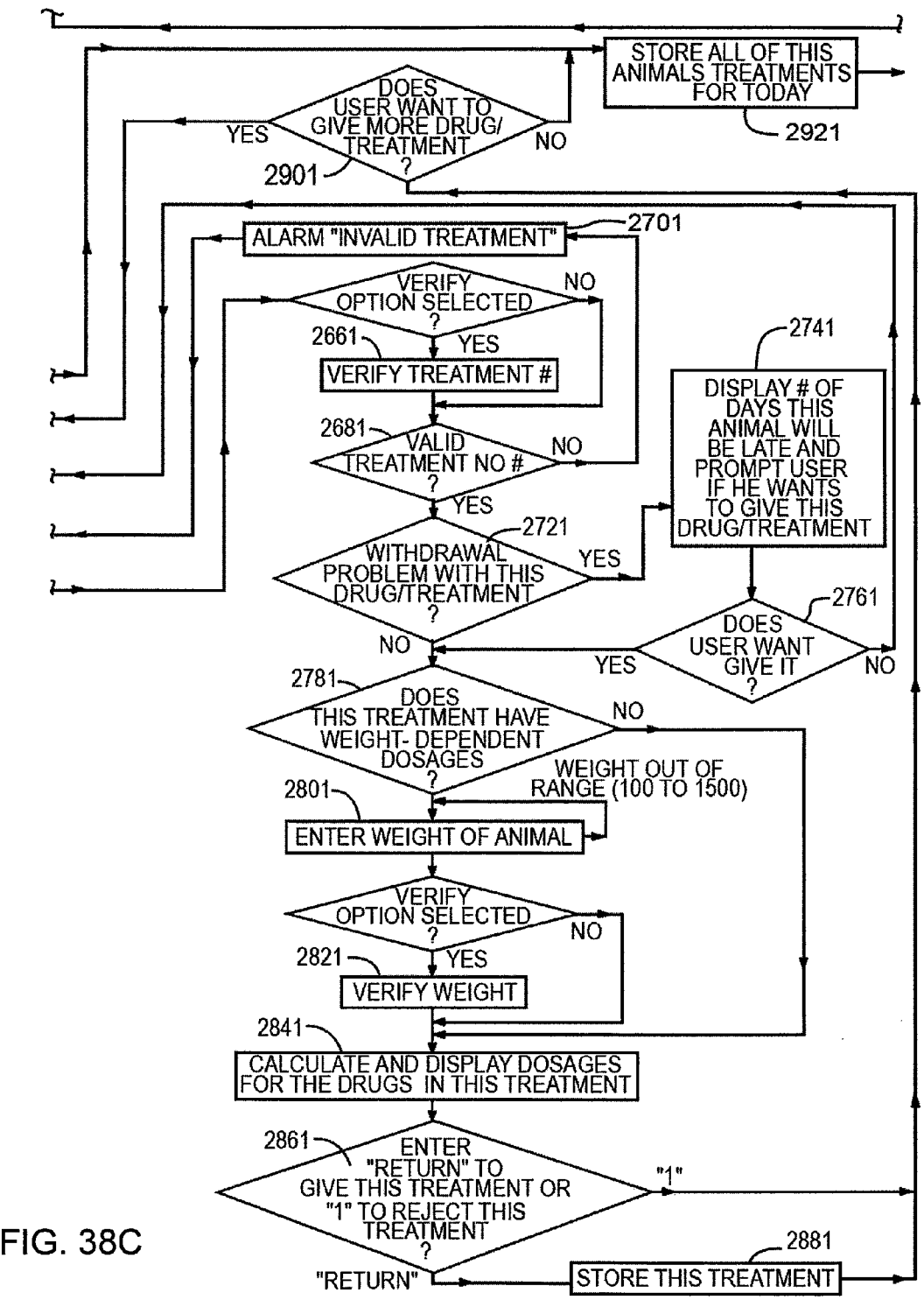
FIG. 38C is a flowchart illustrating a third portion of the programming of the portable unit.

The treatment data recorded in the portable unit 1611 during a treatment session is entered in response to prompts from the instructional program stored within the terminal 2811. FIGS. 38A-38C illustrate the operation of this program. Referring to FIG. 38A, the program prompts the operator 1211 on the display such as video monitor 2511 to enter the date and time of treatment via the keyboard 2911 (2001). A main menu (2021) then appears on the monitor 2511, which gives the operator several choices. One choice allows the operator to include and exclude various prompts and verifications of entered data which appear throughout the figure. Deletion of verifications, shown in these flowcharts, may be made by experienced operators who known the program operation well. The second choice commands the unit 1611 to transfer its data to the host computer 5011. A third choice allows for the entry of treatment data initially.

The operator thus begins treatment with this third choice by scanning the appropriate number on the menu sheet 2411. He is then prompted to scan the ear tag of the animal to be treated or key in the tag number to identify the animal to the unit 1611 (2031). If he scans the tag, the number is automatically verified (2041). If keyed in, the ear tag number is then displayed so that the operator may visually verify his entry (2051) before scanning a CR. Once the ear tag has been verified, the program checks to see if the animal is new or has a previous treatment history (2061). If the animal does have a record, the monitor 2511 displays the last treatment for the animal (2081). The operator can then scroll through previous treatments (2101) via commands on menu sheet 24 to determine the health history of the animal (2121). The operator can also quit the program by scanning the quit command on the menu sheet 2411. The quit option is always available throughout the program, though not repeatedly shown in the figure for clarity. All data entered before the quit command is invoked is recorded. On the other hand, the operator can always "bail out" of the program if trouble develops therein by scanning the numerals 9999. No data entered during a treatment session is saved if the operator "bails out."

If no previous treatments have been administered, the operator enters the lot number through keyboard 2911 (2131) and scans the CR. The program then compares the lot number with those stored in memory. If it is a new lot number, the program alerts the operator that it is included and prompts for reentry. Entering the same number a second time establishes the lot number. The program then prompts the operator to verify his entry (2141), which he does by a CR scan.

The operator is then prompted to enter a sickness code (2161), such as a respiratory or intestinal condition, appearing on the menu sheet 2411. The code is then displayed momentarily for the operator's verification (2201). If the sickness code entered indicates the animal is dead (2221), this data is stored immediately (2241) and the treatment session is ended. If the animal is merely sick, however, the operator is prompted for the severity of the illness and enters a severity code number in response such as 1, 2, or 3 (2261) from the menu sheet 2411.

Following entry of the animal's identity and sickness diagnosis, the operator may be prompted for other physical conditions such as the animal's temperature. Referring to FIG. 38B, he enters the temperature (2321) in response, and it is displayed by the program for operator verification. The last recorded temperature is also displayed (2341). The program then prompts the operator for the animal's destination, and the operator enters the pen type and particular pen number by scanning the corresponding numbers on the menu screen 2411 (2401, 2421). These pen types include home pens, recovery pens, or hospital pens such as hospital 1411.

Following the intended destination, the operator is prompted to enter numbers identifying the drug or hospital treatment to be administered to the animal (2441). Each individual drug and hospital treatment has a unique identification number. If the number entered by the operator is greater than 1000, i.e., has four digits, then the program determines that an individual drug is to be administered (2461). The identification number is then checked against a stored list to determine if it is valid (2481). The operator is alerted if the number is invalid, and he may attempt reentry (2501). Once a valid identification number has been entered, the program checks to determine if the drug requires a withdrawal date (2521). Certain drugs require that the animal be kept in the feedlot for a period of time after it is administered a drug to prevent undesired side effects to consumers. The program has stored within it the time period for each drug and calculates from the treatment data the earliest release date of the animal thereafter. If the drug has a withdrawal problem, the information is displayed (2541) and the operator is given the opportunity to reconsider administering the drug (2561). If no withdrawal date is displayed or if the operator chooses to administer the drug in any event, the program then prompts the operator to enter the number of units to be administered (2581). The amount entered is checked against an allowable dosage range to protect the animal from an overdose. The portable unit 1611 then verifies the number of units to be administered (2601). This drug treatment data is stored within the memory of the terminal 2811 for later transfer to the computer 5011 (2621). The operator is then queried if more treatments are to be given the animal in the present treatment session (2641).

Administering and recording hospital treatments are similar to the steps followed for individual drugs. Returning to step (2461) and then referring to FIG. 38C, an entered number less than 1000, i.e., two digits, is first verified by the operator as a hospital treatment number (2661) via a scanned CR. The program then checks to see if the number entered is a valid treatment number (2681). The operator is alerted if the number is invalid (2701). If the number is valid, the program then determines if there is a withdrawal problem with this treatment (2721) and displays the appropriate information if such problem exists (2741). The operator again has the option to proceed or choose another treatment or drug (2761). The program also determines whether the treatment has a weight dependent dosage (2781). If so, the program prompts the operator to enter the animal's weight (2801), which must fall within a predetermined range to be accepted as valid. The entered weight is then verified by the operator (2821) via a scanned CR, and the program calculates and displays the dosages to be administered (2841). The operator at this point can accept or reject the treatment as calculated (2861). If accepted and administered, the amount of treatment is then stored (2881).

The operator is then prompted to determine if further drugs or treatment is to be administered to the particular animal (2901) in this treatment session. If treatment is finished, all data is then stored within the memory of the terminal 2811 and the operator proceeds to examine the next animal. Once treatment is concluded, the operator quits the program (2921).

At the conclusion of the day or other predetermined reporting period, the unit 1611 is carried to the location of the computer 5011 and the two connected by cable 5211. Referring again to FIG. 38A, the operator then initiates data transfer via the main menu of the program within the unit 1611 (2021). The appropriate commands are first selected on the host computer 5011 (1561-1601). The operator then enters a transfer command in response to a prompt (2941), and the data is transferred (2961). The transferred data is collected to update the health histories of the animals treated in that session. The updated health histories are then transferred back to the terminal 2811 for review and display in steps (2081) through (2121).

Where the "dumb" terminal is employed in place of the portable unit 1611, the instructional program illustrated in FIGS. 38A-C is stored within the memory of the host computer 5011. No recording of data for later transfer, however, is required.

Tissue Analysis

This subsection describes various process steps and system components for measuring tissue characteristics of animals. Many of the process steps and system components described in this subsection can be used to gather information about an animal's respiratory or circulatory condition.

FIG. 39 is a block diagram, which illustrates certain components for an embodiment. FIG. 39 also illustrates certain fluid and electric interconnections between these components. The illustrated embodiment includes switch unit 4161 and handpiece 4181. A monitor 4201 (not shown) also is used. Power source 4221 is electrically coupled to each unit requiring power. More specifically, power source 4221 is electrically coupled to control computer 4241 by cable 4261, to ultrasound computer 4281 by cable 4301, to input/output module 4321 by cable 4341, and to pump 4361 using cable 4381. Pump 4361 is controlled by pump control 4401, which is electrically coupled to a three-way solenoid valve 4421 by cable 4441. A data cable 4461 interconnects control computer 4241 and ultrasound computer 4281. FIG. 39 also illustrates that the ultrasound computer 4281 is electrically coupled to switch unit 4161 by cable 4481. Input/output module 4321 also is electrically coupled to the handpiece 4181 by cable 4501.

Pump 4361 is fluidly coupled to reservoir 4521, which contains a conductive fluid, by fluid conduit 4541. Pump 4361 is further fluidly coupled to switch unit 4161 by fluid line 4561. As shown in FIG. 39, a quick disconnect 4581 may be placed in fluid line 4561. This quick disconnect 4581 is provided solely for convenience, and allows the pump fluid line 4561 to be quickly disconnected from handpiece 4181.

Each of the individual lines, namely electric cables 4481, 4501, and fluid line 4561, are interfaced with the handpiece 4181 by switch unit 4161. Each of the components of the apparatus can be individually actuated using the switches 4601, 4621 and 4641 on switch unit 4161. Thus, by depressing the appropriate switch, each function of the apparatus can be actuated.

The components of the apparatus mentioned above will now be described in more detail. Power source 4221 is a conventional piece of equipment that can be obtained commercially. Virtually any power source now known or hereafter developed that can safely power sensitive electronic apparatuses.

Control computer 4241 also is a conventional piece of equipment, and any computer which has sufficient capability to control and interface with ultrasound computer 4281 will suffice. One example, without limitation, of a control computer 4241 suitable for this operation is an IBM PC. Control computer 4241 controls certain functions of the ultrasound computer 4281. Commercial software is available for operating the control computer 4241 to control ultrasound computer 4281. One example of software suitable for this operation is sold by Animal Ultrasound Services, Inc., of Ithaca, N.Y.

The present apparatus operates by generating and transmitting into livestock an ultrasound energy pulse. This energy pulse is produced and controlled by ultrasound computer 4281 and ultrasound transducer 4661. Each of these components can be purchased. One example of an ultrasound apparatus is an ALOKA 500 V Ultrasound Computer. The ALOKA 500 V is purchased in combination with an ultrasound transducer 4661 and transducer cable 4681 for coupling the transducer 4661 to the computer 4281.

Input/output module 4321 controls the signals input to and from computer 4241 and to the components housed in handpiece 4181. Again, the I/O module 4321 is a conventional piece of equipment, and virtually any input/output module 4321. One prototype was assembled using an OPTO 22 I/O board. The OPTO 22 I/O board includes: a 1AC5Q input module; a PB16HQ circuit board; a B1 brainboard; a PBSA PP/S power supply; and an OAC5Q output module.

A pump 4361 pumps conductive liquid to handpiece 4181. The conductive liquid is contained in reservoir 4521. Any conductive liquid likely will work. The selection of a suitable conductive liquid will best be decided by considering, inter alia, the conductivity of the liquid, the expense of the liquid, the availability of the liquid and the toxicity of the liquid. Solely by way of example, suitable conductive liquids may be selected from the group of conductive liquids consisting of water, vegetable oil and mineral oil. Pump 4361 is liquidly connected to conductive liquid reservoir 4521 using liquid conduit 4541, which was made from flexible TIGON tubing. A pressure equalization tube 4701, also made from TIGON tubing, couples the liquid reservoir 4521 and the pump 4361. Pressure equalization tube 4701 equalizes the pressure between the pump 4361 and the reservoir 4521 when the pump 4361 is not in operation. This helps prevent liquid leaks from reservoir 4521.

Conductive liquid is dispensed from reservoir 4521 upon actuation of the pump 4361. Liquid dispensation is controlled by a three-way solenoid valve 4421, which is electrically coupled to pump control 4401. Three-way valve 4421 can be electrically actuated by switch 4601, which is housed in switch unit 4161. This dispenses conductive liquid from reservoir 4521 through liquid conduits 4541 and 4561 to handpiece 4181. When the pump 4361 is not in use, the solenoid valve is open to pressure equalization tube 4701 to equalize the pressure between the pump 4361 and reservoir 4521. Liquid back flow from handpiece 4181 can be checked by a check valve 4721, which is mechanically coupled to the handpiece 4181.

Figure 40:
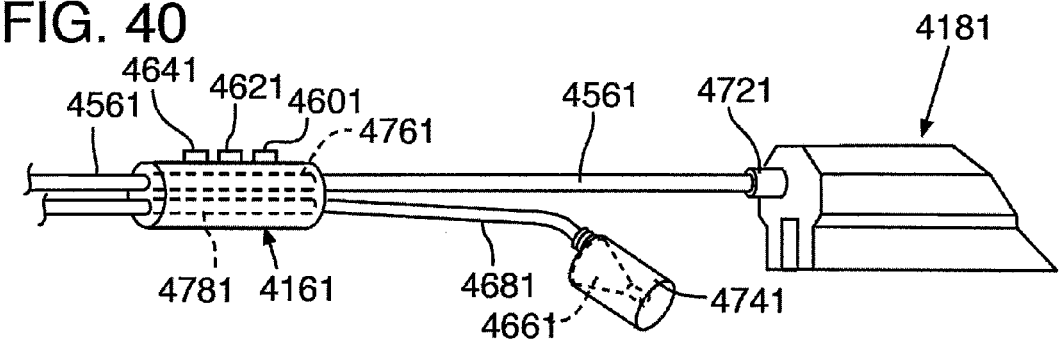
FIG. 40 is a side, partially disassembled view, illustrating an ultrasound transducer and dispensing handpiece unit.

FIG. 40 is a schematic diagram of the switch unit 4161, handpiece 4181, cables 4481, 4501, and liquid conduit 4561. FIG. 40 shows transducer 4661 separated from handpiece 4181. FIG. 40 further shows that ultrasound transducer 4661 is surrounded by a clear protective housing 4741. Housing 4741 performs at least two functions. First, housing 4741 protects ultrasound transducer 4661 from contact damage. Furthermore, protective-housing 4741 facilitates the positioning of transducer 4661 in handpiece 4181 as described below. The protective housing 4741 in a prototype illustrated in FIG. 40 was made from TIGON tubing sized to tightly receive transducer 4661 therein.

Figure 41:
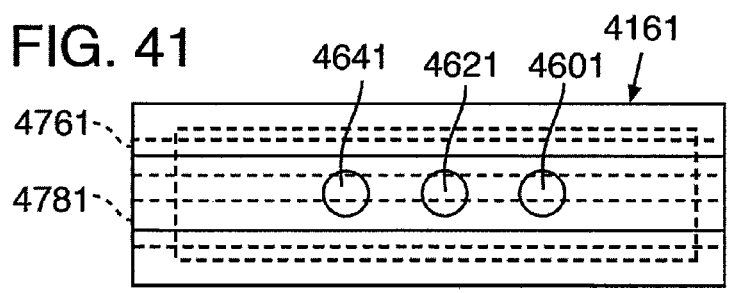
FIG. 41 is a plan view of the switch unit illustrated in FIG. 40.
Figure 42:
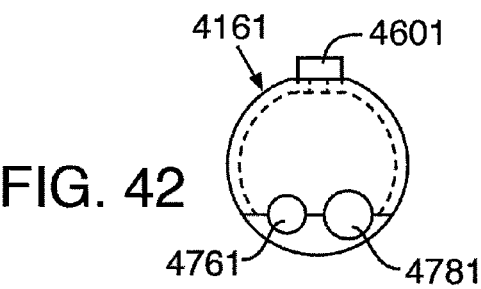
FIG. 42 is a front-end view of the switch unit of FIG. 41.
Figure 46:
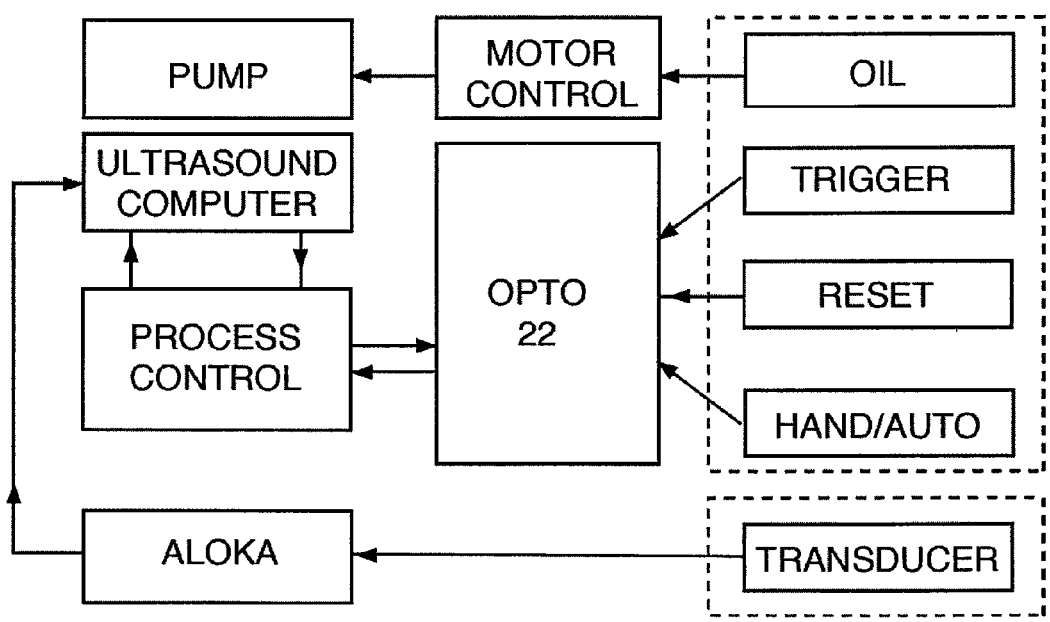
FIG. 46 is a schematic illustrating the switch unit of FIG. 41.

FIG. 41 is a schematic top plan view and FIG. 42 is an end view illustrating switch unit 4161. In a prototype, switch unit 4161 was made from a polypropylene block that was machined to include passages 4761 and 4781 therethrough. Conduit 4761 provides a passage through switch unit 4161 for liquid line 4561. Passage 4781 provides a passage through switch unit 4161 for electric cables 4481 and 4501. Switch unit 4161 includes three switches 4601, 4621 and 4641. The switches include conductive liquid switch 4601, trigger switch 4621 for commanding the computer to read and analyze the image, and reset switch 4641 for clearing a previous reading to prepare for rereading an animal or reading a new animal. These switches and their functions also are illustrated in FIG. 46. Switch 4601 actuates liquid pump 4361 so that conductive liquid from reservoir 4521 is pumped through liquid line 4561 and into handpiece 4181. The amount of time that pump 4361 operates is governed by a timer switch on pump 4361 (not shown). Thus, by actuating switch 4601, pump 4361 is induced to pump conductive liquid from reservoir 4521 for the period of time allowed by the timer switch on the pump. In a current prototype, the pump 4361 is actuated for a period of less than about 5 seconds, and typically about 3 seconds, during which time less than about 50 milliliters, and more typically about 30 milliliters, is pumped from reservoir 4521 to the handpiece 4181.

A second switch 4621 is electrically coupled to the ultrasound computer 4281 by cable 4481. Switch 4621 activates the computer 4281 to read and analyze the ultrasound image that is produced by transducer 4661 as displayed on monitor 4201. Thus, once the transducer 4661 is correctly positioned, operator 4141 depresses switch 4621 to cause the computer 4281 to read the ultrasound image.

A third switch 4641 also is provided on switch unit 4161. Switch 4641 is a reset switch electrically coupled to input/output module 4321 by cable 4501. Switch 4641 is depressed by operator 4141 when the image has been read by computer 4281 or when the operator wants to discard a previous reading and record a new reading of a given animal's image. This can include reapplying conductive liquid from the handpiece 4181 onto the animal. This resets the computer 4241 and input/output module 4321 for receiving new information from a different animal 4101.

Figure 43:
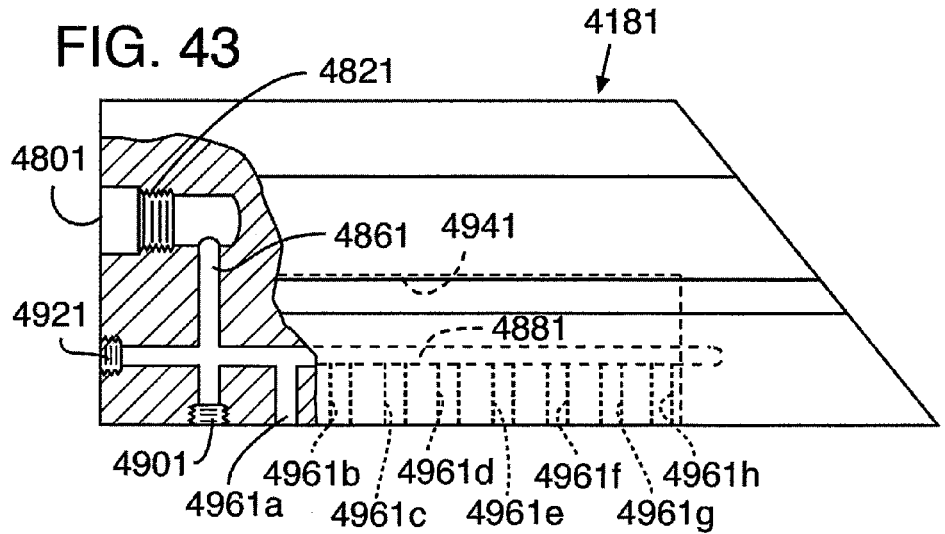
FIG. 43 is an enlarged side view of the handpiece illustrated in FIG. 40.
Figure 44:
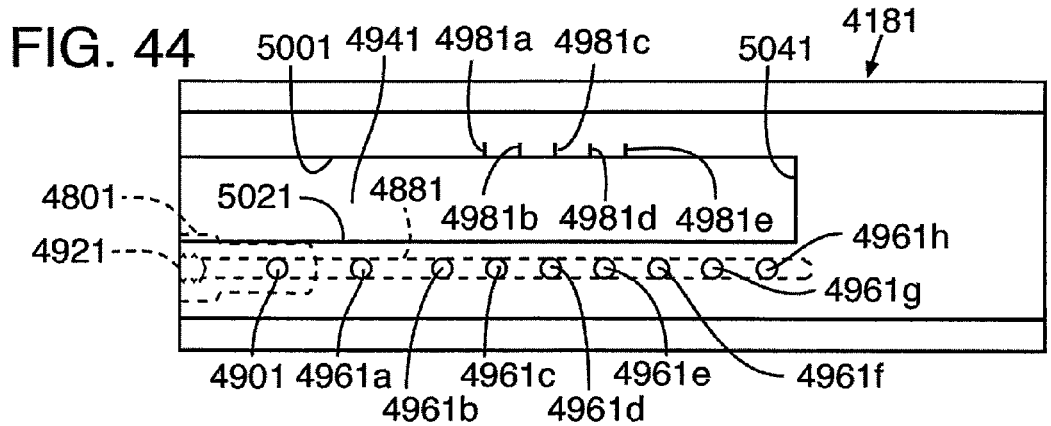
FIG. 44 is a bottom plan view of the handpiece of FIG. 40.

FIGS. 42-44 further illustrate the construction of handpiece 4181. FIG. 43 is a side schematic view of the housing 4181. Housing 4181 is manufactured for this particular application, and can be manufactured from a number of suitable materials. The embodiment of a prototype illustrated in FIGS. 42-44 was manufactured from polypropylene. A block of polypropylene having suitable dimensions was obtained and then machined to have substantially the appearance illustrated in FIGS. 42-44.

More particularly, handpiece 4181 is machined to include a threaded inlet 4801 for receiving liquid line 4561. Any suitable means for coupling the liquid line 4561 to housing 4181 will suffice. FIGS. 42-44 illustrate a male threaded connection 4821 which is inserted into threaded portion 4841 of passage 4801 to couple liquid line 4561 to housing 4181. Housing 4181 also is machined to include a passage 4861 for interconnecting liquid inlet 4801 and a liquid conduit 4881. Liquid conduit 4861 is closed using a threaded plug 4901, and liquid conduit 4881 is closed by a threaded plug 4921.

Figure 45:
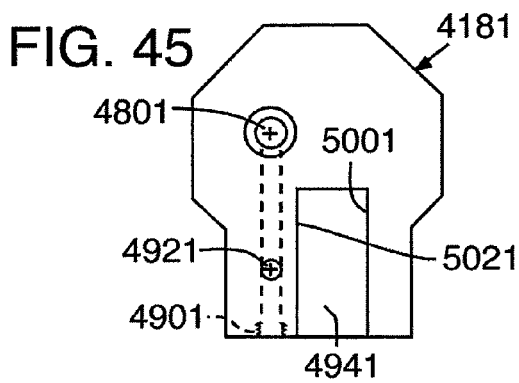
FIG. 45 is a rear end view of the handpiece illustrated in FIG. 40.

FIG. 44 is a bottom plan view and FIG. 45 is an end view of the handpiece 4181. FIGS. 44 and 45 illustrate a longitudinal slot 4941 recessed in the bottom surface of the handpiece 4181. Slot 4941 is sized to receive the transducer 4661 and protective cover 4741. If, however, the transducer 4661 and cover 4741 are not received sufficiently tightly in slot 4941 to hold the ultrasound transducer 4661 securely therein, an additional polypropylene wedge (not shown) can be used to wedge ultrasound transducer 4661 and protective cover 4741 inside the slot 4941.

FIG. 44 also illustrates that leading to and intersecting with the conduit 4881 are plural output orifices 4961a-4961h. These orifices 4961a-4961h are fed by liquid line 4561. Thus, as a conductive liquid enters the handpiece 4181 through liquid line 4561 and inlet 4801, the conductive liquid flows through the passage 4861, into passage 4881 and thereafter through the plural orifices 4961a-4961h and onto animal 4101. The spacing of these plural orifices 4961a-4961h is not critical. The embodiment illustrated in the figures has a relative spacing of approximately one-half inch between each respective orifice 4961a-4961h.

FIG. 44 also illustrates that the handpiece 4181 includes plural position markings 4981a-4981e. As stated above, transducer 4661 and protective cover 4741 are positioned in slot 4941. The transducer 4661 and cover 4741 are firmly wedged into the slot 4941 and between sidewalls 5001 and 5021. A mid-portion of the transducer 4664 is centered on one of these respective positioning marks 4981a-4981e depending upon the size of the animal, before the transducer is fixed in its selected position relative to end wall 5041. More specifically, the smaller the animal, the closer transducer 4661 is positioned to end wall 5041 of slot 4941.

The preceding paragraphs describe one embodiment of an ultrasound apparatus. This section discusses how to operate the apparatus, with particular reference to measuring tissue characteristics of cattle at a packing plant.

Cattle are conveyed seriatim using conveyor 5001 to a tissue analysis zone 5021 in a packing plant. As illustrated in FIGS. 47 and 48, the ultrasound device and computer control system described above can be used to analyze the tissue characteristics of the stunned ruminant at the packing plant. With transducer 4661 transmitting continuous ultrasound signals, the operator positions handpiece 4181 on the back of the animal 5101. The operation of the apparatus is not critically affected by the positioning of the apparatus on the back of the animal, but its positioning is important for obtaining accurate measurement data of a desired internal tissue characteristic. Transducer 4661 can be positioned between the twelfth and thirteenth rib, and typically is focused on the rib-eye muscle approximately three-quarters of the way down the muscle. Once housing 4181 is correctly positioned, the operator then actuates switch 4601 to dispense a predetermined amount of conductive liquid from reservoir 4521 onto the back of the stunned ruminant 5101. A sufficient amount of the conductive liquid is dispensed onto the ruminant 5101 through line 4561, passages 4861 and 4881, and orifices 4961a-4961h to obtain a clear image on a monitor (not shown). The amount of liquid dispensed is not critical, except that there must be enough to obtain a clear signal from the ultrasound transducer 4661. Solely by way of example, less than about 50 milliliters, and more typically about 30 milliliters, of conductive liquid should suffice. Pump 4361 can be actuated for particular predetermined lengths of time. The pump speed also can be controlled. The combination of controlling the pump speed and liquid dispensation time allows operator 5141 to vary the amount of liquid dispensed upon animal 5101 with each actuation of switch 4601.

Positioning the transducer 4661 is facilitated by monitoring the ultrasound tissue image on a monitor. If the monitor indicates that the transducer 4661 is not correctly positioned, the transducer 4661 can be removed from slot 4941 in the handpiece 4181 and repositioned. Once this is done for the first animal in a group of animals the transducer 4661 likely will be correctly adjusted for all animals in the group.

Once a suitable amount of conductive liquid is dispensed, which generally takes less than about 5 seconds, and more typically about 3 seconds, operator 5141 then positions transducer 4661 against the animal 5101 over the oil and between the twelfth and thirteenth rib of the animal 5101. The transducer 4661 is held steady in this position while operator 5141 watches the monitor. Once a suitable image is obtained, operator 5141 actuates trigger switch 4621, which is electrically coupled to the ultrasound computer 4281. By actuating switch 4621, ultrasound computer 4281 records the image and data, and calculates and records particular measurements of the animal 5101. The data acquisition performed by ultrasound computer 4281 is controlled by computer 4241. Software is commercially available for running computer 4241. This software can determine certain tissue characteristics using the ultrasound data, which includes backfat, intramuscular marbling, muscle dimensions and the location of a fat deposit, such as the rib eye fat kernel. Thus, software can be selected to perform particular measurements on each animal, and measurement data obtained can be displayed on the monitor. If insufficient or inaccurate data is received from a reading, and if the plant processing rate provides the operator time, the animal can be remeasured. This is done by pressing reset switch 4641 and again pressing trigger switch 4621 to take a new reading.

The information obtained for each animal 5101 is downloaded into computer 4241. The animal 5101 is continuously conveyed by conveyor 5001 along the processing line as an operator conducts tissue analysis. Once the tissue analysis is completed, then operator 5141 moves the ultrasound tissue imaging and analysis device adjacent another stunned and bled ruminant for tissue imaging and analysis. Prior to applying the transducer 4661 to the back of the next animal, the operator actuates reset switch 4641. This clears the computer 4241 and prepares it to receive new data. The process is then repeated.

FIG. 47 illustrates that the tissue analysis can be performed by a single ultrasound operator 5141 using an ultrasound tissue imaging and analysis device as described above. FIG. 48 illustrates an alternative method for tissue imaging and analysis involving two operators. In this embodiment, the stunned and bled ruminant is conveyed to a first position adjacent a first operator. The first operator can either perform ultrasound analysis on the stunned cattle, with the second operator repeating the ultrasound measurements made by the first operator. Alternatively, the first and second operators can perform ultrasound analysis on every other cow so that operators 5141 can match the conveying speed of conveyor 5001.

Still another alternative method is to have a first operator 5141 apply an ultrasound image enhancing fluid to the animal's hide at the rib-eye portion. This animal is then conveyed to a position adjacent a second operator 5141. The second operator 5141 then performs ultrasound tissue imaging and analysis adjacent the rib-eye portion of the ruminant 5101 as the ruminant is being conveyed by conveyor 5001. The second operator 5141 adjusts the position of the ultrasound tissue analysis device until a good image is obtained. The ultrasound imaging and analysis device is then actuated to obtain and store tissue data.

The method takes less than about fifteen seconds per animal to perform, typically less than about ten seconds to perform, and more typically less than about 10 seconds to perform, and more typically about 5-7 seconds to perform. The information obtained is then used to make calculations as discussed below, and is available to both the packing plant operator and the feedlot operator in real time. This is a significant improvement over conventional methods.

Data obtained using tissue analyses on the stunned and bled ruminant can be used to perform a variety of calculations, such as those discussed in Pratt's U.S. Pat. No. 5,673, 647. For example, yield and quality can be determined. The ultrasound tissue imaging and analysis device is used to make a number of measurements, including rib eye dimensions, backfat thickness and determinations of rib eye area and marbling. To make such measurements, the ultrasound device focuses on and locates particular tissue characteristics, including, for example, a particular fat deposit, such as the rib eye fat kernel. As soon as a good ultrasound tissue image is obtained, the measurements discussed above are made, and are recorded in a computer or on computer readable medium. Such data is correlated with the animals electronic identification tag, as well as information determined for each animal at the feedlot.

The data obtained by ultrasound tissue imaging and analysis at a packing plant is itself indicative of meat quality and/or yield, such as the backfat measurements, or can be used to make other calculations, such as yield grade. Yield grade is a scale from 1 to 5, with 1 being the most lean and 5 the least lean.

Typically, cattle backfat thickness varies from about 0.1 inch to about 1.0 inch thick. Rib eye area typically varies from about 9 square inches to about 15 square inches. Yield grade is determined by considering at least rib eye area and backfat. First though, solely with respect to backfat, backfat measuring greater than about 0.7 inch thick generally results in a yield grade of 4 or better. Average cattle have a backfat thickness ranging from about 0.4 inch to about 0.7 inch, and such backfat generally results in a yield grade of 3. Less backfat results in a yield grade of 1-2.

But, as stated above, yield grade also considers rib eye area. The USDA yield grade is determined by considering backfat thickness, rib eye area, hot carcass weight (which is determined by weighing both halves of a carcass about 15 minutes after initial processing) and pelvic, kidney and heart fat (PKH) values. Thus, for example, if a particular animal has a relatively small rib eye area and relatively thick backfat, then the animal likely will receive a yield grade of 4 or 5. And, if the animal has relatively large rib-eye area and relatively little backfat, then the animal likely would receive a yield grade of 1-2.

Marbling also can be determined using ultrasound tissue imaging and analysis of ruminants at packing plants. Marbling is determined by computer analysis of contrast differences in the ultrasound image. A quality grade is then assigned to the animal to reflect the marbling content. Marbling is specified as standard (which correlates with the least amount of marbling), select, choice and prime (prime correlates with the most amount of marbling).

Data collected at the packing plant is available much sooner than if conventional methods are used, such as waiting for and relying on government grading or area analyses of rib eye tracings. The present method makes such information available in real time to the packing plant operator, who could chose to provide such information virtually simultaneously to the feedlot operator. This accelerates payment all along the ruminant processing chain.

Moreover, the information provided by the method appears more objective than the grading information provided by the government grading system. And, tissue characteristics are obtained prior to processing the stunned ruminant to a carcass by, amongst other things, removing the hide and perhaps simultaneously portions of backfat. Because the present system is based on collecting and analyzing repeated tissue body measurements, it is both more reliable and correlates better with the actual yield of the stunned and bled ruminant.

And, because the information concerning each animal is available sooner and generally is more accurate and reliable than the currently used subjective grading techniques, both the feedlot and packing plant operators can make use of such information for management decisions. As used herein "management decisions" depends on whether this refers to feedlot management or packing plant management. Packing plant management decisions are discussed above, and in Pratt U.S. Pat. No. 5,673,647. "Packing plant management decisions" typically refers to, for example: (a) sorting cattle; (b) further distribution; (c) pricing for either purchase or sell; (d) classifying inventory; (e) valuing inventory; and (f) selecting feedlot suppliers. It should be realized that information provided the feedlot operators can be used to change the subsequent treatment of individual animals at the feedlot, such as to increase or decrease feed, or to administer certain materials, such as growth factors. Because animal grading is done virtually simultaneously with processing of the animal at the packing plant using the method, cattle emerging from the carcasses emerging from the processing area can be sorted into groups based on predetermined criteria, such as customer desires, yield, quality, carcass weights, size of cuts, etc. This, along with the fact that the information is available in real time, provides the packing plant operator better information faster concerning packing plant inventory. The feedlot also can be provided the information sooner, so that feedlot management decisions based on the information provided by the packing plant can be made much sooner and with more reliability than can be achieved using conventional methods.

This example describes a method for performing ultrasound tissue analysis of cattle in a packing plant prior to processing the cattle to carcasses. An electronic I.D. tag was placed on a trolley hook at a point where the rear leg of each animal was transferred from shackle to trolley. A portable tag reader was used to read the tag as it was placed on the hook, and this information was stored to establish the sequence of cattle on the trolley.

Figure 49:
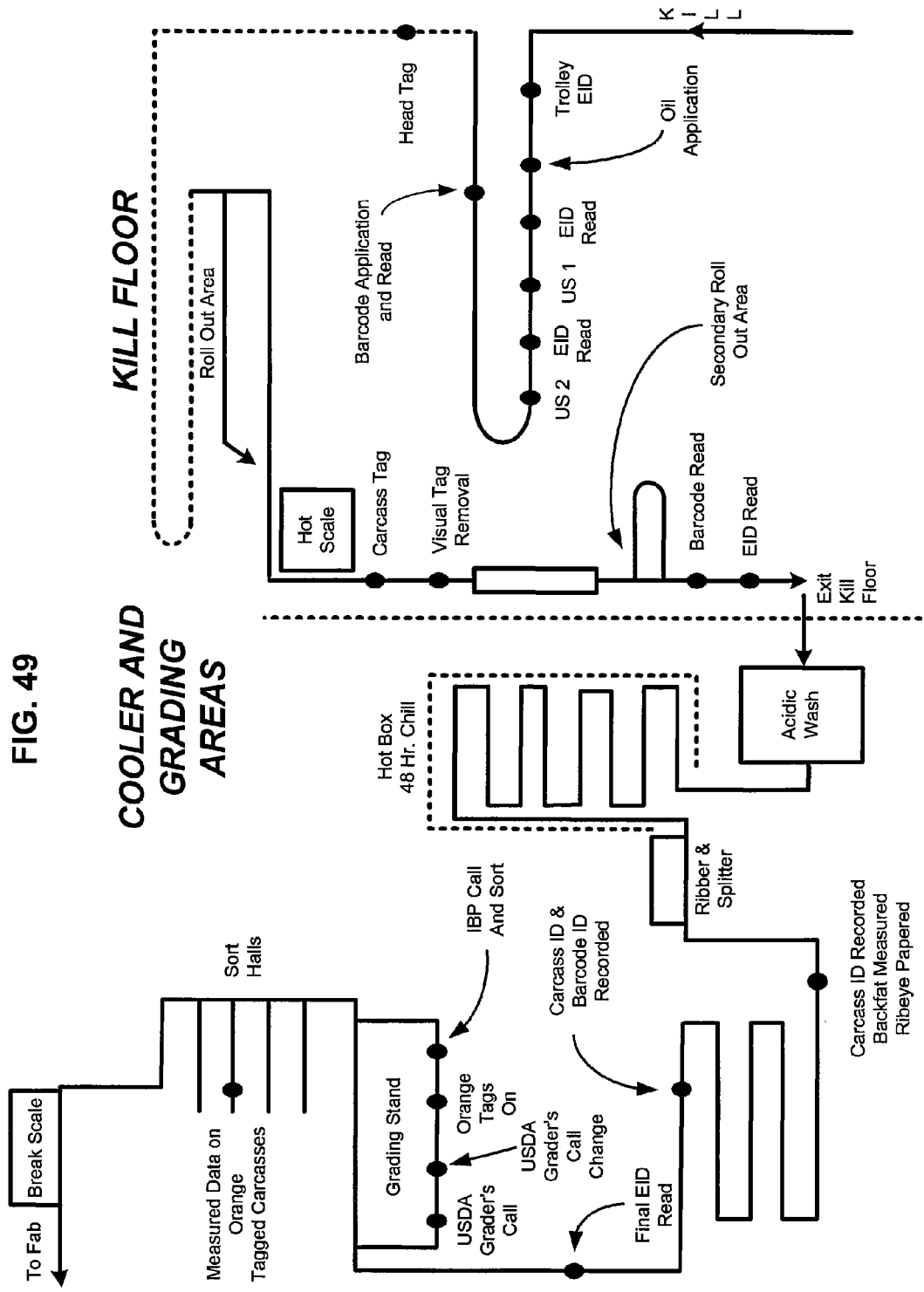
FIG. 49 is a schematic diagram illustrating the layout of a packing plant and ruminant tissue analysis locations in the packing plant.

FIG. 49 is a schematic diagram illustrating how ultrasound tissue imaging and analysis devices were positioned in a packing plant for this procedure. Just past the transfer point for transferring the stunned animal from the shackle to the trolley, the ultrasound tissue analysis zone was defined. Vegetable oil, about 18 milliliters, was applied to the hide on the left side between the 12th and 13th ribs before each animal was conveyed to a position adjacent an ultrasound technician.

FIG. 48 illustrates two ultrasound operators 5141 performing ultrasound analysis on ruminant 10 in a packing plant. Operators 5141 are illustrated as using one embodiment of an ultrasound tissue imaging and analysis system as described in more detail above comprising a switch 5161, and a hand piece 5181. The two successive ultrasound operators 5141 used two identical computer/ultrasound systems, although it will be apparent that the two ultrasound systems need not be the same.

Following ultrasound measurement and prior to removing the head from the animal a portable tag reader was used to read the electronic identification tag which was removed from the ear of the animal. This electronic identification number was matched to the trolley sequence number and electronic identification tag on the trolley.

Ultrasound tissue analysis was performed on cattle processed at the packing plant. The tissue measurements made by the ultrasound device were stored with each animal's individual identification tag number, sequence number and trolley identification number in a computer.

A second I.D. in a form of an USDA-approved edible bar coded label was applied to the exposed brisket area. The edible label had a five-digit number printed thereon for visual reading, in addition to a bar code to be read by a hand-held reader immediately after the label was fixed to the brisket. The carcass was weighed at the hot scale. The packing plant's carcass tag was then fix to the carcass, and the weight was recorded along with the plant's carcass I.D. number on a tablet. The trolley I.D. and bar code label were read electronically to re-establish the sequence of cattle on the trolley in case some ruminants were railed-off by a USDA inspector for trimming and observation before being railed back in the moving chain. After all carcasses in the test left the packing plant for chilling, the hot carcass weight was linked to the ultrasound-derived data of backfat, rib eye area and marbling score in a file in a computer.

Yield grade, quality grade closely trimmed retail yield and pounds of each ruminant were calculated for each cattle processed using published formulas.

This example describes a method for grading carcasses at a packing plant where objectively measured carcass data was used rather than the normal method of visual observation by graders. Immediately after the carcasses were ribbed, a numbered paper was applied to the rib eye of the left side of the carcass. The paper was removed after the rib eye impression had been made, and was traced at a later time for determining actual rib eye area on all carcasses. Immediately after the paper was removed from the rib eye, the backfat was measured with an approved preliminary-grade ruler. This measurement was recorded on a paper that was removed from that rib eye.

Each carcass was graded by a grader employing official procedures of the USDA meat grading service, and stamped accordingly with yield and quality grades. A second person from the USDA meat grading service observed the carcass as trained and then observed a computer screen displaying the yield and quality grades as calculated on day of slaughter by the ultrasound derived data plus the hot carcass weight. If the USDA grader agreed with the calculated value, he pressed the touch screen computer and a label was printed and fixed to the carcass by another worker to confirm the calculated values. If the USDA grader did not agree, he adjusted PYG, RIB EYE, and/or KPH to change the calculated yield grade and marbling score to change the quality grade. When the displayed yield grade and quality grade matched the USDA grader's evaluation, he pressed a print button on the touch screen computer and a label was printed and fixed to the carcass.

A second touch screen computer was made available to the plant grader. He could observe the carcass and compare his subjective value to that displayed on the screen. He could then make changes to PYG, KPH and rib eye to adjust the yield grade and marbling score to adjust the quality grade.

Every thirtieth carcass was railed off for measuring PYG with the official ruler and rib eye using an official grid device. Three people, two USDA meat-grading graders and one IBP selected grader, independently measured each carcass railed off. The three independent measurements were averaged to establish the official reference measurements.

The results from the examples demonstrate that tissue analysis made on ruminants in packing plants can provide yield grades, rib eye areas and marbling, for example, that correlate well with those obtained by the conventional processes. Moreover, the data provided by the tissue analysis at the packing plant is available in real time for analysis by the packing plant, the feedlot, and others in the processing line. This not only expedites payment to all persons in the processing line, but further also allows the feedlot to adjust its methods of processing ruminants, and allows the packing plant operators to better control their inventory.

Animal Tracking

This subsection describes various process steps and system components for tracking animals. These process steps and system components can be used in conjunction with evaluation of an animal's respiratory or circulatory condition, as discussed above. For example, information gather by imaging and evaluating an animal's respiratory or circulatory system, such as respiratory damage designations, can be entered into the described electronic system components and processed alone or with other animal characteristics as described below Protecting animal agriculture by safeguarding animal health is vital to the well-being of people everywhere. In fact, protecting animal agriculture promotes human health, provides wholesome, reliable, and secure food resources, mitigates national economic threats, and enhances a sustainable environment. An element of this goal to safeguard animal health in an effective AIF that allows users to quickly and efficiently trace information concerning an animal, including without limitation, an animal's location history, treatment history, such as drug or feed additive administration, food products made from such animal, and any combination of such information. By doing so, diseased animals, those potentially diseased, and/or those animals that have commingled with the diseased animals may be identified and dealt with, e.g., treated, quarantined, or destroyed when necessary.

The following provides definitions of certain terms used in this subsection. These definitions are provided to aid the reader, and should not be construed to be narrower than would be understood by a person of ordinary skill in the art.

A "cohort" or "cohorts" refers to an animal or animals that occupied a same general location, such as might be identified by a premise identifier, at some time as some other animal or animals, but not necessarily at the same time. Cohorts can refer to a group of animals occupying a same location, and if one or more of these animals is moved to a second location, then the moved animal now is, or animals are, associated with a second cohort group.

"Commingled" is a subset of the term cohort and generally refers to animals that occupy the same general location at a common time. For example, a first group of animals might be owned by the same owner and pastured separately from a second group. Both the first group and the second group may be referred to as cohorts, particularly if the first and second pasture are identified by the same premise identifier, but are not commingled. Animals in the first group are commingled, and animals in the second group are commingled, but animals of the first group are not commingled with animals of the second group. Commingled also can be considered to occur when animals have unrestrained access to each other. Under a program, such as the USAIP, a single premise identifier may be used to identify cohorts, but cohorts may not be sufficiently intimately associated so as to warrant treating all animals in the group in the same manner, such as in case of a detected disease. By providing additional animal identifiers as disclosed in the present application cohorts in this and other examples can be treated differently.

"Intimately associated" typically refers to animals that are in sufficiently close contact that, for example, transmission of a disease might be inferred. Simply because animals are commingled does not necessarily mean that they are intimately associated. Again by way of example, animals located in a large pasture area may be considered commingled, but may not ever be intimately associated.

"Participants" include, without limitation, producers, grazers, auctioneers, feedlots, packers, data service providers, data trustees, and others.

Over the last several years, more than 100 animal industry professionals, academics, and state and federal government representatives have debated the feasibility of implementing a single, nationwide computerized system that utilizes an individual food animal identification tracking and management system. As a result of those debates, the United States Department of Agriculture (USDA) endorsed most of the USAIP that defines the standards and a framework for implementing and maintaining a phased-in, NAIS. Basically, the USAIP would be one method enabling not only the beef industry but all livestock industries and government officials to conduct lifetime tracebacks of all animals and perform disease surveillance on cattle, swine, sheep, and other animals. Tracing back animals would allow government officials, animal producers, animal purchasers, and others to determine where an animal has been and what other animals have been in contact with the "traced" animal.

For example, if a cow is diagnosed with Mad Cow disease, an NAIS would allow government health officials to traceback where an animal has been over its entire lifetime and investigate and control the disease by quarantine or other method animals that have commingled with the diseased animal. The USAIP requires that a complete traceback report be obtainable within 48 hours of the initiation of an investigation following the diagnosis of a sick animal.

Figure 50:
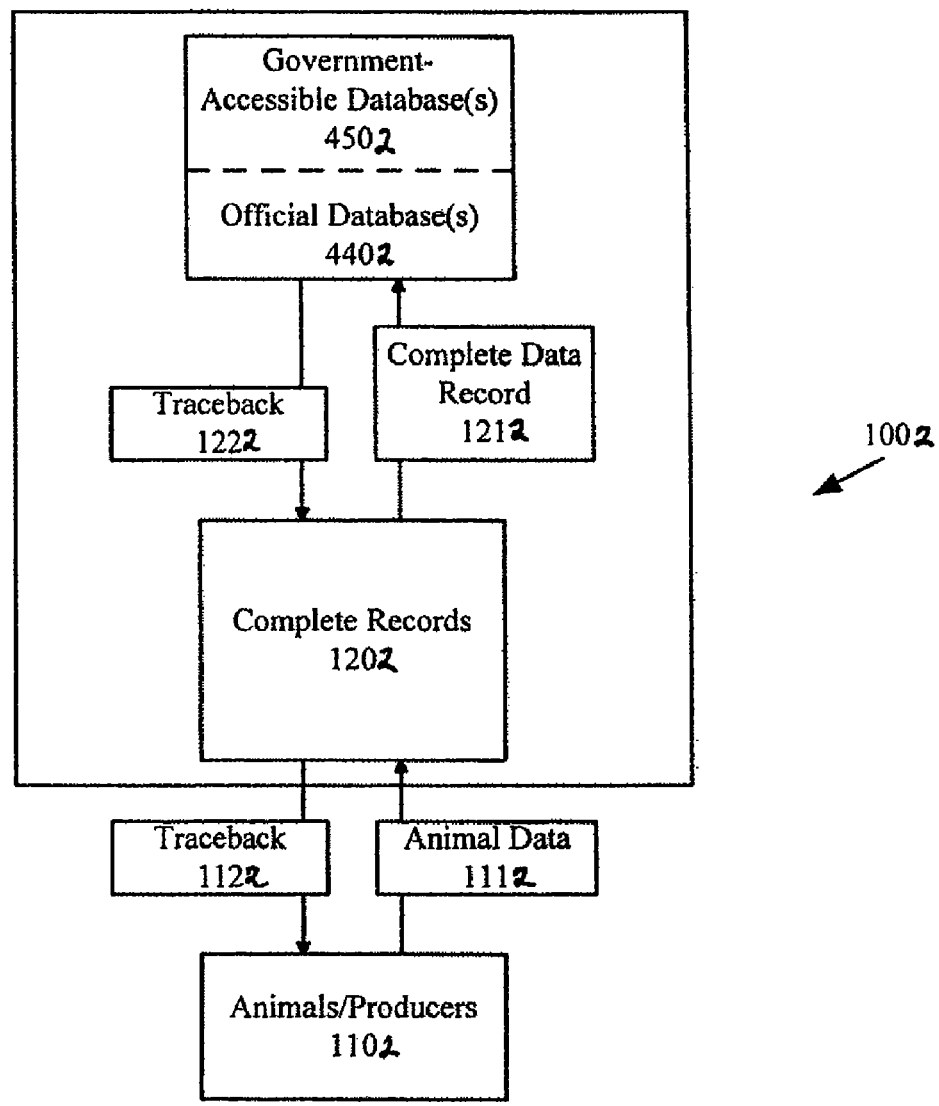
FIG. 50 is a block diagram of a national animal identification system.

The basics of the USAIP are illustrated in FIG. 50. FIG. 50 shows animal producer 1102 collecting data 1112 about his animals and storing that data in a database 1202. The type of data collected by animal producer 1102 varies among animal industries; however, the data typically includes many of the same types of data that are found in a cattle specification. Under the USAIP, that data is supplemented by an official ID tag and may include a couple of additional identifiers to help trace a specific animal. For example, in order to trace an animal's location history, the USAIP includes a premise identifier (PID) and a universal animal identifier (UAID) among the collected data 1212. Whenever an animal is moved to a new location, the new location's PID is linked to the animal's UAID. By doing so, these identifiers help pinpoint where a cow has been during its lifetime.

Data collection usually begins at the animal producer's location. As an animal moves in the stream of commerce and passes through data collection points, additional records or information are collected and uploaded to a national animal information database 1302. According to the USAIP, the national animal information database 1302 is accessible to the USDA and other health officials. Thus, when an animal is discovered with an animal disease, such as an FAD, the USDA determines the assigned UAID of the diseased animal and reviews the animal's records in the NAIS information database. Based on recorded PIDs it is possible to trace where a diseased animal has been. At that point, appropriate measures can be put into effect to prevent those animals that have commingled with the diseased animal as identified solely by a premise identifier from entering the marketplace. The USAIP's goal is to protect people from buying tainted meats and other animal products and to prevent the disease from spreading to other animals.

To put an NAIS in place, the USAIP proposes implementing the following systems: a national premises identification system, an individual animal identification system, and a group/lot identification system.

The national premises identification system assigns a unique number to each premise involved in animal agriculture. Generally, a premise is an identifiable physical location that, in the judgment of animal health officials, area veterinarians, or other designated group, and when appropriate in consultation with the affected producer, represents a unique and describable geographic entity (e.g., where activity affecting the health and/or traceability of animals may occur) or represents the producer contact location when extensive grazing operations exist. By assigning a unique identifier to premises, the location history of animals is more easily tracked. The USAIP-proposed premise identifier is a 7-character alphanumerical value, e.g., A123B45.

Figure 51:
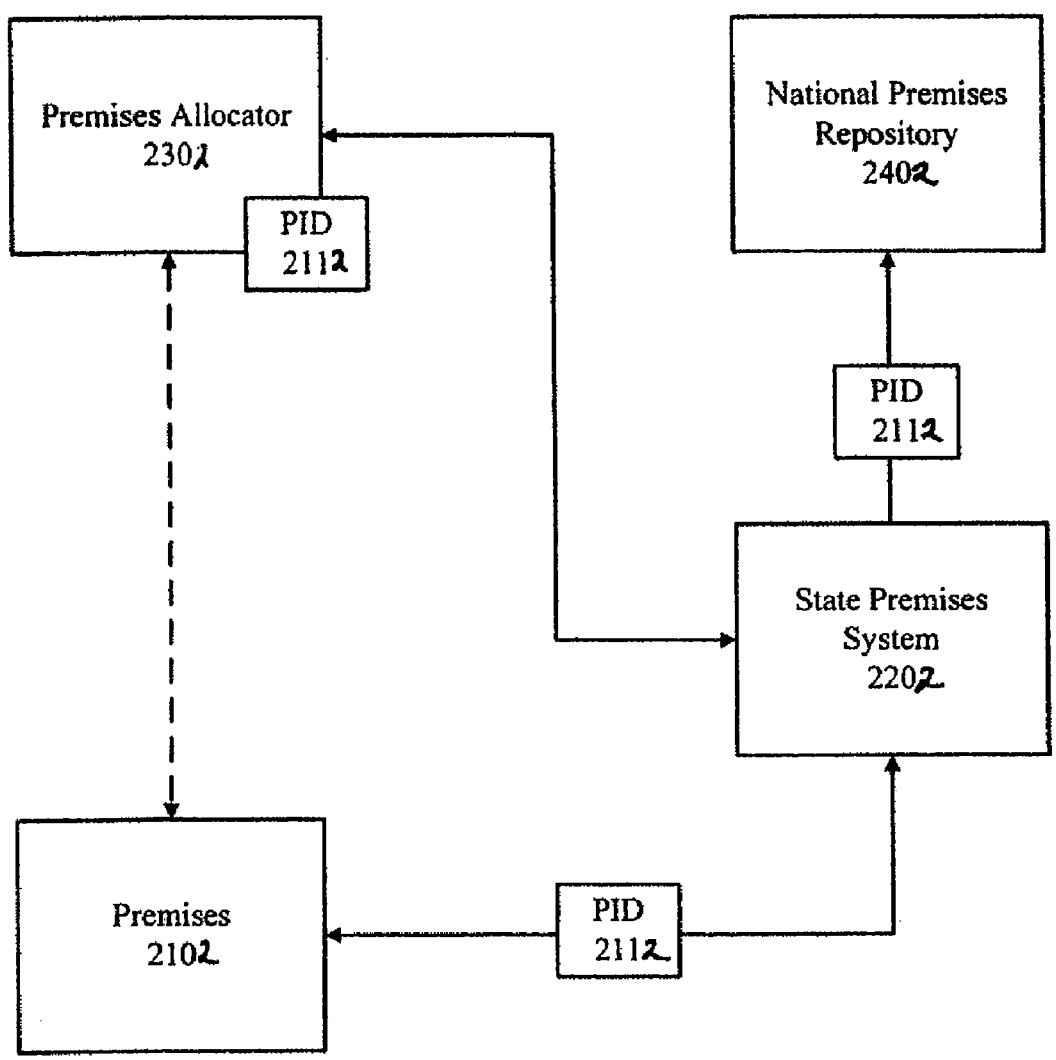
FIG. 51 is a block diagram of an infrastructure for assigning premise identifiers.

FIG. 51 illustrates a simple block diagram of the USAIP's proposed infrastructure for assigning PIDs. Basically, a premise 2102 is required to file a request for a PID with a local government premise system 2202. The state premise system 2202 contacts a national premise allocator 2302 for a PID 2112. The national premise allocator 2302 assigns a PID to the premise and sends it back to the state premise system 2202. The state premise system 2202 forwards it to the requesting premise 2102 and to a National Premises repository 2402. The USDA has access to all PIDs through the national premises repository 2402. Using the PIDs, the USDA can determine where animals have been when doing tracebacks. According to the USAIP, the PID 2112 uniquely identifies a premise.

The USAIP's national premise identification system requires states and local governments to identify and validate "premises".

Figure 52:
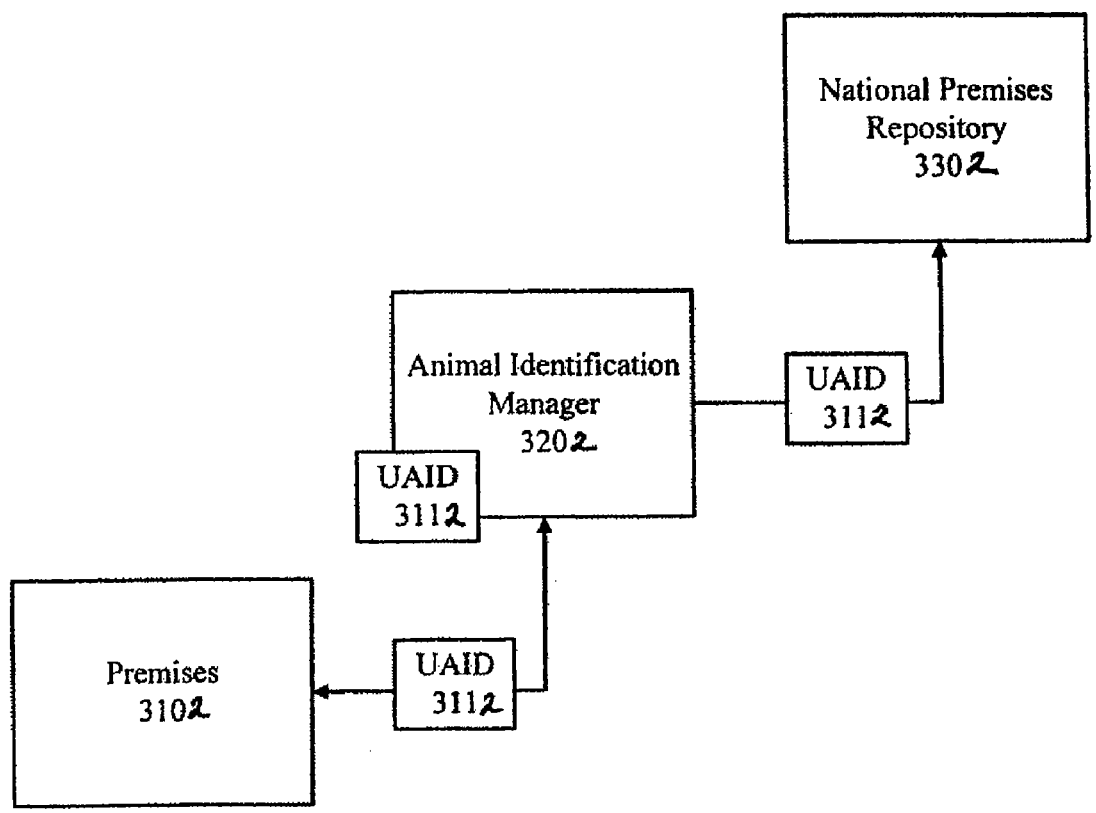
FIG. 52 is a block diagram of infrastructure for assigning animals universal identifiers.

In conjunction with a premise identifier, the USAIP proposes using an individual animal identification system to assign universal identification numbers (UAID) to animals. FIG. 52 illustrates a simple block diagram of the entities involved in assigning an animal a UAID. Typically, requests for a UAID come from animal producers. As illustrated, an animal producer at premise 3102 requests and receives a UAID 3112 from an animal identification number allocator 3202. As before, a copy of the UAID 3112 is forwarded to the requesting animal producer 3102, as well as to a national animal identifier repository 3302. Typically, the UAIDs adhere to the ISO code structure standard for Radio Frequency Identification (RFID). In other words, animals will be assigned a number that is imprinted and encoded on an electronic RFID tag. The tag is attached to an animal and throughout the lifetime of the animal the RFID electronic tag is used to trace animal movements. An exemplary animal ID number, according to the USAIP, the ISO code contains 15 numbers, for example, "840 123456789012".

The USAIP also proposes a group/lot identification system, which assigns different values to specific lots or groups within a much larger premise. For example, a large feedlot may have dozens of separate feeding areas. Each area or lot may receive its own unique number to further distinguish where an animal has been. Another reason for using a group/lot identification system is that animals often are transferred in groups to a premise. Each shipment of animals that comes in or moves out may be considered a group. A group/lot identifier (GID) distinguishes between groups within a premise. The GID is typically based on a date. For example, in some cases, the USAIP adds a six-digit number to the premise ID to reflect the date a group of animals moved in. This means that an animal shipped to a premise on Oct. 3, 2003, has the combined group lot number "A234L69100303," where the final six digits represent the date of arrival. The GID provides a way to further distinguish groups of animals of that have not been commingled.

Based on the above-identified systems, the USAIP proposes an infrastructure that includes a national premises allocator, a national premises database, individual animal ID database, and "Reader" technology in order to trace animal location histories. The reader technology, as mentioned above, includes electronic RFID tags and RFID readers placed at various collection points. For example, the reader technology would be most likely implemented at markets, expositions, slaughter facilities, feedlots, etc. By recording the PID and UAID of animals, an accurate history of their movement through the streams of commerce can be recorded and traced.

Notably, within the USAIP, the identification devices used to identify animals may vary across species groups. A USDA official device may be required.

Major opposition from the livestock industry has delayed implementation of the USAIP. One of the main drawbacks to implementing the USAIP's NAIS relates to the ability to protect the confidentiality of collected data. For example, many livestock producers are concerned that the Freedom of Information Act (FOIA) would require the government to release all collected traceback data. Releasing such information could cause irrevocable harm to the livestock industry just as it did when the first Mad Cow case was discovered in the U.S. Moreover, releasing confidential business information could also damage reputations and cause producers to lose money.

For example, inaccurate tracking results may result in treating animals, such as by a quarantine, that were healthy and did not require segregation. This would cause a producer to lose money since quarantine interferes with the movement and management of animals in normal commerce. Moreover, because of an inappropriate quarantine, a livestock producer and its herds generally may be perceived as being "bad," which hurts the reputation of the producer and its other herds. Furthermore, livestock producers and marketers are concerned that they may incur consumer liability (or at least legal costs) despite inaccurate tracking results.

Protecting records also is important to prevent unfair speculation and manipulation of pricing at sourcing and markets. For example, if the government obtains and releases industry proprietary information, buyers or sellers of livestock can artificially inflate or deflate prices based on the released data. Ultimately, collected traceback data should be safeguarded. Hence, there is a need for a NAIS that ensures the confidentiality of that data.

The USAIP's NAIS is difficult and costly to implement. The USAIP creates a separate NAIS dedicated exclusively to animal traceback. This means livestock producers that already use commercial systems to track their animals would have to finance their current tracking systems as well as the NAIS. Hence, the cost may become prohibitive for small herd owners. Moreover, the USAIP experts failed to recognize the need to utilize commercial tracking and management information systems that actually would add enough value to the process to cover the cost of the official government requirements. Furthermore, the USAIP failed to recognize the inherent resistance to additional government mandated identification, reporting and costs to industry when more then 99 percent of animals are healthy, disease free, non-quarantined animals. These additional costs would be implemented in order to identify the less than 1 percent of livestock requiring FAD management.

The proposed NAIS restricts animal movement in commerce and provides no method for a real time confirmation of the official records. Real time confirmation could be an important feature for buyers and sellers of animals. Again by way of example, a buyer would like to know, virtually immediately upon inspection, whether the animal has an appropriate movement record, and further that such record can be accessed as desired. If a move-in or move-out event occurs reasonably close in time to a buyer wanting to purchase an animal, then these recent events would be important information that should be available to the purchaser. The proposed NAIS does not allow for real time reconciliation of such events, whereas the embodiments disclosed herein do allow real time reconciliation.

The USAIP's NAIS also rely solely on RFID identifiers to identify an animal. A producer may lose an assigned RFID, or the RFID may fail to operate correctly. As a result, the animal's identification cannot be properly recorded, or if initially recorded correctly, cannot be verified upon a move-in or move-out event. RFIDs also would have to be requested by a producer, provided by a government agency, associated with an individual animal, and then such information reported to the agency. This scenario requires time and compliance with the requirements by each producer. Embodiments of the disclosed method and system allow for other animal identifiers to be used, which increases appropriate identification of problematic animals and compliance by participants.

The components and systems of an AIF (AIF) accomplish what the USAIP proposes, while overcoming its limitations. The animal identification framework incorporates computerized data management system tools and techniques to timely process information regarding the movement of livestock from one location to another. The framework helps maintain the normal speed of commerce in buy/sell transactions, helps provide records making the animals more valuable to the buyer and seller, improves the accuracy of movement and animal sales transactions, protects the animal owners from liability due to inaccuracies, protects the confidentiality of producer data, and lowers the cost of tracking animals.

In commercial and private settings, the information collected through this framework is beneficial in a variety of ways. For example, when an animal change of possession occurs, the new owners or custodians may be easily provided with the historical animal records and current records necessary to move the animal. Suppose, for example, a purchaser buys an animal without first obtaining a traceback history of the animal. Owning animals purchased without records violates regulatory rules and purchasing animals without historical records incurs a risk of being unable to resell the animal.

Additionally, this framework may protect purchasers against liability in case of a disease outbreak. Moreover, because information is collected in an organized and strong framework, it is possible to share commercial data among the diverse and segmented livestock industries, thereby adding value to the overall system, and helping offset the costs associated with the implementation of the AIF. There are other private benefits and uses for the AIF.

In a public sense, the framework is beneficial because it allows health officials to identify and quarantine animals that have commingled with diseased animals. Thus, it reduces the chance that a consumer will purchase infected meats or tainted animal products. For example, suppose a cow is diagnosed with Mad Cow disease. To protect consumers from purchasing tainted meat, health officials or industry members, using the embodiments of the disclosed system and methods of the AIF, may traceback and ascertain where an animal has been. Based on that information, other animals that have commingled with the diseased animal can be examined or quarantined for the same disease.

To trace animals, within the framework, animal information is recorded as animals pass through data collection points. At minimum, the recorded information includes location history information (e.g., a PID) and an animal identifier (e.g., a UAID). However, in many situations, animal information includes other information, including commercial and confidential information. For example, it may include the height, weight, size, age, sex, color, type of feed, drug treatment history, actual animal location, such as by GPS, name of owner, and other relevant animal information. Conducting a computerized trace of an animal involves ascertaining the animal identifier and searching the recorded animal information to find previous locations where the identified animal occupied.

Within the framework are various tools and techniques for collecting animal information. The MBPs, the disclosures of which are hereby incorporated by reference, describe various tools and techniques for collecting and tracking animal histories. For example, some of the tools and techniques described in U.S. Pat. No. 5,673,647 (the '647 patent), such as the electronic ID tag, which is encoded with an animal identifier, may be used to uniquely and universally identify an animal. Using those identifiers, tools in the MBPs may collect and store animal information. For example, as the animal passes through data collection points, such as those described in the MBPs, animal information is collected. Typically, the data collection points use sensors, scanners, or other reader technology to record animal information as it passes through a gate or chute. Additional information may be collected when an animal is examined, weighed, measured, or otherwise analyzed. With that information, authorized health officials and others may trace an animal's location history.

In some implementations, the AIF includes an integrated database system that shares non-confidential animal information among industry members and authorized health officials. The database system may be located at a single location, at multiple locations, with identical, redundant information, or multiple, networked locations sharing different information. The database system also may be in different countries to integrate information collected by multiple countries. Filtering tools and techniques are used by a data trustee to screen confidential from the shared access database. The shared information includes enough data for the USDA and health officials to accomplish their traceback objectives, yet still protects animal producers' interests.

For example, the AIF includes the official database specifically containing all reported animals records and administered and regulated by a data trustee. The data trustee screens sensitive information from the government and other third-parties by removing any information regarded as confidential. The data trustee official database only forwards to a government-accessible database the information necessary to use for requesting animal trace information from the official database to identify an animal. When a diseased animal is discovered, the USDA looks up the animal in its database and requests a traceback history from the data trustee database for the animal to be entered into the government database. By implementing a data trustee in the AIF, animal producers maintain control and access to confidential information, and avoid many of the problems associated with inaccurate or leaked information.

The tools and techniques associated with the AIF use or adopt proven existing technologies wherever possible. For example, implementations utilize state-of-the-art national and international animal identification standards with the best available and practical technologies to create a plan that is dynamic and flexible, and that incorporates new and proven technologies as they become available.

The techniques and tools described herein can be implemented in various ways, and may be used in combination or separately.

Figure 53:
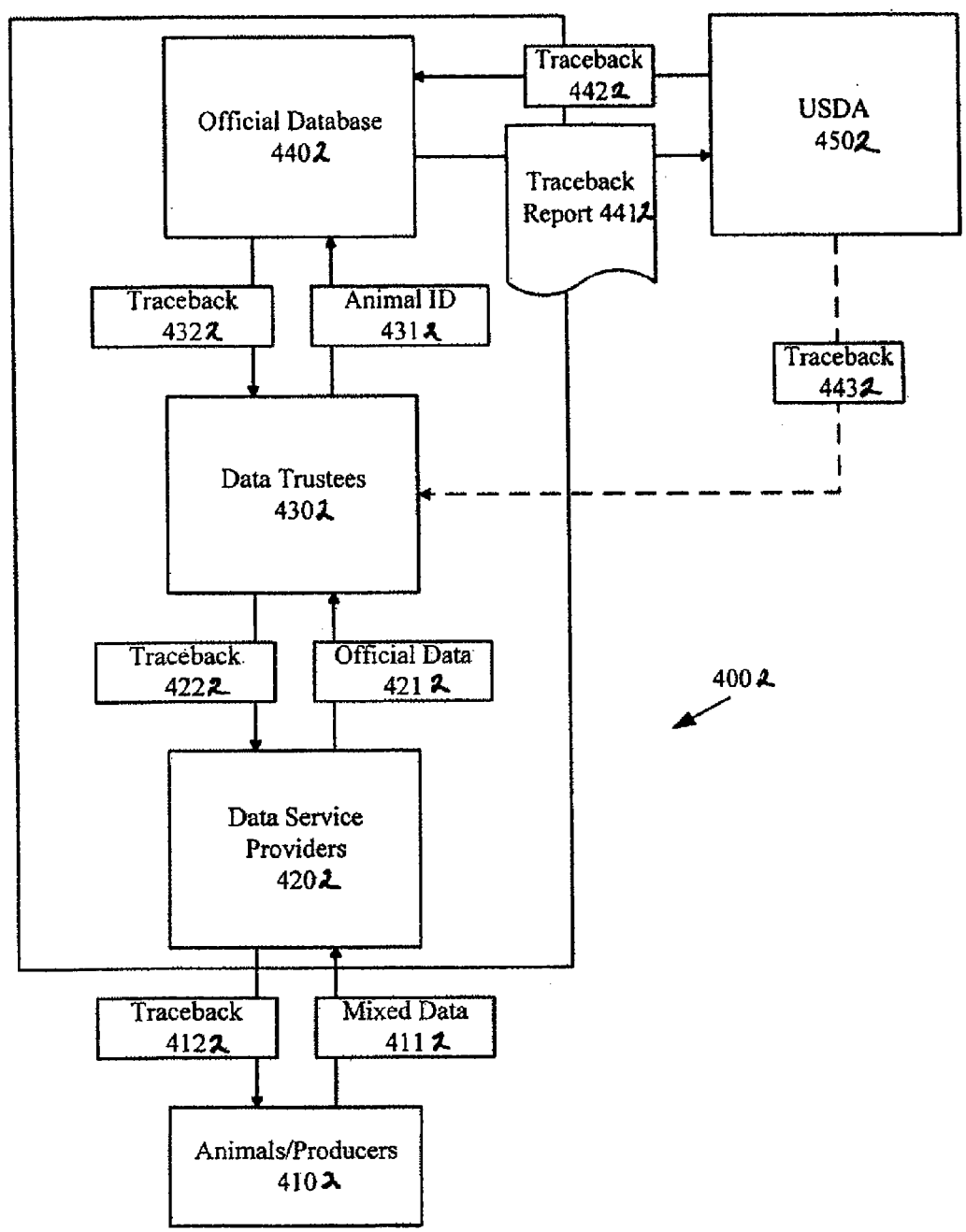
FIG. 53 is a block diagram of an AIF for tracing animal location histories.

An AIF ("AIF") is an extensible framework designed to facilitate the collection and traceback of animal data, including their location histories. Within this framework are included both hardware and software components that identify animals, that transmit data about the animals, that collect the transmitted data, that filter out confidential information from the collected data, and that release the confidential data when necessary. FIG. 53 shows an exemplary AIF 4002 in which various techniques described herein may be implemented. Basically, the AIF 4002 has tools that collect and store (or work with hardware and software that collect and store) animal identification data, including the animal's location history. The AIF 4002 filters confidential information and releases the information upon proper request.

AIF 4002 is a cross-system framework that can be used with multiple database systems, hardware devices, and applications in many configurations. It provides a strong foundation upon which animal traceback tools and techniques can be implemented. The AIF 4002 may use tools and techniques described in the MBPs, but this is not a requirement of the framework 4002.

FIG. 53 shows various components of the AIF 4002. Among those components are a data service provider 4202 for receiving and storing transmitted data 4112, a data trustee 4302 for screening the confidential parts of the received data 4212, and an official database, or potentially multiple databases, 4402 for storing non-confidential data 4312.

The AIF 4002 collects data from an animal or animal producer 4102 and provides a traceback history report 4412 for government and health officials 4502. A variety of tools and techniques may be used for transmitting animal information 4112 to the framework 4002. Some of these tools and techniques are hardware-based and others are software-based. For example, an electronic identification device ("EID") may be attached to the animal 4102. As the animal 4102 passes through an AIF data collection point, the EID transmits pre-encoded animal information 4112 to the AIF 4002. The data service provider 4202 detects the transmission of data 4112, receives the data 4112, and stores the data.

Data service providers 4202 as illustrated in FIG. 53 include commercial data system organizations that have the necessary personnel, computer management expertise, and data gathering capabilities to detect, receive, store, and report animal information. Alternatively, or in conjunction with a commercial data system, a data service provider 4202 includes, without limitation, animal producers, marketers, and purchasers that own and operate the necessary reader and data storage technology to receive, store, and report animal information.

Within the context of an NAIS, there may be a multitude, e.g. hundreds of data service providers 4202 to collect animal information. These data service providers 4202 are ratified by industry members.

The information 4112 received by the data service provider 4202 typically includes a mix of commercial and official data 4112. Official data includes the data necessary for the USDA to traceback an animal. The data service provider 4202 forwards the official data 4212 to data trustee 4302. Or, the data service provider 4202 forwards both the commercial and official data 4212 to data trustee 4302.

Within the AIF 4002, a data trustee 4302 serves as a buffer between commercial animal identification systems and any government system. The functions of a data trustee 4302 are to receive forwarded data 4212 from data service provider 4202, screen and filter the forwarded data 4212 to maintain the official database 4402, which may be a multiple database system, and generate reports.

As a component within the AIF, a data trustee 4302 includes those individuals, groups, organizations, and tools designated by industry members, perhaps approved by government, to screen the forwarded animal information 4212 before it is sent to the official government-accessible database 4502. The actual number of data trustees may vary based on cost to implement, size and growth of the cattle industry, improving network and database technologies, and other such factors.

After receiving forwarded data 4212, the data trustee 4302 screens and filters the data to remove confidential information. The data trustee then forwards the filtered data to the official database 4402. Typically, the filtered data includes the necessary information for the USDA database 4502 to start tracing an animal's location history. For example, the data trustee 4302 filters all the forwarded information except for an animal identifier and a data record address to a record in the data trustee database. Knowing the animal identifier is sufficient to retrieve the other animal information from the data trustee 4302. In other implementations, the data trustee 4302 may filter more or less data. The amount and type of data forwarded to the official database 4402 may change as government and industry needs change.

The official database 4402 contains official data. It is the repository of data trustee filtered data 4312. In the AIF 4002, a data trustee 4302 is the administrator and arbiter of all the data that is stored in the official database. In some implementations, the official database is the only database the government 4502 has access to. In other implementations, the data trustee is the only entity to have access to the official database 4402. More than one official database may be maintained in order to provide quicker access to data and to provide redundancy and fail-safes in case a connection or system goes down. Data in multiple databases is synchronized periodically to ensure consistency throughout the databases.

In some implementations, multiple databases are maintained to further protect confidential animal information. For example, the data trustee 4302 maintains the official database 4402, and the government 4502 maintains a separate database. The other database under control of the data trustees contains official, yet confidential information, e.g. sensitive data, that the government can request when needed, but that will not be subject to standard government FOIA rules unless requested by the government. This allows industry members to keep data confidential until requested by the government. For example, a rancher wants to keep his ranch premise identifier confidential. The government does not actually need access to the premise identifier until an animal health or safety issue arises. Thus, the data trustee filters the premise ID from being forwarded to a government controlled database. When the need arises, the government may submit a request to the official database administrator trustee for that information based upon an identified animal. After a proper request, the data trustee sends the requested information to the government. The number of filtered fields in the official database may vary depending on implementation, government regulations, logistical concerns, ease of implementation, and other such factors. Using data requested from the official database 4402, government and health officials 4502 have access to sufficient data to traceback an animal within the currently mandated 48-hour time period. In other implementations, tracing an animal may take more or less time to complete, and much faster traceback results likely can be achieved with the present method and system, such as within minutes.

The AIF 4002 provides a variety of traceback reports 4122, 4222, 4322, 4422 to confirm events as they occur. For example, when a cow is shipped to a feedlot, a confirmation report 4122 is sent to the animal producer 4102 confirming animal arrival. Similarly, when animal information 4212 is forwarded to the data trustee, a traceback report 4222 is sent confirming receipt of the data. The report 4222 also may include a reconciliation of premise and animal information. After data has been filtered and forwarded to the official database, another report 4322 is generated and sent to the data service provider 4202 confirming receipt of the information. The report may reconcile information from the report against data stored in national identifier repositories. The format and delivery methods of these reports may vary. For example, some reports are sent via text email. Other reports are accessed over a webpage. Some are sent as text files, PDFs, or other standardized format. Alternatively, the reports are text messages, paper copies, or some other readable format.

In some other implementations, animal producers 4102 are allowed to request a report from the data trustee 4302 in order to view their current inventory as recorded in the official database 4402. This function allows producers 4102, data service providers 4202, and data trustees 4302 to correct any potential database errors by reconciling information.

For example, upon request, a rancher files a move out report with a service provider and receives a move in report from the service provider. The rancher checks the record reporting move-out/move-in information against each other. If there are any errors, the rancher submits a request to correct the information. By generating confirmation reports as data passes from one component of the AIF 4002 to another, errors and inconsistencies in the data are identified throughout the process, avoiding major discrepancies or errors in the future. They also provide an automated chain of custody to ensure the database information is synchronized with actual animal movements. To not implement a chain of custody and reconciliation process compromises the integrity of the NAIS and increases producer liability concerns.

Alternatively, the data trustee 4302 and the official database 4402 allow animal producers 4102 or other users to perform the essential functions of reading, updating, and deleting records. To do so, an interface, such as a web-based interface, a database interface, or customized software application, is provided so animal producers 4102 or others may securely connect to the database to read and/or update records. In some implementations, error correction is done directly by the animal producer 4102, e.g. they log onto a secure system and manually correct errors. Preferably, an animal producer submits a request to correct erroneous data to the data trustee 4302. The data trustee verifies the submitted data and makes appropriate updates. Other techniques for updating and correcting information also may be available.

Finally, within the AIF 4002, government and health officials 4502 trace animal location histories. To do so, the USDA 4502 accesses data in the USDA database 4502 and then submit a formal request for a complete trace of an animal to the official database 4402. Upon receipt of a request, the official data base 4402 generates a location history report 4412. The location history report includes a list of every premise the animal has occupied during its traceable lifetime. The location history report also includes other information, such as the date, time, and group number associated with an animal when it lived at a premise.

Using the information from the location history report, the government officials 4502, alternatively, contact the listed premises for more information or request further information from the official base 4402. In some implementations, the initial history location report 4412 includes all animal identifiers that have ever commingled with the traced animal.

Notably, when officials 4502 make a direct request to official database 4402 for information, all official data is granted within the guidelines set forth by government and industry regulatory bodies. Other confidential information is released at the data trustee's discretion.

The AIF 4002 includes elements of software and/or hardware. The relationships shown between components in FIG. 53 indicate the main flow of information; other relationships are not shown for the sake of simplicity. Depending on implementation, components can be added, omitted, split into multiple components, combined with other components, and/or replaced with like components or systems. Alternatively, a framework with different components and/or other configurations perform one or more of the AIF techniques described herein.

Various implementations of the components in the AIF 4002 are described below.

Figure 54:
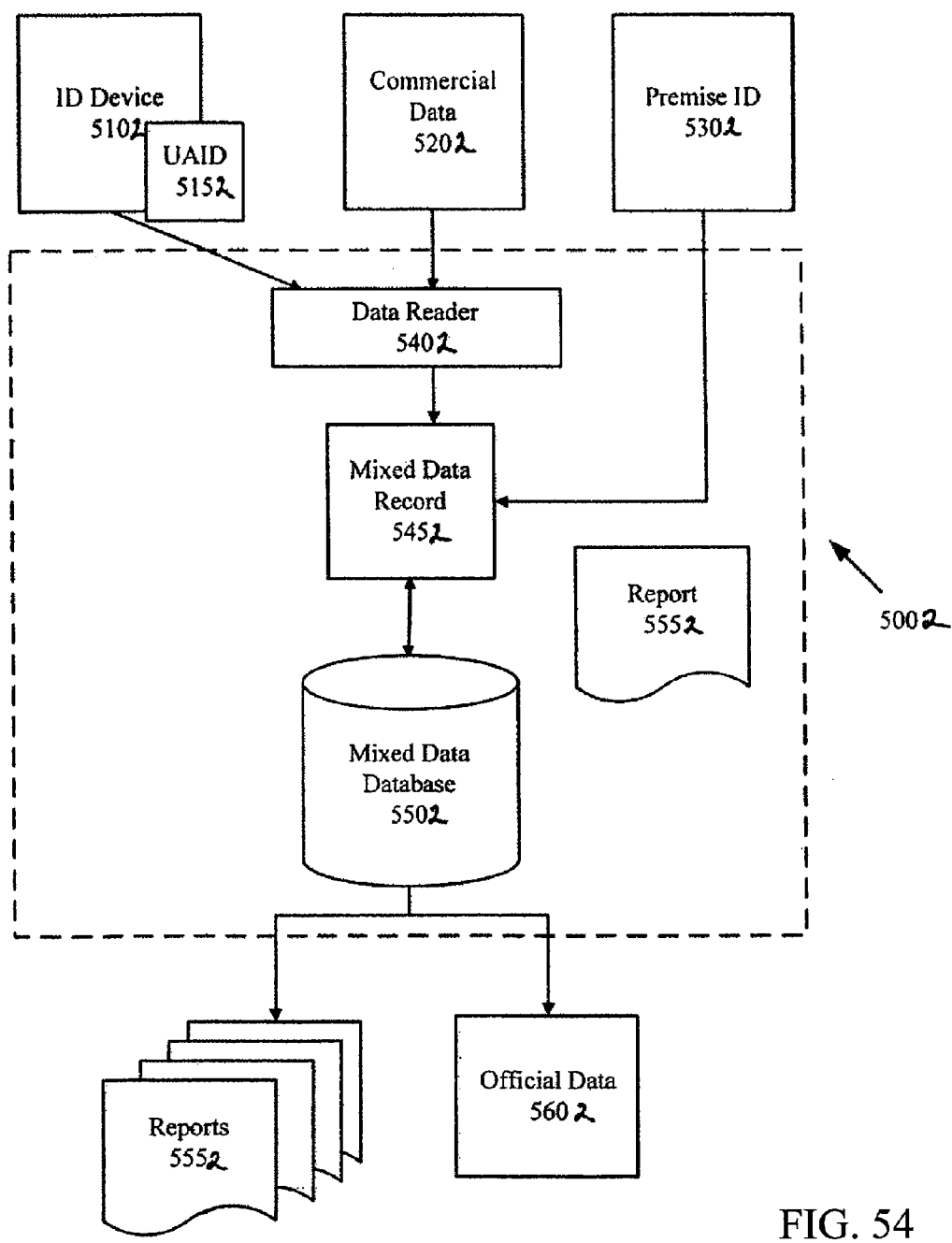
FIG. 54 is a block diagram of a data service provider for receiving, storing, and reporting animal information.

Data service providers provide the necessary data collection tools, reporting systems and services, customer support and education to enable the transfer of data from animal producers to data trustees. FIG. 54 illustrates a simple block diagram of a data service provider 5002 such as data service provider 4202 discussed in connection with FIG. 53. The data service provider 5002 collects and stores animal information in a single or multiple databases 5502, generates reports 5552 confirming receipt of the information, and then forwards official data 5602 to a data trustee. As illustrated in FIG. 54, the data service provider 5002 includes elements of software and/or hardware. The relationships shown between the components in FIG. 54 indicate the main flow of information; other relationships are not shown for the sake of simplicity. Depending on implementation, components can be added, omitted, split into multiple components, combined with other components, and/or replaced with like components or systems. Alternatively, a data service provider with different components and/or other configurations perform one or more of the techniques described herein.

The data service provider 5002 receives data from multiple sources. Some of those sources include an EID 5102 and other commercial data entry tools 5202. Also, the data service provider may add premise identifying information 5302.

An electronic identification device (EID) 5102 provides animal information to the data service provider 5002. The EID includes elements of software and/or hardware. Various implementations of EIDs are discussed in the MBPs, which are incorporated herein. For example, in the '647 patent an electronic identification tag that uses radio frequency technology (RFID) to transmit signals to an RF reader is disclosed. An RF reader collects and stores the information sent by the RFID tag. In other implementations, the EID may use other wireless and microwave technologies, such as Wi-Fi, WiMax, etc. to transmit animal information to the data service provider 5002. Moreover, in yet other implementations, the EID is a transponder, a chipcard, a biometric device, a magnetic device, scan code, bar code, a visual cue such as a cattle brand, or any other state-of-the-art and/or cost effective technology. Alternatively, the EID 5102 is implemented as a combination of these technologies. The EID tag also can be used to provide specific location information for each individual animal, such as by using GPS, as opposed to just general location information.

For example, under the USAIP, a specific type and design of radio frequency identification (RFID) official tags are used as the official identification device to identify animals. However, any RFID tags following ISO standards create numbers that can universally identify animals without needing any additional setup. Therefore, the AIF RFID numbering system provides producers the flexibility to utilize readily available ISO compliant identification devices from a source of their choice. For example, there are nonofficial RFID ISO compliant tags that may be used one time or multiple times to reduce the cost. Moreover, by using non-official, ISO compliant tags the industry is not burdened with sourcing restrictions and managing official tags inventory for the USDA. Different species of animals may use different types of tags.

In some implementations, the EID is programmable, e.g., animal producers or others can encode information onto the EID. At the very least, the EID 5102 includes an animal identifier 5152 as described below that uniquely identifies an animal in the NAIS. However, other information, including but not limited to, age, sex, weight, breed, owner, drug history, feed history, etc. also may be encoded into the EID.

An animal identifier 5152 is a value recorded in the official database, which also may be encoded onto animal tracking devices 5102. The animal identifier is a unique value assigned to individual animals to which all of its collected information including the physical animal identifier is linked in the various databases described herein. For example, when the data service provider collects animal information, the universal database animal identifier 5152 (UAID) serves as the value that distinguishes one animal's record from others'.

As discussed above in connection with FIG. 52, the animal identifier is an assigned UAID. Alternatively, the animal identifier is a different value. A UAID establishes permanent, tamperproof database identification for each animal to which all identification devices like RFID, visual identification or other identification methods can be linked. UAIDs are official 15-digit-ISO identification numbers allocated by the USDA. These UAID numbers may be encoded on the RFIDs or an alternate ISO or other numbers may be used. However, in some cases, at the producer's option, those official numbers are not required to be on the animal and an alternate physical identifier is used. For example, in a small herd of 20 animals, the animal producer keeps a list of his animals' UAIDs. When an animal identified by an ID device, method or system 5102 is moved or sold, animal information, including tracking information, may be scanned from the producer's records (e.g., scanning bar codes from paper), entered manually, or input in some other way.

To maintain consistency throughout the database, if an EID is lost or becomes unreadable, the animal identifier encoded into the first EID is re-encoded into the new EID, or alternatively the EID is replaced by a new EID. Thus, the universal animal identifier UAID 5152 tracks the animal over its lifetime by linking all ID devices, methods or systems 5102 to the same UAID 5152.

Assigned UAIDs are placed in an animal identifier repository. The reason for the repository is to ensure the uniqueness and universality of the identifier and ensure animal data is available for access when needed. Moreover, in some implementations, an animal identifier allocator assigns UAIDs to animals upon request. For example, under a nationwide animal identification system as described herein (NAIS), as new animals are born, a rancher requests animal identifiers for each newborn animal. The UAID allocator, in response, sends the identifier values to the rancher, which is encoded in EIDs for the calves or, for example, the rancher uses the UAID to link with the EID as reported to the official database. Animals other than food animals also can be tracked by the system, as they also may come into sufficiently close contact with a food animal to transmit disease. For example, pets and wild animals that are tracked by pet owners or wildlife officials also can be tracked using disclosed embodiments of the method and system.

As an animal identification system, either a nationwide (NAIS) or worldwide system, is implemented, there may be difficulties in assimilating and converting current tracking systems. To reduce costs, to allow producers and data service providers to maintain their current system while the transition occurs, and to allow time to install approved EIDs on animals, animal information may be linked to other values until a permanent system is in place. For example, the name of a company and its proprietary animal identifier may uniquely identify an animal. Thus, during the transition phase, an additional field in the various databases lists that temporary identifier value, until a new conforming identifier is in place. Animal information is updated and linked to the new animal identifier as it becomes available.

In some implementations, the animal identifier is associated with meat shipments during processing and even after the animal has been slaughtered. For example, packaging containing processed food products can be tracked, and the food products correlated with the animal history from which such products were produced.

Referring again to FIG. 54, data service provider 5002 also receives and stores commercial data from commercial data sources 5202. Commercial data includes commercially valuable data, e.g., the type of data used by animal producers in the course of business. For example, commercially valuable information includes, but may not be limited to, an animal's owner, breed, size, weight, age, sex, feed type, vaccination or other treatment reports, pricing terms, veterinarian reports, and any other data that is commercially useful. The amount and type of commercial information collected by the commercial data sources 5202 may vary based on individual producer needs. Commercial information sent by commercial data sources are collected by the data reader 5402.

In some implementations, commercial data sources are the tools and techniques described in the MBPs, which are incorporated herein by reference. For example, one aspect of the '647 patent tracks the historical and projected weights of animals using external measurement tools at feedyards. That information may be valuable for commercial purposes. Using such tools and techniques described in the '647 patent information is collected so that it can be transferred to data service provider 5002. The actual transfer involves transmitting information from the animal producer's computer systems to the data service provider 5002. The data reader 5402 receives the commercial data about an animal and adds it to the animal's complete data record 5452.

A premise identifier 5302 identifies a premise, which is an identifiable physical location that conducts animal agriculture. In FIG. 53, premises include both animal producers 4102 and some, if not all, data service providers 4202. Referring again to FIG. 54, the premise identifier 5302 is submitted by the participant and automatically added to animal data records by the data trustee whenever an animal is moved from one premise to another. For example, a cattle rancher auctions an animal locally. When the cow moves from the ranch to the auction house, the animal's data records are updated to reflect this move. When the cow arrives at the auction house a new data entry, including the auction house's premise identifier, is added to the cow's records showing the cow's arrival and submitted to a service provider. Thus, an animal's location history can be tracked using the UAID to obtain the premise identifiers. In some implementations, the premise identifier is the PID described in connection with the USAIP described above. Alternatively, it is a different value. It also may be possible to track movements of cattle according to shipping method. For example, animals commingled on a single transport, such as a truck or train, also might be identified by assigning particular identifiers to the transport method used.

As suggested by the USAIP, in some implementations a national or worldwide premise allocator assigns PIDs upon request. Referring back to FIG. 51, however, there are other implementations for allocating premise identifiers not described by the USAIP. For example, an animal producer 2102 fills out on electronic request form and submits it to the premise allocator via the Internet. In response, the premise allocator assigns and sends a premise identifier to the requesting animal producer 2102. Notably, in this implementation, the premise allocator assigns the identifier without prior screening by state officials. In other implementations, the premise allocator files a request with the state for verification information before assigning the identifier. Alternatively, the premise allocator verifies some minimal pieces of data, such as name, address, and phone number, before allocating the identifier.

Another implementation for assigning premise identifiers involves a data trustee. A data trustee is given a range of premise identifiers that are allocated to when an animal producer or premise reports animal information for the first time. For example, a non-registered premise sends animal information to a data service provider. Since there was no valid premise identifier, the information is immediately forwarded to a data trustee. The data trustee obtains and allocates a premise identifier for the non-registered premise and notifies the premise of the new value. Moreover, a copy of the premise identifier with accompanying premise identification information is deposited in a national premise identification repository. As before, the data trustee may ask for verification information from the requesting premise before allocating a premise identifier.

In some cases, the premise allocator or data trustee assigns a temporary identifier to a premise until the premise can be certified by either the allocator, government agency, or the data trustee. Under these circumstances, the temporary identifier may be only allocated for a short period of time after which the premise needs to be authenticated by an appropriate entity.

If a temporary identifier is used, after a premise is authenticated the temporary identifier is made permanent. Alternatively, a new permanent identifier is assigned and all records with the temporary identifier are updated with or linked to the new identifier. Again in the alternative, records received from a premise with a temporary identifier are maintained in a separate database until the premise has been authenticated. At that point, all of its records are moved to a valid premise database. Temporary identifiers may be distinguished from permanent ones based on their format, based on a table listing temporary identifiers, or in some other way.

The actual format of the premise identifier may vary. According to the USAIP, a PID is a 7 character alphanumeric value. In other implementations, the premise identifier may have more or less characters. Moreover, a premise identifier 5302 may be randomly generated according to a defined format, it may be assigned from a master list or database of values, it may be derived from animal producer information (e.g., a hash of the premise's name or other proprietary information), it may incorporate letters or numbers from a premise company name or brand, or it may be derived in some other way.

In some implementations, a value such as a NULL, zero, or other random non-conforming value may be inserted into a data record until a proper premise identifier is received.

Animal producers and premises 2102 are notified of their new premise identifier via a receipt web page, an email, mail, telephone call, or some other mechanism. In every case, the newly-generated PID is sent to a national or worldwide premise repository, such as the repository 2302 described in connection with FIG. 51.

Referring again to FIG. 54, once a premise identifier 5202 has been assigned and sent to the proper premise, the premise should include the premise identifier 5202 anytime it sends data to a data service provider 5002 or to a data trustee.

It is worth noting that, although the premise allocator is described herein as a single entity, implementations may include more than one allocator, each designated by government and industry members.

Related to premise identifiers are group identifiers (GIDs), which distinguish groups of animals from each others as they move through a premise as noted in connection with the USAIP. According to the USAIP, a GID is a six-digit identifier representing a premise arrival date and in some cases is combined with the premise ID. Thus, unlike the premise identifiers, GIDs are generated by the participant or data service provider 5002, and they may not necessarily be unique. For example, all the cattle that arrive at a feedlot on a specific date may be assigned the same GID. Alternatively, a GID may represent other information, for example, the building where an animal was housed. The GID may be combined with the PID to form a new identifier, or alternatively it may be a separate value in the mixed data database 5502.

FIG. 54 shows data reader 5402, which collects animal information for the data service provider 5002. The data reader includes elements of software and/or hardware. Various implementations of data readers are discussed in the MBPs, which are incorporated herein. For example, the '647 patent describes computer systems that record, measure, sort, and track individual animals. The data reader 5402 described herein performs the same and additional functions.

In some implementations, the data reader 5402 collects wireless and microwave technology transmissions (e.g., RFID transmissions) from devices directly attached to animals. Moreover, the data reader 5402 may collect signals and data from transponder devices, chipcards, biometric devices, magnetic devices, and other devices attached to or implanted into an animal. Alternatively, the data reader 5402 receives data transmissions from computing devices, such as computers, PDAs, scanners, cell phones, flash memory cards, and other similar electronic devices containing data, such as commercial data. In yet other implementations, the data reader uses video imaging and ultrasound technology to gather data. In other implementations, light or laser technology to scan bar codes or other visual cues (e.g., a cattle brand or mark) is used. In some case, animal information is read manually (e.g., visually) and input manually (e.g., through data entry or voice recognition means). Alternatively, other state-of-the-art and/ or cost effective data reader technology is used.

Data readers 5402 are installed at designated reader locations. For example, since participants include producers, grazers, auctioneers, feedlots, packers, and other animal marketers, data readers are installed at their premises b themselves or a data service provider. When an animal is sent to a participant that serves as a data service provider, an animal typically passes through an entrance gate or chute. Hence, an exemplary data reader is installed at the entrance gate or chute of data service provider 5002. Alternatively, the data reader is installed in animal barns, pens, stalls, or other similar locations.

As an animal passes through the data reader 5402, it collects animal information. At minimum, this includes an animal identifier. Other commercial and official data also may be collected at this time. Alternatively, the other data is transmitted separately, e.g., via a computer disk, paper copy, an email, a computer file, etc., and the data is later correlated to the animal identifier in the data service provider database 5502.

After the data reader 5402 collects information from the animal information sources 5102, 5202, AID, the data is added to the data service provider's database 5602 as a mixed data record 5452. A mixed data record 5452 combines confidential/commercial data with non-confidential/official data, typically in a single entry, in the data service provider database or databases 5502. Other animal information such as a premise identifier may be added automatically by the data service provider 5002. In some implementations, the database is indexed by the animal identifier.

The database 5502 is built from commercially available database services. For example, the database 5502 is an SQL database with various fields, such as breed, weight, date and time of arrival, animal identifier, premise identifier, etc., defined for the types of information received from the data reader. Alternatively, a different database builder is used, e.g., an XML database, an Access database, a web-enabled database, or any other well-known database management system (DBMS). In other implementations, a custom database is developed.

For ease of administration, the database 5502 may be spread over multiple computer systems. For example, a feed lot serves as a data service provider that receives data for thousands of animals every day. Due to the volume of the information being collected, multiple instances of the database are distributed across many different computer systems and perhaps even multiple computer networks in order to handle the information. To maintain consistency throughout the instances of the database and to keep the information current, the databases are synchronized periodically.

Defined fields are filled as animal information is collected into a record 545. Not every field needs to be filled to be complete a record. A complete animal record may include a subset of the information in the database, such as the animal identifier, premise identifier, event type and date and time of arrival.

At least some of the data stored in database 5502 is forwarded to a data trustee.

Data service provider 5002 provides reports 5552 to producers and data trustees confirming data has been received, recorded, meets NAIS standards, etc. These reports 5552 provide information regarding the status of an animal event and also provide a chain of custody that shows where an animal has been. Exemplary animal events include having an EID applied, moving from one location to another, branding, sightings, shipment to a slaughterhouse, processing into food products, shipping as food products, etc.

When a move-out transaction from one premise to another has been initiated then a corresponding move-in (receipt) transaction needs to acknowledge that the animals, or food products made therefrom, arrived at a valid premise within a specified time period. For example, a rancher sends an animal to a commercial feedlot (in this case serving as a data service provider) before sending it to be slaughtered. Moving the animal from one location to another is recorded by data readers. A data reader at the ranch records when the cow leaves and, in addition to other information, a data reader at the feedlot records when the animal arrives. Upon arrival at the feedlot, a confirmation report is generated notifying the rancher that the animal arrived. This report typically includes the animal identifier, premise identification, and event being confirmed. Alternatively, it includes a complete report of all recorded animal information, or any combination of sortable recorded information.

The reports 555 also are used to verify that data has been accurately recorded and to reconcile data with other databases. In the example above, a rancher may determine from the confirmation report that the animal EID listed is incorrect. To correct the error, the rancher contacts the data service provider and provides it with the correct data. Now, suppose in the above example, the commercial feedlot, as part of a normal verification process, checks with the repository or data service provider to validate the rancher's premise identifier. If an error is detected a report detailing this inconsistency is generated and sent to the commercial feedlot and to the rancher. Again the rancher corrects the error, even if it means requesting a valid premise identifier.

The number and type of reports generated by the data service provider may vary, depending on, for example, government and industry regulations, animal producer and data service provider wants and needs, and other such factors. Exemplary reports include a move-out report, a ship and traceback report, a move-in and reconcile report, and a termination report.

FIGS. 55A-55D show sample reports generated by a data service provider. For example, FIG. 55A shows a move-out confirmation report. The report confirms that 38 animals were shipped from a premise with PID S200971 and all the cows arrived at the destination premise (premise F201565).

FIG. 55B shows a move-in report. This report notifies the animal producer that seven of his animals are unaccounted for. The animal producer can then follow-up with the data service provider to reconcile this discrepancy. Reasons for this type of error include the fact that the cows may never have arrived at the destination premise, the premise identifiers may be unknown or unregistered, the animal identifiers may be invalid, or there was a hardware or software failure. Whatever the reason, the animal producer should know that he needs to check on his animals.

FIG. 55C illustrates a tag-applied confirmation report. FIG. 55D illustrates a slaughtered or termination report for an animal. Notably, FIGS. 55A-55D illustrate a technique for outputting confirmation reports. In other implementations, the report may be made via email, a web confirmation page, printed report, electronic text, or some other technique.

Throughout its entire process, data service provider 5002 uses secure network, database, and computing technologies. At least some of the data collected by data service provider 5002 is forwarded to a data trustee.

Data trustees establish a private sector infrastructure to insure that confidential animal information is not released to the public sector. A number of data trustees, approved by the livestock industry as well as the government, serve as a buffer between commercial animal information systems and any government sponsored systems. They are certified with standardized criteria and consent to be audited by industry associations and other oversight groups. Once certified, data trustees contribute data to the official database and provide government officials with animal traceback reports. Data trustees provide tools to receive, store and report data to the USDA for various purposes, including disease surveillance and health management purposes.

Figure 56:
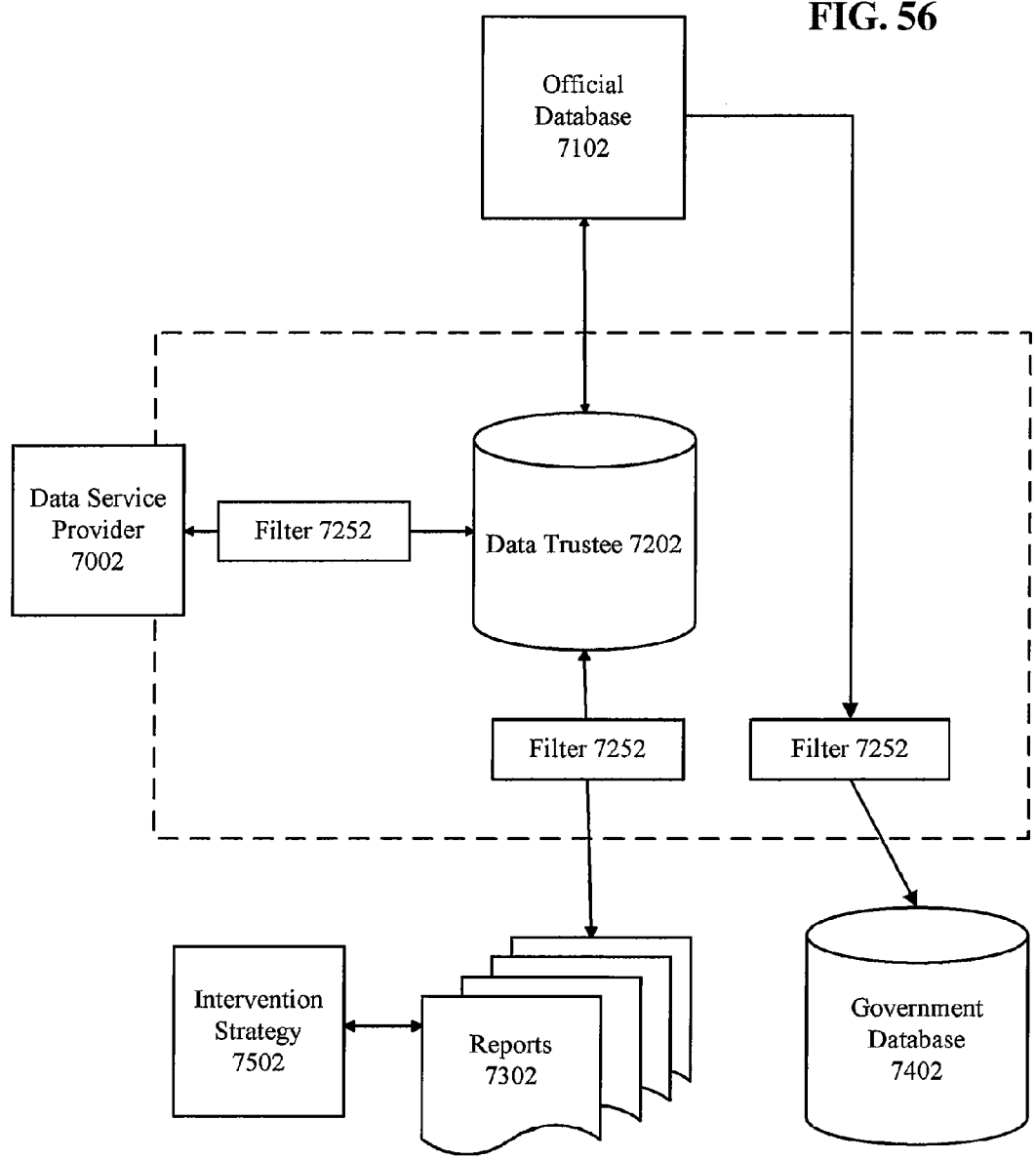
FIG. 56 is a block diagram of a data trustee for screening confidential information from received animal information.

As illustrated in FIG. 56, the data service provider 7002 includes elements of software and/or hardware. The relationships shown between the components in FIG. 56 indicate the main flow of information; other relationships are not shown for the sake of simplicity. Depending on implementation, components can be added, omitted, split into multiple components, combined with other components, and/or replaced with like components or systems. Alternatively, a data trustee with different components and/or other configurations perform one or more of the techniques described herein.

FIG. 56 illustrates a block diagram of a data trustee 7202. In some implementations the data trustee is data trustee 4302 described in connection with FIG. 53. A data trustee 7202 receives official data 7102 from a data service provider. The official data 7102 is stored in the official database 7102 to ensure that the integrity, security, confidentiality, liability, normal commerce, performance and efficiency goals of the NAIS are met. The official data is then screened by a filter 7252 to remove confidential information. Screened, non-confidential information is forwarded to the government database 7402. Using data from the government database, health officials may request a traceback report on a given animal. The data trustee 7202 generates the traceback report 7302 upon request. Preferably, the report is returned within a specified, agree-upon time period, such as within 48-hours of request or less.

A data service provider sends the data trustee 7202 official data 7102. Official data 7102 includes the data necessary to traceback an animal. For example, the official data may include an animal identifier, a premise identifier, group/lot identifiers, the date and time an animal was at a premise, etc. The official data 7102 also may include other non-official data. In fact, in some implementations, the data forwarded by the data service provider 7002 includes all of the animal information collected by the data service provider. The reasons for doing this include centralizing animal data records and providing wider data access to industry members.

Alternatively, the government may impose requirements on what constitutes official data. For example, currently the government requires access upon request to information describing specific animal events such as when a tag is allocated, when a tag is applied, when an animal is moved-in to a premise, moved out of a premise, when a tag is lost, when a tag is replaced, when an animal is imported or exported, sightings of animals, when an animal is slaughtered or dies, when a tag is retired, when an animal is missing, veterinarian inspections, drug information, and other such data. Some of this data is confidential, some of it is not.

Government and health officials are only granted access to the data after making a formal request to the official database. Alternatively, access is granted only at the discretion of the official database according to specific business and industry guidelines. This protects confidential information from being released to the public at large.

After the data trustee 7102 receives official data from a data service provider, the official data 7102 is added to the official database 7102 by the data trustee 7202. Preferably, the official database operates and is supported 24 hours per day, seven days a week, and 365 days per year.

The official database 7102 is built from commercially available database services and includes the underlying data, hardware, and software application required to manage, view, access, add to, delete from, modify, etc., the database. An exemplary official database 7102 is an SQL database with application software built to access the underlying data. Within the database are various tables and fields, such as animal identifier, premise identifier, move-in date, move-out date, etc., defined to receive and store information from a data service provider. Alternatively, a different database builder is used, e.g., an XML database, an Access database, a web-enabled database, or any other well-known database management system (DBMS). In other implementations, a custom database built from the ground up is used.

For ease of administration, the official database 7102 may be spread over multiple computer systems. For example, a data trustee receives data for thousands of animals every day. Due to the volume of the information being collected, multiple instances of the database may be distributed across many different computer systems, perhaps at different locations, and perhaps even multiple computer networks, in order to handle the load. To maintain consistency throughout the instances of the database and to keep the information current, the databases typically are synchronized periodically.

In addition, to protect the integrity of the official database 7102, data trustee 7002 uses advanced and state-of the art security measures to protect the database's underlying hardware, software, and data. For example, during transmission to or from the data trustee, the official data 7102 may be encrypted using strong encryption algorithms (e.g., those algorithms provided in the Data Encryption Standard (DES), the International Data Encryption Algorithm (IDEA), the RSA algorithm, and Advanced Encryption Standard (AES)). Alternatively, or in conjunction with the strong data encryption algorithms, secure protocols are used to transmit the official data 7102 over a data network. For example, the data may be sent to a secure website, using the secure hypertext transfer protocol (HTTPS). Pretty good privacy (PGP) and secure sockets may also be used to protect the data during transmission. These and other security measures are designed to prevent non-authorized parties from reading or changing the official data 7102.

Furthermore, once the data is stored in the official database other security measures may be used to protect the data. In some implementations, the data trustees are required to implement strict procedures, such as requiring data trustee employees to display security badges, performing background checks on key personnel, securing computers in restricted-access facilities, requiring users to log on using a registered IP address or network-interface car, and implementing strong authentication requirements for accessing data, to control access to the official database 7102.

Moreover, additional security measures may be applied to the database 7102. Exemplary measures include encrypting the data within the database, adding security policies to the database that attach privileges and roles to people with access to confidential information, monitoring and logging a user's activities on the database to detect misuse or serve as an intrusion detection system, labeling certain types of data as confidential and creating strict rules for accessing the data, and auditing connections.

To provide redundancy and back-up in the event of disaster or failure, backup copies of the official database 7102 may be located in at least two secure and private locations. As a matter of procedure, occasional system checks are run to verify the consistency of the data in the official database 7102.

Other security measures, such as firewalls and other hardware and software measures, may be used to maintain the integrity of the system.

After the official data is secured, typically at least a portion of it is screened, filtered, and transmitted to the government database 7402.

A filter 7252 screens the official data 7102 to ensure confidential information is removed from official data being forwarded to a government-accessible database 7402. In some implementations, the data is filtered automatically. For example, as animal information is received from a data service provider, specific database rules are created to automatically forward designated fields of data, e.g., the animal identifier, to the government database 7402. Alternatively, data trustee personnel filter the data manually, e.g. they visually review data records and remove confidential information. Or, they copy the non-confidential information into a new data record. Then the new data record is forwarded to the government database 7402. Preferably, a combination of both automatic and manual filtering is used.

For example, a filter is programmed into the official database that automatically removes all data except for the animal identifier. When a new record arrives, the filter is automatically applied. Then the filtered data record is sent to a separate repository until it can be reviewed manually to determine if there is any remaining confidential information. This process provides an additional security measure and allows the data to be checked for accuracy before being forwarded to the government database 7402.

In some cases, there is no government database, only the data trustee's official database 7202. Under these circumstances, the filter 7252 may be applied after receiving an official request for information from a government official. In other words, a government official has to request even non-confidential information before it is released to the government. In this situation, the filter 7252 is applied just before sending the requested data. Alternatively, the government official may be granted limited access to the official database, e.g., the rights of the government official would be limited to non-confidential information In some implementations, received data is checked for accuracy before being filtered. For example, the data trustee, before filtering the data 7102, verifies the accuracy of some of the received data by checking a national premise identification repository to see if a received premise identifier is correct. Additionally, the data trustee may verify the accuracy of any received animal identifiers by checking an official database to see if the received numbers are valid. If invalid data is received, the data trustee likely will report the error to a data service provider or the animal producer, so that appropriate corrections are made. Alternatively, the identifier checks are performed after filtering.

The amount of data being filtered is based on predetermined government and business guidelines. In some implementations, all the animal information is filtered except for the animal identifier. The animal identifier is forwarded to the government database 7402 along with the data record address that corresponds to the animal's information in the official database 7102. Alternatively more or less data may be forwarded to the government database.

This filter 7402 allows the system to effectively address the concerns and the requirements of industry and health officials, protecting producer interests and enabling animal traceback within a short period of time without impeding the normal movement and commerce of animals.

Figure 57:
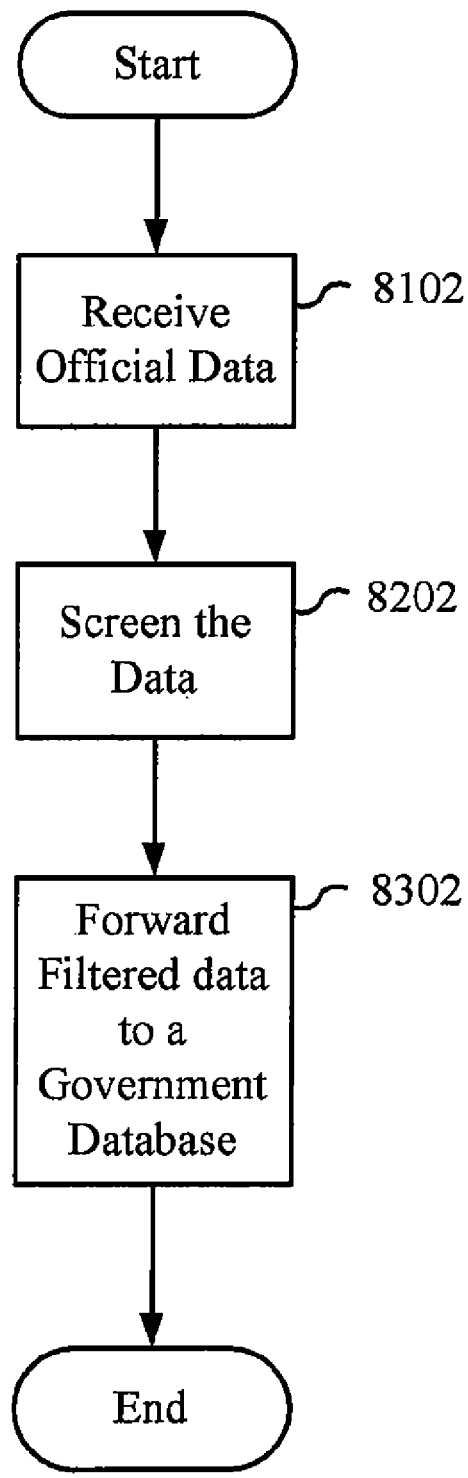
FIG. 57 is a flowchart illustrating a technique filtering confidential data.

FIG. 57 shows a technique 8002 for screening official data in an AIF. A tool such as the data trustee 7202 shown in FIG. 56 performs the technique 8002. Alternatively, another system, component, group, tool, and/or application perform the technique 8002.

A data trustee tool receives (8102) data records from a data service provider. The received data records include official data that allows government officials to traceback animals. For example, the received data records include an animal identifier, a premise identifier, and other official data. Alternatively, the received data contains both commercial and official data.

Upon receipt of data records from a service provider, the data trustee tool screens (8202) the data for confidential and/or non-official content. If any confidential information is found, the tool filters that data out before forwarding the data record. In some implementations, any data not specifically required by the USDA is filtered. The filter process is subject to modification based on government and industry regulations.

After filtering confidential information from the received data, the data trustee tool passes (8302) the screened data to a government database. The government database provides government officials with access to information that allows the government to begin tracing an animal's location history. For example, an animal is diagnosed with a Mad Cow disease. Out of concern for public health and safety, a government official uses the animal's identifier to look up traceback data in the government database. The traceback data stored in the database allows the government to request a trace history report of the diseased animal. Using the reports, other animals that have been in sufficiently intimate contact with the diseased animal, such as being commingled with the diseased animal, are investigated and treated in an appropriate manner, such as by being quarantined.

Alternatively, various stages of the technique 8002 are separately or in various combinations performed in conjunction with other stages.

Referring back to FIG. 56, the data trustee 7202 uses a filter 7252 to remove confidential information from received official data. The filtered data is forwarded to a government database.

The government database 7402, like the official database, is built from commercially available database services. Included within the term government database are the underlying data, hardware, and software application required to manage, view, access, add to, delete from, modify, etc., the database. An exemplary government database 7202 is an SQL database with application software included to access the underlying data. Alternatively, a different database builder is used, e.g., an XML database, an Access database, a web-enabled database, or any other well-known database management system (DBMS). In other implementations, a custom database is developed. The application which accesses the government database is preferably web-based, although alternative interfaces may be used. Within the database are various tables and fields, such as animal identifier, data trustee data record, etc., defined to receive and store information received from the data trustee.

For ease of administration, the database 7102 may be spread over multiple computer systems. For example, due to the volume of the information being forwarded from a data trustee, multiple instances of the database may be distributed across many different computer systems and perhaps even multiple computer networks in order to handle the load. To maintain consistency throughout the instances of the database and to keep the information current, the databases are synchronized periodically.

The government database 7402 stores only animal identification information. When a health related investigation is initiated the database 7402 receives additional information. In some implementations, for every animal record, the database stores an animal identifier and a data record address that points to a location in the official database 7102 from which additional animal information is retrieved. For this reason, the government database 7402 may not implement all of the security measures used to protect the official database 7102, but could if desired. However, to communicate with the official database 7102, the government database 7402 makes use of some of the same security measures. For example, the government database may employ the tools necessary to decrypt encoded data transfers and data packets from a data trustee 7202. Moreover, in some implementations, other security measures, such as adding security policies to the database, monitoring and logging user activity on the database, and auditing connections, are used to prevent non-authorized parties from reading or changing the official data 7102.

To provide redundancy and a fail-safe in the event of a disaster or system failure, the government database 7402 is backed up on a periodic basis. This may be done by maintaining duplicate instances of the database on separate computer systems. If one system fails, the secondary system begins operating. Moreover, storing a duplicate copy of the database at an off-site location, backing up the data using a back-up system such as a tape drive, and other similar mechanisms, all insure the consistency of the government database 7402. Occasional system checks may be run to verify the consistency of the data in the government database 7402.

As with the official database 7102, other security measures such as firewalls and other hardware and software measures may be used to maintain the integrity of the system.

Data trustee 7202 provides various reports 7302 to producers, data service providers, and government officials. Similar to the reports generated by the data service provider, some of the reports confirm data has been received, recorded, meets NAIS standards, etc. These reports 7302, like those 5552 described in connection with FIG. 54, provide information regarding the status of an animal and also provide a chain of custody that shows where an animal has been. The data trustee 7202 also provides animal traceback reports 7302, which unlike the confirmation reports created by the data trustee, are generated in response to a request from government officials and show a complete animal history.

The confirmation reports 7302 are made in response to animal move events. The confirmation reports disclose the factual information regarding the shipping and receiving premises without necessarily disclosing the premise identification numbers of previous premise locations. They allow data service providers and animal producers to verify that data has been accurately recorded and that data has been properly reconciled within the database.

For example, an animal is moved from a ranch to a commercial feedlot. This triggers at least two events: an animal move-out event from the ranch and an animal move-in event at the commercial feedlot. The data service provider records these events and forwards official data such as the new premise identifier to the data trustee. Upon receipt of the forwarded information, in some implementations, the data trustee generates in real-time a confirmation report to the animal producer. In other implementations, the data trustee reconciles the received data against its own records and those records stored at the national premise identifier repository and the official database. If no errors are found, a confirmation report is sent to the data service provider and/or the animal producer. Similarly, when an error is found, the report notifies the data service provider and/or the animal producer of the error.

In order to protect industry privacy interests, some premises receive a lifetime premise identifier. In the confirmation reports 7302, this information is not disclosed. On the commerce reports the premise identifier is reported as "confirmed."

The number and type of reports generated by the data service provider varies based on government and industry regulation, animal producer and data service provider wants and needs, and other such factors.

Related to a confirmation report is a traceback report 7302. Traceback reports 7302 include a location history for a given animal. For example, whenever an animal is moved, that animal identifier, the new premise identifier, date, time, etc. are all recorded in the official database 7102. In response to a request from a government official, the official database 7102 provides data to the government to generate a report tracing an animal's location history.

In some implementations, generating the report involves searching in the official database for every location an animal has been and reporting the information on that animal alone. Alternatively, when government officials request data for an animal traceback, the official database provides the data to generate a comprehensive list of animals that have at one time or another commingled, or have been more intimately in contact, with the "traced" animal. This search involves determining every premise where an animal has stayed. Then the search continues by identifying every animal that has stayed at the same premise. Such a search likely would be computing resource intensive (and may end up listing every cow in the country). Thus, to narrow the search, the data trustee 7202 adds additional search terms to its queries, such as the date an animal was at a premise, a GID, or other piece of data. By focusing the search, the data trustee can provide a reasonably accurate report of all animals that have commingled with the traced animal. Generally, this is done to identify diseased animals.

This type of investigation generally returns only a small percentage of the national herd. Thus, only a small percentage of animals need to be treated as deemed appropriate. Moreover, the privacy and security concerns of animal producers are protected.

FIG. 58 shows a report similar to what a traceback report 7302 for a single animal looks like. As listed, an animal with an animal identifier of 840 123456789012 lives at three different premises during its lifetime. The animal is tagged at premise AB12345. On Mar. 15, 2005, the animal is sighted on the same premise. Later, the animal is moved to a second premise GHI90JK, where the animal stays for about 5 months. On Dec. 20, 2005, the animal is moved to a slaughter house where it waits to be slaughtered.

After a traceback report 7302 is generated, if necessary, government and health officials develop a strategy 7502 to keep diseased animals out of the stream of commerce. For example, animals may be quarantined, treated, or slaughtered as the need arises. Alternatively, the animals are dealt with in any other suitable manner.

Figure 59:
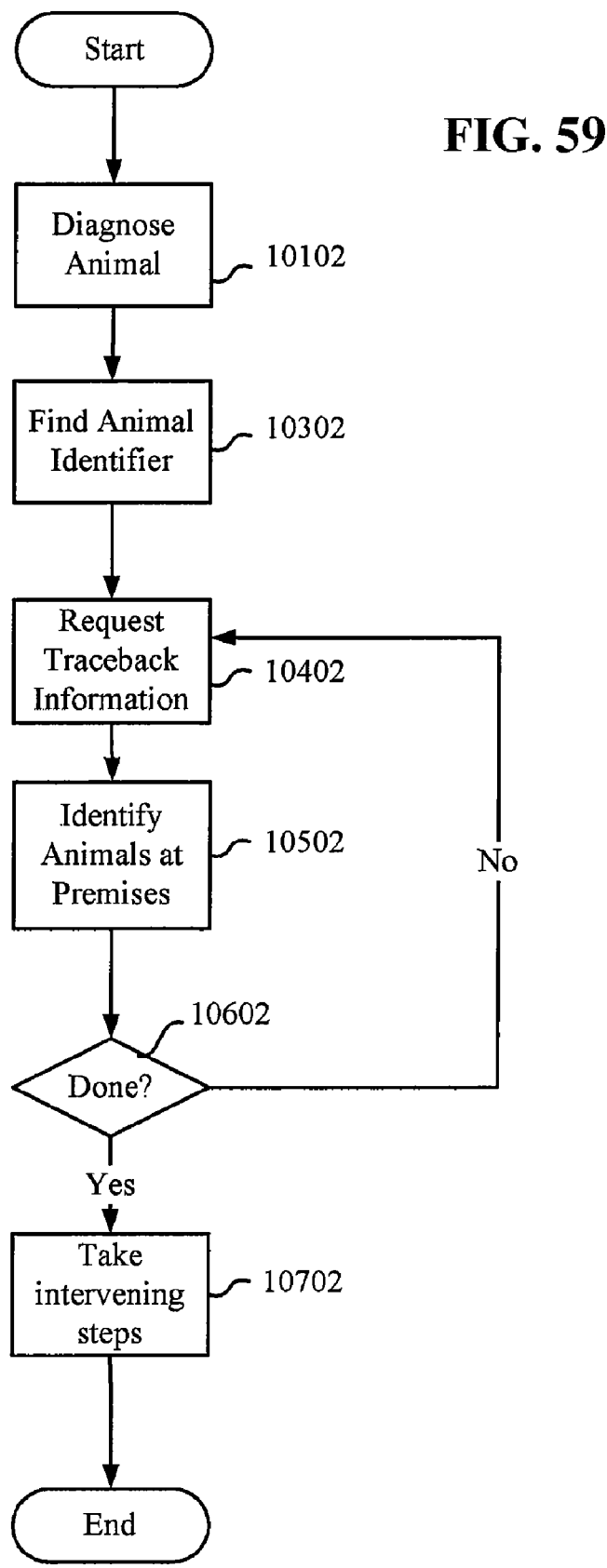
FIG. 59 is a flowchart illustrating a technique for tracing an animal's location history.
Figure 60:
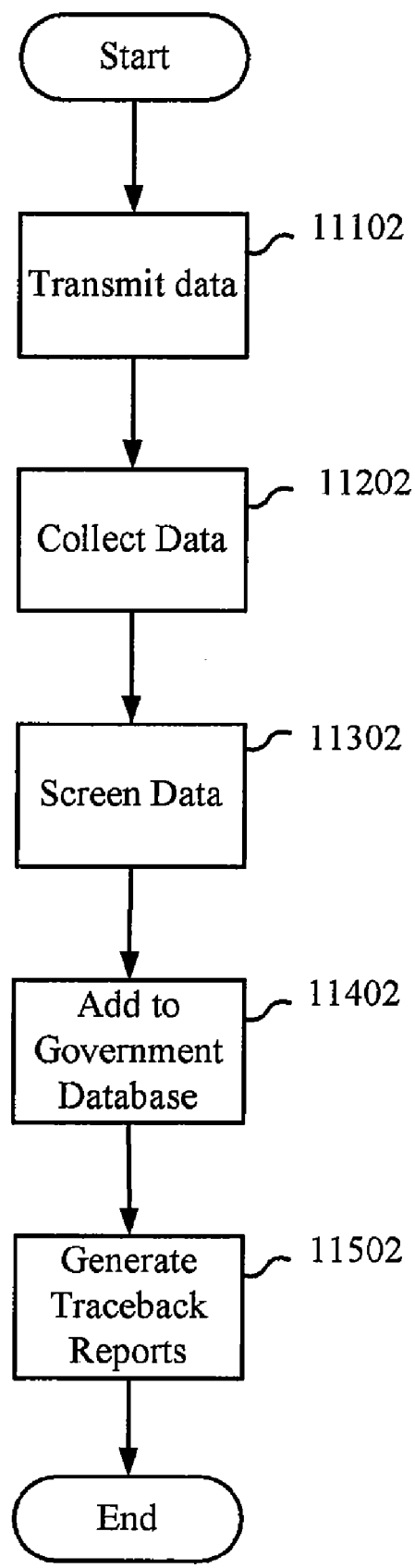
FIG. 60 is a flowchart illustrating a technique identifying diseased animals.

FIG. 59 illustrates a technique 10002 for tracing an animal. Tracing back generally includes identifying an animal 10302 (usually a diseased one), requesting a traceback report for the animal 10302, identifying other potentially infected animals 10402, and finally developing a strategy 10502 to protect people from being infected by tainted meat and to reduce the other effects a diseased animal has on commerce. Tools, components, and systems such as those illustrated in FIG. 53 perform the technique 11002. Alternatively, another tool and/or system perform the technique 10002.

In a first stage, an animal is discovered to have an infectious disease such as Mad Cow disease (10102). To prevent spread of the disease, health officials attempt to determine what animals have commingled with the diseased animal. This can be done in one of at least two ways. First the health officials using the diseased animal's identifier look up (10302) the data record address for the diseased animal in the official database and submit (10402) a formal request for a traceback report on the diseased animal. The formal request may be submitted electronically, e.g. through a web page, through a link in a government database application, or by some other means.

An official database system then processes the request, searching through relevant records to find where the animal has been (10502). Confidential premise identifiers, such as the PIDs listed in conjunction with FIG. 51, identify more specifically premise locations the animal has stayed. An initial traceback search finds the premise identifiers of locations where the diseased animal has lived and commingled with other animals.

Subsequent recursive searches (10602) using additional search terms, such as the time and date of move-in, a group number, narrow the search scope and limit the number of animals that need to be quarantined. This process is repeated until a complete list of animals that have commingled with the diseased animal is generated. Then the health officials can take the necessary precautions and intervening steps to quarantine, treat, or slaughter potentially infected animals.

Alternatively, various stages of the technique (10002) are separately or in various combinations performed in conjunction with other stages.

Systems such as those described in connection with the input data sources 5102, 5202 of FIG. 54 transmit (11102) animal information. In some implementations, the data is transmitted to data collection tools such as those described in connection with the data service provider 5002. The transmitted data is received (11202) by the data collection system and stored in a repository. The transmitted data includes animal information, such as an animal identifier, a premise identifier, and other data that is typically associated with commercial animal data collection services.

For example, an owner may have a small herd and each animal has been tagged with an identification device properly encoded with universal animal identifiers. To prepare the animals for processing, the owner moves his small herd to a commercial feedlot, which acts as a designated data service provider, so the animals will fatten up before sale. The animals' movements are tracked. When the animals are sent to the commercial feedlot, the animal identifier and other information encoded on the identification devices are transmitted to a service provider, which stores the information and reports to the owner that the animals arrived.

The data collector system then forwards all or part of the collected data to a data trustee system such as the data trustee 7002 discussed in connection with FIG. 56.

The data trustee system confirms receipt of the information, stores the forwarded information, and removes and/or hides confidential portions of the information (11302).

For example, in the scenario described above, the collected data from the small animal herd is forwarded to the data trustee system. The data trustee verifies the owner's premise identifier and the animals' identifiers. A report is sent to the owner either confirming entry of the data in the database or detailing errors found in the data. In either case, the cattle owner has the opportunity to reconcile the data against his own records and correct any errors.

A portion of the screened data may be sent (11402) to a government-accessible database system, such as the government database 7302 described in connection with FIG. 56.

For example, in the above scenario, the data trustee filters confidential information from the data it received and only forwards non-confidential information, such as the animal identifier, to the government-accessible database system.

Now suppose one of the cattle owner's animals is diagnosed with an infectious disease, such as Mad Cow disease. Using the animal identifier as a starting point, government and health officials request a traceback report on the sick animal (11502). Per the technique (10002) described in connection with FIG. 59, a traceback history is generated by the data trustee system. The traceback history provides enough data for government and health officials to impose proper quarantines and other measures to protect the health and well-being of animals, as well as human beings. For example, the diagnosed cow is slaughtered and burned to avoid spreading the disease to other animals. Those animals that had contact with the diseased animal may be quarantined for a period of time to be treated and to see if they manifest any symptoms of the disease.

Many of the tools and techniques herein can be described in the general context of computer-executable instructions, such as those included in program modules, being executed in a computing environment on a target real or virtual processor. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing environment.

For the sake of presentation, the detailed description uses terms like "determine," "generate," "adjust," and "apply" to describe computer operations in a computing environment. These terms are high-level abstractions for operations performed by a computer and, in less the context indicates otherwise, should not be confused with acts performed by a human being. The actual computer operations corresponding to these terms vary depending on implementation.

Feed Delivery 1

This subsection describes various process steps and system components for delivering feed to animals. These process steps and system components can be used in conjunction with evaluation of an animal's respiratory or circulatory condition, as discussed above. Information gather by imaging and evaluating an animal's respiratory or circulatory system, such as respiratory damage designations, can be used as the basis for management decisions regarding feed delivery. For example, an animal with damaged lungs may be administered an inexpensive maintenance diet, whereas an animal with healthy lungs is administered a more expensive weight gain diet.

The microingredient feed additive concentrates include such potent substances as hormones, antibiotics, and vitamins that are typically administered to cattle and poultry at feeding operations, such as cattle feedlots, in gram amounts or less. It is often essential that a prescribed amount of a microingredient be delivered to an animal, and no more. Too little of a microingredient has no effect, while too much of it may be toxic or fatal. The range between too much or too little of some additives is often no more than 0.5 gram. The apparatus and method disclosed in this detailed description is intended to accurately dispense dry and liquid additive concentrates within this range of accuracy.

With reference to the drawings, FIG. 61 illustrates an apparatus shown generally at 1013 for measuring, dispensing, and delivering microingredient feed additive concentrates in small but accurate proportions in a liquid carrier slurry to livestock shortly before delivery of the feed ration to the animals for consumption. The apparatus 1013 includes several separate components including a main cabinet 1113, and a remote control unit 2013, shown for convenience near cabinet 1113 but normally located at a remote control station such as at a feed truck filling station in a feedlot. Additional separate components include multiple liquid additive concentrate storage containers 7613, 7813 (only one being shown in FIG. 61) supported on a stand 7913, and their dispensing pumps 7913 (see FIG. 62). Typically, a separate water supply tank 1953 (FIG. 64) supplies the necessary carrier and flush water to the cabinet through fill and flush conduits (FIG. 10), via a booster pump 1933 (FIG. 64).

Figure 64:
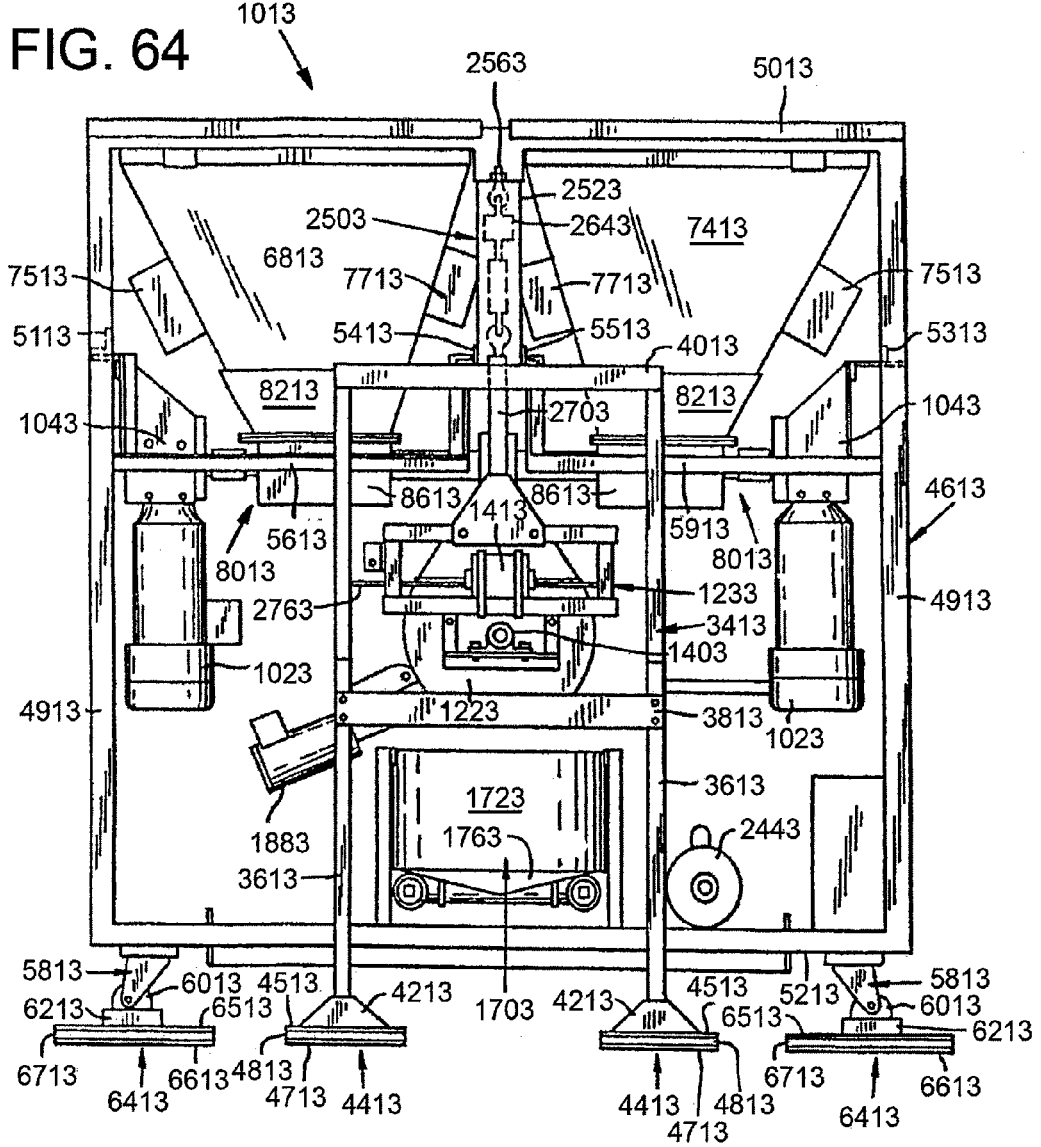
FIG. 64 is an enlarged, front elevational view of the main cabinet shown in FIG. 61, the cabinet panels having been removed to show the internal parts of the machine.

Another separate cabinet (not shown) houses a weigh micro computer, or central processing unit, shown schematically at 4243 in FIG. 64. A second microcomputer, or central processing unit, shown schematically at 4303 in FIG. 64, for controlling the machine sequencing and volumetric metering functions, is housed within one end portion 1313 of cabinet 1113. Various speed controls and electrical relay interfaces and circuitry of the control system shown in FIG. 64 are also housed within cabinet end portion 1313. Such end portion is a separate compartment of cabinet 1113 that can be swung open about a hinged vertical axis for access.

Cabinet 1113 houses the major mechanical components of the apparatus. The exterior of the cabinet, with its protective panels 1213, completely encloses and shields such components from external dust, dirt and other contaminants common in a feedlot environment. The panels also protect the internal components, especially the weight-sensitive ones, from external forces such as wind, jarring contact, and the like, that would otherwise affect the accuracy of weight measurements.

Referring to FIG. 64 showing the major components inside the cabinet 1113, such components include a main frame 4613 and an entirely separate and independently mounted subframe 3413, each mounting certain components. Access to the components mounted on these frames is gained through access doors 1513, 1713, 1913 in a front wall of the cabinet 1113, and through hinged lids 1613, 1813 on a top wall of the cabinet.

In general, weigh subframe 3413 mounts those components which are necessary to the weighing function of the apparatus, and main frame 4613 mounts the remaining components that could, during their operation, induce undesirable movements in the weigh components to adversely affect the weighing function. Accordingly, the weigh subframe serves as a means for isolating the weight components from internal machine movements induced through operation of components on the main frame.

The main frame components include storage bins 6813, 7013, 7213, 7413 for storing different dry additive concentrates, dry additive dispensing means 8013 for dispensing additives from the storage bins, and an additive-receiving means comprising a mixing vessel or tank 1703. Other main frame-mounted components include a discharge pump 2443 for pumping slurry from mixing vessel 1703, slurry mixers 1803, and various plumbing components for supplying carrier and flush water to the mixing vessel and discharging slurry liquid from the vessel. Cabinet lids 1613, 1813 provide access to the storage bins for refilling them.

The subframe 3413 includes an entire subassembly of weigh components, including a weigh hopper means comprising the compartmented weigh hopper 1223, and a suspension means for suspending the weigh hopper from a weighing means 2503. The suspension means includes a pair of suspension frames 1233, one at either end of the weigh hopper. Each such frame rotatably supports weigh hopper 1223. Each suspension frame 1233 includes a suspension arm 2703 suspending the suspension frame from the weigh means 2503. The weigh means includes, at each end of the subframe 3413, a weigh tower 2523 projecting upwardly from the subframe and suspending therein a load cell 2643. The load cell in turn suspends the weigh hopper through an appropriate connection to suspension arm 2703 of suspension frame 1233.

Remote control unit 2013 includes a computer terminal 2213 supported on a stand 3013 having a base plate 3213. Terminal 2213 includes a primary keyboard 2413, a primary display screen 2613, a small, secondary keyboard 2713 and a small, secondary display screen 2913. Various control switches and indicators are provided on a control switch box 2813 mounted on a shelf 3113 of the stand below the terminal 2213.

Figure 65:
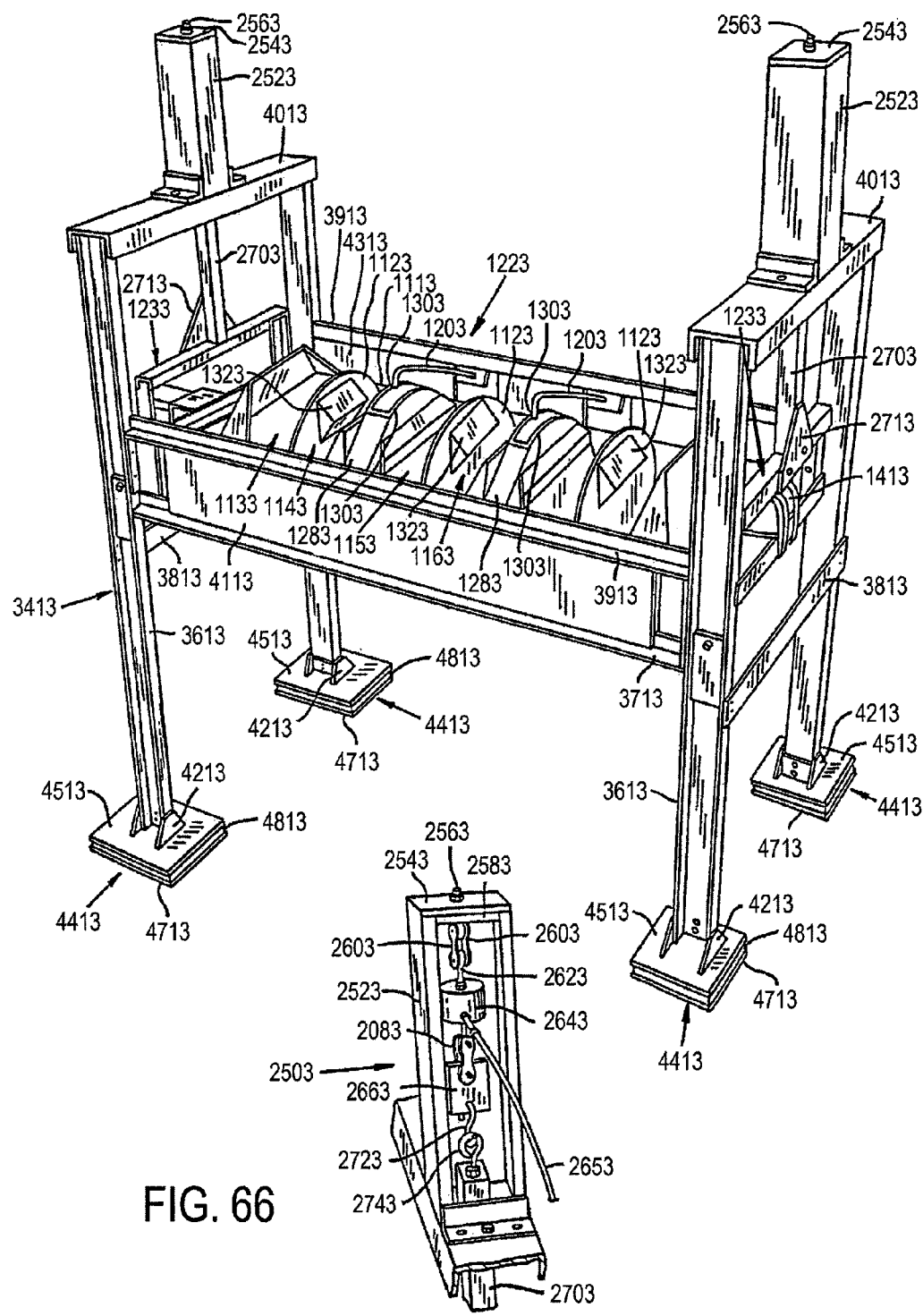
FIG. 65 is an enlarged, perspective view of the weigh frame subassembly of the apparatus shown in FIG. 64.

Apparatus 1013 is seen therein and in FIG. 65 to comprise a weigh frame 3413 having four uprights 3613 and two each of parallel crossbeams 3813, 4013 and longitudinal beams 3713, 3913 rigidly interconnecting the four uprights 3613. A vertical slat 4113, 4313 is carried between each pair of beams 3713, 3913. Each of uprights 3613 has an enlarged foot 4213 to enhance the stability of weigh frame 3413. Each foot 4213 is mounted on an elastomeric isolation pad 4413 (FIG. 63) which absorbs vibrations or other environmental influences that may affect the accuracy of the functions performed by weigh frame 3413. Each pad 4413 includes a square upper plate 4513 to which foot 4213 is secured, the upper plate having a peripheral, downwardly depending flange which forms an enclosure. A square lower plate 4713 is attached to a floor with bolts below plate 4513 and has a peripheral, upwardly extending flange that forms an enclosure. A rubber cushion 4813 is placed between plates 4513, 4713 within the enclosures formed by the flanges on the plates. Cushion 4813 is thick enough to maintain the upwardly and downwardly extending flanges in spaced relationship so that vibrations are not communicated between plates 4513, 5713.

Separate mounting or main frame 4613 substantially surrounds weigh frame 3413, the mounting frame 4613 comprising four uprights 4913 interconnected by four top support beams 5013 and four bottom support beams 5213. Two intermediate parallel support beams 5113, 5313 extend across opposing parallel faces of frame 4613, and two parallel support beams 5413, 5513 extend across the middle of frame 4613 parallel to beams 5113, 5313. A pair of parallel, U-shaped brackets 56, 57 are fixed to and suspend from beams 5113, 5413 (FIG. 68), and a pair of similar U-shaped brackets are fixed to and suspend from beams 5313, 5513. Only one U-shaped bracket 5913 is shown in FIG. 64, although it will be understood that a second, parallel U-shaped bracket extends between beams 5313, 5513 in an arrangement similar to that shown in FIG. 68 for U-shaped brackets 5613, 5713.

Figure 63:
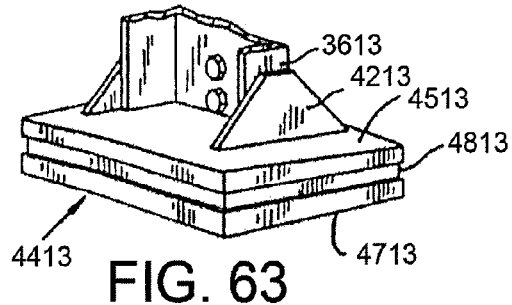
FIG. 63 is an enlarged, perspective view of a typical foot portion and isolation pad of a support leg of the apparatus of FIG. 61.

Mounting frame 4613 is supported by casters 5813 each having a roller 6013 that is received within a cup 6213 that is attached to an isolation pad 6413 which is similar in structure to pad 4413 shown in FIG. 63. Pad 6413 comprises a top plate 6513 having a peripheral, downwardly depending flange and a bottom plate 6613 bolted to the floor and having a peripheral, upwardly extending flange. A rubber cushion 6713 is positioned between plates 6513, 6613 within the enclosures formed by their peripheral flanges, the width of cushion 6713 being great enough to keep the peripheral flanges in spaced relationship to one another and avoid metal to metal contact which might transfer vibrations.

FIGS. 62 and 64 show multiple storage means such as dry additive concentrate storage bins 6813, 7013, 7213, and 7413 for storing separately a plurality of different dry microingredient feed additive concentrates. Each of the bins has a square top opening and square bottom opening, the bottom opening having a smaller area than the top opening such that the cross-sectional area of each bin diminishes in the direction of the bottom opening. A pair of vibrator motors 7513, 7713 (FIG. 64) are placed on each bin 6813-7213 to assist in moving dry microingredient concentrates out of the bins during dispensing.

A plurality of liquid containers 7613, 7813 are also shown in FIG. 62 for storing separately different liquid microingredient feed additive concentrates. The liquid containers are supported on a table 7913 (FIG. 61) adjacent cabinet 1113 and connected to the apparatus through flexible tubes described later.

A separate dry dispensing means 8013 is provided for each dry bin 6813-7413. A separate liquid dispensing means 1203 is provided for each liquid container 7613-7813. Each liquid and dry dispensing means is independently operated and controlled for dispensing separately several selected additive concentrates from their respective bins and liquid containers in predetermined weights during a machine operating cycle.

Figure 68:
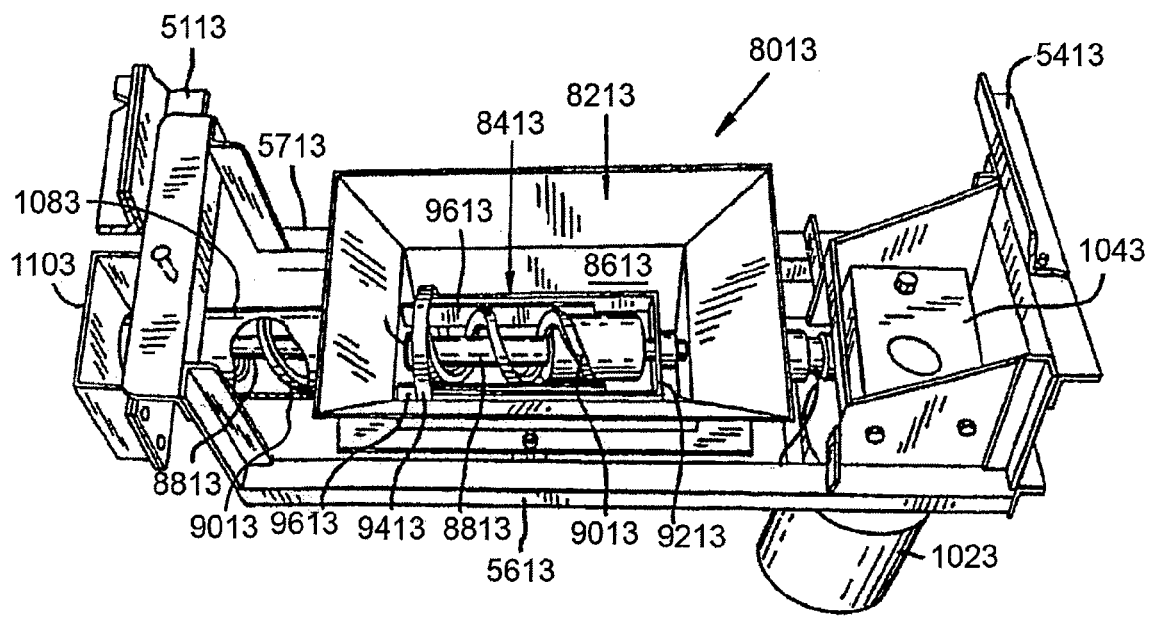
FIG. 68 is a fragmentary top perspective view of a dry additive dispensing means portion of the apparatus of FIG. 64, shown mounted on the main frame assembly of FIG. 64.

One of the dry dispensing means 8013 for a dry microingredient is shown best in FIGS. 64 and 68. It includes an annular collar 8213 having a square cross section. The collar fits closely about the open bottom of a bin 6813-7413 and extends partially up its sidewalls. Collar 8213 has a square frusto-pyramidal configuration which defines a flow passageway of progressively decreasing cross section from the bottom bin opening to a top opening into a coreless metering screw assembly 8413 within a rectangular lower extension section 8613 of collar 8213 having a curved bottom. Screw assembly 8413 includes a rotatable core 8813 which carries a helical metal screw 9013 and rectangular screw agitator 9213 with a circular band 9413 around one end thereof. A stationary rear one-half tube extension 9613 of a conveyor tube 1083 projects into the interior of agitator 9213 to start the conveyance of material that is moved by the screw 9013 into conveyor tube 1083. Agitator 9213 helps maintain a uniform microingredient density around rotating screw 9013.

Agitator 9213 is rotated by a shaft 1003 which is driven through a right-angle gear box 1043 by a variable-speed motor 1023, with three pre-set speeds. Core 8813 and screw 9013 project through opening 1063 and into conveyor tube 1083 having an open end that terminates adjacent a deflection plate 1103 above the top opening of weigh hopper 1223. Thus the metering screw assembly conveys additive from the supply bin into a compartment of the weigh hopper.

Each of liquid containers 7613, 7813 is provided with a separate dispensing means 1203. Each liquid dispensing means is, for example, a variable-speed or displacement rotary or piston pump 7913 (FIG. 62). The liquid dispensing means pumps liquid additive from a container 7613, 7813 through a flexible feed conduit which connects to a rigid dispensing tube end 1203 (FIG. 65) on the weigh subframe to deliver the additive into a liquid compartment 1173-1183 of weigh hopper 1223.

The hopper 1223 (FIGS. 62, 64, 65, and 67) is carried by weigh subframe 3413 between frame slats 4113, 4313 below the open end of extension tube 1083 of screw conveyor 8013. Hopper 1223 is an elongated trough having a substantially semicylindrical cross section and a plurality of partitions 1123 which divide the hopper transversely into several dry microingredient receiving compartments 1133, 1143, 1153, 1163. Each of the dry compartments 1133-1163 is provided with a deflector 1323 on its partition wall having a triangular cross section that directs additive concentrates to the interior of the compartments during both filling and emptying of the hopper.

Additional partitions 1113 of hopper 1223 cooperate with some partitions 1123 and upper walls 1283 to define liquid additive-receiving compartments 1173, 1183 having narrow openings 1303 into which liquid dispensing tubes 1203 direct liquid additives from containers 7613, 7813.

The liquid and dry additive compartments of hopper 1223 maintain dispensed additives separated until the hopper discharges its contents, after weighing, into the diluting liquid carrier within the mixing vessel 1703 positioned vertically below the hopper.

Figure 67:
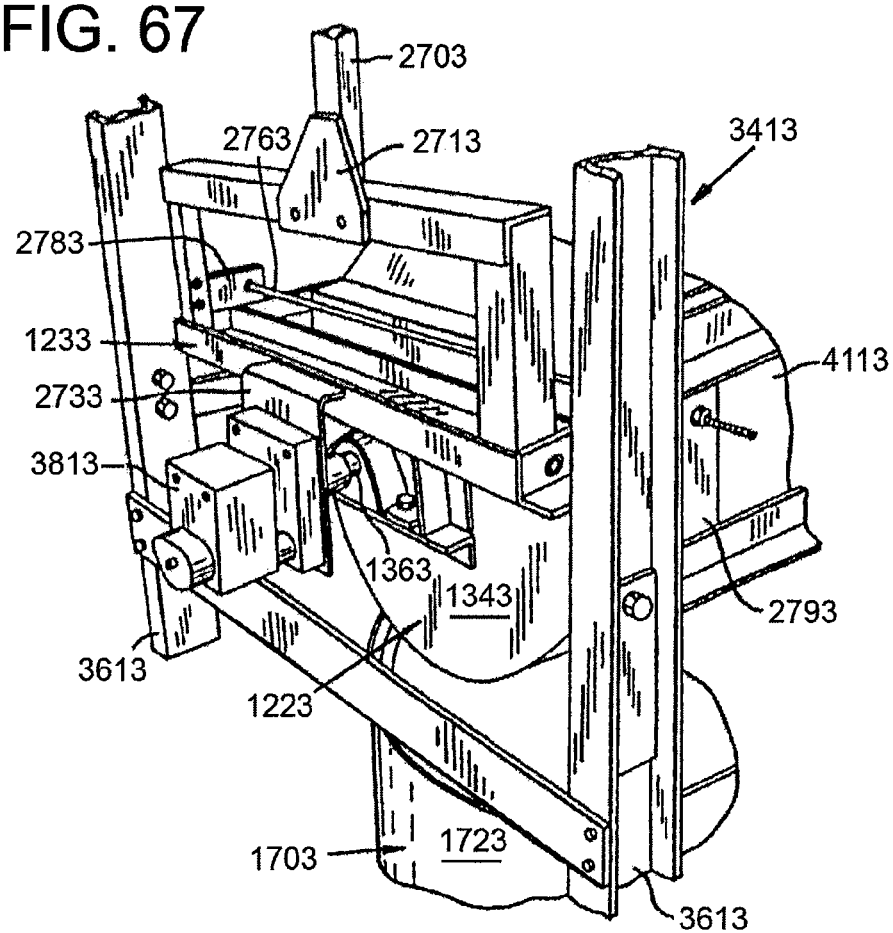
FIG. 67 is an enlarged, fragmentary perspective view of a portion of the weigh hopper subassembly of the weigh frame shown in FIG. 65.

Hopper 1223 is supported by weigh frame 3413 such that it is free to rotate about its longitudinal axis. Each semicircular end plate 1343 (one being shown in FIG. 67) of hopper 1223 is secured to a shaft 1363. The shaft 1363 at the hopper end shown in FIG. 67 is drivingly connected to a motor 1383 that is fixed to hopper suspension frame 1233 by a mounting bracket 2733. The shaft at the opposite end of the hopper is mounted in a bearing 1403 (FIG. 64). Motor 1383 operates first to rotate hopper 1223 to an inverted position for emptying (FIG. 71); then to an upright position (in the same direction) for the next dispensing and weighing cycle.

Figure 71:
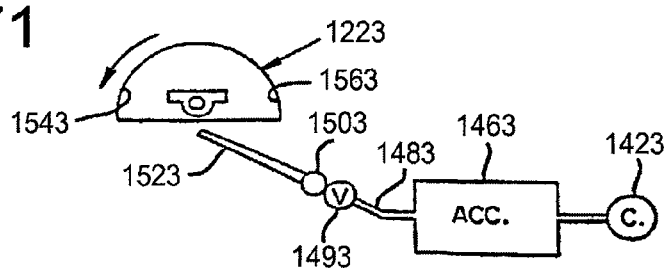
FIG. 71 is a schematic view of the air flush system for the weigh hopper portion of the apparatus.

An air flush means for compartments 1133-1163 of hopper 1223 is shown in FIG. 71. The air flush means is carried by the main frame and comprises a compressor 1423 in fluid communication through passageway 1443 with air pressure accumulator tank 1463. A solenoid valve 1493 regulates the flow of air through passageway 1483 to header 1503. The header in turn fluidly communicates with a plurality of hoses 1523 that project into each compartment 1133-1163 of hopper 1223 when the hopper is inverted. Each of hoses 1523 is positioned to direct a stream of air against far wall 1543 of the hopper. It is not necessary to direct the air stream against near wall 1563 because that wall will have already been scraped relatively clean by the movement of dry additives against the wall and out of the hopper as hopper 1223 rotates to an inverted position.

A vibrator motor 1413 is carried by suspension frame 1233 at the end of hopper 1223 opposite hopper rotating motor 1383. Vibrator motor 1413 operates during inversion of the hopper to promote emptying of the hopper compartments by vibrating the hopper.

An elongated mixing vessel 1703 which serves as a receiving means for receiving additives from the hopper 1223 and also as a mixing means for mixing such additives with water, is placed below hopper 1223. Vessel 1703 is an elongated tub that is longer and wider than hopper 1223. Vessel 1703 comprises a continuous, annular upright wall 1723 around a sloping bottom formed from a plurality of triangular sections 1763 that slope towards a pair of central bottom openings including an inlet port 1773 and discharge port 1783.

Variable speed flow inducing means, such as variable two-speed mixers 1803, serve as part of the mixing means and are provided in mixing vessel 1703 for inducing a turbulent flow of liquid within the mixing vessel. Each mixer 1803 is comprised of four angled mixing blades 1823 connected to the end of a rotary mixing shaft 1843 that is connected to a gearbox 1863 and motor 1883 for rotating shaft 1843. Each of motors 1883 is mounted on a motor mounting frame 1903 along an outside face of vessel wall 1723. Level sensors 1923, 1943 are also mounted over the edges of wall 1723 and project downwardly into the tub for determining the level of water contained therein and shutting off a supply of water to the tub when a predetermined level is reached. Sensors 1923, 1943 are, for example, electrodes through which an electrical circuit is completed or a timing circuit energized when the water surface in the tub reaches the predetermined level. Sensor 1923 is the primary sensor, while sensor 1943 is a backup sensor which detects a near overflow condition, closes fill solenoid 2063, and interrupts the fill cycle.

Figure 70:
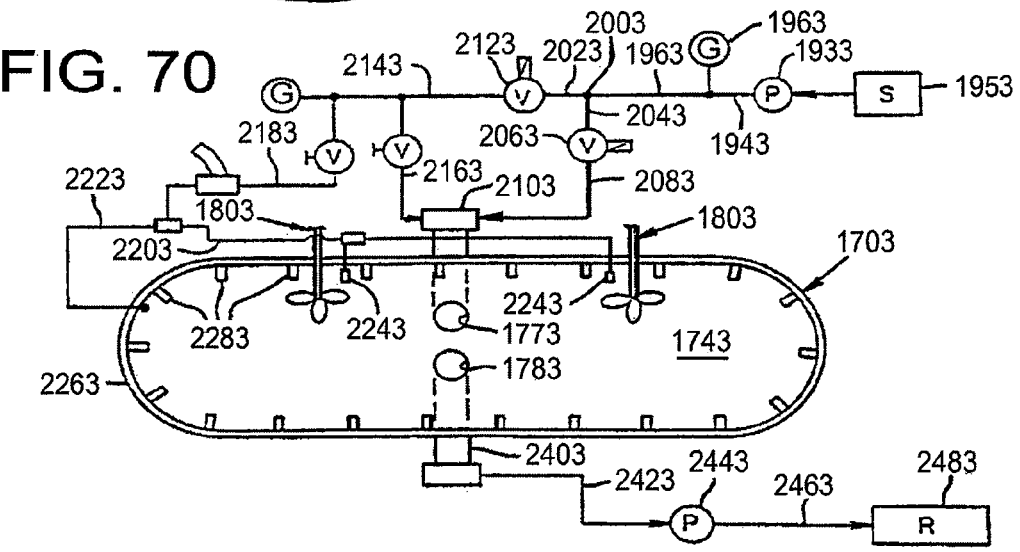
FIG. 70 is a plumbing diagram for the fluid components of the feed delivery apparatus.

FIG. 70 shows a plumbing system for apparatus 1013 which delivers and removes carrier and flush water from vessel 1703. Water is introduced from a source 1953 by pump 1933 through line 1943 where its pressure is detected by pressure gauge 1963. Water then continues to flow through line 1983 where it is divided by tee 2003 into water lines 2023, 2043. The flow of water through fill line 2043 is controlled by solenoid valve 2063 which, when open, allows water to flow through line 2083, thence to conduit 2103 and into vessel 1703 through port 1773. When solenoid valve 2063 is open, a second solenoid valve 2123 in line 2023 remains closed such that all of the supply of water moves through line 2043 to fill vessel 1703.

Figure 69:
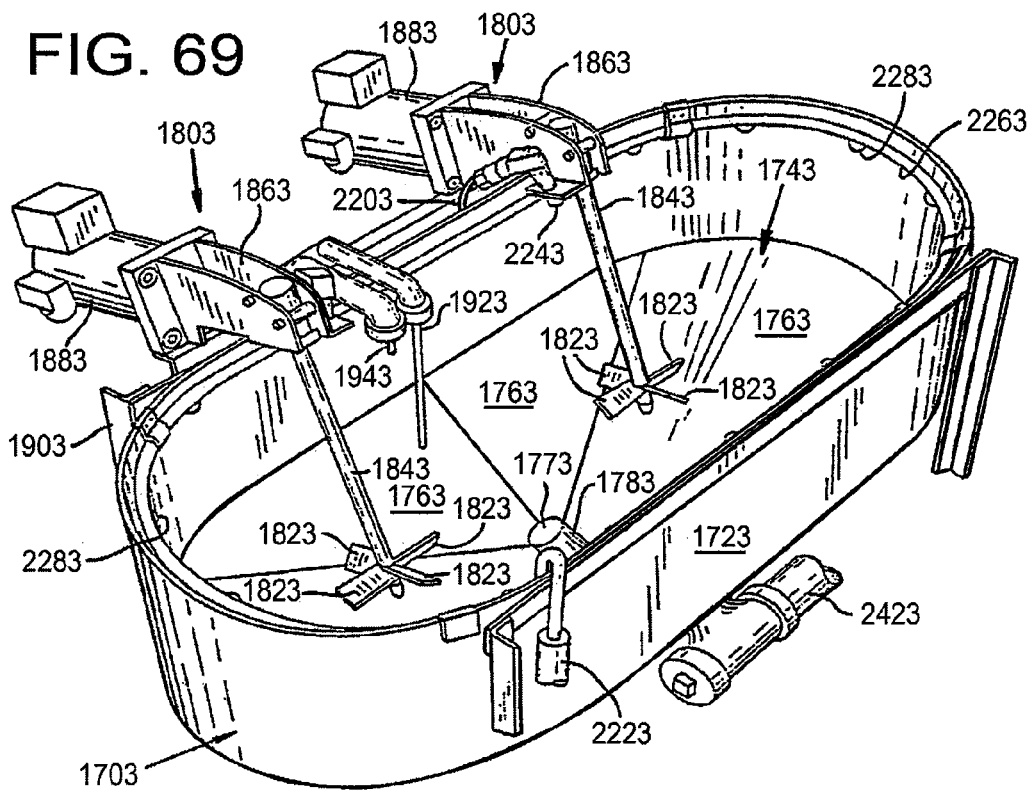
FIG. 69 is a fragmentary top perspective view of the mixing vessel and associated components of the main frame assembly shown in FIG. 64.

Solenoid valve 2123 is interposed between line 2023 and flush line 2143 that in turn communicates with line 2163 to establish fluid communication with conduit 2103. Line 2143 also fluidly communicates with line 2183 having branches 2203, 2223. Branch 2203 fluidly communicates with a pair of nozzles 2243, one positioned above blades 1823 of each mixer 1803, nozzle 2243 directing a flow of water onto the blades to clean them. Line 2223 provides a passageway through which the water moves to flush ring 2263 (FIGS. 69 and 70) which is positioned around the upper inner periphery of vessel 1703 adjacent its top edge. Ring 2263 has a number of flush nozzles 2283 which direct a flow of water downwardly against wall 1723 of vessel 1703 to flush it.

Apparatus 1013 also has a delivery means for delivering slurry from vessel 1703 to a receiving station for mixing with an animal feed ration at a location remote from the mixing vessel. This delivery means includes discharge opening 1783 in fluid communication with conduit 2403 that empties into discharge line 2423. Discharge pump 2443 withdraws slurry through line 2423 and sends it through line 2463 to receiving station 2483 where, typically, it is sprayed into a livestock feed ration and mixed therewith.

Figure 66:
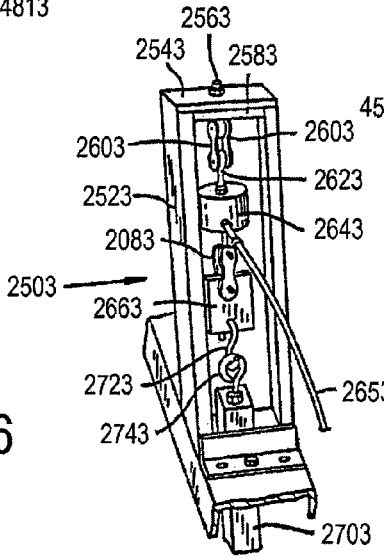
FIG. 66 is an enlarged, fragmentary, perspective view of a load cell in a weigh tower of the weigh frame of FIG. 65, the remainder of the weigh frame being broken away.

A weighing means 2503 (FIG. 66) is provided on weigh frame 3413 for weighing predetermined weights of the different additive concentrates dispensed from bins 6813-7413 and containers 7613, 7813. Weighing means 2503 includes a weigh tower 2523 extending vertically upward from a crossbeam 4013 of weigh frame 3413 midway between uprights 3613 at each end of frame 3413. Each tower 2523 has a flat top plate 2543 with a central opening through which the threaded shank of an eye member 2563 is placed and secured with a nut. A rubber pad 2583 is placed against the interior face of plate 2543 before member 2563 is secured to top plate 2543 with the nut. A pair of suspension members 2603 pivotally interconnect eye member 2563 and a second eye member 2623 from which a load cell 2643 is suspended. The amount of strain on load cell 2643 is communicated to a control unit through line 2653. The load cell 2643 in the preferred embodiment is capable of weighing to an accuracy of 0.5 grams.

A rubber isolator pad 2663 is pivotally suspended beneath load cell 2643 by suspension members 2683. A suspension arm 2703 of the hopper suspension frame 1233 is in turn suspended from isolation pad 2663 by hook 2723 and eye 2743 secured to arm 2703. Arms 2703 of suspension frames 1233 thus suspend hopper 1223 such that the entire weight of the hopper is freely suspended from load cells 2643. Arms 2703 are braced by gussets 2713 to their rectangular weigh frames 1233. Hopper 1223 is suspended interior to frames 1233 between slats 4113, 4313 of frame 3413 by suspending shafts 1363, one of which is driven (FIG. 67) and the other of which is mounted in a bearing 1403 (FIG. 64). The hopper is therefore free to rotate between frames 1233 to an inverted position. This arrangement allows the weight of the hopper to be transferred through frames 1233 to arms 2703 for acting on load cells 2643. The weight of additive concentrates in hopper means 1223 can therefore be accurately determined.

As best shown in FIG. 67, a transverse vibration and sway dampening rod 2763 extends between a bracket 2783 carried by an upright of hopper suspension frame 1233 and a bracket 2793 carried by two longitudinal beams 3713, 3913 of weigh frame 3413. Such a rod 2763 is provided at each end of weigh frame 3413 adjacent face 1343 of hopper 1223 for preventing or damping transverse movements of the hopper. A similar longitudinal rod (not shown) extends along one longitudinal side of hopper 1223 to prevent or dampen longitudinal vibratory or swaying movements of hopper 1223, one end of the longitudinal rod being fixed to longitudinal beam 3913 and the other end being fixed to weigh frame 3413. Such sway dampening rods provide part of the means isolating the weight-sensitive components of the apparatus from movements that could affect accurate weight measurements.

Apparatus 1013 is provided with a control means, such as a central processing unit, for controlling the operation of apparatus 1013. In the preferred embodiment, two-programmed central processing units are used, one for operating the weighing functions of apparatus 1013 and the other for operating all other machine functions.

Figure 72:
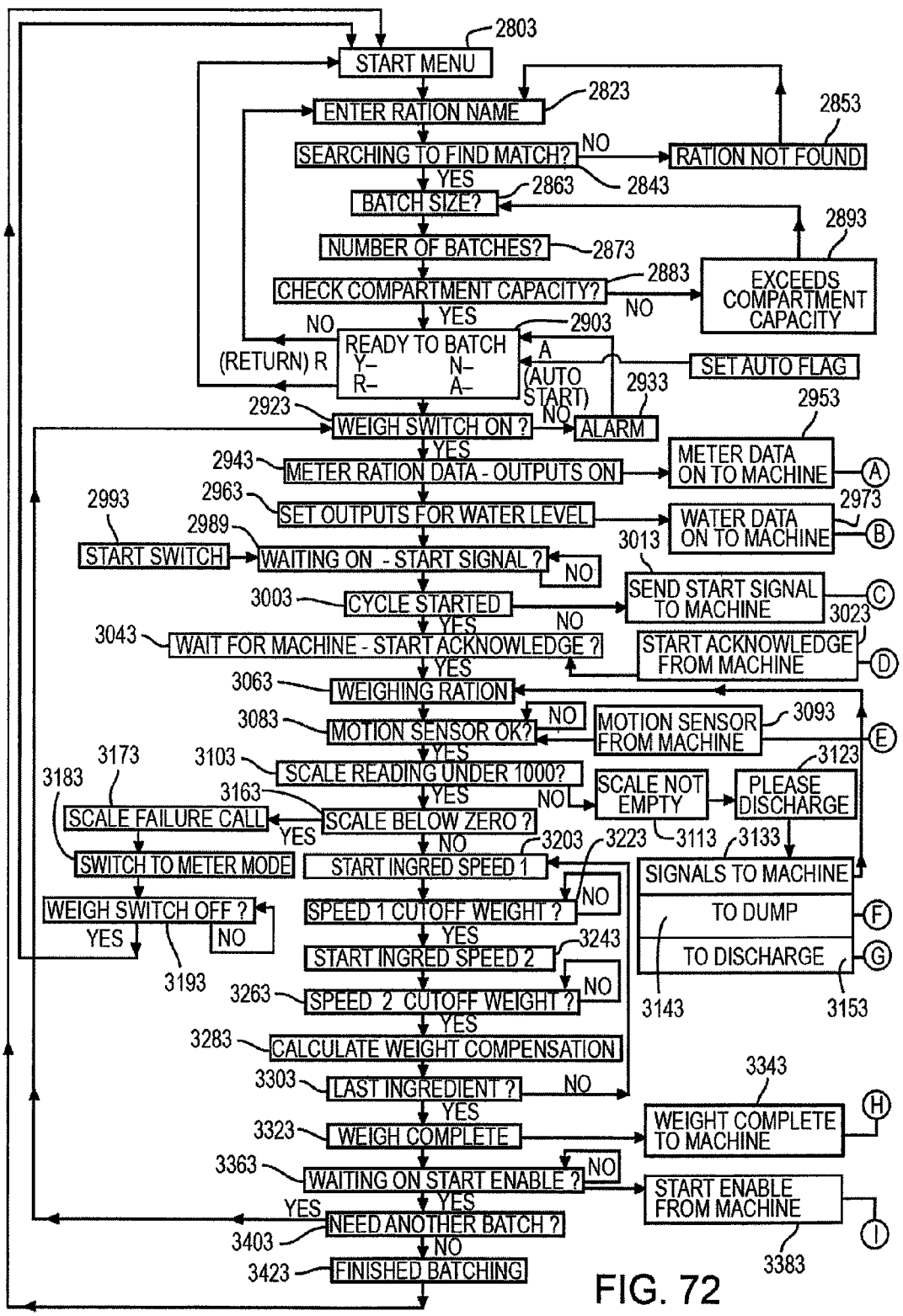
FIG. 72 is a flow diagram illustrating the logic of a computer program which controls the weigh means of the present apparatus.

The logic of the program for operating the weighing functions of the machine is shown in FIG. 72. The weighing CPU is activated by starting the menu at 2803 and then entering ration data with keyboard 2413 for a particular feedlot or data for one of a series of desired batches at a feedlot. The formulation of each desired batch has been preprogrammed into the computer such that a batch formulation can be chosen by entering a code number at 2823. The computer then searches at 2843 for a match to this encoded formulation until the match is found and the machine is ready to batch. If a match is not found, the program at 2853 returns to step 2803 and a prompt is sent to screen 2613 to enter ration data.

Once a match is found at 2843, a program prompt at 2863 appears on screen 2613 requesting the size of the batch to be prepared. After this information is entered, the program prompt at 2873 requests the number of batches to be prepared, and if the batch size exceeds the capacity of the preprogrammed limit for the feed lot ration mixer or the compartments 1133-1183 of hopper 1223, this is computed at 2883. If capacity has been exceeded, a prompt is sent to screen 2613 at box 2893, and the program will request that new data concerning batch size and number be entered by returning to step 2863. If capacity has not been exceeded, the machine is ready to batch at 2903.

The weighing computer first checks to determine if a weigh switch is on at 2923, and if the weigh switch is off, an alarm is sounded at step 2933 and the program returns to ready at 2903. The alarm will alert an operator that the weighing switch must be turned on in order for batching to continue.

Figure 73:
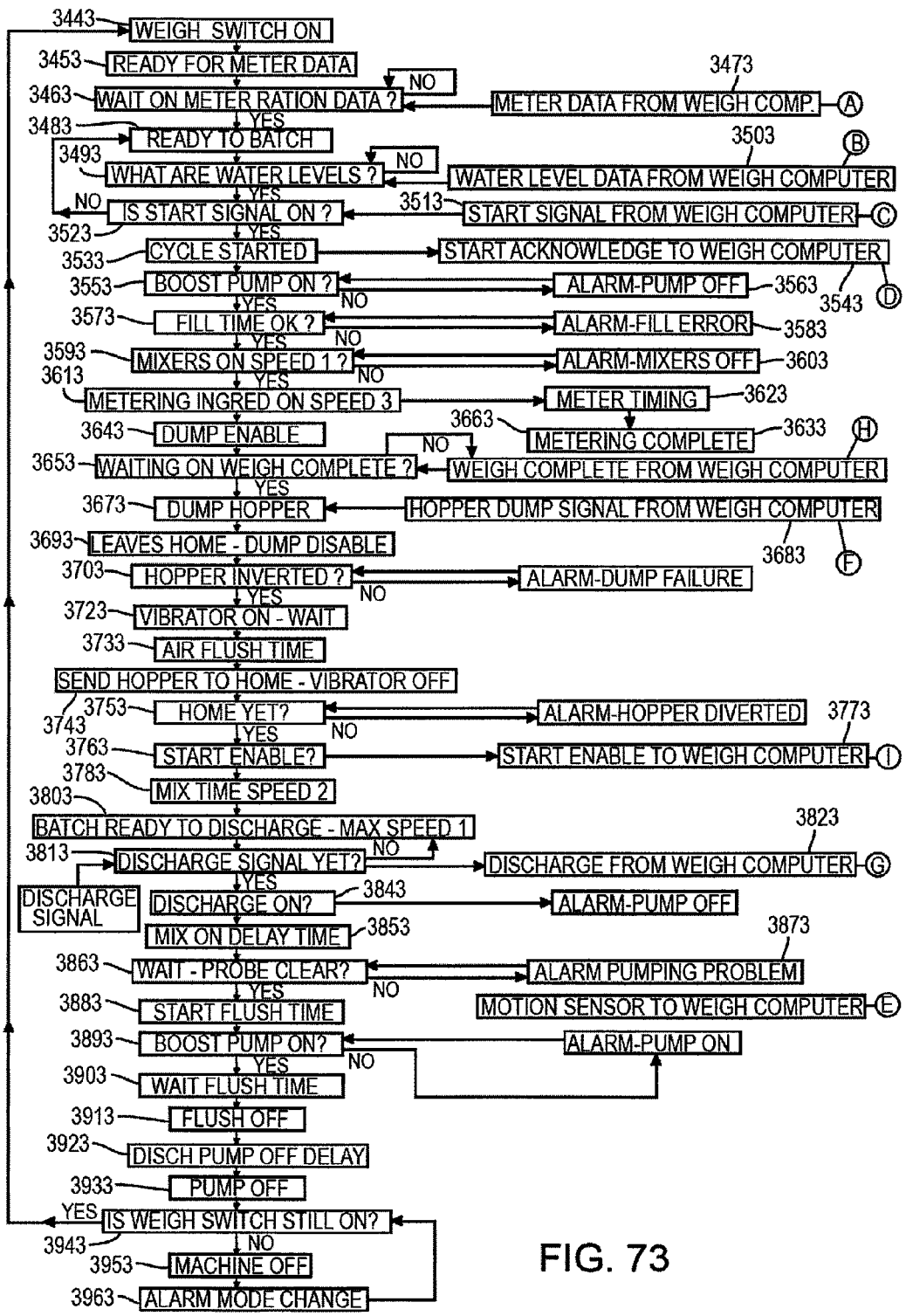
FIG. 73 is a flow diagram illustrating the logic of a computer program which controls all machine operating sequences and functions other than the weigh functions illustrated in FIG. 72.

The program next calculates metering ration data at 2943 and sends it to the machine operating program at 2953 as indicated by A in FIGS. 72 and 73. The metering data is calculated for any additives that have been selected for dispensing in the metering mode during the weigh cycle. Dispensing a portion of the additives by volume is more fully set forth in connection with steps 3613-3633 of FIG. 73 below.

The program then sets an output for the water level at 2963, the level of the water determining how much fluid carrier will be present in the slurry which is ultimately delivered to receiving station 2483. Water level information is sent to the machine operating program at 2973, as indicated by B in FIGS. 72 and 73. The program next waits at 2983 for a start signal which the operator gives by activating start switch 2993 on switch panel 2813. The weighing cycle is then started at 3003 by sending a start signal at 3013 to the machine operating program as indicated by C in FIGS. 72 and 73. Even though the weighing cycle has started, no weighing of microingredients actually commences until a signal is received back from the machine operating program at 3023 as indicated by D in FIGS. 72 and 73 that indicates weighing should begin at 3043. This communication between the programs at D enables the machine operating program to begin its initial checks while microingredients are being dispensed and weighed.

Once the signal to begin weighing is received at 3043, the weighing sequence begins at 3063. It is first determined at 3083 whether a motion sensor is detecting movement of hopper means 1223. Information is received from the motion sensor on the hopper at 3093, as indicated by E in FIGS. 72 and 73. The program will not progress beyond 3083 until the motion sensor indicates that hopper means 1223 is not moving, since movement of the hopper means will adversely affect weight determinations of load cell 2643. Hopper means 1223 can be put in motion by a variety of influences, such as wind gusts, floor vibration, personnel contact, or movement of machine parts. Although the effect of these movements on load cell 2643 may not be great, the extreme accuracy required in dispensing microingredient feed additive concentrates makes absence of movement desirable.

It is next determined at 3103 whether the scale reading is less than 1000 grams. If the reading is greater than 1000 grams, it is probably because the hopper means is not empty, as indicated at 3113, and a signal is sent at 3123, 3133 to dump hopper means 1223 so that weighing of a new lot of microingredients can begin. The signal to dump is sent to the machine operating program as indicated at step 3143 and F in FIGS. 72 and 73. The mixers 1823 are also started at 3153 as indicated by G in FIGS. 72 and 73 so that the microingredients dumped from hopper means 1223 will be mixed into a slurry and discharged to receiving station 2483 in accordance with normal operation of the machine operating program described in connection with FIG. 73 below.

If the scale reading is less than 1000 grams, it is determined at 3163 if the scale reads below zero. If that is the case, a message is given to the operator by 3173 on screen 2613 that the scale has failed and the supervisor should be called. Then at 3183 the program prompts the operator to switch to a backup metering mode system which dispenses additive concentrates by volume instead of by weight, and a prompt is sent at 3193 to screen 2613 directing that the weigh switch 3213 at panel 2813 be turned off. The operator then performs as outlined in FIG. 75 by turning the meter switch on at step 5003 and entering ration data at 5023. Volumetric metering of additive concentrates is performed by activating motor 1023 of each bin 6813-7413 to rotate screw 9013 for a predetermined period of time. Since screw 9013 will dispense an approximate known amount of concentrate per unit of time, a volumetric approximation of the desired amount of concentrate can be dispensed without weighing.

If the scale reads above zero at 3163, the weighing mode of the program is instead used. Ingredient flow is started at 3203 by activating motor 1023 for screw 9013 below bin 6813. Motor 1023 has at least two speeds so that it initially operates at a higher speed during the initial phase of dispensing additive concentrates from bin 6813 into a first compartment 1133 of hopper means 1223. The weight of concentrate introduced into compartment 1133 is sensed by load cell 2643 and that information is continually fed back to the computer through line 2653. As the weight of concentrate dispensed from bin 6813 approaches the predetermined amount of that concentrate for the batch formulation chosen at 2823, motor 1223 is switched to a lower speed at 3223 and 3243 that more slowly dispenses the concentrate from bin 6813 during a final phase of dispensing. In this manner, a more accurate weight of microingredient can be dispensed from bin 6813 into compartment 1133 since the dispensing of additive will have slowed before it is finally stopped when the correct weight of this first concentrate is sensed at 3263.

The program contains a weight compensation step at 3283. It sometimes happens that the actual weight of additive concentrate dispensed by dispensing means 8013 into compartment 1133 will be slightly greater or less than the desired weight set by the ration data at 2823. The program compensates for such inaccuracies by adding or subtracting a weight compensation factor to the ration amount set for the additive concentrate at 2823. In this manner, the weight inaccuracy will be corrected the next time a microingredient additive is dispensed from bin 6813 into compartment 1133.

When the predetermined weight of microingredient additive concentrate is sensed at 3263 and the weighing of that component has been completed, the computer determines if the just dispensed concentrate was the last microingredient dispensed at 3303. Assuming the microingredient concentrate in bin 6813 was not the only concentrate to be dispensed in this formulation, the program then returns to box 3203, and the flow of ingredients from bin 7013 is initiated by activating motor 1023 beneath bin 7013 to turn screw 9013 at a fast speed and begin moving microingredient additive from bin 7013 into compartment 1143 of hopper means 1223. Load cell 2643 continues to sense the weight of concentrate added to hopper means 1223 from bin 7013 until that weight begins to approach the final predetermined weight desired of the second concentrate. This predetermined weight will be the total actual net weights of the first additive concentrate plus the predetermined weight of the second additive concentrate since hopper means 1223 has not yet inverted and the first additive concentrate still remains in compartment 1133. As the total combined actual weight of additive concentrate in compartments 1133, 1143 approaches the predetermined amount, motor 1023 is switched to a slower speed, and additive concentrate is continued to be slowly dispensed with screw 9013 from bin 7013 until the total combined weight of additive concentrate is reached, and motor 1203 is shut off.

This same procedure is repeated until the predetermined weight of additive from each of bins 7213, 7413 is similarly dispensed into compartments 1153, 1163. Liquid microingredient additive concentrates from containers 7613 and 7813 are dispensed by activation of a liquid pump which sequentially dispenses liquid additive from containers 7613, 7813 into liquid receiving compartments 1173, 1183 of hopper means 1223 until a predetermined amount of each liquid additive has been dispensed.

Once the last additive has been dispensed, as determined at 3303, the computer determines that weighing has been completed at 3323, which sends at 3343 a signal to the machine sequence program as indicated by H in FIGS. 72 and 73. The computer pauses at 3363 to wait on discharge of hopper means 1223. Once dumping of hopper means 1223 has been completed by inversion of the hopper and its return to an upright position, this information is sent from the machine operating program of FIG. 73 to the weighing program of FIG. 72 as shown at 1 and 3383. It is then determined at 3403 whether another batch of microingredient is required. If not, the program returns from 3423 to its starting point at 2803. If another batch is required, the program returns to box 2923 and the sequence repeats itself as described above.

Although not shown in FIG. 72, the weigh program can be modified to keep a running inventory of additive concentrates. This can be accomplished by entering into the weigh computer the weight of additive concentrate placed in each of bins 6813-7413 and containers 7613, 7813. The weight of each concentrate actually dispensed and sensed by load cells 2643 is then subtracted from the original weight of concentrate to determine the inventory of concentrate remaining.

The control means can also be programmed to perform other functions that enhance the accuracy of weight determinations by the weighing means. For example, the isolating means can include programming the control means to prevent acceptance of the measured weight by the control means following operation of dispensing means 8013 until motion of hopper means 1223 sensed by motion sensors has subsided to a level that will not affect load cells 2643. The same result can be achieved by programming the control means to delay operation of all other movable machine components (such as dispensing means 8013, 1203 or mixers 1823) for a predetermined period of time sufficient for hopper 1223 to settle or until any oscillatory movements subside. Alternatively, the isolating means can include programming the control means to prevent operation of moving components (such as dispensing means 8013, 1203 or mixers 1823) while weight determinations are being made by the load cells 2643.

FIG. 73 schematically illustrates the logic of a program for actuating the sequence of operations of apparatus 1013. The program begins by determining at 3443 if the weigh switch on switch panel 2813 has been turned on. Once the weigh switch is on, the program is ready for a metering data signal at 3453. It waits at 3463 until the metering ration data is received at 3463 from steps 3473 and 2953 as indicated by A.

Once the metering data is received, the program is ready to batch at 3483. It receives water level data at 3493 from 3503 and 2973 as indicated by B. The start signal from 3013 is then relayed via C to 3513 and 3523. The machine cycle is then started at 3533, and initiation of the cycle is signaled to the weighing program from 3543 through D to 3023.

Boost pump 1933 is then turned on at 3553 for introducing water through line 1943 in FIG. 70 with solenoid 2063 open and solenoid 2123 closed. It is determined at step 3553 if the boost pump is on, and if it is not, an alarm is sounded at 3563 that the pump is switched off. Boost pump 1933 introduces water through line 2083, conduit 2103, and port 1773 until a predetermined water level set at 2943 is sensed by level probe 1923. If the predetermined water level is not reached within a set period of time as indicated by 3573, an alarm sounds at 3583 to indicate that an error has occurred. Otherwise, if mixing vessel 1703 fills within the set time, this condition is detected by level probe 1923 and mixing blade motors 1883 are activated at 3593 on a slow speed to cause the water in mixing vessel 1703 to flow. If the motors 1883 do not turn on, an alarm is given at 3603 to alert the operator of this malfunction.

It is possible to accurately dispense some liquid microingredient additives such as those in containers 7413, 7613 by volumetric metering instead of weighing. Such accurate volumetric metering is possible since the density of most liquids is quite constant over the range of environmental conditions in which apparatus 1013 is used. Volumetric metering of liquid additives selected by the metering ration data is achieved at 3613 by activating the piston pump in dispensing means 1203 for a period of time determined by 3623, 3633. Once the metering step is completed, the dumping mechanism is enabled at 3643 for proceeding to weigh complete step 3653 before inverting hopper 1223.

The program waits at step 3653 for the weighing sequence shown in FIG. 72 step 3203 through step 3343 to be complete. Once the weighing sequence is completed at step 3343, a signal is sent to 3653 through 3663 at H from the weigh program, and the sequence program progresses to 3673 where a signal is given at 3683 from 3143 via F to actuate motor 1383 and invert hopper means 1223 to dispense the additive concentrates contained in compartments 1133-1183 separately but simultaneously into the flowing water of vessel 1703. The dumping mechanism is disabled at 3693 once the hopper leaves its upright position. Once hopper means 1223 is inverted at 3703, vibrators on the hopper are activated at step 3723 to promote complete removal of all microingredient particles from bins 1133-1183. Compressor 1423 is next actuated at 3733 to compress air in air tank 1463, and a solenoid to header 1503 is opened which moves a flow of air through hoses 1523 and toward wall 1543 of each of compartments 1133-1163 to remove any traces of solid additive concentrates from the compartments. Air flushing continues for a predetermined period of time at step 3733.

Hopper means 1223 is then sent to its home position at step 3743 by activating hopper motor 1383 to continue to turn shaft 1363 in the same direction it turned to invert the hopper. When the hopper returns to its upright position, this is sensed by a switch as indicated by step 3753, and a signal is sent at 3763, 3773 to 3383 through I that the contents of hopper means 1223 have been dumped, and another weigh cycle (FIG. 72) can begin. Meanwhile the machine operating program of FIG. 73 progresses to step 3783 which switches motors 1883 of mixers 1803 to a higher speed. The lower motor speed is used until hopper means 1223 leaves its inverted position since high speed mixing while the hopper is inverted could cause water drops to be splashed into containers 1133-1163. Step 3783 also begins to measure a predetermined mixing time. When the period for the preselected mixing time expires, as determined at 3803, the mixing motors 1883 are switched back to their lower speed. Once the weighing program receives a discharge signal at 3813 from step 3153 through G and 3823, or alternatively from actuation of a discharge switch 3833 on switch panel 2813, a discharge signal is sent by the program at 3843 to discharge the slurry in vessel 1703. A solenoid valve in line 2403 then opens, and pump 2443 (FIG. 70) is activated to remove the slurry through outlet 1783 in vessel 1703. Mixer blades 1823 continue turning at a slow speed until a predetermined period of time expires, as set by step 3853. Pump 2443 continues operating as the water level lowers and finally clears the bottom of probe 1923, as illustrated by step 3863. If the level probe is not cleared within a predetermined period of time, an alarm is given at 3873 to indicate a pumping malfunction.

After the water level clears the bottom of probe 1923, pump 2443 continues operating and a timed flush cycle begins at 3883. Boost pump 1933 is activated at 3893 for introducing water through line 1943 as solenoid 2063 is closed and solenoid 2123 is opened. In this manner, flush water is introduced through line 2143 so that it enters vessel 1703 through nozzles 2283 of flush ring 2263, blade flush nozzles 2243, and port 1773. The interior of vessel 1703 and the surfaces of blades 1823 are thereby flushed, completely removing any residue of microingredient additives from the vessel through inlet 1793.

The boost pump continues introducing a water flush into vessel 1703 until the flush time period expires at 3903, and the flush is terminated at 3913. Discharge pump 2443 continues pumping for a delay period following the end of the flush cycle, as shown at 3923; then discharge pump 2443 is turned off at 3933.

The program then determines if the weigh switch is still on at 3943 and if it is, the program returns to step 3443 to repeat the sequence described in steps 3443-3933. If the weigh switch has been turned off, the apparatus 1013 is turned off at 3953 and an alarm is given at 3963 to indicate that a mode change has been made.

The control means includes means for operating mixers 1803 and discharge pump 2443 at the same time as dispensing means 8013 such that a first batch of additive concentrate slurry can be mixed and delivered to a receiving station while a second batch of additive concentrates are dispensed and weighed prior to their deposit into the mixing vessel.

Figure 74:
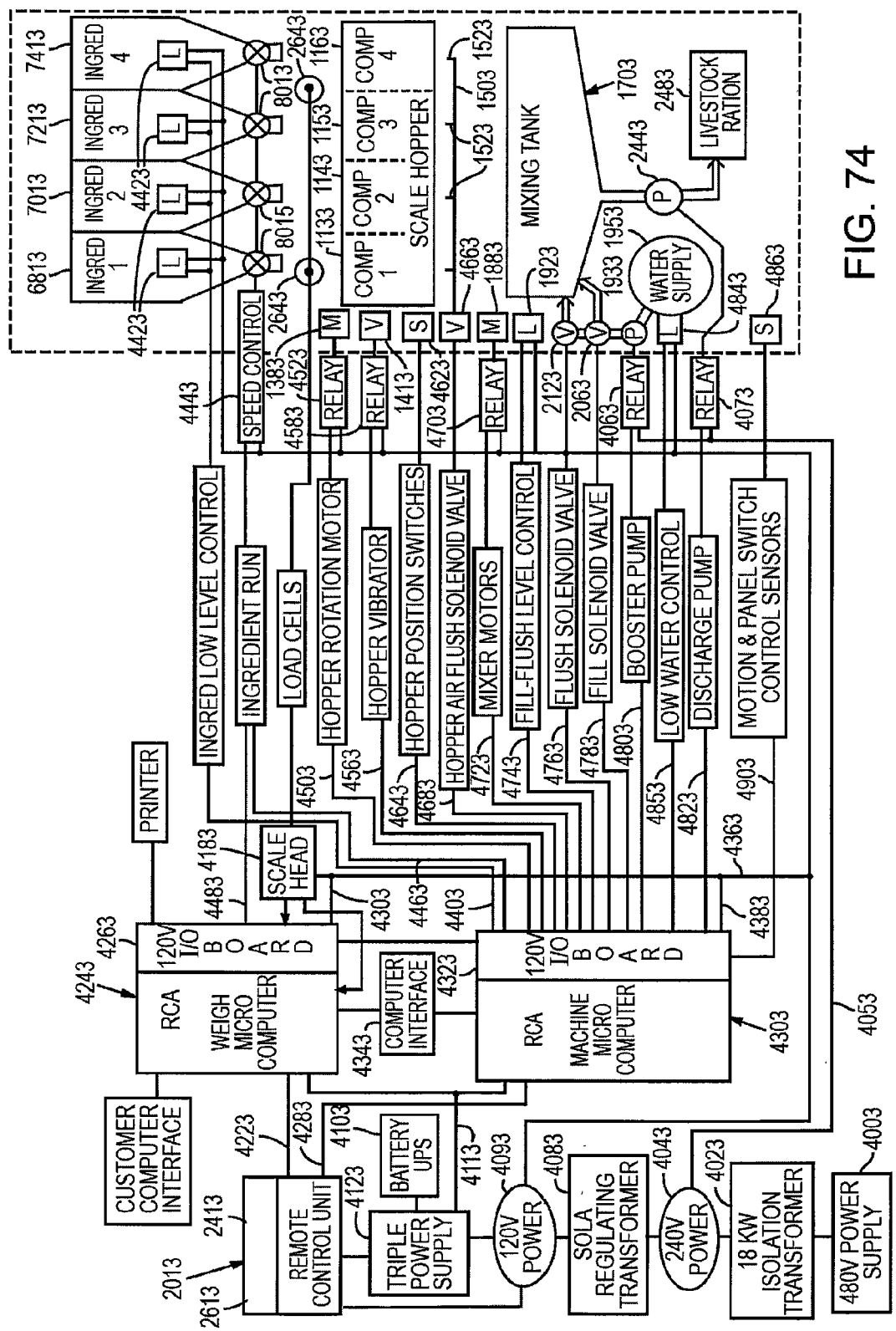
FIG. 74 is an electrical control schematic diagram for the illustrated apparatus.

A schematic diagram of the electrical connections for apparatus 1013 is shown in FIG. 74.

It is important to the proper operation of a computer that it be supplied with electrical power of a constant and consistent quality. This is a serious drawback in rural areas where the electrical power being supplied is often at the end of a long supply line into which fluctuations are introduced by intervening power users. Most cattle yards and other users of apparatus 1013 are located in rural areas where variations in power would adversely affect operation of the computers which control weighing and sequencing of machine function. For that reason, the system employs a series of transformers to selectively filter the electrical energy, isolate the power source, and damp variations in the power before it is supplied to the computers.

Four hundred eighty volts of power are supplied at 4003 by a rural electrical utility, and that power first passes through 10 kw isolation transformer 4023 where it is transformed into 240 V power, illustrated by 4043 in FIG. 74. This initially filtered 240 V power is supplied to electrical connection line 4053 through relay 4063 to booster pump 1933 that introduces water into mixing tank 1703 during the filling and flushing cycles. The 240 V power is also supplied through relay 4073 to pump 2443 that helps drain the mixing tank. This relatively unfiltered power can be supplied to pumps 1933, 2443 since they are not as sensitive to power variations as the computers.

The 240 V power is also sent to a sola-regulating transformer 4083 where it is transformed to 120 V power, as illustrated at 4093. This filtered, 120 V power is used to provide electrical energy to all components of apparatus 1013 other than pumps 1953, 2443. If electrical energy is interrupted, three 12 V batteries 4103 connected in series are provided as an uninterruptable power supply through triple power supply 4123.

Remote control unit 2013 has monitor screens 2613, 2913 and keyboards 2413, 2713 for weighing and metering functions. Remote control unit 2013 is electrically connected through line 4223 with a weigh microcomputer 4243 (RCA 1800 Micro System Z80 Microprocessor) having a 120 V optically isolated input/output relay board 4263. Remote control unit 2013 is also connected through line 4283 with machine sequencing microcomputer 4303 (RCA 1800 Micro System Z80 Microprocessor) having an optically isolated input/output relay board 4323 (Opto PB 24Q). Computer interface 4343 provides a data bus between weigh microcomputer 2413 and machine sequencing computer 4303.

Machine sequencing computer 4303 and weigh computer 4343 are supplied with 5 V power from triple power supply 4123 through line 4113. Both I/O boards 4263, 4323 are supplied with 120 V power through line 4363 at 4383.

Weigh computer 4243 contains an eight slot card cage with three 6623 RAM memory cards that contain the programs for operation of the weighing functions and monitoring of microingredient additive inventory. Weigh computer 4243 also contains a service box 6413 card to connect the service box to the computer, a printer 6413 output card, a 6003 system operating program card, and a 6264 memory card.

The machine computer 4303 has a six slot card cage, including two 6623 RAM memory cards, as well as a 6593, 6503, 6413 and 6003 CPU card. When apparatus 1013 is functioning in the metering mode, it uses only machine computer 4303. A complete set of ration data is stored on the machine computer's ROM memory separate from the ration data stored on the RAM memory cards of weigh computer 4243.

I/O board 4263 is connected through line 4483 with a speed control 4443 for controlling the speed of dispensing means 8013 in the weigh mode during a weigh cycle. For additives dispensed in weigh mode, speed control 4443 determines whether screw 9013 rotates at a fast speed during the initial weighing period of a given concentrate, or at a slow speed during the terminal phase of weighing as the weight of the concentrate approaches its predetermined amount. Since it is necessary to sense the weight of each concentrate that has been dispensed before the speed of dispensing means 8013 can be reduced and then stopped, load cells 2643 are electronically connected through scale head 4183 to the weigh microcomputer 4243. Weight determinations of the weighing means can therefore be sensed and sent to speed control 4443. For additives dispensed by volume during a weigh cycle, speed control 4443 determines that screw 9013 rotates at the preset third speed during the predetermined time of volumetric dispensing controlled by micro computer 4303.

I/O board 4323 is connected through line 4463 with speed control 4443 for controlling the speed of dispensing means 8013. Speed control 4443 determines that screw 9013 rotates at the preset metering speed on the third speed of speed control 4443 for a predetermined amount of time of volumetric dispensing controlled by microcomputer 4303.

Input/Output board 4323 is connected through line 4403 with ingredient level controls 4423 in each of bins 6813-7413 and containers 7613, 7813. These level controls are conventional switches located within the bins and containers for sensing when the level of additive concentrate in each bin has reached a predetermined low level. When the low level of additive concentrate is sensed by low level control 4213, a signal is sent to the operator indicating that more concentrate should be added.

I/O board 4323 of machine sequencing microcomputer 4303 is connected through line 4503 and relay 4523 with hopper rotation motor 1383 that inverts hopper means 1223. Line 4563 connects I/O board 4323 through relay 4583 with vibrator 1413 on hopper means 1223. A switch 4623 is also provided on hopper means 1223 for sensing whether the hopper is in an upright or inverted position, switch 4623 being connected to I/O board 4323 through line 4643. Finally, hopper means 1223 is provided with hopper air flush solenoid valve 4663 in header 1503 for controlling the introduction of air flush into compartments 1133-1163 of the hopper after it reaches its inverted position. Solenoid valve 4663 is connected to I/O board 4323 through line 4683.

Mixer motors 1883 on mixing vessel 1703 are connected through relay 4703 and line 4723 with I/O board 4323. Level control 1923 of the mixing vessel is connected with I/O board 4323 through line 4743. Solenoid valve 2123 in flush line 2023 is connected to I/O board 4323 through line 4763, and solenoid 2063 in fill line 2043 is connected to I/O board 4323 through line 4783. Booster pump 1953 for pumping water into vessel 1703 is connected through relay 4063 and line 4803 with I/O board 4323, while pump 2443 for withdrawing slurry and flush water from vessel 1703 is connected through relay 4073 and line 4823 with I/O board 4323. Low water control 4843 for the water supply is connected through line 4853 with the I/O board. Motion and panel control sensors 4863, which detect any oscillatory movements of hopper means 1223 and determine if any of the panels 1213 have been removed from apparatus 1013, are interconnected with I/O board 4323 through line 4903.

As earlier described in connection with FIG. 72, in the event of scale failure at step 3173, apparatus 1013 switches to a meter mode at 3183 and the weigh switch is turned off at 319. The off position of the weigh switch at 3193 is sensed as the meter switch being on at step 500 in FIG. 75. The numeral 1 is entered at keyboard 2413 at step 5023 to begin batching in the metering mode, and a ration code name is entered at 5043. The metering mode program of FIG. 75 searches at 5063 for a ration corresponding to the code entered at 5043. If the corresponding ration is not found at 5063, the program returns at 5083 to step 5043 so that another ration name can be entered.

Once the entered code has been matched with a ration at 5063, the program prompts for entry of information concerning batch size, which is entered at 5093. The program next prompts for entry of information concerning the number of batches to be processed, which is entered at 5103. The machine is then ready to batch at 5123 by volumetric metering instead of by weighing.

The program waits at step 5143 for a start signal 5163, which is supplied by a start switch 2993 on control panel 2813. It is then determined at 5183 if boost pump 1933 is on, and if it is not, an alarm is given at 5203 to indicate that the pump is off. Boost pump 1933 fills mixing vessel 1703 during a predetermined amount of time at step 5223. If the water level in mixing vessel 1703, as detected by water level sensor 1923, does not reach a predetermined level within a set period of time, an alarm sounds at 5243 to indicate a filling error.

Once level sensor 1923 determines that the water level in mixing vessel 1703 has reached a predetermined level, mixing motors 1883 are activated at 5263 to rotate mixing blades 1823 at a slow speed. An alarm sounds at step 5283 if the mixers are not on. While mixer blades 1823 induce a turbulent flow of water in mixing vessel 170, motor 1023 for screw 9013 below bin 6813 is activated at 5303. The metering speed of motor 1023 is a third speed, intermediate the fast and slow speeds used in dispensing additive concentrates by weight. Screw 9013 turns for a predetermined period of time sufficient to dispense a required volume of additive concentrate. The screw of each dispensing means 8013 below the bin containing desired additive concentrates turn simultaneously. Dispensing means 1203 for liquid additive concentrates in containers 7613, 7813 also operate simultaneously with dispensing means 8013 to volumetrically deliver predetermined amounts of liquid concentrate to compartments 1173, 1183.

When metering is complete at 5323, a signal is sent to motor 1383 at step 5343 to invert hopper means 1223 and dump its contents into the flowing water of vessel 1703. A switch determines at 5363 whether the hopper is inverted, and if it is not, an alarm is given at 5383 to indicate a dump failure. Hopper vibrators are then actuated at 5403 while hopper means 1223 is inverted to remove, by vibration, additive concentrate particles that remain stuck to the walls or bottom of containers 1133-1163. The air flush (FIG. 71) is actuated at 5423, and the program sends a signal at 5443 to send the hopper to its home, upright position by actuating motor 1383 to continue rotation of shaft 1363. If hopper means 1223 does not reach its home, upright position within a predetermined period of time set by 5463, an alarm sounds at 5483 to indicate that a malfunction has occurred and the hopper is still inverted.

When hopper means 1223 leaves its inverted position, mixing motors 1883 are switched to their second, higher speed at 5483. High speed mixing continues for a predetermined amount of time and then returns to low speed at step 5503 until a discharge signal 5543 is received at 5523 from a discharge switch 3833 on panel 2813 to turn on discharge pump 2443. It is determined at 5563 whether discharge pump 2443 is on, and if it is not, an alarm is given at 5583 to indicate a pump malfunction.

A predetermined, mix delay time period is initiated at 5583 during which period motors 1883 continue to move mixing blades 1823 at low speed. If the bottom of level probe 1923 is not cleared at 5603 within the predetermined period of time set in step 5583, an alarm is given at 5623 to indicate pumping problems. Once probe 1923 has been cleared, a predetermined flush cycle time is initiated at 5643, and boost pump 1933 is actuated at 5663 to move water through flush line 2143 while solenoid 2123 is open and solenoid 2063 is closed. Boost pump 1933 continues introducing water through line 2143 and into flush ring 2263, blade cleaning nozzles 2243, and port 1773 until a flush period has expired at 5683 and pump 1933 is turned off at 5703. Discharge pump 2443 continues operating for a period of time set by 5723 until all of the flush water residue has been removed through drain 1783 and sent to receiving station 2483. Discharge pump 2443 is then turned off at 5743 when the delay period set at step 5723 expires.

The metering mode program then determines whether another batch is needed at 5763, the need for another batch having been determined by the number of batches entered at 3103. If another batch is not needed, the program returns to step 5023 which prompts the operator to enter the code for another batch. If, on the other hand, another batch is required at 5763, the program checks at 5783 to determine if the meter switch is still on. If the metering switch is on (and conversely the weigh switch is off), the program returns to step 5123 where it repeats steps 5123-5763. If it is determined at 5783 that the meter switch is off, apparatus 1013 is turned off at 5803 and an alarm is given at 5823 indicating a mode change.

Figure 76:
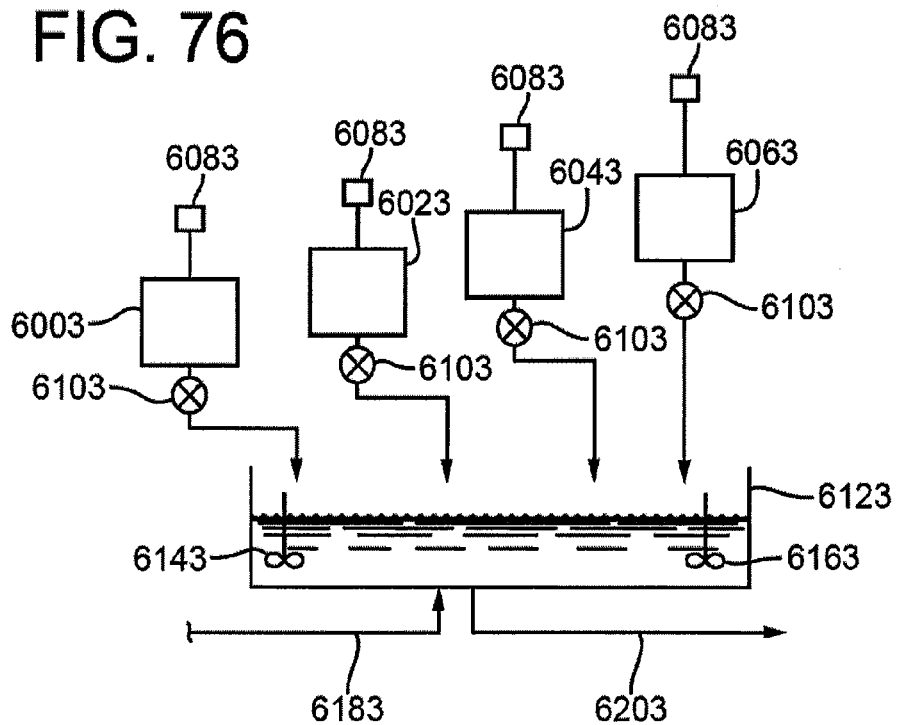
FIG. 76 is a schematic view illustrating a system in which microingredient additive concentrates are dispensed directly into a mixing vessel from individually weighed storage containers.

FIG. 76 shows a second embodiment of apparatus 1013 in which hopper means 1223 has been eliminated. In this embodiment, the weight of each microingredient concentrate dispensed is determined on a "loss of weight" basis. Each of dry concentrate bins 6003, 6023, 6043, 6063 is provided with a load cell 6083 for determining the weight of each container. The program in this embodiment activates a dispensing means 6103 (similar to dispensing means 8013 in apparatus 1013) to selectively sequentially or simultaneously deliver dry microingredients separately from bins 6003-6063 into mixing vessel 6123 having mixers 6143, 6163. Tank 6123 is filled and flushed through water supply line 6183 and emptied through discharge line 6203 after concentrates have been mixed with water in mixing vessel 6123.

Liquid microingredient concentrates may also be dispensed on a "loss of weight" basis by mounting containers of liquid microingredient on load cells.

The control means for the FIG. 76 embodiment includes a means for controlling the dispensing rate of each dispensing means 6103 in response to loss of weight sensings of load cell 6083 for each bin 6003-6063. Such a control means is similar to speed control 4443 for dispensing means 8013 in FIG. 74.

In a variation of the embodiment of FIG. 76, the control means includes a means for operating dispensing means 5103 for several cycles in the volumetric metering mode wherein additives are dispensed using a weight per unit time formula instead of load cell 6083. The actual weight of each additive concentrate dispensed will be determined by the loss of weight measured by each load cell 6083. The actual weight of concentrate lost will be compared by the computer to the theoretical amount dispensed. The discrepancy between the actual and theoretical amounts will then be corrected by adjusting the formula to dispense more accurately the desired amount of additive concentrate. Since the remaining concentrate in each bin has substantially the same density as that already dispensed, the remaining additive can be dispensed accurately by volume.

Correction of the weight per unit time formula used for volumetric dispensing in the metering mode can be used in connection with any embodiment employing a weighing means. For example, volumetric metering into hopper means 1223 of FIG. 62 can be adjusted by comparing actual weights of additive concentrate dispensed into compartments 1133-1163 with the desired amounts determined on a weight per unit time formula. The computer can then correct the formula to account for the density and other properties of the particular batch of additive concentrate being dispensed.

Alternatively, dispensing means 8013 can be operated in a weigh mode from the beginning through a major portion of a dispensing cycle for a particular additive concentrate. The load cell 2643 monitors the weight of concentrate dispensed at a given speed of screw 9013. This information is used by the control means to prepare a weight per unit time formula for volumetric dispensing of the particular additive being dispensed. The dispensing means 8013 is then operated in a volumetric metering mode independently of the weighing means for the final portion of the dispensing cycle.

Figure 77:
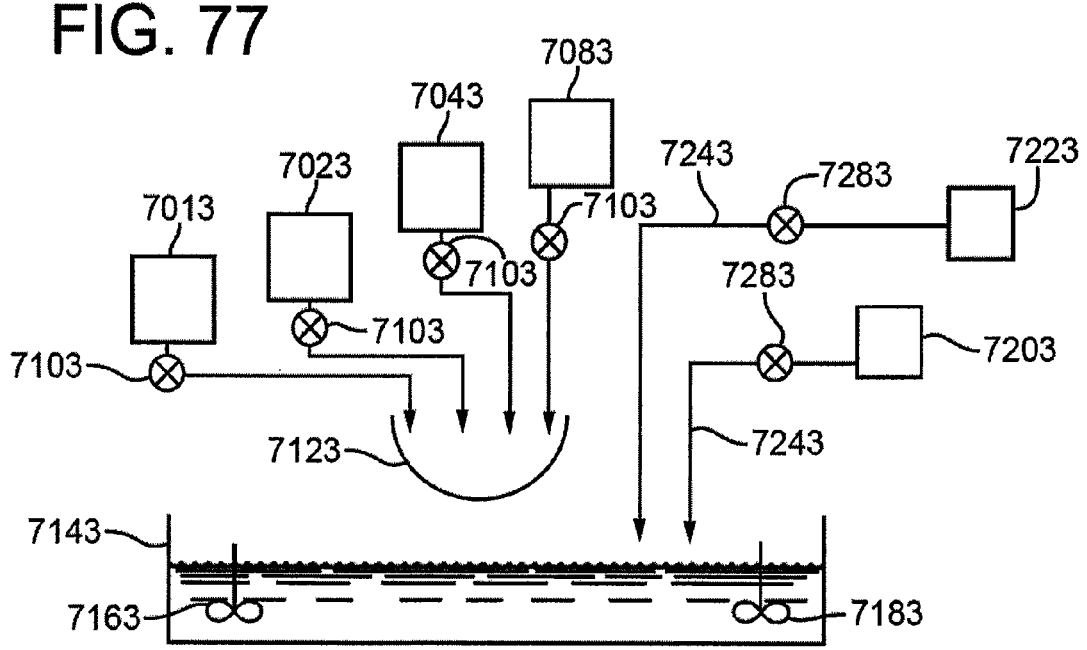
FIG. 77 is a schematic view illustrating a system in which dry additive concentrates are dispensed by weight into a weigh hopper while liquid additive concentrates are metered by volume directly into the mixing vessel.

Yet another embodiment of the system is shown in FIG. 77 which takes advantage of the fact that the density of liquid microingredient concentrates does not vary as greatly as solid microingredients. For this reason, it is possible to accurately meter liquid microingredients by volume while measuring the solid microingredients by weight. In the embodiment of FIG. 77, four dry microingredient containing supply means 7013, 7023, 7043, 7083 are shown to each be connected to a dispensing means 7103 similar to the dispensing means 8013 of apparatus 1013. Each of dispensing means 7103 conveys dry additive concentrate to a hopper means 7123 similar to hopper means 1223 in FIG. 65, the hopper means 7123 being suspended from a pair of weigh cells. Each additive concentrate is dispensed sequentially into hopper means 7123 from containers 7013, 7023, 7043, 7083 using dispensing means 7103 until a predetermined weight of each concentrate has been sensed by a load cell from which hopper means 7123 is suspended. Hopper means 7123 is then inverted to separately and simultaneously empty the dry microingredient contents of hopper means 7123 into flowing water in mixing vessel 7143 which is being agitated by mixers 7163, 7183.

In the FIG. 77 embodiment, liquid microingredients are separately stored in containers 7203, 7223 which are provided with tubes 7243 that empty into vessel 7143. Rotary of piston pumps 7283 are interposed in each tube 7243 to pump microingredients from containers 7203, 7223 directly into mixing vessel 7143, thereby bypassing entirely hopper means 7123.

The control means for the FIG. 77 embodiment may, in some embodiments, include means for selectively operating some dispensing means simultaneously and others sequentially. Pumps 7283 for the liquid additive concentrates in containers 7203, 7223 may, for example, be operated simultaneously with each other and with dispensing means 7103. Dispensing means 7103 for dry additives should, however, be operated sequentially in this embodiment since the overall weight of hopper means 7123 is sensed by the load cells from which the hopper is suspended. If the dry additives were dispensed simultaneously into hopper means 7123, it would not be possible to weigh accurately the amount of each additive dispensed. It is through cumulative weight determinations of sequentially dispensed additives that accurate weight determinations are made in the compartmented hopper. A first additive concentrate is delivered into a compartment of the hopper until its load cells register a first predetermined weight, and delivery of the first additive concentrate is stopped. Delivery of a second additive concentrate is then started and continued until the load cells register a second predetermined weight, and so on until predetermined weights of all selected additives have been delivered into the hopper.

In yet other embodiments which are not shown in the drawings, the control means is programmed to operate the dispensing means in an interrupted, on-off-on-off sequence to dispense selected microingredients into a weighing means such as hopper 1223. Weight determinations sensed by load cells 2643 would only be accepted when the dispensing means is switched off during the interrupted sequence. In this manner, weighing inaccuracies caused by movement of the dispensing means or settling of additives would not affect weight determinations.

In another disclosed embodiment, the isolating means includes programming the control means to prevent operation of any other moving components of apparatus 1013 while weight determinations are being made by the weighing means. The operation of dispensing means 8013 and mixer blades 1823 would, for example, be prevented by the control means while weight determinations were being made by load cell 2643.

Figure 78:
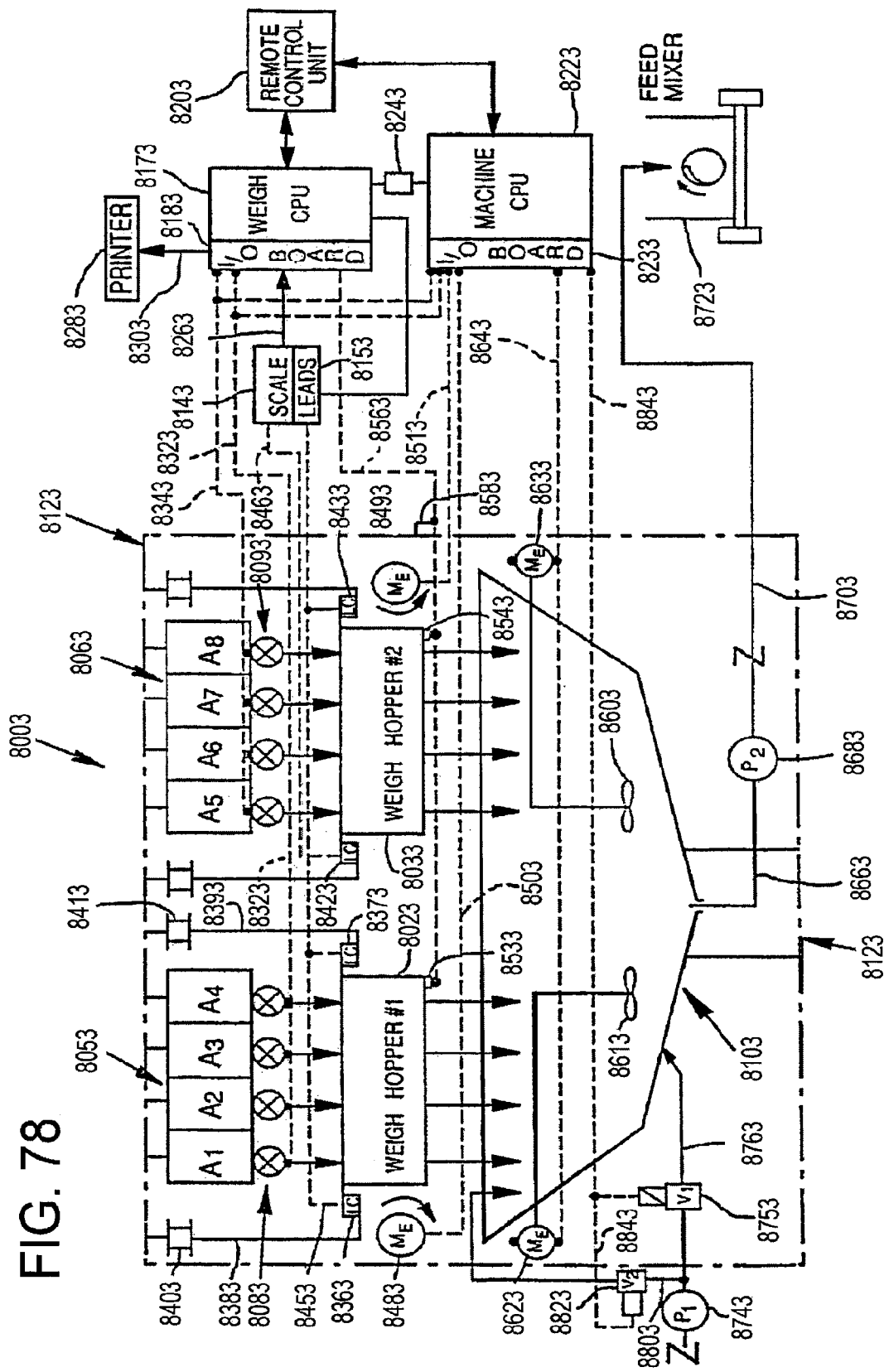
FIG. 78 is a schematic view showing a system in which different additive concentrates can be dispensed into different weigh hoppers simultaneously and the different weigh hoppers discharged either independently or simultaneously and either after the weighing of each additive or cumulatively after the cumulative weighing of multiple additives in each hopper.

FIG. 78 shows an apparatus indicated generally at 8003, which is somewhat similar to the embodiment of FIGS. 61-75 but having two separate weigh hoppers 8023, 8033 for weighing the multiple additive concentrates dispensed from additive concentrate storage means 8053, 8063 by dispenser means 8083. The weigh means of the apparatus 8003 includes separate weigh means for each weigh hopper 8023, 8033, thereby giving the apparatus the capability of weighing multiple additives simultaneously in different weigh hoppers. This capability gives the apparatus 8003 an advantage over the apparatus of FIG. 61 in being able to dispense, weigh and discharge all of the multiple microingredients of a given formulation into the mixing vessel 8103 and thereby complete the batching of a formulation, more quickly than the apparatus of FIG. 61.

The apparatus 8003 also includes a support frame means 8123 which may include either separate support and weigh frames as in the apparatus of FIG. 61 or a common support frame for all of the major mechanical components of the apparatus as depicted schematically in FIG. 78. Support frame 8123 rigidly supports the multiple microingredient concentrate storage containers 8053, 8063 and their associated dispensers or metering devices 8083, 8093. The support frame means 8123 also rigidly supports the mixing vessel 8103 which is shown as a mixing vessel common to both weigh hopper 8023 and weigh hopper 8033.

Other major components of the system of FIG. 78 include control and other components which would normally be mounted apart from support frame means 8123, including a pair of scale heads 8143, 8153, one for each weigh hopper, a weigh computer or central processing unit 8173 with its associated input/output board 8183, and a remote control unit or terminal 8203 for controlling the operation of the computer 8173. A separate machine computer or central processing unit 8223 has an associated input/out board 8233. An interface 8243 enables communication between the machine computer 8223 and the weigh computer 8173. Scale heads 8143, 8153 transmit weight determination data through line 8263 to the input/output board of the weigh computer 8173. There is also a printer 8283 connected to the input/output board of weigh computer 8173 through line 8303 for printing desired output data from the weigh computer 8173.

In the apparatus 8003 there are four microingredient additive concentrate storage containers 8053 associated with weigh hopper 8023 and another four such storage containers 8063 associated with the other weigh hopper 8033, thereby giving each weigh hopper the capability of weighing and discharging four different additives into the mixing vessel 8103. The dispensers 8083 associated with the different additive storage containers 8053 are capable of operating independently of one another upon an appropriate command signal from a weigh computer 8173 transmitted from the input/output board 8183 through line 8323. Similarly, each of the dispensers 8093 for the four other storage containers 8063 are capable of operating independently of one another to dispense additives into the weigh hopper 8033 upon a suitable command signal from weigh hopper 8173 transmitted from input/output board 8183 through line 8343.

Weigh hopper 8023 is mounted at its opposite ends on a pair of load cells 8363, 8373 connected by suspension members 8383, 8393 and a pair of resilient isolator members 8403, 8413 to support frame 8123.

Weigh hopper 8033 is mounted in a similar manner by load cells 8423, 8433 to support frame 8123. Thus, each weigh hopper is independently mounted by separate weigh means to the frame 8123 for independent weighing of ingredients. The two load cells 8363, 8373 for weigh hopper 8023 are operatively connected by a line 8453 to scale head 8153. Weigh hopper 8033 is separately connected by a line 8463 to a separate scale head 8143. Both of the scale heads in turn are connected to the input/output board 8183 of weigh computer 8173 through line 8263. Thus each weigh hopper and its contents can be weighed separately and its contents cumulatively through its associated scale head simultaneously with the other weigh hopper. That is, both weigh hoppers can carry out their weighing functions at the same time and independently of one another.

Each weigh hopper 8023, 8033 is preferably similar in construction to the weigh hopper disclosed in FIGS. 62, 63, 65, 66 and 67. That is, each weigh hopper is mounted in a manner shown in such prior figures for rotation from its normal additive receiving upright position to an inverted discharge position by discharge means including an electric motor 8483 in the case of weigh hopper 8023 and electric motor 8493 in the case of weigh hopper 8033. Each is connected independently to the input/output board 8233 of the machine computer 8223 through suitable electrical conductors 8503 and 8513, respectively.

Each weigh hopper, 8023, 8033 also is provided with a motion sensor 8533, 8543, respectively, connected to the input output board 8183 of weigh computer 8173 through line 8563 for detecting any motion in either weigh hopper during the weighing process. The software for the weigh computer 8173 prevents a final weight determination from being made for a given weigh hopper whenever the motion sensor for that hopper senses motion that might give a false or highly inaccurate reading.

The support frame means 8123 for the weighing and delivery components of the apparatus is preferably enclosed by housing panels (not shown) in a manner similar to that shown in FIG. 61 to shield and isolate the weighing components of the apparatus from external ambient forces that could cause undesirable motion and thus inaccurate weight readings. Such forces typically might include the effects of wind or jarring of the components by direct contact of personnel. The support frame means 8123 is provided with a sensor 8583 which is also connected by line 8563 to the input/output board of weigh computer 8173. Sensor 8583 is operable to prevent a weight determination from being made whenever a panel is removed from the support frame 8123. Thus the motion sensors 8533, 8543 for the weigh hoppers and the panel sensor 8583 for support frame 8123 provide additional means for isolating the weighing components of the apparatus from influences that could affect weight determinations and the accuracies of such determinations.

A further means of enhancing the accuracy of the weight determinations of the apparatus disclosed in FIG. 78 is the mounting of the discharge motors 8483 and 8493 in conjunction with their respective weigh hoppers 8023, 8033 so that such motors become part of the tare weight of the hoppers in making additive weight determinations. Because very lightweight, flexible electrical conductors can connect such electric motors to the operable control components of the apparatus, such conductors will have no appreciable effect on the weight determinations of the weigh means. This should be contrasted with the hydraulically actuated discharge means in conjunction with the weigh hoppers of prior apparatus. With a prior hydraulically actuated discharge means, relatively stiff hydraulic conduit must connect the hydraulic motor associated with the hopper to the source of hydraulic fluid remote from the hopper. Typically such hydraulic conduit affects weight determinations of the hopper in such instances because it inherently provides some structural support for the hopper, thereby influencing load cell weight sensings as ingredients are added to the hopper because the conduit is partially supporting some of the load of the added weight.

The apparatus in FIG. 78 also includes positive mixing means within the mixing vessel 8103 in the form of a pair of mixing blades 8603, 8613, each driven by an electric motor 8623, 8633. The mixer motors are connected by electrical conductor means 8643 to the input/output board 8233 of the machine computer 8223. A slurry discharge line 8663 leads from a bottom opening of mixing vessel 8103 to the input side of a discharge pump 8683. The discharge line continues at 8703 from the discharge side of discharge pump 8683 to a conventional feed mixer such as typically the truck-mounted feed mixer 8723. A booster pump 8743 pumps a liquid carrier such as water from a source (not shown) through a fill line 8763 into the mixing vessel. A solenoid operated valve 8783 in fill line 8763 controls the admission of the water carrier into the mixing vessel and is operated by the machine computer 8223 through a suitable conductor 8783 connected to the input/output board 8233 of such computer.

A flush line 8803 branches from fill line 8763 downstream of booster pump 8743 and upstream of fill valve 8743. Another solenoid actuated valve 8823 in the flush line connected to the input/output board 8233 of machine computer 8223 through conductor 8843, controls the admission of flush fluid into the mixing vessel.

The hardware components of the control system including the weigh computer 8173, machine computer 8233 and their associated input/output boards, the printer 8283, and the remote control unit 8203, may be similar to those same units described with respect to the embodiment of FIG. 61. Similarly, the software controlling the operation of such computers can be varied to vary the operating sequence of the machine of FIG. 78.

A typical operating sequence of the machine of the apparatus of FIG. 78 is as follows:

A driver drives a feedtruck into a feed-receiving station in a cattle feedlot. The driver departs his vehicle, approaches the remote control unit 8203 and selects the formulation of feed additive concentrates to be batched and delivered into his truck, depending on the specific lot of animals to be fed within the feedlot. The formulation is selected typically by the operator depressing a key corresponding to the formulation selected on the computer terminal of the remote control unit.

Assuming that predetermined weights of two additives A1, A2 in storage containers 8053 and two additives A5, A6 from storage containers 8063 are to be included in the formulation, the dispenser 8083 for container A1 begins to dispense the additive A1 into weigh hopper 8023. At the same time, the dispenser 8093 for container A5 begins to dispense additive A5 into weigh hopper 8033. The dispensing of additive A1 into weigh hopper 8023 continues until a predetermined weight of such additive has been added to such hopper as determined by the load cells 8363, 8373 and the associated scale head 8153, at which point the weigh computer 8173 stops the dispensing of additive A1 from its storage container by stopping its associated dispensing means 8083. At the same time, a weight determination of the additive A5 added to weigh hopper 8033 is determined in the same manner, but independently of the weight determination occurring in hopper 8023.

When the predetermined weight of additive A1 has been added to weigh hopper 8023, depending on programming, two alternative functions can occur. Either the weigh hopper 8023 can be inverted by motor 8483 to discharge the additive A1 into the mixing vessel 8103 and then returned to its upright position to receive the next additive A2, or the weigh hopper can remain in its upright position while the dispenser 8083 for additive A2 operates to add, cumulatively, the predetermined weight of additive A2 to weigh hopper 8023. If the latter sequence is used, weigh hopper 8023 is inverted by its discharge motor 8483 to discharge the predetermined weights of additive A1 and additive A2 together into the mixing vessel 8103. The same options are available with respect to the addition of additives A5 and A6 to weigh hopper 8033 and the discharge of the contents of the weigh hopper 8033 into the mixing vessel 8103. It is important to note that both weigh hoppers 8023 and 8033 can operate entirely independently to weigh and discharge their preselected additives into the mixing vessel 8103, although the machine and weigh computers could also be programmed to cause both weigh hoppers 8023, 8033 to wait until all of the selected additives have been added and weighed within each weigh hopper and then both weigh hoppers inverted simultaneously by their respective motors to discharge all of the weighed additives at once into the mixing vessel. That is, each additive can be added, weighed and discharged either separately or cumulatively with other additives, depending on the programming selected for the control system.

Regardless of which of the above described dispensing, weighing and discharge options are selected, preferably booster pump 8743 pumps the carrier water through open valve 8743 and fill line 8763 to fill the mixing vessel 8103 to a predetermined level before any additive is discharged into the mixing vessel. This will prevent different and possibly incompatible additives from intermixing in concentrated form and also prevent additives from sticking to the inside walls of the vessel, making it difficult to remove such additives even after carrier water or flush water is added to the vessel.

Also preferably before the discharge of any additives into the mixing vessel in making up a batch, mixing blades 8603, 8613 rotate to create a turbulent flow within the mixing vessel so that additives entering the liquid carrier are quickly intermixed with and dispersed throughout the carrier, thereby diluting the concentrates.

When the predetermined weights of the selected additives A1, A2, A5 and A6 all have been weighed in their respective weigh hoppers 8023, 8033 and discharged into the water carrier within mixing vessel 8103, mixing blades 8603, 8613 continue to rotate for a time to ensure a uniform dispersal of all additives throughout the carrier liquid slurry thus formed. Of course at this time, booster pump 8743 shuts off and fill line valve 8743 closes, as does flush line valve 8823.

When mixing is complete within mixing vessel 8103, discharge pump P2 operates to pump the slurry formulation from the mixing vessel through discharge line 8663 and to the waiting feed mixer truck 8723 through discharge line 8703. When the level of slurry within the mixing vessel drops below a predetermined level as determined by level sensors (not shown) within the vessel, booster pump 8743 restarts and flush line valve 8823 opens to pump flush water into the mixing vessel through its top and along its side walls to flush all slurry residue from the vessel. Flushing continues as the discharge of slurry proceeds through the discharge lines 8663, 8703. Discharge pump 8683 continues to operate during the complete flush period, pumping the flush liquid with the slurry into the feed mixer truck 8723. After a predetermined length of time sufficient to enable the complete flushing of the mixing vessel and discharge lines, and the pumping of all slurry into the feed mixer 8723, booster pump 8743 stops and flush valve 8823 closes. Pump 8683 continues to operate until all of the slurry and most of the flush liquid is pumped into the feed mixer 8723. Thereafter the truck operator returns to his truck and drives away as the mixing of the feed and slurry continues. Typically, the driver drives to the feed bunks of selected pens or lots of animals and delivers the additive-bearing feed into the bunks immediately upon departure from the additive receiving station. Thereafter, typically, another feed mixer truck arrives at the additive receiving station represented by the position of truck 8723 and that operator goes through the same procedure as just described, selecting the same or a different formulation depending on the requirements of the animals within the lot or pens that are to be fed with the feed ration from such truck.

During the additive formulating process as just described, the system will not allow a weight determination of a given additive to be made so long as a panel is removed from the support frame 8123 as detected by sensor 8583. Nor will a weight determination be made if either one of the motion sensors 8533, 8543 associated with each weigh hopper detects movement of a weigh hopper that could affect the weight determination to be made in such weigh hopper.

Typically, scale heads 8143, 8153 receive weight sensings from their respective load cells 6 to 8 times per second. The scale heads then average such readings for that given unit of time and send the average reading via line 8263 to the input/output board 8183 of the weigh computer 8173. Computer 8173 then records the averaged weight per unit of time as the weight upon which the computer acts to control the operation of the additive dispensing means and discharge means.

Because of the large number of readings being averaged before the average is transmitted to the weigh computer, any single erroneous reading transmitted to a scale head by the load cells will have an insignificant effect on the accuracy of the averaged reading transmitted from the scale head to the weigh computer for processing. This slow updating of the weigh computer (about once per second or less) with an average of a large number of weight sensings received by the scale head is further insurance against inaccurate weight readings and enhances the accuracy of the entire system. If the computer updating were faster (such as twice per second or more), an erroneous reading would have a greater effect on the accuracy of weights recorded and processed by the computer.

Figure 75:
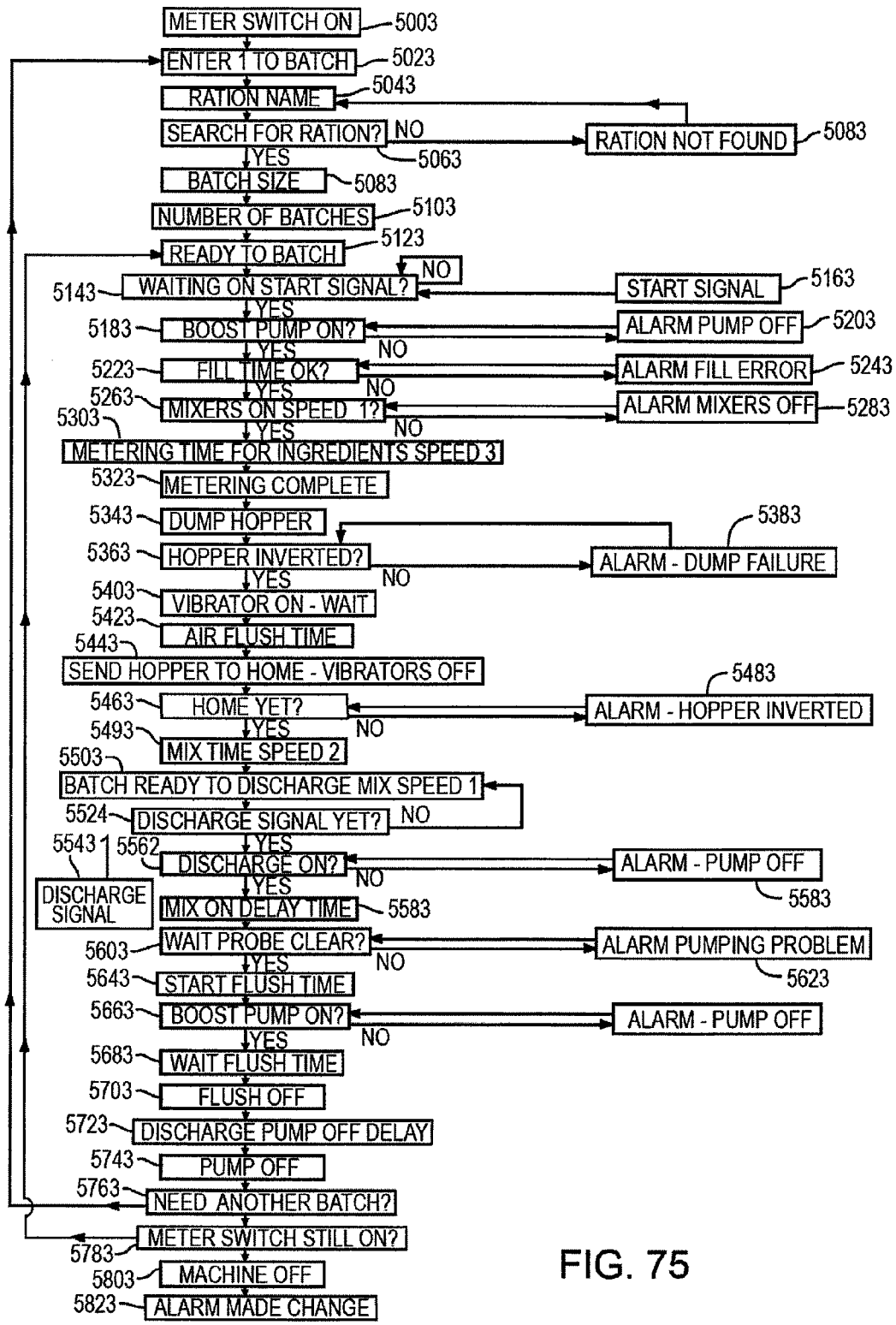
FIG. 75 is a flow diagram illustrating the logic of a computer program which controls alternative volumetric metering and dispensing functions of the illustrated apparatus.
Figure 79:
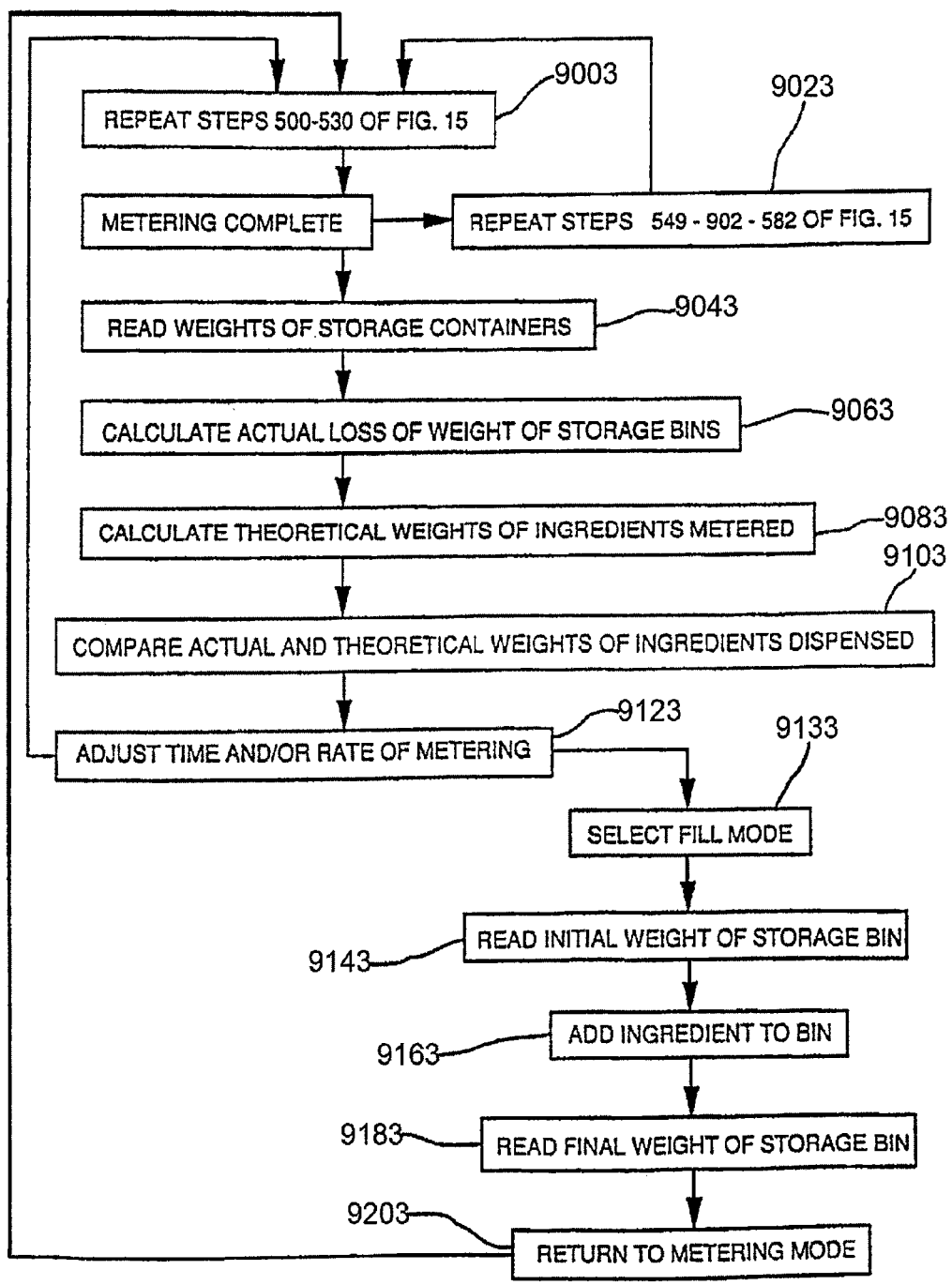
FIG. 79 is a flow diagram illustrating the logic of a modification of the computer program of FIG. 75 which controls a hybrid volumetric-weight system of measuring the amounts of microingredients dispensed using apparatus of the general type shown in FIG. 76.

FIG. 79 is a flowchart of a computer program applicable to the computers of FIG. 74 and representing a modification of the program of FIG. 75 for operating the apparatus of, for example, FIG. 76 on a weight-compensated metering basis.

The flowchart of FIG. 79 incorporates steps 5003-5303 of the FIG. 75 program in box 900 and also the completion-of-metering step 5323 of the same program. When all microingredients have been metered into the mixing vessel 6123, the program continues to sequence through steps 5493-5823 of the metering program of FIG. 75, skipping steps 5343-5483 because the apparatus of FIG. 76, unlike the apparatus of FIGS. 74 and 78, does not use a weigh hopper.

As the program continues to sequence through mixing and discharge steps 5493-5823 as indicated at box 9023 in FIG. 79, the program also, at least after so many metering cycles, or if desired after every metering cycle, reads the weight of each microingredient storage container 6003, 6023, 6043, 6063 as indicated at 9043. Thereafter, as indicated at box 9063, the program commands the computer to calculate the actual loss of weight of the ingredient storage containers to determine the actual weight of each microingredient metered, by subtracting the weight of each storage container sensed after metering at 9043 from the initial weight of each storage container prior to such metering steps.

The program also commands the computer to calculate the theoretical weight loss of each storage container, which is also the theoretical weight of each ingredient used, by multiplying the metering rate of each metering device 6103 in, for example, grams per minute, by the length of time each metering device 6103 has operated, as indicated at box 9083. The program then commands the computer to compare the actual weight of ingredient used as calculated at 9063 with the theoretical or target weight of ingredient used as calculated at 9083, as indicated at box 9103. From this comparison the program commands the computer to adjust either the time that each metering device 6103 operates, or the rate of speed at which each such device operates, or both, during a metering cycle so that the actual weight of ingredient used as determined by weighing equals the desired or theoretical weight of ingredient used as determined by metering. This adjustment command occurs at box 9123 in the computer program. When the metering speed or time adjustment is made, the program returns to the start of the metering cycle as indicated at box 9003.

The program also includes a fill mode or routine which is used whenever a microingredient storage bin 6003, 6023, 6043, 6063 is refilled. In such mode, the program commands a reading of the initial weight of the storage container being refilled at box 9143. The additional microingredient is then added to the storage container as indicated in box 9163. The program then commands a reading of the filled weight of the storage container at box 9183 and enters such weight in computer memory. At this point the fill subroutine has been completed and the apparatus is conditioned to start another metering cycle.

The foregoing described program operates the apparatus of FIG. 76 primarily as a metering apparatus. However, the metering devices 6103 are adjusted after completion of a predetermined number of metering cycles based on actual loss-of-weight determinations of each storage bin as registered by the weighing means 6083 for each storage container. Thus the apparatus of FIG. 76 when operated in accordance with the program of FIG. 79 is actually a hybrid weigh-metering system in which the metering components are periodically readjusted so that the theoretical or target weights of ingredients metered will closely approximate the actual weights of ingredients dispensed.

The described weight-compensated metering system can also be used in a continuous mill application in contrast to the batch mill application described with respect to FIG. 76. In a continuous mill system, the metering devices meter the additive concentrates continuously at predetermined rates from their storage bins into a liquid carrier, which in turn flows into a feed ration at a predetermined rate. In such a system, weight losses of the storage bins can be determined periodically and then used to calculate the necessary adjustments of metering rates of the metering devices to bring the actual weights of additives dispensed per unit of time by metering into line with the theoretical weights desired. This can be done without interruption of metering, simply by adjusting the speed controls or the metering devices.

Feed Delivery 2

This subsection describes additional process steps and system components for delivering feed to animals. These process steps and system components can be used in conjunction with evaluation of an animal's respiratory or circulatory condition, as discussed above. Information gather by imaging and evaluating an animal's respiratory or circulatory system, such as respiratory damage designations, can be used as the basis for management decisions regarding feed delivery. For example, an animal with damaged lungs may be administered an inexpensive maintenance diet, whereas an animal with healthy lungs is administered a more expensive weight gain diet.

Figure 80:
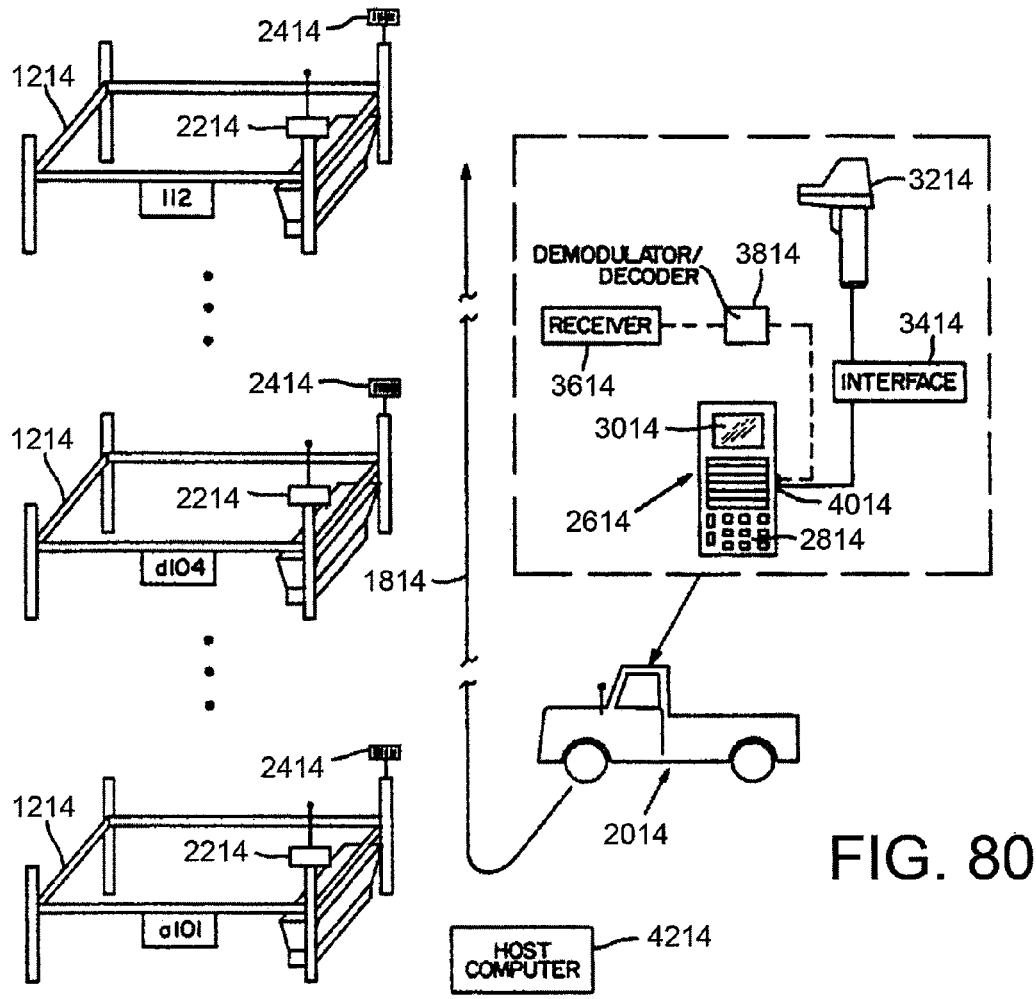
FIG. 80 is a schematic of a system for assigning feed to each feed bunk.

Referring now to FIG. 80 of the drawings, there is shown several cattle pens 1214 in a feedlot, each having an associated feed bunk. A feed bunk holds a ration, i.e., a type of feed, in a selected quantity for the cattle contained within the pen. The arrow 1814 represents a route that a truck 2014 may take for the driver to view the condition of each feed bunk from the truck cab. That route, as will be described, depends on which cattle pens contain cattle and are thus currently receiving feed.

Each pen and associated feed bunk have means of identification such as an alphanumeric symbol (i.e., a101, d104, 112, etc.) mounted near the truck route that can be read by the person viewing the bunks. Alternatively, the identification may be through automated means such as an RF signal transmitted locally by a transmitter 2214 or a bar code 2414 affixed to the cattle pen. Such means provide an accurate identification of the pen without the driver having to attempt a written entry onto a feed card.

To "read" the bunks, i.e., identify the bunks and assignment data regarding feed rations, the driver carries in the cab a portable computer 2614 such as a PDT111 manufactured by the MSI Data Corporation. The computer 2614 includes a data entry means such as a keyboard 2814 for entering feed assignment data and a display screen 3014 for optimally viewing yard sheet data while making a feed assignment. If the cattle pens include automated identification means such as the transmitter 2214 or bar code 2414, a corresponding data entry means such as a machine capable of reading the identification signal is coupled to the computer 2614. For reading the bar codes 2414, a bar code scanner 3214, such as the SYMBOLTEC LS8100 available from the MSI Corporation, is connected to the computer 2614 via a conventional laser interface module 3414. For reading the RF signals generated by transmitters 2214, a conventional RF receiver 3614 may be connected to the computer 2614 via a conventional demodulator/decoder module 3814. Whichever of the scanner 3214 or receiver 3614 is utilized, the machine is coupled to one of the computer's serial I/O port 4014. Alternative means of automatic cattle pen identification may include Loran-type radio frequency triangulation, sound waves, etc.

Figure 81:
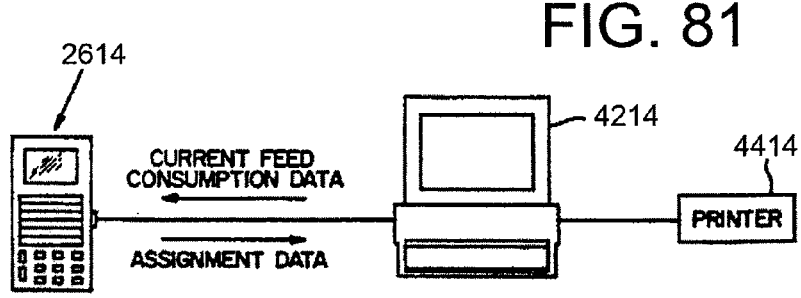
FIG. 81 is a schematic view showing data transfer between the portable and host computer of FIG. 80.

The portable computer 2614 is adapted to receive the feed consumption data before a reading of the feed bunks so that the driver may review that data while entering assignment data. The portable computer 2614 is also adapted to communicate with a host computer 4214 for transferring the assignment data to it after all the feed bunks have been read. The movement of data between computers is illustrated in FIG. 81. The assignment data is utilized by the host computer to update its feed consumption data for each of the corresponding cattle pens. The feed consumption data includes consumption history for each pen, weather history (which affects feeding), physical condition of the feed bunk, which bunks should presently be read, and other data relevant to feeding. The assignment data may include a change in the ration quantity to be assigned and the present physical condition of the bunk, i.e., whether the bunk is completely empty, needs to be cleaned, whether the feed needs to be mixed with hay, or the time of feeding to be changed, etc.

The host computer 4214 is normally located remote from the cattle pens because this computer is required for a number of additional feedlot operational and management tasks that require central access. It should be noted, however, that the portable computer 2614 could be replaced by a "dumb" terminal and linked to the host computer continuously by radio signal instead of a physical connection. It should also be understood that the use of a host computer is not required. The feed consumption data could be stored and updated solely in the portable computer 2614. This approach is usually not done because the feed consumption data is utilized for other purposes, such as management and invoicing, and must be made available for those purposes in a computer 4214 located centrally in the feedlot.

The host computer 4214 is programmed to utilize the newly entered assignment data for a number of tasks. One task is to determine the best or most efficient route for the truck 2014 to read the selected feed bunks in the feedlot. As different cattle pens are emptied and filled with cattle, this data is entered in the host computer 4214 to update the feed consumption data. The computer 4214 calculates therefrom the best route through the cattle lot to read the currently used bunks. The route is transferred to the portable computer as part of the feed consumption data at the beginning of a bunk reading. At each pen during the route, pen numbers may be displayed on screen 3014 after the previous bunk is read. The entered assignment data is also used to organize feed rations to be delivered to each feed bunk. This data is defined as feed delivery data and may be printed out for a feed truck operator by means of a printer 4614 coupled to the computer 4214 as shown in FIG. 81 and as will be described.

Figure 82A:
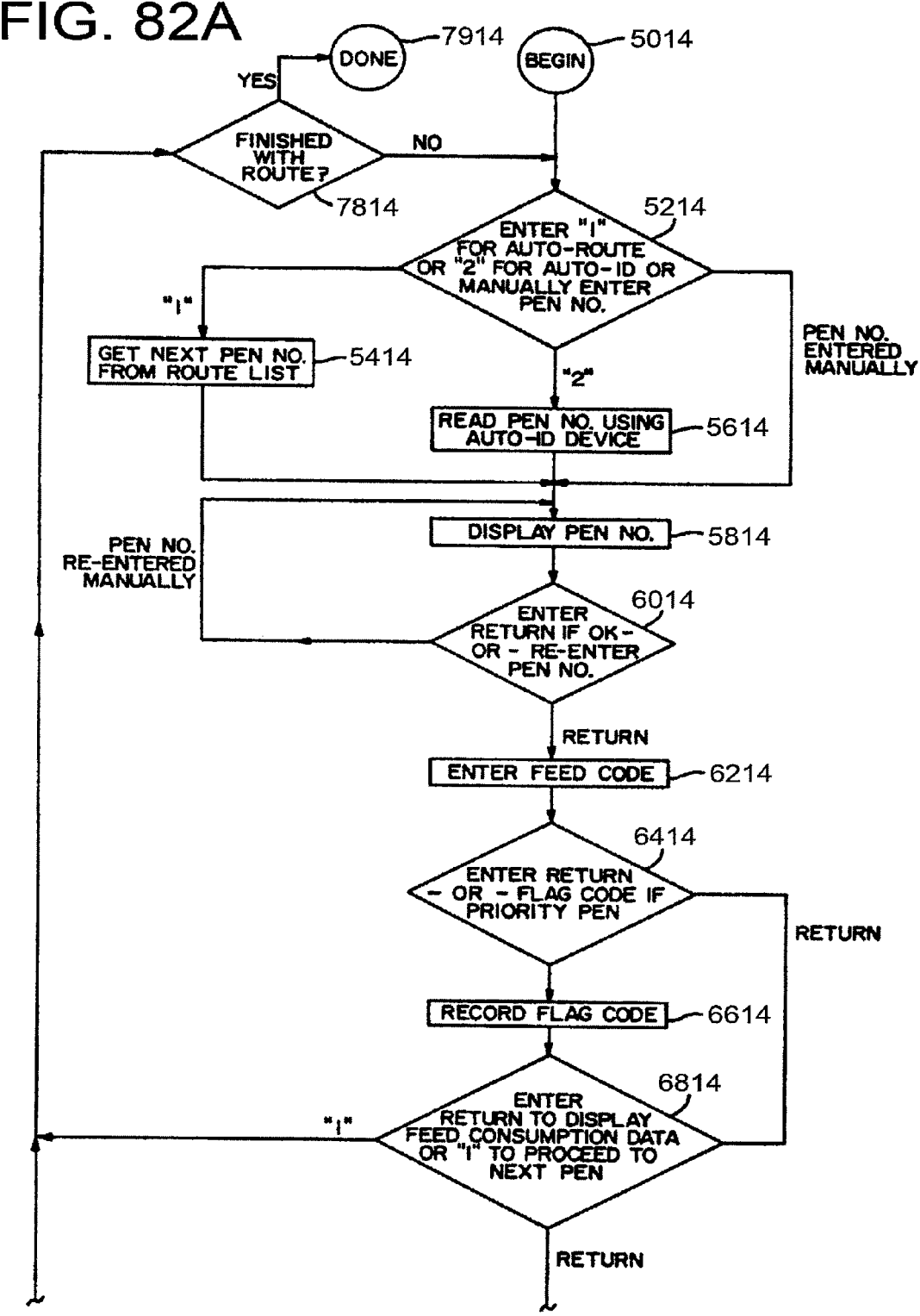
FIGS. 82A and 82B are a flowchart illustrating the computerized operation of the system of FIG. 80.
Figure 82B:
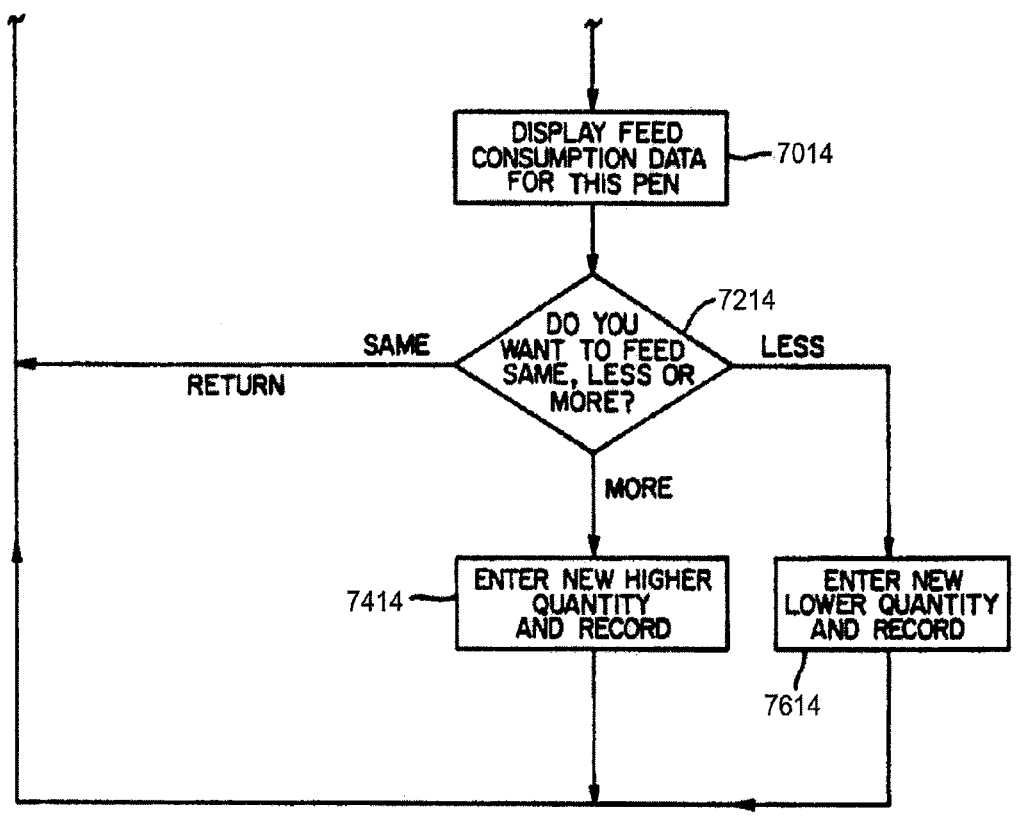

FIGS. 82A and 82B are a flowchart illustrating the computerized operation of the bunk reader system. For clarity, each step of the flowchart described herein is followed by a numeral in parenthesis corresponding to the flowchart steps in the figure. Prior to beginning a reading of the bunks, the feed consumption data is downloaded from the host computer 4214 into the portable computer 2614 and the computer 2614 placed in the truck cab.

With the driver approaching a feed bunk, the program within the computer 2614 is called (5014). The driver is first prompted to enter a number to determine the identification means for the cattle pen (5214). If he enters the number 1 in response, for example, the computer 2614 displays an expected pen number from the bunk reader route list generated by the host computer 4214 and contained within the feed consumption data transferred to the computer 2614 (5414). If the number 2 is entered, an automated identification means such as described is employed by the driver (5614). The driver may also enter the pen number manually if desired. The pen number is then displayed for the driver to confirm its correctness (5814). He confirms by entering a carriage return on the keyboard 2814 or reenters the number if it is incorrect (6014).

With the correct pen number confirmed, the driver is prompted to enter a feed code corresponding to a change in the ration quantity assigned to the pen's feed bunk (6214). The code is simple: +1 is entered to increase the ration quantity; 0 is entered for no change in the ration quantity; and −1 is entered to decrease the ration quantity. These entries are later translated by the host computer 4214 into a percentage change in the base amount of the ration quantity, e.g., 5%. Note that the driver need not identify the ration type explicitly. This identification is made by the host computer from the entered pen number.

At this point, the driver has the option of entering a flag code (6414). Flag codes correspond to the physical condition of the bunk, feeding priority, feeding mix changes, or other actions to be taken while or before more feed is delivered (6614). For example, if the driver notices a feed bunk is wiped clean or "slick," he enters a number code indicating that condition. If the bunk should be cleaned, another code number is entered. If hay should be mixed in with the next ration quantity, still another code number is entered, etc.

Once the feed code and flag codes, if desired, have been entered, the computer 2614 prompts the driver on whether to display the historical feed consumption data for the pen (6814). The driver typically evaluates this data only if the feeding of the cattle in the pen appears to be unusual. For example, a bunk that is slick several days in a row may indicate the base amount of feed is too small. Conversely, too much feed left over from a prior feeding may indicate the base amount is excessive. The consumption data indicates the actual ration quantities dispensed previously, as well as weather history that may affect prior feeding (7014). The driver then has the option of changing the base amount of the next ration quantity (7214) by entering a command. He may increase it (7414), decrease it (7614), or leave it unchanged. If the base amount of the ration quantity is to remain the unchanged, the driver simply enters a return on keyboard 2814.

The computer 2614 then checks to determine if the route is finished (7814). If not, the driver is prompted to proceed to the next pen and the bunk reading continues. Once all feed bunks have been read, the driver is prompted to confirm that the bunk reading route is finished (7914).

The assignment data entered during the feed bunk reading is transferred to the host computer 4214 for generating feed delivery data. This data, organized by ration type, is used for loading feed trucks and for organizing feed truck routes though the feed lot. An example of the delivery data produced by the host computer 4214 for the feed trucks is shown in Table I below.

TABLE I

FEED LOADOUT REPORT

| Pen | Pounds to Feed |
|---|---|
| *a101 | 500 |
| b102 | 1000 |
| c103 | 2000 |
| d104 | 1500 |
| e105 | 1300 |
| *F106 | 2000 |
| g107 | 3000 |
| h108 | 4000 |
| i109 | 3000 |
| j110 | 1500 |
| *k111 | 3000 |
| 112 | 3500 |
| m113 | 3500 |
| MAXIMUM LOAD SIZE = 6000 lbs. | |
| LOAD NO. 1 | |
| *a101 | 500 |
| *F106 | 2000 |
| *k111 | 3000 |
| Total | 5500 |
| LOAD NO. 2 | |
| b102 | 1000 |
| c103 | 2000 |
| d104 | 1500 |
| e105 | 1300 |
| Total | 5800 |

*denotes first priority to feed

Normally, each feed truck carries one type of feed ration and is filled with selected ration quantities to its maximum load. For example, in Table I above, the ration quantities for pen number a101, F106, and k111 have been combined in a single load of 5500 lbs., that is near the maximum load of 6000 lbs. for a feed truck. These quantities were determined from the amount of ration quantity for each pen plus whatever changes have been made to the base amount from prior readings of the feed bunks. Note also that the flag code for feeding priority was entered during the last bunk readings. The priority loads are thus combined by the computer 42 into the first load to be delivered to the cattle pens.

Figure 83:
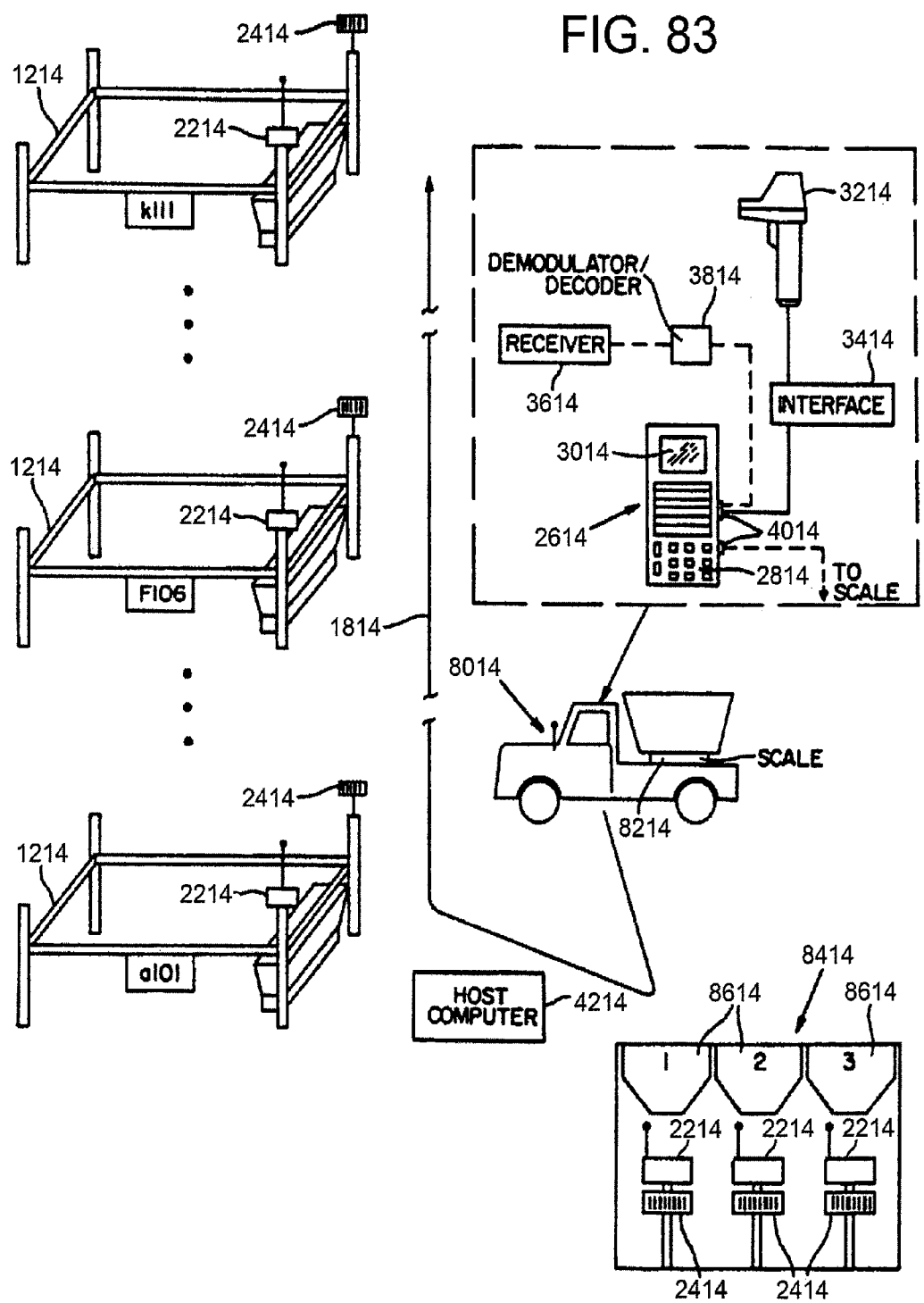
FIG. 83 is a schematic diagram of a system for delivering feed to each feed bunk.

Referring now to FIG. 83, there is shown a drawing of a computerized feed delivery system. A feed truck 8014 includes a weighing scale 8214 for weighing the total load in the truck hopper and for weighing individually the ration quantities to be dispensed into each feed bunk. The scale is conventional and is adapted to provide an output signal indicating the weight of the load. Accompanying the truck operator is another portable computer 2614 the same as or similar to the type used for bunk reading. It includes a keyboard 2814, display screen 3014, and one or more I/O ports 4014. The computer 2614 is adapted to connect to the scale 8214 through an I/O port 4014. As in the bunk reader system, the computer 2614 may be associated with other data entry means such as an RF receiver 3614 or bar code scanner 3214. The feed bunks, of course, may include corresponding automated identification means such as RF transmitters 2214 or bar code 2414. FIG. 83 further shows a feed mill 8414 from which feed is obtained for delivery to the feed bunks. The mill 8414 has a number of ration bins 8614 each holding a different type of ration and having means of identification such as an alphanumeric symbol, radio signal from a transmitter 2214, or a bar code 2414 affixed to the bin.

The type of feed ration and base amount of ration quantity for each cattle pen when initially filled with cattle is entered into host computer 42 by a feedlot supervisor. The ration quantities may be modified by the assignment data from the bunk readings. However, if the type of ration for the pen is changed or if drugs are added to the basic ration, this information is entered directly into the host computer. Certain drugs cannot be taken by cattle immediately before they are shipped from the feedlot for slaughter. One of the functions of the feed delivery system is to make certain that cattle ready for slaughter have drugs withdrawn from their feed rations in a timely manner, as will be shown.

Figure 84A:
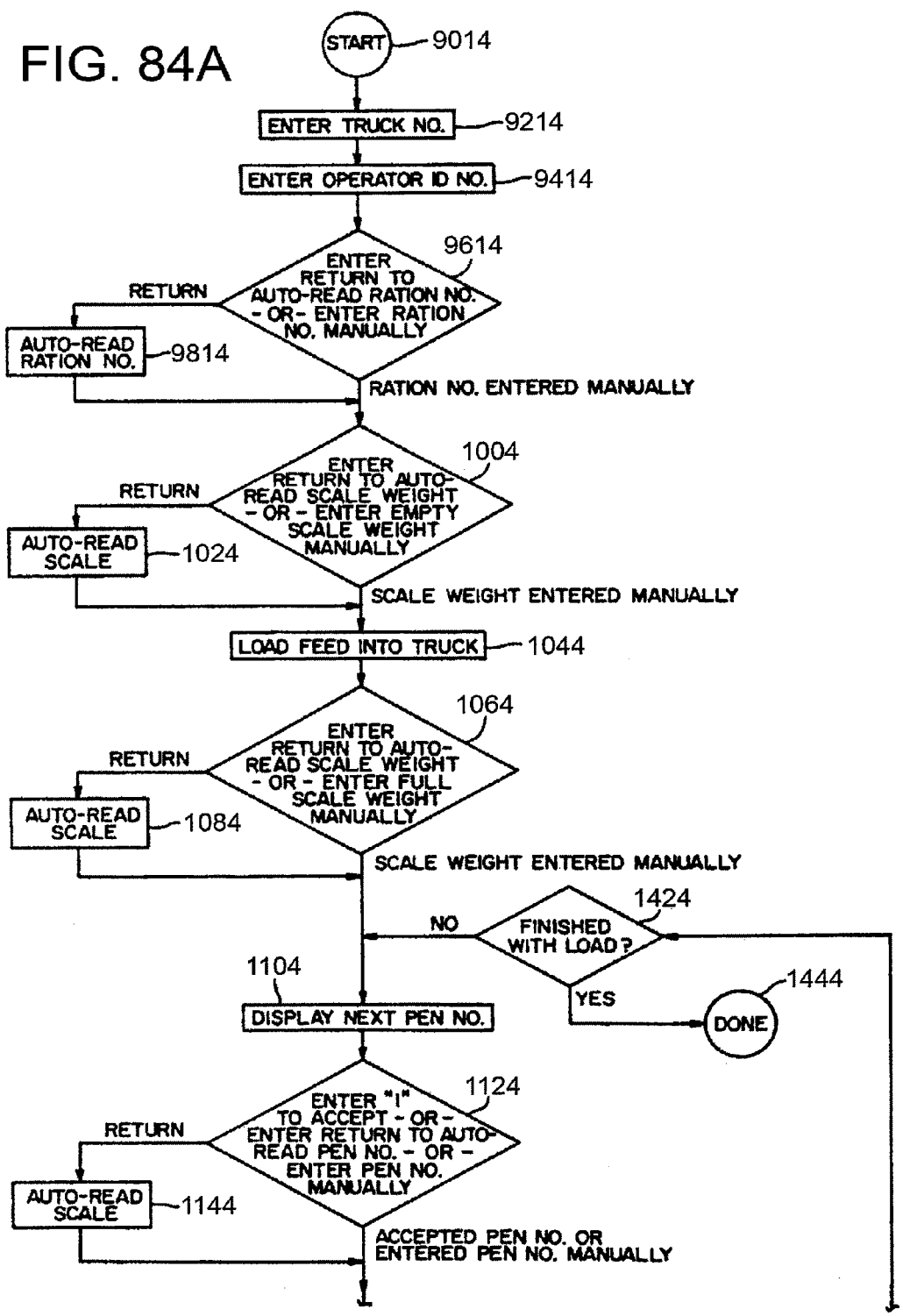
FIGS. 84A and 84B are a flowchart illustrating the computerized operation of the system of FIG. 83.
Figure 84B:
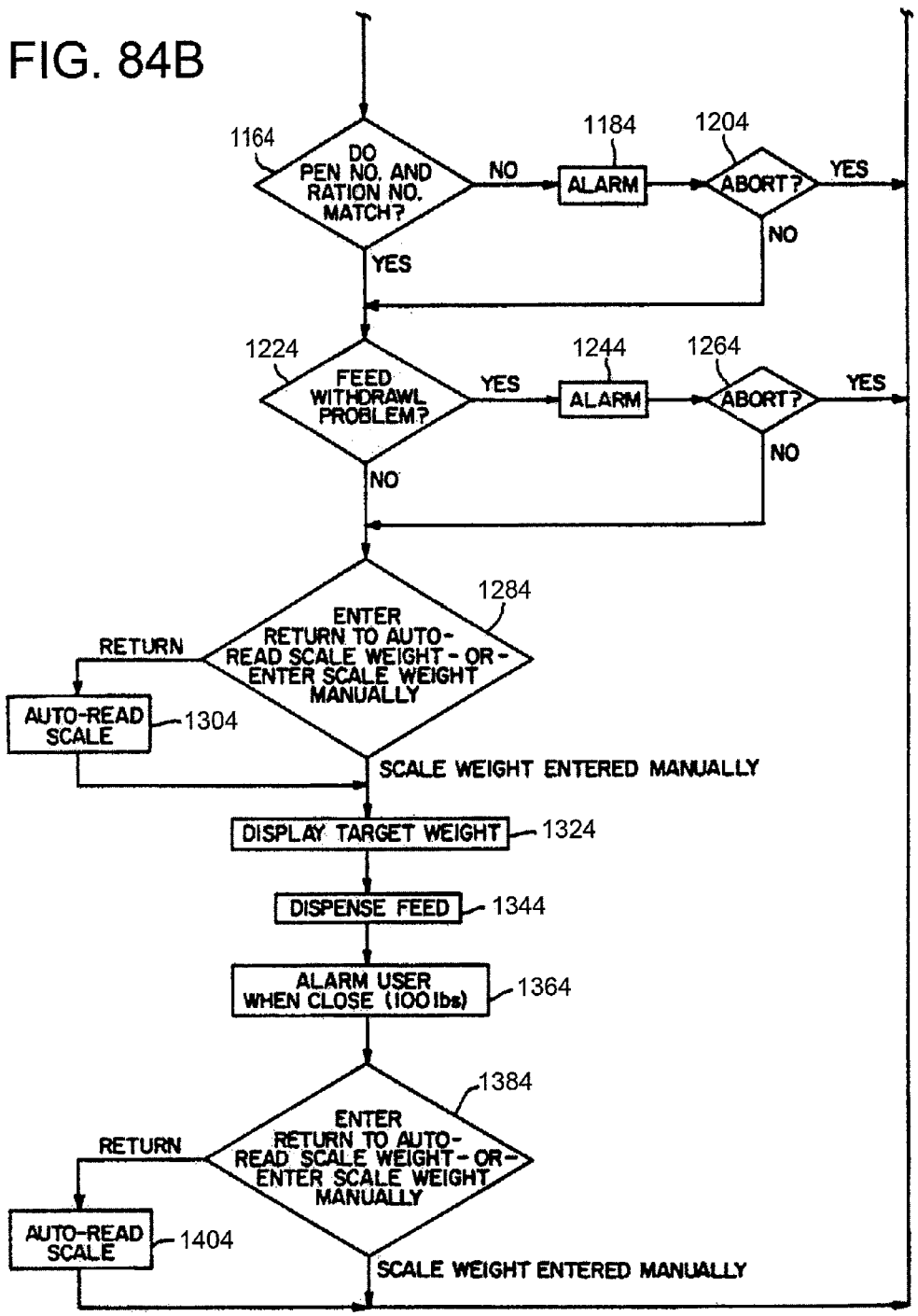

FIGS. 84A and 84B are a flowchart that illustrates the interactive programming of the computer 2614 for directing the feed truck operator to deliver the appropriate ration and quantity to each pen. Initially, the host computer 4214 has generated the feed delivery data for each pen from the assignment data received from the bunk reading. Prior to delivery, the feed delivery data shown in Table I is downloaded into the portable computer 2614 via an I/O port 4014. The present manner of transfer is the same as in FIG. 81, the difference being that in this step feed delivery data is transferred from the host computer 4214 to the portable computer 2614 prior to the delivery and feed dispensed data is transferred from the portable 2614 to the host computer 4214 after delivery.

The operator first proceeds to the mill 8414 for loading the feed truck and calls the program (9014). At the mill, he enters his feed delivery truck number and operator number (9214, 9414). If the operator is using an RF receiver 3614 or bar code scanner 3214 to identify the particular feed bin, he enters a return on the keyboard 2814 to automatically read the identifying ration number, e.g., "2," on the bin (9614, 9814). Otherwise, the ration number is entered manually. The operator then connects the computer 2614 through its I/O port 4014 to the scale 8214 and enters a return to record the empty scale weight (1004, 1024). That information may be entered manually as well (1004). The operator proceeds to load the feed truck to the level specified in Table I, provided to him on a printout (1044). The scale is again read to determine the total weight of feed loaded, either automatically (1064, 1084) or manually (1064). At this point, the ration number and the total ration quantity loaded into the truck have been recorded in the computer 2614, as well as the ration quantity or amount to be delivered to each pen in Table I.

The driver then proceeds to the first pen 1214 whose number, a101, is retrieved from the route list produced by the host computer 4214 and displayed on the display screen 3014 (1104). Upon arriving at the indicated pen, the driver identifies the pen using a machine (1124, 1144) or manually (1124). The computer 2614 in response compares the entered pen number against the pen numbers that are to receive that ration number to determine if the operator has driven to a correct pen (1164). If the two numbers do not match, an alarm is given (1184). The operator is then asked via the screen 3014 if dispensing feed for that pen should be aborted (1204). An affirmative answer aborts the feeding at the pen, and the screen 3014 directs the driver to proceed to the next pen. The operator gives a negative answer to override and dispense the feed. The computer then determines if there is a feed withdrawal problem, as described (1224). As before, an alarm is given if a potential problem exists (1244) and the operator is given the chance to abort the pen feeding (1264).

Immediately before the operator proceeds to dispensing the feed, the scale is again read manually or automatically (1284, 1304). The computer 2614 then displays on the screen 3044 the target weight for the truck operator (1324). The operator dispenses feed (1344), with the computer 2614 monitoring the scale weight as the weight dispensed approaches the desired ration quantity for the feed bunk. The operator is notified by alarm or otherwise when the dispensed quantity is close to the desired quantity, such as within a hundred pounds (1364). Once the ration quantity for the pen has been dispensed, the operator enters the remaining scale weight into the computer (1384) to confirm the quantity. This entry can be made manually or automatically (1404).

The program then checks to determine if the delivery route is finished (1424). If not, the driver is prompted to proceed to the next pen and its number is displayed (1104). The program continues until each pen on the route has received its ration quantity (1444).

On returning to the host computer, the portable computer 2614 is taken from the feed truck 8014 and the data and actual feed dispensed is transferred from the computer 2614 to the host computer 4214. This data is used to charge feed costs to the lot owners whose cattle are contained in the pens. An example of data generated by host computer 4214 after comparing the feed delivery data against the feed dispensed data is shown in Table II.

TABLE II

FEED TRUCK NO. 1 REPORT

| Pen | Ration | Ordered | Fed | Diff | Date | Time |
|---|---|---|---|---|---|---|
| a101 | 2 | 500 | 505 | 5 | 1/21 | 5:17 PM |
| F106 | 2 | 2000 | 1998 | -2 | 1/21 | 5:19 PM |
| k111 | 2 | 3000 | 3002 | 2 | 1/21 | 5:20 PM |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for managing at least one animal, comprising:
    receiving a live animal at a feedlot;
    entering into a computer system information relating to the animal, wherein the computer system comprises a feedlot business system (FBS) computer capable of performing accounting functions and passing data back and forth between the FBS computer and one or more various computers used in the computer system;
    measuring the animal at a processing location and entering first measurement characteristic data into the computer system including at least weight;
    associating the first measurement data with a unique identifier for the animal in the computer system;
    imaging at least one lung of the animal to produce a first image and determine a degree of respiratory damage in the animal;
    comparing the first image to at least one other lung image to determine whether the first image indicates active or past disease;
    assigning the animal a respiratory damage designation corresponding to the animal's degree of respiratory damage;
    recording the respiratory damage designation in an electronic database;
    associating the respiratory damage designation with the unique identifier for the animal in the computer system;
    determining in the computer system, from at least in part the first measurement characteristic data and the respiratory damage designation, a projected condition for the animal; and
    selecting at least one aspect of treatment, care, and/or disposition of the animal based on the respiratory damage designation and whether the first image indicates active or past disease.

2. The method according to claim 1, further comprising performing an auditory evaluation of internal tissue characteristics.

3. The method of claim 1 where at least one of the one or more various computers is at a location remote from the FBS computer.

4. The method according to claim 1 where the computer system further comprises a computerized animal drug inventory control and animal health history and drug treatment system, a computerized feed additive delivery system, a computerized bunk reader system, or each and every combination thereof.

5. The method of claim 4 further comprising receiving and storing data from the computerized animal drug inventory control and animal health history and drug treatment system, the computerized feed additive delivery system, the computerized bunk reader system, or each and every combination thereof.

6. The method of claim 5 where the data includes drug usage information, feed ration usage information, feed additive usage information, or each and every combination thereof.

7. The method of claim 5 where the FBS computer is capable of receiving and storing data concerning an amount of feed ration delivered to at least one or more feed pens from the computerized bunk reader system.

8. The method according to claim 4 where the FBS computer further comprises the animal drug inventory control, animal health history and drug treatment system, the feed additive delivery system, the bunk reader system, or a combination of such systems.

9. The method according to claim 4 where each of the FBS computer and the computerized animal drug inventory control, animal health history and drug treatment system, the computerized feed additive delivery system, and the computerized bunk reader system is a separate computer in communication with one another.

10. The method according to claim 4 where the FBS computer records and stores data from the computerized feed additive delivery system and utilizes such information to calculate a cost of production and feed additive costs for the animal.

11. The method according to claim 4 where selecting at least one aspect of treatment, care, and/or disposition of the animal comprises:
    determining in the computer system for the animal a projected feed intake, a projected gain and an estimated time required to reach the projected condition, from at least in part the first measurement characteristic data, the respiratory damage designation, the projected condition, feed ration information, and if used, growth promotants; and
    directing the animal to a feed pen and there feeding the animal with a sort group of animals for a feeding period.

12. The method according to claim 11, further comprising:
    measuring and recording at least one physical characteristic of the animal in a subsequent measuring step, including at least a second weight measurement, and matching second measurement data with the animal's unique identifier and with the first measurement data;

determining in the computer system performance characteristics for the animal, based at least in part on the first and second measurement data; and re-sorting the animal into one of multiple sort groups of animals based at least in part on the performance characteristics and the respiratory damage designation.

13. The method of claim 12 where the animal is re-sorted into a salvage group and removed from the feedlot.

14. The method according to claim 11, further comprising:
administering a feed additive growth promotant to the sort group based at least in part on an estimated time required to reach a projected condition for the sort group;

dispensing the feed additive growth promotant into a feed ration by the computerized feed additive delivery system for administering the feed additive growth promotant to the sort group; and dispensing the feed additive growth promotant at a determined time prior to shipment of the sort group from the feedlot for substantially optimizing economic value for the sort group.

15. The method according to claim 14 where the feed additive growth promotant is selected from a group of growth promotants including ionophores.

16. The method according to claim 14 further comprising discontinuing dispensing the feed additive growth promotant into the feed ration for the sort group to provide a withdrawal period for the feed additive growth promotant.

17. The method according to claim 1 where the projected condition includes a projected weight gain and selecting at least one aspect of the treatment, care or disposition of the animal comprises selecting the amount or type of feed provided to the animal.

18. The method of claim 17 where the type of feed is a weight maintenance diet.

19. The method of claim 1, further comprising imaging the animal's lungs at another time during the animal's lifecycle to provide a second lung image.

20. The method of claim 19, further comprising comparing the second lung image to the first lung image.

21. The method of claim 1 where selecting at least one aspect of the care, treatment, or disposition of the animal comprises determining whether or not to treat the animal for a respiratory illness diagnosed after assigning the respiratory damage designation.

22. The method of claim 21 where determining whether to treat the animal comprises determining whether or not to administer a drug to the animal.

23. The method of claim 22, further comprising:
administering the drug to the animal; and
adjusting the estimated time required to reach the projected condition based upon a drug withdrawal period for the drug prior to selecting the animal for a sort group.

24. The method of claim 1 where selecting at least one aspect of the care, treatment, or disposition of the animal comprises selecting how long the animal should remain at the feedlot prior to slaughter.

25. The method of claim 24 where the animal is sent to slaughter without spending any time at the feedlot.

26. The method of claim 1 where selecting at least one aspect of the care, treatment, or disposition of the animal comprises providing the respiratory damage designation to a buyer to aid the buyer in a decision regarding purchasing the animal.

27. The method of claim 1, further comprising:
entering into the computer system location data for the animal for a location or locations occupied by the animal;

enabling confidential information to be filtered from data in the computer system, where the confidential information includes at least a previous location identifier; and generating a filtered record for the animal that includes the animal's respiratory damage designation, a location identifier for a present location of the animal, and that the animal occupied a previous location without disclosing the previous location identifier.

28. The method of claim 27 further comprising entering into the computer system data for animals commingled from different locations.

29. The method of claim 28 further comprising identifying in the computer system a subsequently identified animal that shared a location with the animal.

30. The method of claim 27, further comprising:
requesting a trace report from a data trustee upon discovering the animal has active respiratory disease;
generating a trace report that filters confidential information; and
identifying locations of identified animals that have commingled with the animal.

31. The method of claim 30 further comprising implementing a treatment strategy for the identified animals that commingled with the animal with active respiratory disease.

32. The method of claim 31 where the treatment strategy comprises treating the respiratory disease, quarantining the identified animals, slaughtering the identified animals, or a combination thereof.

* * * * *